US008735599B2

(12) United States Patent
Wang et al.

(10) Patent No.: US 8,735,599 B2
(45) Date of Patent: *May 27, 2014

(54) SUBSTITUTED IMIDAZOLE DERIVATES

(75) Inventors: Weibo Wang, Moraga, CA (US); Paul A. Barsanti, Pleasant Hill, CA (US); Xia Yia, Palo Alto, CA (US); Rustum S. Boyce, New York, NY (US); Sabina Pecchi, Oakland, CA (US); Nathan Brammeier, Walnut Creek, CA (US); Megan C. Phillips, Lake Orion, MI (US); Kris Mendenhall, Concord, CA (US); Kelly Wayman, San Rafael, CA (US); Liana Marie Lagnition, Oakland, CA (US); Ryan N. Constantine, Salt Lake City, UT (US); Hong Yang, Fremont, CA (US); Elizabeth Mieuli, Redwood City, CA (US); Savithri Ramurthy, Walnut Creek, CA (US); Elisa Jazan, Siena (IT); Anu Sharma, El Cerrito, CA (US); Rama Jain, Fremont, CA (US); Sharadha Subramanian, San Ramon, CA (US); Paul A. Renhowe, Danville, CA (US); Kenneth W. Bair, Oakland, CA (US); David Duhl, Oakland, CA (US); Annette Walter, Mill Valley, CA (US); Tinya Abrams, Richmond, CA (US); Kay Huh, San Mateo, CA (US); Eric Martin, El Cerrrito, CA (US); Mark Knapp, Oakland, CA (US); Vincent P. Le, San Francisco, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/613,977

(22) Filed: Sep. 13, 2012

(65) Prior Publication Data

US 2013/0017196 A1    Jan. 17, 2013

Related U.S. Application Data

(60) Continuation of application No. 12/455,798, filed on Jun. 5, 2009, now Pat. No. 8,318,791, which is a division of application No. 11/158,574, filed on Jun. 20, 2005, now Pat. No. 7,576,221.

(60) Provisional application No. 60/580,927, filed on Jun. 18, 2004.

(51) Int. Cl.
    *A61K 31/4174*    (2006.01)
    *C07D 233/00*     (2006.01)
    *C07D 233/54*     (2006.01)

(52) U.S. Cl.
    CPC ........................ *C07D 233/54* (2013.01)
    USPC ...................... 548/338.1; 514/400

(58) Field of Classification Search
    CPC ........................ C07D 233/64; A61K 31/4174
    USPC ...................... 514/268, 400; 548/338.1
    See application file for complete search history.

(56) References Cited

U.S. PATENT DOCUMENTS

| | | | |
|---|---|---|---|
| 4,152,440 A | 5/1979 | Gebert et al. | 42/269 |
| 6,545,004 B1 | 4/2003 | Finer et al. | 514/266.2 |
| 6,562,831 B1 | 5/2003 | Finer et al. | 514/266.3 |
| 6,630,479 B1 | 10/2003 | Finer et al. | 514/266.3 |
| 7,291,641 B2 | 11/2007 | De Lassauniere et al. | 514/400 |
| 7,504,405 B2 * | 3/2009 | Wang et al. | 514/259.4 |
| 7,576,221 B2 * | 8/2009 | Wang et al. | 548/338.1 |
| 7,662,581 B1 * | 2/2010 | Bussiere et al. | 435/7.71 |
| 2004/0106608 A1 | 6/2004 | Munchhof et al. | 514/227.8 |
| 2004/0132788 A1 | 7/2004 | De Lassauniere et al. | 514/365 |
| 2005/0187277 A1 | 8/2005 | Mjalli et al. | 514/400 |
| 2005/0215546 A1 | 9/2005 | Hurnaus et al. | 415/221 |

FOREIGN PATENT DOCUMENTS

| | | |
|---|---|---|
| RU | 2219171 | 12/2003 |
| WO | WO 98/27108 | 6/1998 |
| WO | WO 00/23487 | 4/2000 |
| WO | WO 00/59887 | 10/2000 |
| WO | WO 01/26656 A2 | 4/2001 |
| WO | WO 01/30768 A1 | 5/2001 |
| WO | WO 01/83575 | 11/2001 |
| WO | WO 01/94317 | 12/2001 |

(Continued)

OTHER PUBLICATIONS

Shirley et al., "The Metalation of 1-Methyl-13 1-Bensyl—and 1-Phenylimidazole with n-Butyllithium" 79:8922-8927, Sep. 20, 1957.
Whitten et al. "A One Step Synthesis of 4-Substituted Imidazoles. An Important Observation When *N*-Alkylating Imidazoles" 1845-4847, Nov.-Dec. 1988.
Matthews et al., "Synthesis and Cardiotonic Activity of Nevel Biimidazoles" *J. Med. Chem.* 33:327-327, 1990.
Deng and Hlasta, "Synthetic Applications of Azolium Ylides to a Traceless Solid-Phase Synthesis of 2-Substituted Azoles" *Org. Lett.* 4(23):4017-4020, 2002.
Gerbert et al. Justus Liebigs Annalen Der Chemie. 1974, 644-654 (abstract) Database Beilstein 1988 XP002347720.
Garber, *J. Natl Cancer Inst.* 37(12), Jun. 15, 2005.
http://www.oncolink.com/types/index.htm, Oncolink list of cancers, 2007.

*Primary Examiner* — Jennifer M Kim
(74) *Attorney, Agent, or Firm* — Michael G. Smith

(57) ABSTRACT

The present invention relates to new substituted imidazole compounds and pharmaceutically acceptable salts, esters or prodrugs thereof, compositions of the new compounds together with pharmaceutically acceptable carriers, and uses of the new compounds. The compounds of the invention have the following general formula:

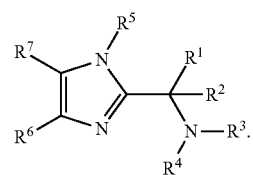

11 Claims, No Drawings

(56) References Cited

FOREIGN PATENT DOCUMENTS

| | | |
|---|---|---|
| WO | WO 01/94318 | 12/2001 |
| WO | WO 02/10140 | 2/2002 |
| WO | WO 02/28839 A1 | 4/2002 |
| WO | WO 02/056880 A1 | 7/2002 |
| WO | WO 02/057244 A1 | 7/2002 |
| WO | WO 02/050877 | 8/2002 |
| WO | WO 03/039450 A2 | 5/2003 |
| WO | WO 03/043995 A1 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/059289 A2 | 7/2003 |
| WO | WO 03/070701 A2 | 8/2003 |
| WO | WO 03/076432 | 9/2003 |
| WO | WO 03/079973 A2 | 10/2003 |
| WO | WO 03/093263 | 11/2003 |
| WO | WO 03/094839 | 11/2003 |
| WO | WO 03/094839 A2 | 11/2003 |
| WO | WO 03/097053 A1 | 11/2003 |
| WO | WO 03/097643 | 11/2003 |
| WO | WO 03/099211 A2 | 12/2003 |
| WO | WO 03/103575 A2 | 12/2003 |
| WO | WO 03/105855 A1 | 12/2003 |
| WO | WO 03/106417 A1 | 12/2003 |
| WO | WO 2004/004652 A2 | 1/2004 |
| WO | WO 2004/006865 A2 | 1/2004 |
| WO | WO 2004/009036 A2 | 1/2004 |
| WO | WO 2004/001489 B | 2/2004 |
| WO | WO 2004/018058 A2 | 3/2004 |
| WO | WO 2004/024086 A2 | 3/2004 |
| WO | WO 2004/026226 A1 | 4/2004 |
| WO | WO 2004/031174 | 4/2004 |
| WO | WO 2004/041808 | 5/2004 |
| WO | WO 2004/041809 | 5/2004 |
| WO | WO 2004/007144 B | 8/2004 |
| WO | WO 2004/071448 A2 | 8/2004 |
| WO | WO 2005/073198 | 8/2005 |
| WO | WO 2005/100322 | 10/2005 |
| WO | WO 2005/105802 | 11/2005 |
| WO | WO 2005/107762 | 11/2005 |

\* cited by examiner

SUBSTITUTED IMIDAZOLE DERIVATES

This application is a continuation application of Ser. No. 12/455,798, filed 5 Jun. 2009, now U.S. Pat. No. 8,318,791, which is a divisional of Ser. No. 11/158,574, filed 20 Jun. 2005, now U.S. Pat. No. 7,576,221, which claims the benefit under 35 U.S.C. §119(e) of U.S. Provisional Application Ser. No. 60/580,927 filed Jun. 18, 2004, which is hereby incorporated by reference in its entirety.

BACKGROUND OF THE INVENTION

1. Field of the Invention

The present invention relates to substituted imidazole compounds and pharmaceutically acceptable salts, esters or prodrugs thereof, compositions of these compounds together with pharmaceutically acceptable carriers, and uses of these compounds.

2. State of the Art

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmic reticulum. Several KRPs interact with the microtubules of the mitotic spindle or with the chromosomes directly and appear to play a pivotal role during the mitotic stages of the cell cycle. These mitotic KRPs are of particular interest for the development of cancer therapeutics.

Kinesin spindle protein (KSP) (also known as Eg5, HsEg5, KNSL1, or KIF11) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., *Cell* 83:1159-1169, 1995). Mutations in bimC and cut7 genes, which are considered to be homologues of KSP, cause failure in centrosome separation in *Aspergillus nidulans* (Enos, A. P., and N. R. Morris, *Cell* 60:1019-1027, 1990) and *Schizosaccharomyces pombe* (Hagan, I., and M. Yanagida, *Nature* 347:563-566, 1990). Treatment of cells with either ATRA (all trans-retinoic acid), which reduces KSP expression on the protein level, or depletion of KSP using antisense oligonucleotides revealed a significant growth inhibition in DAN-G pancreatic carcinoma cells indicating that KSP might be involved in the antiproliferative action of all trans-retinoic acid (Kaiser, A., et al., *J. Biol. Chem.* 274, 18925-18931, 1999). Interestingly, the *Xenopus laevis* Aurora-related protein kinase pEg2 was shown to associate and phosphorylate XlEg5 (Giet, R., et al., *J. Biol. Chem.* 274:15005-15013, 1999). Potential substrates of Aurora-related kinases are of particular interest for cancer drug development. For example, Aurora 1 and 2 kinases are overexpressed on the protein and RNA level and the genes are amplified in colon cancer patients.

The first cell permeable small molecule inhibitor for KSP, "monastrol," was shown to arrest cells with monopolar spindles without affecting microtubule polymerization as do conventional chemotherapeutics such as taxanes and vinca alkaloids (Mayer, T. U., et al., *Science* 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., *Biochemistry* 42:338-349, 2003; Kapoor, T. M., et al., *J. Cell Biol.* 150:975-988, 2000).

In light of the importance of improved chemotherapeutics, there is a need for KSP inhibitors that are effective in vivo inhibitors of KSP and KSP-related proteins.

SUMMARY OF THE INVENTION

This invention is directed to substituted imidazole compounds which modulate the activity of KSP represented by the formula I:

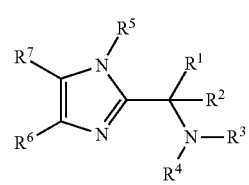

wherein:

$R^1$ is selected from the group consisting of aminoacyl, acylamino, carboxyl, carboxyl ester, aryl, and alkyl optionally substituted with hydroxy or halo;

$R^2$ is selected from the group consisting of hydrogen, alkyl, and aryl;

$R^3$ is selected from the group consisting of hydrogen and —X-A, wherein X is selected from the group consisting of —C(O)—, —C(S)—, —S(O)—, —S(O)$_2$—, and —S(O)$_2$—N(R)—, where R is hydrogen or alkyl; and A is selected from the group consisting of hydrogen, optionally substituted alkyl, optionally substituted alkoxy, optionally substituted aryl, carboxyl, carboxyl ester, aminoacyl, optionally substituted heteroaryl, optionally substituted heterocyclic, and optionally substituted cycloalkyl, wherein the optionally substituted groups are substituted with 1 to 4 substituents selected from the group consisting of alkyl, substituted alkyl, alkoxy, substituted alkoxy, amino, substituted amino, aryloxy, substituted aryloxy, cyano, aryl, substituted aryl, heteroaryl, substituted heteroaryl, heterocyclic, substituted heterocyclic, heterocyclyloxy, substituted heterocyclyloxy, acyl, carboxyl, carboxyl ester, oxo (except when A is optionally substituted aryl or optionally substituted heteroaryl), halo, hydroxy, —S(O)$_2$—R$^9$ where R$^9$ is alkyl, substituted alkyl, aryl, substituted aryl, heteroaryl or substituted heteroaryl, and nitro;

or $R^1$ and $R^3$, together with the carbon atom attached to $R^1$ and the nitrogen atom attached to $R^3$ form a heterocyclic or substituted heterocyclic group;

$R^4$ is selected from the group consisting of hydrogen, linear alkyl, -alkylene-aminoacyl, -alkylene-oxyacyl, -alkylene-acyloxy, -alkylene-hydroxy, -[alkylene]$_p$-nitrogen-containing heterocyclic, -[alkylene]$_p$-nitrogen-containing substituted heterocyclic, -[alkylene]$_p$-nitrogen-containing heteroaryl, -[alkylene]$_p$-nitrogen-containing substituted heteroaryl, and -[alkylene]$_p$-NR$^{10}$R$^{11}$ wherein p is an integer from 0 to 1, alkylene is a straight chained alkylene optionally mono- or disubstituted with one of the foregoing substituents selected from the group consisting of amino, substituted amino, hydroxy, alkyl, substituted alkyl, carboxyl, carboxyl ester, oxo, spirocycloalkyl, and halo;

$R^{10}$ and $R^{11}$ are independently selected from the group consisting of hydrogen, alkyl, substituted alkyl, —S(O)-alkyl, —S(O)-substituted alkyl, —S(O)$_2$-alkyl, —S(O)$_2$-substituted alkyl, heterocyclic, substituted heterocyclic, acyl, aryl, substituted aryl, heteroaryl, substituted heteroaryl, cycloalkyl, and substituted cycloalkyl, or when $R^{10}$ is hydrogen, $R^{11}$ is hydroxy, alkoxy or substituted alkoxy;

or when $R^1$ and $R^3$, together with the carbon and nitrogen atoms bound respectively thereto, do not form a heterocyclic or substituted heterocyclic group, then $R^3$ and $R^4$, together with the nitrogen atom bound thereto, form a heterocyclic or substituted heterocyclic group;

$R^5$ is selected from the group consisting of L-$A^1$, wherein L is selected from the group consisting of —S(O)$_q$— where q is one or two, and $C_1$ to $C_5$ alkylene optionally substituted with hydroxy, halo, or acylamino; and $A^1$ is selected from the group consisting of aryl, substituted aryl, heteroaryl, substituted heteroaryl, heterocyclic, substituted heterocyclic, cycloalkyl, and substituted cycloalkyl; and one of either $R^6$ or $R^7$ is selected from the group consisting of heterocyclic, aryl and heteroaryl, all of which may be optionally substituted with —$(R^8)_m$ where $R^8$ is as defined herein and m is an integer from 1 to 3, and the other of $R^6$ or $R^7$ is selected from the group consisting of hydrogen, halo, and alkyl;

or $R^6$ and $R^7$ are both hydrogen;

$R^8$ is selected from the group consisting of cyano, alkyl, alkenyl, alkynyl, —CF$_3$, alkoxy, halo, and hydroxy;

or pharmaceutically acceptable salts, esters or prodrugs thereof.

In another embodiment, the invention is directed to compounds represented by formula II:

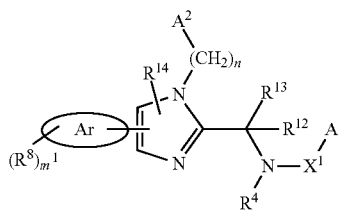

II wherein:

Ar is selected from the group consisting of phenyl, pyridinyl, pyrazinyl, and thiazolyl;

$X^1$ is selected from the group consisting of —C(O)— and —S(O)$_2$—;

$A^2$ is selected from the group consisting of aryl, heteroaryl, heterocyclic, and cycloalkyl, all of which may be optionally substituted with 1 to 4 substituents selected from the group consisting of alkyl, substituted alkyl, alkoxy, substituted alkoxy, amino, halo, hydroxy, and nitro;

A is selected from the group consisting of hydrogen, optionally substituted alkyl, optionally substituted alkoxy, optionally substituted aryl, carboxyl, carboxyl ester, aminoacyl, optionally substituted heteroaryl, optionally substituted heterocyclic, and optionally substituted cycloalkyl, wherein the optionally substituted groups are substituted with 1 to 4 substituents selected from the group consisting of alkyl, substituted alkyl, alkoxy, substituted alkoxy, amino, substituted amino, aryloxy, substituted aryloxy, cyano, aryl, substituted aryl, heteroaryl, substituted heteroaryl, heterocyclic, substituted heterocyclic, heterocyclyloxy, substituted heterocyclyloxy, acyl, carboxyl, carboxyl ester, oxo (except when A is optionally substituted aryl or optionally substituted heteroaryl), halo, hydroxy, —S(O)$_2$—$R^9$ where $R^9$ is alkyl, substituted alkyl, aryl, substituted aryl, heteroaryl or substituted heteroaryl, and nitro;

$R^4$ is selected from the group consisting of hydrogen, linear alkyl, -alkylene-aminoacyl, -alkylene-oxyacyl, -alkylene-acyloxy, -alkylene-hydroxy, -[alkylene]$_p$-nitrogen-containing heterocyclic, -[alkylene]$_p$-nitrogen-containing substituted heterocyclic, -[alkylene]$_p$-nitrogen-containing heteroaryl, -[alkylene]$_p$-nitrogen-containing substituted heteroaryl, and -[alkylene]$_p$-NR$^{10}$R$^{11}$ wherein p is an integer from 0 to 1, alkylene is a straight chained alkylene optionally mono- or disubstituted with one of the foregoing substituents selected from the group consisting of amino, substituted amino, hydroxy, alkyl, substituted alkyl, carboxyl, carboxyl ester, oxo, spirocycloalkyl, and halo;

$R^{10}$ and $R^{11}$ are independently selected from the group consisting of hydrogen, alkyl, substituted alkyl, —S(O)-alkyl, —S(O)-substituted alkyl, —S(O)$_2$-alkyl, —S(O)$_2$-substituted alkyl, heterocyclic, substituted heterocyclic, acyl, aryl, substituted aryl, heteroaryl, substituted heteroaryl, cycloalkyl, and substituted cycloalkyl or when $R^{10}$ is hydrogen, $R^{11}$ is hydroxy, alkoxy or substituted alkoxy;

or when $R^{13}$ and A, together with the carbon atom and the $X^1$ group bound respectively thereto, do not form a heterocyclic or substituted heterocyclic group, then $X^1$-A and $R^4$, together with the nitrogen atom bound thereto, form a heterocyclic or substituted heterocyclic group;

$R^8$ is selected from the group consisting of cyano, alkyl, alkenyl, alkynyl, —CF$_3$, alkoxy, halo, and hydroxy;

$R^{12}$ is hydrogen, alkyl;

$R^{13}$ is alkyl or aryl;

$R^{13}$ and $X^1$-A, together with the carbon atom attached to $R^{13}$ and the nitrogen atom attached to $X^1$ join to form a heterocyclic or a substituted heterocyclic group;

$R^{14}$ is hydrogen or $C_1$ to $C_4$ alkyl;

$m^1$ is an integer equal to 0 to 2;

n is an integer equal to 1 to 3; or pharmaceutically acceptable salts, esters or prodrugs thereof.

In yet another embodiment, the invention is directed to compounds represented by formula III:

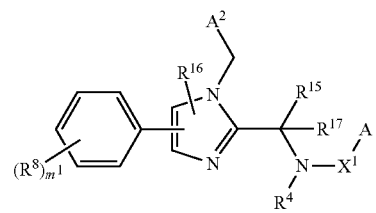

III wherein:

$X^1$ is —C(O)— or —S(O)$_2$—;

$A^2$ is selected from the group consisting of aryl, heteroaryl, heterocyclic, and cycloalkyl, all of which may be optionally substituted with 1 to 4 substituents selected from the group consisting of alkyl, substituted alkyl, alkoxy, substituted alkoxy, amino, halo, hydroxy, and nitro;

A is selected from the group consisting of hydrogen, optionally substituted alkyl, optionally substituted alkoxy, optionally substituted aryl, carboxyl, carboxyl ester, aminoacyl, optionally substituted heteroaryl, optionally substituted heterocyclic, and optionally substituted cycloalkyl, wherein the optionally substituted groups are substituted with 1 to 4 substituents selected from the group consisting of alkyl, substituted alkyl, alkoxy, substituted alkoxy, amino, substituted amino, aryloxy, substituted aryloxy, cyano, aryl, substituted aryl, heteroaryl, substituted heteroaryl, heterocyclic, substituted heterocyclic, heterocyclyloxy, substituted heterocyclyloxy, acyl, carboxyl, carboxyl ester, oxo (except when A is optionally substituted aryl or optionally substituted heteroaryl), halo, hydroxy, —S(O)$_2$—R$^9$ where R$^9$ is alkyl, substituted alkyl, aryl, substituted aryl, heteroaryl or substituted heteroaryl, and nitro;

R$^8$ is selected from the group consisting of alkyl, alkenyl, alkynyl, —CF$_3$, alkoxy, halo, and hydroxy;

R$^4$ is selected from the group consisting of hydrogen, linear alkyl, -alkylene-aminoacyl, -alkylene-oxyacyl, -alkylene-acyloxy, -alkylene-hydroxy, -[alkylene]$_p$-nitrogen-containing heterocyclic, -[alkylene]$_p$-nitrogen-containing substituted heterocyclic, -[alkylene]$_p$- nitrogen-containing heteroaryl, -[alkylene]$_p$-nitrogen-containing substituted heteroaryl, and -[alkylene]$_p$-NR$^{10}$R$^{11}$ wherein p is an integer from 0 to 1, alkylene is a straight chained alkylene optionally mono- or disubstituted with one of the foregoing substituents selected from the group consisting of amino, substituted amino, hydroxy, alkyl, substituted alkyl, carboxyl, carboxyl ester, oxo, spirocycloalkyl, and halo;

R$^{10}$ and R$^{11}$ are independently selected from the group consisting of hydrogen, alkyl, substituted alkyl, —S(O)-alkyl, —S(O)-substituted alkyl, —S(O)$_2$-alkyl, —S(O)$_2$-substituted alkyl, heterocyclic, substituted heterocyclic, acyl, aryl, substituted aryl, heteroaryl, substituted heteroaryl, cycloalkyl, and substituted cycloalkyl or when R$^{10}$ is hydrogen, R$^{11}$ is hydroxy, alkoxy or substituted alkoxy; or when R$^{15}$ and A, together with the carbon atoms and X$^1$ bound respectively thereto, do not form a heterocyclic or substituted heterocyclic group, then X$^1$, A and R$^4$, together with the nitrogen atom bound thereto, form a heterocyclic or substituted heterocyclic group;

R$^{15}$ is selected from the group consisting of ethyl, isopropyl, t-butyl, or phenyl;

R$^{15}$ and X$^1$-A, together with the carbon atom attached to R$^{15}$ and the nitrogen atom attached to X$^1$ join to form a heterocyclic or a substituted heterocyclic group;

R$^{16}$ is hydrogen or methyl;

R$^{17}$ is hydrogen or methyl;

m$^1$ is an integer equal to 0, 1 or 2;

or pharmaceutically acceptable salts, esters or prodrugs thereof.

In still another preferred embodiment, the compounds of this invention are represented by formula IV:

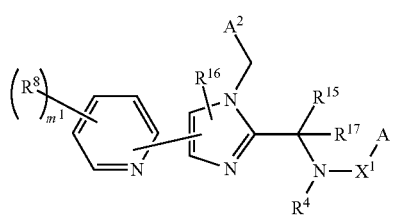

wherein X$^1$, A, A$^2$, R$^4$, R$^8$, R$^{15}$, R$^{16}$, R$^{17}$, and m$^1$ are as defined above.

In another embodiment, the compounds of this invention are represented by formula V:

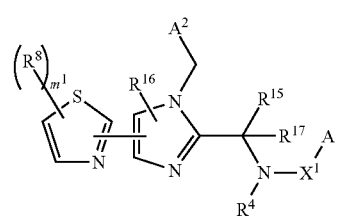

wherein X$^1$, A, A$^2$, R$^4$, R$^8$, R$^{15}$, R$^{16}$, R$^{17}$, and m$^1$ are as defined above.

In yet another embodiment, the invention is directed to compounds of formula VI:

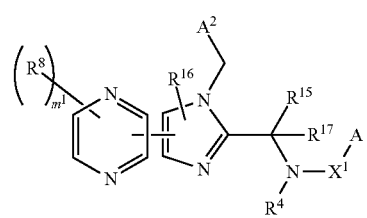

wherein X, A, A$^2$, R$^4$, R$^4$, R$^8$, R$^{15}$, R$^{16}$, R$^{17}$, and m$^1$ are as defined above.

Also provided is a composition comprising a compound of formulae I-VII (including mixtures thereof) and a pharmaceutically acceptable excipient or carrier.

EMBODIMENTS OF THE INVENTION

The following embodiments are selected from embodiments in which the compound is any of formula I-VII, depending on the variable discussed.

In one embodiment, R$^1$ (or R$^{13}$ or R$^{15}$) is a group such as methyl, iso-propyl, t-butyl, 1-methyl-n-prop-1-yl, phenyl, and 2-hydroxy-iso-propyl.

In one embodiment, R$^2$ (or R$^{12}$ or R$^{17}$) is a group such as hydrogen, methyl, and ethyl.

In one embodiment, X or X$^1$ is C(O) or S(O)$_2$ and A is an unsubstituted group such as 1,3-benzothiadiazol-4-yl, t-butoxy, butoxy, n-butoxy, carboxyl, cyclohexyl, 2,2-dimethylpropoxy, ethoxy, furan-3-yl, hydrogen, isoxazol-3-yl, methoxy, methyl, 2-methylpropoxy, phenyl, piperidin-3-yl, piperidin-4-yl, n-propoxy, pyridin-2-yl, pyrazin-2-yl, tetrahydrofuran-2-yl, tetrahydrofuran-3-yl, tetrahydro-2H-pyran-4-yl, 1H-tetrazol-1-yl, 2H-tetrazol-2-yl, and thiazol-4-yl.

In another embodiment, X or X$^1$ is C(O) or S(O)$_2$ and A is an unsubstituted group such as 1,3,4-thiadiazol-2-yl, 1,3-benzothiadiazol-6-yl, 3,3-dihydrobenzo[1,2,3]thiadiazol-4-yl, benzimidazol-2-yl, benzimidazol-6-yl, benzo[1,2,5]thiadiazole, benzoxadiazol-4-yl, cyclopentyl, imidazol-4-yl, indazol-6-y, isooxazol-5-yl, morpholin-2-yl morpholino, oxazol-4-yl, piperidin-N-yl, pyrazol-3-yl, pyrrolidin-2-yl pyrrolidin-3-yl, pyrrolidin-N-yl, tetrazol-5-yl, and thiadiazol-4-yl.

In one embodiment, X or X$^1$ is C(O) or S(O)$_2$ and A is a substituted aryl or heteroaryl group such as 5-methyl-2H-imidazol-4-yl, 2-aminothiazol-4-yl, 4-t-butylphenyl, 2-chlorophenyl, 2-chloro-6-methylpyrid-4-yl, 3-chlorophenyl, 4-chlorophenyl, 6-chloropyridin-3-yl, 3,4-dichlorophenyl, 2,4-difluorophenyl, 1,5-dimethyl-1H-pyrazol-3-yl, 2,4-dimethylthiazol-5-yl, 1-ethyl-3-methyl-1H-pyrazol-5-yl, 2-methoxyphenyl, 4-methoxyphenyl, 4-methylisoxazol-3-yl, 5-methylisoxazol-4-yl, 4-methylphenyl, 1-methyl-3-trifluoromethyl-1H-pyrazol-4-yl, 1-methyl-5-chloro-1H-pyrazol-4-yl, 5-methyl-1H-pyrazol-3-yl, 6-methylpyridin-3-yl, 2-pyrrolidin-3-ylphenyl, 4-(trifluoromethyl)phenyl, and 6-(trifluoromethyl)pyridin-3-yl.

In another embodiment, X or $X^1$ is C(O) or $S(O)_2$ and A is a substituted aryl or heteroaryl group such as 2,5-dimethyloxazol-4-yl, 2-aminothiazol-4-yl, 4-methylpyrazol-5-yl, 3-trifluoromethylpyrazol-4-yl, 2-methyl-3-trifluoromethylpyrazol-5-yl, 4-chloro-1,3-dimethylpyrazolo[3,4]pyridine, and 1-methylbenzimidazol-2-yl.

In one embodiment, X or $X^1$ is C(O) or $S(O)_2$ and A is a substituted heterocyclic or cycloalkyl group such as 3-[(aminoacetyl)amino]cyclohexyl and 3-(2-aminoethylsulfonylamino)cyclohexyl.

In another embodiment, X or $X^1$ is C(O) or $S(O)_2$ and A is a substituted heterocyclic or cycloalkyl group such as 1-methylpiperazin-4-yl, 1-methylcarbonylpiperidin-4-yl, 1-methoxycarbonylpiperidin-4-yl, quinuclidin-3-yl, 2-oxopyrrolidin-5-yl, 2-oxopyrrolidin-4-yl, 2-oxo-dihydrofuran-5-yl, 2-oxothiazolidin-4-yl, and 3-hydroxypyrrolidin-5-yl.

In one embodiment, X or $X^1$ is C(O) or $S(O)_2$ and A is a substituted alkyl group such as 3-amino-2-oxo-1(2H)-pyridinylmethyl, cyanomethyl, (N,N-dimethylamino)methyl, ethoxymethyl, p-fluorophenoxymethyl, hydroxymethyl, 1H-imidazol-1-ylmethyl, methoxymethyl, (N-methylamino)methyl, methylsulfonylmethyl, (5-methyl-1H-tetrazol-1-yl)methyl, (5-methyl-2H-tetrazol-2-yl)methyl, morpholin-4-ylmethyl, 1H-pyrazol-1-ylmethyl, 1H-1,2,3-triazol-1-ylmethyl, 2H-1,2,3-triazol-2-ylmethyl, 1H-1,2,4-triazol-1-ylmethyl, 2H-1,2,4-triazol-2-ylmethyl, 4H-1,2,4-triazol-4-ylmethyl, 1H-tetrazol-1-ylmethyl, 1H-tetrazol-5-ylmethyl, and 2H-tetrazol-2-ylmethyl.

In another embodiment, X or $X^1$ is C(O) or $S(O)_2$ and A is a substituted alkyl group such as imidazol-4-ylmethyl, 1-methylpyrazol-3-ylmethyl, piperidin-4-ylmethyl, trifluoromethyl, dimethylaminoethyl, and 2-oxo-3-aminopyrrolidin-1-ylmethyl.

In one embodiment, X or $X^1$ is C(O) or $S(O)_2$ and $R^1$ and $R^3$ are cyclized to form a divalent heterocyclic group such as 2-oxopiperidin-N-6-yl or pyrrolidin-1-yl.

In one embodiment, $R^3$ and $R^4$ (Or $R^4/X^1$-A) cyclize to form 1-oxa-3,7-diazaspiro[4.4]nonan-2-one or 6-oxa-2,9-diazaspiro[4.5]decan-8-one.

In one embodiment, A is N-methylaminocarbonyl.

In one embodiment, $R^4$ is a group such as hydrogen, piperidin-4-yl, —(CH$_2$)$_2$—NH$_2$, —CH$_2$-azetidin-3-yl, —CH$_2$-(2,5-dihydropyrrol-3-yl), —(CH$_2$)$_3$-imidazol-1-yl, —CH$_2$-(1H-imidazol-4-yl), —CH$_2$-pyridin-3-yl, —CH$_2$-(2-hydroxypyridin-4-yl), —CH$_2$-(6-hydroxypyridin-3-yl), —CH$_2$-morpholin-2-yl, —CH$_2$-pyrrolidin-3-yl, —CH$_2$-(3-fluoropyrrolidin-3-yl), —CH$_2$-(3-hydroxypyrrolidin-3-yl), —CH$_2$-(4-fluoropyrrolidin-3-yl), —CH$_2$-(4-hydroxypyrrolidin-3-yl), —CH$_2$-(2-hydroxymethylpyrrolidin-3-yl), —CH$_2$-piperidin-3-yl, —CH$_2$-[1H-(1,2,3-triazol-4-yl)], —CH$_2$CH(NH$_2$)CH$_2$OH, —(CH$_2$)$_3$—OH, —(CH$_2$)$_3$—O(CO)-phenyl, —(CH$_2$)$_3$—NH$_2$, —(CH$_2$)$_3$—NHCH$_3$, —(CH$_2$)$_3$—N(CH$_3$)$_2$, —(CH$_2$)$_3$—NHOCH$_3$, —(CH$_2$)$_3$—NHSO$_2$CH$_3$, —(CH$_2$)$_3$NH-(5-cyanopyridin-2-yl), —(CH$_2$)$_3$NH-cyclopropyl, —(CH$_2$)$_3$NH-cyclobutyl, —(CH$_2$)$_3$-(1H-imidazol-2-yl), —(CH$_2$)$_3$-(2-hydroxyethylpiperidin-1-yl), —(CH$_2$)$_3$NH(2-hydroxymethylphenyl), —(CH$_2$)$_3$NH-(5-trifluoromethylpyridin-2-yl), —(CH$_2$)$_3$NHCH$_2$-cyclopropyl, —(CH$_2$)$_3$NHCH$_2$-{5-(pyridin-3-yloxy)-1H-indazol-3-yl}, —(CH$_2$)$_3$NHCH$_2$-(5-methoxy-1H-indazol-3-yl), —(CH$_2$)$_3$NHCH$_2$-(6-fluoro-1H-indazol-3-yl), —CH$_2$CHOHCH$_2$NH$_2$, —CH$_2$CH(CH$_2$OH)CH$_2$NH$_2$, —CH$_2$C(CH$_3$)$_2$CH$_2$—N(CH$_3$)$_2$, —CH$_2$C(CH$_3$)$_2$CH$_2$-(4-methylpiperazin-1-yl), —(CH$_2$)$_2$C(O)NH$_2$, —(CH$_2$)$_2$CH(NH$_2$)C(O)NH$_2$, —(CH$_2$)$_2$CH(NH$_2$)C(O)OH, —(CH$_2$)$_2$CH(NH$_2$)CH$_2$C(O)NH$_2$, —(CH$_2$)$_2$CH(NH$_2$)CH$_2$OH, —(CH$_2$)$_2$CH(NH$_2$)CH$_3$, —(CH$_2$)$_3$NHC(O)CH$_2$NH$_2$, —(CH$_2$)$_3$NHC(O)CH(NH$_2$)CH(CH$_3$)$_2$, —CH$_2$CHFCH$_2$NH$_2$, —(CH$_2$)$_2$NHC(O)CH$_2$NH$_2$, —(CH$_2$)$_3$—NHCH$_2$CH$_2$OH, —(CH$_2$)$_3$—NHCH$_2$CO$_2$H, —(CH$_2$)$_3$—NHCH$_2$CO$_2$CH$_2$CH$_3$, —(CH$_2$)$_3$—N(CH$_2$CH$_2$OH)$_2$, —(CH$_2$)$_3$—NHCH(CH$_2$OH)$_2$, —(CH$_2$)$_2$CH$_3$, —(CH$_2$)$_2$CH(NH$_2$)CH$_2$OH, —(CH$_2$)$_2$C(CH$_3$)$_2$NH$_2$, —(CH$_2$)$_2$CH(NH$_2$)CH$_2$OCH$_3$, —(CH$_2$)$_2$CH(NH$_2$)CH$_2$F, —CH$_2$CHFCH(NH$_2$)CH$_2$OH, and —(CH$_2$)$_2$spirocylcopropyl-NH$_2$.

In one embodiment, L is methylene (n=1 in formula II) and $A^1$ or $A^2$ is a group such as phenyl, 6-aminopyridin-2-yl, 3-chlorophenyl, 3-cyanophenyl, 2,4-difluorophenyl, 2,5-difluorophenyl, 3,5-difluorophenyl, 2-fluorophenyl, 3-fluorophenyl, 4-fluorophenyl, 3-hydroxyphenyl, 3-methoxyphenyl, 1-(5-methyl)-isoxazol-3-yl, 2-methylphenyl, 3-methylphenyl, 4-methylphenyl, pyridin-2-yl, pyridin-3-yl, pyridin-4-yl, tetrahydropyran-4-yl, thiazol-4-yl, and 5-trifluoromethylfuran-2-yl.

In one embodiment, $R^7$ ($R^{14}/R^{16}$) is hydrogen, halo, or methyl and $R^6$ (Ar—$(R^8)_{m1}$) is a group such as phenyl, 3-bromophenyl, 3-chlorophenyl, 4-cyanophenyl, 2,5-difluorophenyl, 3-fluorophenyl, 2-methoxyphenyl, 3-methoxyphenyl, 4-methoxyphenyl, 4-methylphenyl, pyrazin-2-yl, pyridin-2-yl, thiazol-2-yl, 2-trifluoromethylphenyl, and 3-trifluoromethylphenyl.

In another embodiment, $R^6$ is hydrogen, halo, or methyl and $R^7$ is a group such as 3-fluorophenyl.

In one embodiment, $m^1$ is 0, 1 or 2. In another embodiment, n is 1.

Embodiments of the invention also include the following:

1. A compound of formula I:

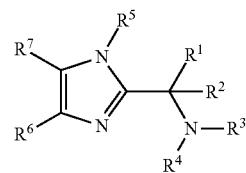

I wherein:

$R^1$ is selected from the group consisting of aminoacyl, acylamino, carboxyl, carboxyl ester, aryl, and alkyl optionally substituted with hydroxy or halo;

$R^2$ is selected from the group consisting of hydrogen, alkyl, and aryl;

$R^3$ is selected from the group consisting of hydrogen and —X-A, wherein X is selected from the group consisting of —C(O)—, —C(S)—, —S(O)—, —S(O)$_2$—, and —S(O)$_2$—N(R)—, where R is hydrogen or alkyl; and A is selected from the group consisting of hydrogen, optionally substituted alkyl, optionally substituted alkoxy, optionally substituted aryl, carboxyl, carboxyl ester, aminoacyl, optionally substituted heteroaryl, optionally substituted heterocyclic, and optionally substituted cycloalkyl, wherein the optionally substituted groups are substituted with 1 to 4 substituents selected from the group consisting of alkyl, substituted alkyl, alkoxy, substituted alkoxy, amino, substituted amino, aryloxy, substituted aryloxy, cyano, aryl, substituted aryl, heteroaryl, substituted heteroaryl, heterocyclic, substituted heterocyclic, heterocyclyloxy, substituted heterocyclyloxy, acyl, carboxyl, carboxyl ester, oxo (except when A is optionally substituted aryl or optionally substituted heteroaryl), halo, hydroxy, —S(O)$_2$—R$^9$ where R$^9$ is alkyl, substituted alkyl, aryl, substituted aryl, heteroaryl or substituted heteroaryl, and nitro;

or R$^1$ and R$^3$, together with the carbon atom attached to R$^1$ and the nitrogen atom attached to R$^3$ form a heterocyclic or substituted heterocyclic group;

R$^4$ is selected from the group consisting of hydrogen, linear alkyl, -alkylene-aminoacyl, -alkylene-oxyacyl, -alkylene-acyloxy, -alkylene-hydroxy, -[alkylene]$_p$-nitrogen-containing heterocyclic, -[alkylene]$_p$-nitrogen-containing substituted heterocyclic, -[alkylene]$_p$-nitrogen-containing heteroaryl, -[alkylene]$_p$-nitrogen-containing substituted heteroaryl, and -[alkylene]$_p$-NR$^{10}$R$^{11}$ wherein p is an integer from 0 to 1, alkylene is a straight chained alkylene optionally mono- or disubstituted with one of the foregoing substituents selected from the group consisting of amino, substituted amino, hydroxy, alkyl, substituted alkyl, carboxyl, carboxyl ester, oxo, spirocycloalkyl, and halo;

R$^{10}$ and R$^{11}$ are independently selected from the group consisting of hydrogen, alkyl, substituted alkyl, —S(O)-alkyl, —S(O)-substituted alkyl, —S(O)$_2$-alkyl, —S(O)$_2$-substituted alkyl, heterocyclic, substituted heterocyclic, acyl, aryl, substituted aryl, heteroaryl, substituted heteroaryl, cycloalkyl, and substituted cycloalkyl, or when R$^{10}$ is hydrogen, R$^{11}$ is hydroxy, alkoxy or substituted alkoxy;

or when R$^1$ and R$^3$, together with the carbon and nitrogen atoms bound respectively thereto, do not form a heterocyclic or substituted heterocyclic group, then R$^3$ and R$^4$, together with the nitrogen atom bound thereto, form a heterocyclic or substituted heterocyclic group;

R$^5$ is selected from the group consisting of L-A$^1$, wherein L is selected from the group consisting of —S(O)$_q$— where q is one or two, and C$_1$ to C$_5$ alkylene optionally substituted with hydroxy, halo, or acylamino; and A$^1$ is selected from the group consisting of aryl, substituted aryl, heteroaryl, substituted heteroaryl, heterocyclic, substituted heterocyclic, cycloalkyl, and substituted cycloalkyl; and one of either R$^6$ or R$^7$ is selected from the group consisting of heterocyclic, aryl and heteroaryl, all of which may be optionally substituted with —(R$^8$)$_m$ where R$^8$ is as defined herein and m is an integer from 1 to 3, and the other of R$^6$ or R$^7$ is selected from the group consisting of hydrogen, halo, and alkyl;

or R$^6$ and R$^7$ are both hydrogen;

R$^8$ is selected from the group consisting of cyano, alkyl, alkenyl, alkynyl, —CF$_3$, alkoxy, halo, and hydroxy;

or pharmaceutically acceptable salts, esters or prodrugs thereof.

2. The compound of claim 1, wherein the compound is represented by formula II:

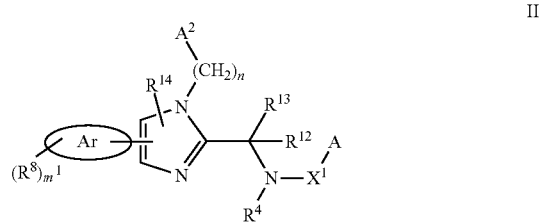

wherein:
Ar is selected from the group consisting of phenyl, pyridinyl, pyrazinyl, and thiazolyl;

X$^1$ is selected from the group consisting of —C(O)— and —S(O)$_2$—;

A$^2$ is selected from the group consisting of aryl, heteroaryl, heterocyclic, and cycloalkyl, all of which may be optionally substituted with 1 to 4 substituents selected from the group consisting of alkyl, substituted alkyl, alkoxy, substituted alkoxy, amino, halo, hydroxy, and nitro;

A is selected from the group consisting of hydrogen, optionally substituted alkyl, optionally substituted alkoxy, optionally substituted aryl, carboxyl, carboxyl ester, aminoacyl, optionally substituted heteroaryl, optionally substituted heterocyclic, and optionally substituted cycloalkyl, wherein the optionally substituted groups are substituted with 1 to 4 substituents selected from the group consisting of alkyl, substituted alkyl, alkoxy, substituted alkoxy, amino, substituted amino, aryloxy, substituted aryloxy, cyano, aryl, substituted aryl, heteroaryl, substituted heteroaryl, heterocyclic, substituted heterocyclic, heterocyclyloxy, substituted heterocyclyloxy, acyl, carboxyl, carboxyl ester, oxo (except when A is optionally substituted aryl or optionally substituted heteroaryl), halo, hydroxy, —S(O)$_2$—R$^9$ where R$^9$ is alkyl, substituted alkyl, aryl, substituted aryl, heteroaryl or substituted heteroaryl, and nitro;

R$^4$ is selected from the group consisting of hydrogen, linear alkyl, -alkylene-aminoacyl, -alkylene-oxyacyl, -alkylene-acyloxy, -alkylene-hydroxy, -[alkylene]$_p$-nitrogen-containing heterocyclic, -[alkylene]$_p$-nitrogen-containing substituted heterocyclic, -[alkylene]$_p$-nitrogen-containing heteroaryl, -[alkylene]$_p$-nitrogen-containing substituted heteroaryl, and -[alkylene]$_p$-NR$^{10}$R$^{11}$ wherein p is an integer from 0 to 1, alkylene is a straight chained alkylene optionally mono- or disubstituted with one of the foregoing substituents selected from the group consisting of amino, substituted amino, hydroxy, alkyl, substituted alkyl, carboxyl, carboxyl ester, oxo, spirocycloalkyl, and halo;

R$^{10}$ and R$^{11}$ are independently selected from the group consisting of hydrogen, alkyl, substituted alkyl, —S(O)-alkyl, —S(O)-substituted alkyl, —S(O)$_2$-alkyl, —S(O)$_2$-substituted alkyl, heterocyclic, substituted heterocyclic, acyl, aryl, substituted aryl, heteroaryl, substituted heteroaryl, cycloalkyl, and substituted cycloalkyl or when R$^{10}$ is hydrogen, R$^{11}$ is hydroxy, alkoxy or substituted alkoxy;

or when R$^{13}$ and A, together with the carbon atom and the X$^1$ group bound respectively thereto, do not form a heterocyclic or substituted heterocyclic group, then X$^1$-A and R$^4$, together with the nitrogen atom bound thereto, form a heterocyclic or substituted heterocyclic group;

R$^8$ is selected from the group consisting of cyano, alkyl, alkenyl, alkynyl, —CF$_3$, alkoxy, halo, and hydroxy;

R$^{12}$ is hydrogen, alkyl;

R[13] is alkyl or aryl;

R[13] and X[1]-A, together with the carbon atom attached to R[13] and the nitrogen atom attached to X[1] join to form a heterocyclic or a substituted heterocyclic group;

R[14] is hydrogen or $C_1$ to $C_4$ alkyl;

$m^1$ is an integer equal to 0 to 2;

n is an integer equal to 1 to 3; or pharmaceutically acceptable salts, esters or prodrugs thereof.

3. The compound of claim 1, wherein the compound is represented by formula III:

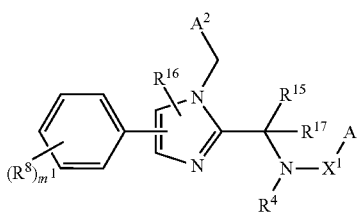

III wherein:

X[1] is —C(O)— or —S(O)$_2$—;

A[2] is selected from the group consisting of aryl, heteroaryl, heterocyclic, and cycloalkyl, all of which may be optionally substituted with 1 to 4 substituents selected from the group consisting of alkyl, substituted alkyl, alkoxy, substituted alkoxy, amino, halo, hydroxy, and nitro;

A is selected from the group consisting of hydrogen, optionally substituted alkyl, optionally substituted alkoxy, optionally substituted aryl, carboxyl, carboxyl ester, aminoacyl, optionally substituted heteroaryl, optionally substituted heterocyclic, and optionally substituted cycloalkyl, wherein the optionally substituted groups are substituted with 1 to 4 substituents selected from the group consisting of alkyl, substituted alkyl, alkoxy, substituted alkoxy, amino, substituted amino, aryloxy, substituted aryloxy, cyano, aryl, substituted aryl, heteroaryl, substituted heteroaryl, heterocyclic, substituted heterocyclic, heterocyclyloxy, substituted heterocyclyloxy, acyl, carboxyl, carboxyl ester, oxo (except when A is optionally substituted aryl or optionally substituted heteroaryl), halo, hydroxy, —S(O)$_2$—R[9] where R[9] is alkyl, substituted alkyl, aryl, substituted aryl, heteroaryl or substituted heteroaryl, and nitro;

R[8] is selected from the group consisting of alkyl, alkenyl, alkynyl, —CF$_3$, alkoxy, halo, and hydroxy;

R[4] is selected from the group consisting of hydrogen, linear alkyl, -alkylene-aminoacyl, -alkylene-oxyacyl, -alkylene-acyloxy, -alkylene-hydroxy, -[alkylene]$_p$-nitrogen-containing heterocyclic, -[alkylene]$_p$-nitrogen-containing substituted heterocyclic, -[alkylene]$_p$-nitrogen-containing heteroaryl, -[alkylene]$_p$-nitrogen-containing substituted heteroaryl, and -[alkylene]$_p$-NR[10]R[11] wherein p is an integer from 0 to 1, alkylene is a straight chained alkylene optionally mono- or disubstituted with one of the foregoing substituents selected from the group consisting of amino, substituted amino, hydroxy, alkyl, substituted alkyl, carboxyl, carboxyl ester, oxo, spirocycloalkyl, and halo;

R[10] and R[11] are independently selected from the group consisting of hydrogen, alkyl, substituted alkyl, —S(O)-alkyl, —S(O)-substituted alkyl, —S(O)$_2$-alkyl, —S(O)$_2$-substituted alkyl, heterocyclic, substituted heterocyclic, acyl, aryl, substituted aryl, heteroaryl, substituted heteroaryl, cycloalkyl, and substituted cycloalkyl or when R[10] is hydrogen, R[11] is hydroxy, alkoxy or substituted alkoxy; or when R[15] and A, together with the carbon atoms and X[1] bound respectively thereto, do not form a heterocyclic or substituted heterocyclic group, then X[1], A and R[4], together with the nitrogen atom bound thereto, form a heterocyclic or substituted heterocyclic group;

R[15] is selected from the group consisting of ethyl, isopropyl, t-butyl, or phenyl;

R[15] and X[1]-A, together with the carbon atom attached to R[15] and the nitrogen atom attached to X' join to form a heterocyclic or a substituted heterocyclic group;

R[16] is hydrogen or methyl;

R[17] is hydrogen or methyl;

$m^1$ is an integer equal to 0, 1 or 2;

or pharmaceutically acceptable salts, esters or prodrugs thereof.

4. The compound of claim 1, wherein the compound is represented by formula IV:

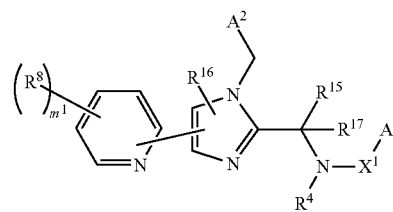

IV wherein X[1], A, A[2], R[4], R[8], R[15], R[16], R[17], and $m^1$ are as defined above.

5. The compound of claim 1, wherein the compound is represented by formula V:

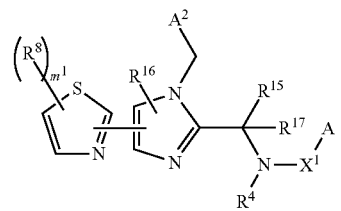

V wherein X[1], A, A[2], R[4], R[8], R[15], R[16], R[17], and $m^1$ are as defined above.

6. The compound of claim 1, wherein the compound is represented by formula VI:

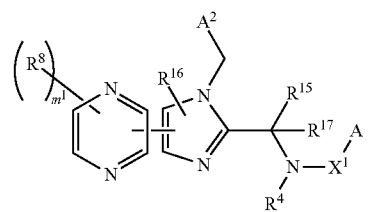

VI wherein X[1], A, A[2], R[4], R[8], R[15], R[16], R[17], and $m^1$ are as defined above.

7. The compound of claim 1, wherein R[1] is selected from the group consisting of phenyl, methyl, iso-propyl, t-butyl, 1-methyl-n-prop-1-yl, and 2-hydroxy-iso-propyl.

8. The compound of claim 1, wherein $R^2$ is selected from the group consisting of hydrogen, methyl, and ethyl.

9. The compound of claim 1, wherein X or $X^1$ is C(O) or $S(O)_2$ and A is unsubstituted and selected from the group consisting of 1,3-benzothiadiazol-4-yl, t-butoxy, butoxy, n-butoxy, carboxyl, cyclohexyl, 2,2-dimethylpropoxy, ethoxy, furan-3-yl, hydrogen, isoxazol-3-yl, methoxy, methyl, 2-methylpropoxy, phenyl, piperidin-3-yl, piperidin-4-yl, n-propoxy, pyridin-2-yl, pyrazin-2-yl, tetrahydrofuran-2-yl, tetrahydrofuran-3-yl, tetrahydro-2H-pyran-4-yl, 1H-tetrazol-1-yl, 2H-tetrazol-2-yl, thiazol-4-yl, 1,3,4-thiadiazol-2-yl, 1,3-benzothiadiazol-6-yl, 3,3-dihydrobenzo[1,2,3]thiadiazol-4-yl, benzimidazol-2-yl, benzimidazol-6-yl, benzo[1,2,5]thiadiazole, benzoxadiazol-4-yl, cyclopentyl, imidazol-4-yl, indazol-6-y, isooxazol-5-yl, morpholin-2-yl morpholino, oxazol-4-yl, piperidin-N-yl, pyrazol-3-yl, pyrrolidin-2-yl pyrrolidin-3-yl, pyrrolidin-N-yl, tetrazol-5-yl, and thiadiazol-4-yl.

10. The compound of claim 1, wherein X or $X^1$ is C(O) or $S(O)_2$ and A is a substituted aryl or heteroaryl group selected from the group consisting of 5-methyl-2H-imidazol-4-yl, 2-aminothiazol-4-yl, 4-t-butylphenyl, 2-chlorophenyl, 2-chloro-6-methylpyrid-4-yl, 3-chlorophenyl, 4-chlorophenyl, 6-chloropyridin-3-yl, 3,4-dichlorophenyl, 2,4-difluorophenyl, 1,5-dimethyl-1H-pyrazol-3-yl, 2,4-dimethylthiazol-5-yl, 1-ethyl-3-methyl-1H-pyrazol-5-yl, 2-methoxyphenyl, 4-methoxyphenyl, 4-methylisoxazol-3-yl, 5-methylisoxazol-4-yl, 4-methylphenyl, 1-methyl-3-trifluoromethyl-1H-pyrazol-4-yl, 1-methyl-5-chloro-1H-pyrazol-4-yl, 5-methyl-1H-pyrazol-3-yl, 6-methylpyridin-3-yl, 2-pyrrolidin-3-ylphenyl, 4-(trifluoromethyl)phenyl, 6-(trifluoromethyl)pyridin-3-yl, 2,5-dimethyloxazol-4-yl, 2-aminothiazol-4-yl, 4-methylpyrazol-5-yl, 3-trifluoromethylpyrazol-4-yl, 2-methyl-3-trifluoromethylpyrazol-5-yl, 4-chloro-1,3-dimethylpyrazolo[3,4]pyridine, and 1-methylbenzimidazol-2-yl.

11. The compound of claim 1, wherein X or $X^1$ is C(O) or $S(O)_2$ and A is a substituted heterocyclic or cycloalkyl selected from the group consisting of 3-[(aminoacetyl)amino]cyclohexyl, 3-(2-aminoethylsulfonylamino)cyclohexyl, 1-methylpiperazin-4-yl, 1-methylcarbonylpiperidin-4-yl, 1-methoxycarbonylpiperidin-4-yl, quinuclidin-3-yl, 2-oxopyrrolidin-5-yl, 2-oxopyrrolidin-4-yl, 2-oxo-dihydrofuran-5-yl, 2-oxothiazolidin-4-yl, and 3-hydroxypyrrolidin-5-yl.

12. The compound of claim 1, wherein X or $X^1$ is C(O) or $S(O)_2$ and A is a substituted alkyl selected from the group consisting of 3-amino-2-oxo-1(2H)-pyridinylmethyl, cyanomethyl, (N,N-dimethylamino)methyl, ethoxymethyl, p-fluorophenoxymethyl, hydroxymethyl, 1H-imidazol-1-ylmethyl, methoxymethyl, (N-methylamino)methyl, methylsulfonylmethyl, (5-methyl-1H-tetrazol-1-yl)methyl, (5-methyl-2H-tetrazol-2-yl)methyl, morpholin-4-ylmethyl, 1H-pyrazol-1-ylmethyl, 1H-1,2,3-triazol-1-ylmethyl, 2H-1,2,3-triazol-2-ylmethyl, 1H-1,2,4-triazol-1-ylmethyl, 2H-1,2,4-triazol-2-ylmethyl, 4H-1,2,4-triazol-4-ylmethyl, 1H-tetrazol-1-ylmethyl, 1H-tetrazol-5-ylmethyl, 2H-tetrazol-2-ylmethyl, imidazol-4-ylmethyl, 1-methylpyrazol-3-ylmethyl, piperidin-4-ylmethyl, trifluoromethyl, dimethylaminoethyl, and 2-oxo-3-aminopyrrolidin-1-ylmethyl.

13. The compound of claim 1, wherein X or $X^1$ is C(O) or $S(O)_2$ and $R^1$ and $R^3$ are cyclized to form a divalent heterocyclic group such as 2-oxopiperidin-N-6-yl or pyrrolidin-1-yl.

14. The compound of claim 1, wherein A is N-methylaminocarbonyl.

15. The compound of claim 1, wherein $R^4$ is selected from the group consisting of: hydrogen, piperidin-4-yl, —$(CH_2)_2$—$NH_2$, —$CH_2$-azetidin-3-yl, —$CH_2$-(2,5-dihydropyrrol-3-yl), —$(CH_2)_3$-imidazol-1-yl, —$CH_2$-(1H-imidazol-4-yl), —$CH_2$-pyridin-3-yl, —$CH_2$-(2-hydroxypyridin-4-yl), —$CH_2$-(6-hydroxypyridin-3-yl), —$CH_2$-morpholin-2-yl, —$CH_2$-pyrrolidin-3-yl, —$CH_2$-(3-fluoropyrrolidin-3-yl), —$CH_2$-(3-hydroxypyrrolidin-3-yl), —$CH_2$-(4-fluoropyrrolidin-3-yl), —$CH_2$-(4-hydroxypyrrolidin-3-yl), —$CH_2$-(2-hydroxymethylpyrrolidin-3-yl), —$CH_2$-piperidin-3-yl, —$CH_2$-[1H-(1,2,3-triazol-4-yl)], —$CH_2CH(NH_2)CH_2OH$, —$(CH_2)_3$—OH, —$(CH_2)_3$—O(CO)-phenyl, —$(CH_2)_3$—$NH_2$, —$(CH_2)_3$—$NHCH_3$, —$(CH_2)_3$—$N(CH_3)_2$, —$(CH_2)_3$—$NHOCH_3$, —$(CH_2)_3$—$NHSO_2CH_3$, —$(CH_2)_3NH$-(5-cyanopyridin-2-yl), —$(CH_2)_3NH$-cyclopropyl, —$(CH_2)_3NH$-cyclobutyl, —$(CH_2)_3$-(1H-imidazol-2-yl), —$(CH_2)_3$-(2-hydroxyethylpiperidin-1-yl), —$(CH_2)_3NH$(2-hydroxymethylphenyl), —$(CH_2)_3NH$-(5-trifluoromethylpyridin-2-yl), —$(CH_2)_3NHCH_2$-cyclopropyl, —$(CH_2)_3NHCH_2$-{5-(pyridin-3-yloxy)-1H-indazol-3-yl}, —$(CH_2)_3NHCH_2$-(5-methoxy-1H-indazol-3-yl), —$(CH_2)_3NHCH_2$-(6-fluoro-1H-indazol-3-yl), —$CH_2CHOHCH_2NH_2$, —$CH_2CH(CH_2OH)CH_2NH_2$, —$CH_2C(CH_3)_2CH_2$—$N(CH_3)_2$, —$CH_2C(CH_3)_2CH_2$-(4-methylpiperazin-1-yl), —$(CH_2)_2C(O)NH_2$, —$(CH_2)_2CH(NH_2)C(O)NH_2$, —$(CH_2)_2CH(NH_2)C(O)OH$, —$(CH_2)_2CH(NH_2)CH_2C(O)NH_2$, —$(CH_2)_2CH(NH_2)CH_2OH$, —$(CH_2)_2CH(NH_2)CH_3$, —$(CH_2)_3NHC(O)CH_2NH_2$, —$(CH_2)_3NHC(O)CH(NH_2)CH(CH_3)_2$, —$CH_2CHFCH_2NH_2$, —$(CH_2)_2NHC(O)CH_2NH_2$, —$(CH_2)_3$—$NHCH_2CH_2OH$, —$(CH_2)_3$—$NHCH_2CO_2H$, —$(CH_2)_3$—$NHCH_2CO_2CH_2CH_3$, —$(CH_2)_3$—$N(CH_2CH_2OH)_2$, —$(CH_2)_3$—$NHCH(CH_2OH)_2$, —$(CH_2)_3CH_3$, —$(CH_2)_2CH(NH_2)CH_2OH$, —$(CH_2)_2C(CH_3)_2NH_2$, —$(CH_2)_2CH(NH_2)CH_2OCH_3$, —$(CH_2)_2CH(NH_2)CH_2F$, —$CH_2CHFCH(NH_2)CH_2OH$, and —$(CH_2)_2$spirocylcopropyl-$NH_2$.

16. The compound of claim 1, wherein L is methylene and $A^1$ is selected from the group consisting of phenyl, 6-aminopyridin-2-yl, 3-chlorophenyl, 3-cyanophenyl, 2,4-difluorophenyl, 2,5-difluorophenyl, 3,5-difluorophenyl, 2-fluorophenyl, 3-fluorophenyl, 4-fluorophenyl, 3-hydroxyphenyl, 3-methoxyphenyl, 1-(5-methyl)-isoxazol-3-yl, 2-methylphenyl, 3-methylphenyl, 4-methylphenyl, pyridin-2-yl, pyridin-3-yl, pyridin-4-yl, tetrahydropyran-4-yl, thiazol-4-yl, and 5-trifluoromethylfuran-2-yl.

17. The compound of claim 1, wherein $R^7$ is hydrogen, halo, or methyl.

18. The compound of claim 17, wherein $R^6$ is selected from the group consisting of phenyl, 3-bromophenyl, 3-chlorophenyl, 4-cyanophenyl, 2,5-difluorophenyl, 3-fluorophenyl, 2-methoxyphenyl, 3-methoxyphenyl, 4-methoxyphenyl, 4-methylphenyl, pyrazin-2-yl, pyridin-2-yl, thiazol-2-yl, 2-trifluoromethylphenyl, and 3-trifluoromethylphenyl.

19. The compound of claim 1, wherein $R^6$ is hydrogen, halo, or methyl.

20. The compound of claim 19, wherein $R^7$ is a group such as 3-fluorophenyl.

21. The compound of claim 1, wherein $R^3$ and $R^4$ cyclize to form 1-oxa-3,7-diazaspiro[4.4]nonan-2-one or 6-oxa-2,9-diazaspiro[4.5]decan-8-one.

22. A compound selected from the group consisting of:
N-(3-aminopropyl)-N-[(1R)-1-(1-benzyl-4-phenyl-1H-imidazol-2-yl)-2-methylpropyl]-4-methylbenzamide;
N-(3-aminopropyl)-N-[(1R)-1-(1-benzyl-4-phenyl-1H-imidazol-2-yl)-2-methylpropyl]benzamide;
N-(3-aminopropyl)-N—[(R)-(1-benzyl-4-phenyl-1H-imidazol-2-yl)(phenyl)methyl]-4-methylbenzamide;

N-(3-aminopropyl)-N—[(R)-(1-benzyl-4-phenyl-1H-imidazol-2-yl)(phenyl)methyl]benzamide;
N-(3-aminopropyl)-N-{(1R)-1-[1-benzyl-4-(3-bromophenyl)-1H-imidazol-2-yl]-2-methylpropyl}benzamide;
N-(3-aminopropyl)-N-{(1R)-1-[1-benzyl-4-(3-bromophenyl)-1H-imidazol-2-yl]-2-methylpropyl}-4-methylbenzamide;
N-(3-aminopropyl)-N-{(1R)-1-[1-benzyl-4-(3-bromophenyl)-1H-imidazol-2-yl]-2-methylpropyl}-4-(trifluoromethyl)benzamide;
N-(3-aminopropyl)-N-{(1R)-1-[1-benzyl-4-(3-bromophenyl)-1H-imidazol-2-yl]-2-methylpropyl}-2,4-difluorobenzamide;
N-(3-aminopropyl)-4-methyl-N-{2-methyl-1-[1-(3-methylbenzyl)-4-phenyl-1H-imidazol-2-yl]propyl}benzamide;
N-(3-aminopropyl)-N-{(1R)-1-[1-benzyl-4-(3-methoxyphenyl)-1H-imidazol-2-yl]-2-methylpropyl}benzamide;
N-(3-aminopropyl)-N-{(1R)-1-[1-benzyl-4-(3-methoxyphenyl)-1H-imidazol-2-yl]-2-methylpropyl}-4-methylbenzamide;
N-(3-aminopropyl)-N-{(1R)-1-[1-benzyl-4-(3-methoxyphenyl)-1H-imidazol-2-yl]-2-methylpropyl}-4-(trifluoromethyl)benzamide;
N-(3-aminopropyl)-N-{(1R)-1-[1-benzyl-4-(3-methoxyphenyl)-1H-imidazol-2-yl]-2-methylpropyl}-2,4-difluorobenzamide;
N-(3-aminopropyl)-N-{(1R)-1-[1-benzyl-4-(3-chlorophenyl)-1H-imidazol-2-yl]-2-methylpropyl}benzamide;
N-(3-aminopropyl)-N-{(1R)-1-[1-benzyl-4-(3-chlorophenyl)-1H-imidazol-2-yl]-2-methylpropyl}-4-methylbenzamide;
N-(3-aminopropyl)-N-{(1R)-1-[1-benzyl-4-(3-chlorophenyl)-1H-imidazol-2-yl]-2-methylpropyl}-4-(trifluoromethyl)benzamide;
N-(3-aminopropyl)-N-{(1R)-1-[1-benzyl-4-(3-chlorophenyl)-1H-imidazol-2-yl]-2-methylpropyl}-2,4-difluorobenzamide;
N-(3-aminopropyl)-N-{(1R)-1-[1-benzyl-4-(4-methylphenyl)-1H-imidazol-2-yl]-2-methylpropyl}benzamide;
N-(3-aminopropyl)-N-{(1R)-1-[1-benzyl-4-(4-methylphenyl)-1H-imidazol-2-yl]-2-methylpropyl}-4-methylbenzamide;
N-(3-aminopropyl)-N-{(1R)-1-[1-benzyl-4-(4-methylphenyl)-1H-imidazol-2-yl]-2-methylpropyl}-4-(trifluoromethyl)benzamide;
N-(3-aminopropyl)-N-{(1R)-1-[1-benzyl-4-(4-methylphenyl)-1H-imidazol-2-yl]-2-methylpropyl}-2,4-difluorobenzamide;
N-(3-aminopropyl)-N-[(1R)-1-(1-benzyl-4-phenyl-1H-imidazol-2-yl)-2,2-dimethylpropyl]-4-methylbenzamide;
N-(3-aminopropyl)-N-[(1R)-1-(1-benzyl-4-phenyl-1H-imidazol-2-yl)-2,2-dimethylpropyl]benzamide;
N-(3-aminopropyl)-N-{(1R)-1-[1-(3,5-difluorobenzyl)-4-phenyl-1H-imidazol-2-yl]-2-methylpropyl}-4-methylbenzamide;
N-(3-aminopropyl)-N-{(1R)-1-[1-(3,5-difluorobenzyl)-4-phenyl-1H-imidazol-2-yl]-2-methylpropyl}benzamide;
N-{(1R)-1-[1-benzyl-4-(3-bromophenyl)-1H-imidazol-2-yl]-2-methylpropyl}-4-methyl-N-{3-[(methylsulfonyl)amino]propyl}benzamide;
N-[(1R)-1-(1-benzyl-4-phenyl-1H-imidazol-2-yl)-2-methylpropyl]-N-[(3R)-piperidin-3-ylmethyl]benzamide;
N-[(1R)-1-(1-benzyl-4-phenyl-1H-imidazol-2-yl)-2-methylpropyl]-N-[(3S)-piperidin-3-ylmethyl]benzamide;
N-(3-aminopropyl)-4-methyl-N-{(1R)-2-methyl-1-[1-(4-methylbenzyl)-4-phenyl-1H-imidazol-2-yl]propyl}benzamide;
N-(3-aminopropyl)-N-{(1R)-2-methyl-1-[1-(4-methylbenzyl)-4-phenyl-1H-imidazol-2-yl]propyl}benzamide;
N-(3-aminopropyl)-4-methyl-N-{(1R)-2-methyl-1-[1-(2-methylbenzyl)-4-phenyl-1H-imidazol-2-yl]propyl}benzamide;
N-(3-aminopropyl)-N-{(1R)-2-methyl-1-[1-(2-methylbenzyl)-4-phenyl-1H-imidazol-2-yl]propyl}benzamide;
N-[(1R)-1-(1-benzyl-4-phenyl-1H-imidazol-2-yl)-2-methylpropyl]-N-[2,2-dimethyl-3-(4-methylpiperazin-1-yl)propyl]benzamide;
N-[(1R)-1-(1-benzyl-4-phenyl-1H-imidazol-2-yl)-2-methylpropyl]-N-[2,2-dimethyl-3-(4-methylpiperazin-1-yl)propyl]-4-methylbenzamide;
N-[(1R)-1-(1-benzyl-4-phenyl-1H-imidazol-2-yl)-2-methylpropyl]-4-methyl-N-[(3R)-piperidin-3-ylmethyl]benzamide;
N-[(1R)-1-(1-benzyl-4-phenyl-1H-imidazol-2-yl)-2-methylpropyl]-4-methyl-N-[(3S)-piperidin-3-ylmethyl]benzamide;
N-(3-aminopropyl)-N-((1R)-1-{1-benzyl-4-[2-(trifluoromethyl)phenyl]-1H-imidazol-2-yl}-2-methylpropyl)benzamide;
N-(3-aminopropyl)-N-((1R)-1-{1-benzyl-4-[2-(trifluoromethyl)phenyl]-1H-imidazol-2-yl}-2-methylpropyl)-4-methylbenzamide;
N-(3-aminopropyl)-N-((1R)-1-{1-benzyl-4-[2-(trifluoromethyl)phenyl]-1H-imidazol-2-yl}-2-methylpropyl)-2,4-difluorobenzamide;
N-(3-aminopropyl)-N-{(1R)-1-[1-benzyl-4-(3-chlorophenyl)-1H-imidazol-2-yl]-2-methylpropyl}-4-methoxybenzamide;
N-(3-aminopropyl)-N-{(1R)-1-[1-benzyl-4-(3-chlorophenyl)-1H-imidazol-2-yl]-2-methylpropyl}-3-chlorobenzamide;
N-(3-aminopropyl)-N-{(1R)-1-[1-benzyl-4-(3-chlorophenyl)-1H-imidazol-2-yl]-2-methylpropyl}-4-chlorobenzamide;
N-(3-aminopropyl)-N-{(1R)-1-[1-benzyl-4-(3-chlorophenyl)-1H-imidazol-2-yl]-2-methylpropyl}-4-tert-butylbenzamide;
N-(3-aminopropyl)-N-{(1R)-1-[1-benzyl-4-(3-chlorophenyl)-1H-imidazol-2-yl]-2-methylpropyl}-3,4-dichlorobenzamide;
N-{(1R)-1-[1-benzyl-4-(3-bromophenyl)-1H-imidazol-2-yl]-2-methylpropyl}-N-{3-[(5-cyanopyridin-2-yl)amino]propyl}benzamide;
N-{(1R)-1-[1-benzyl-4-(3-bromophenyl)-1H-imidazol-2-yl]-2-methylpropyl}-N-(3-{[5-(trifluoromethyl)pyridin-2-yl]amino}propyl)benzamide;
N-[(1R)-1-(1-benzyl-4-phenyl-1H-imidazol-2-yl)-2-methylpropyl]-N-piperidin-4-ylbenzamide;
N-[(1R)-1-(1-benzyl-4-phenyl-1H-imidazol-2-yl)-2-methylpropyl]-4-methyl-N-piperidin-4-ylbenzamide;
N-[(1R)-1-(1-benzyl-4-phenyl-1H-imidazol-2-yl)-2-methylpropyl]-2,4-difluoro-N-piperidin-4-ylbenzamide;
N-(3-aminopropyl)-N-{(1R)-1-[1-benzyl-4-(3-chlorophenyl)-1H-imidazol-2-yl]-2-methylpropyl}cyclohexanecarboxamide;
N-(3-aminopropyl)-N-{(1R)-1-[1-benzyl-4-(3-chlorophenyl)-1H-imidazol-2-yl]-2-methylpropyl}-6-chloronicotinamide;
N-(3-aminopropyl)-N-{(1R)-1-[1-benzyl-4-(3-chlorophenyl)-1H-imidazol-2-yl]-2,2-dimethylpropyl}benzamide;
N-(3-aminopropyl)-N-{(1R)-1-[1-benzyl-4-(3-chlorophenyl)-1H-imidazol-2-yl]-2,2-dimethylpropyl}-4-methylbenzamide;

N-(3-aminopropyl)-N-{(1R)-1-[4-(3-chlorophenyl)-1-(2,4-difluorobenzyl)-1H-imidazol-2-yl]-2,2-dimethylpropyl}benzamide;

N-(3-aminopropyl)-N-{(1R)-1-[4-(3-chlorophenyl)-1-(2,4-difluorobenzyl)-1H-imidazol-2-yl]-2,2-dimethylpropyl}-4-methylbenzamide;

N-[(1R)-1-(1-benzyl-4-phenyl-1H-imidazol-2-yl)-2-methylpropyl]-N-[3-(dimethylamino)-2,2-dimethylpropyl]benzamide;

N-[(1R)-1-(1-benzyl-4-phenyl-1H-imidazol-2-yl)-2-methylpropyl]-N-[3-(dimethylamino)-2,2-dimethylpropyl]-4-methylbenzamide;

N-(3-aminopropyl)-N-{(1R)-1-[1-benzyl-4-(3-chlorophenyl)-1H-imidazol-2-yl]-2,2-dimethylpropyl}-6-chloronicotinamide;

N-(3-aminopropyl)-6-chloro-N-{(1R)-1-[4-(3-chlorophenyl)-1-(3,5-difluorobenzyl)-1H-imidazol-2-yl]-2,2-dimethylpropyl}nicotinamide;

N-(3-aminopropyl)-N-[(1R)-1-(1-benzyl-5-methyl-4-phenyl-1H-imidazol-2-yl)-2-methylpropyl]benzamide;

N-(3-aminopropyl)-N-[(1R)-1-(1-benzyl-5-methyl-4-phenyl-1H-imidazol-2-yl)-2-methylpropyl]-4-methylbenzamide;

N-(3-aminopropyl)-N-[(1R)-1-(1-benzyl-5-methyl-4-phenyl-1H-imidazol-2-yl)-2-methylpropyl]-2,4-difluorobenzamide;

N-(3-aminopropyl)-N-[(1R)-1-(1-benzyl-5-methyl-4-phenyl-1H-imidazol-2-yl)-2-methylpropyl]-6-chloronicotinamide;

N-(3-aminopropyl)-N-{(1R)-1-[1-benzyl-4-(3-chlorophenyl)-1H-imidazol-2-yl]-2-methylpropyl}-2-chlorobenzamide;

N-(3-aminopropyl)-N-{(1R)-1-[1-benzyl-4-(3-chlorophenyl)-1H-imidazol-2-yl]-2-methylpropyl}-2-chloro-6-methylisonicotinamide;

N-(3-aminopropyl)-N-{(1R)-1-[1-benzyl-4-(3-chlorophenyl)-1H-imidazol-2-yl]-2-methylpropyl}-3-furamide;

N-(3-aminopropyl)-N-{(1R)-1-[1-benzyl-4-(3-chlorophenyl)-1H-imidazol-2-yl]-2-methylpropyl}-5-methyl-2H-imidazole-4-carboxamide;

N-(3-aminopropyl)-N-{(1R)-1-[1-benzyl-4-(3-chlorophenyl)-1H-imidazol-2-yl]-2-methylpropyl}-2-methoxybenzamide;

N-(3-aminopropyl)-N-{(1R)-1-[1-benzyl-4-(3-chlorophenyl)-1H-imidazol-2-yl]-2-methylpropyl}pyridine-2-carboxamide;

N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide;

N-(3-aminopropyl)-N-[(1R)-1-(1-benzyl-4-phenyl-1H-imidazol-2-yl)-1,2-dimethylpropyl]benzamide;

N-(3-aminopropyl)-N-[(1R)-1-(1-benzyl-4-phenyl-1H-imidazol-2-yl)-1,2-dimethylpropyl]-4-methylbenzamide;

N-(2-aminoethyl)-N-[(1R)-1-(1-benzyl-4-phenyl-1H-imidazol-2-yl)-2-methylpropyl]-4-methylbenzamide;

N-(2-aminoethyl)-N-[(1R)-1-(1-benzyl-4-phenyl-1H-imidazol-2-yl)-2-methylpropyl]benzamide;

N-(3-aminopropyl)-N-{(1R)-1-[1-benzyl-4-(3-chlorophenyl)-1H-imidazol-2-yl]-2-methylpropyl}-1,3-thiazole-4-carboxamide;

N-{(1R)-1-[1-benzyl-4-(3-chlorophenyl)-1H-imidazol-2-yl]-2,2-dimethylpropyl}-N-(pyrrolidin-3-ylmethyl)benzamide;

N-{(1R)-1-[4-(3-chlorophenyl)-1-(3,5-difluorobenzyl)-1H-imidazol-2-yl]-2,2-dimethylpropyl}-N-(pyrrolidin-3-ylmethyl)benzamide;

N-(3-aminopropyl)-N-{(1R)-1-[1-benzyl-4-(3-chlorophenyl)-1H-imidazol-2-yl]-2-methylpropyl}benzenesulfonamide;

N-(3-aminopropyl)-N-{(1R)-1-[1-benzyl-4-(3-chlorophenyl)-1H-imidazol-2-yl]-2-methylpropyl}-4-methylisoxazole-3-carboxamide;

N-(3-aminopropyl)-N-{(1R)-1-[1-benzyl-4-(3-chlorophenyl)-1H-imidazol-2-yl]-2-methylpropyl}isoxazole-3-carboxamide;

N-(3-aminopropyl)-N-{(1R)-1-[1-benzyl-4-(3-chlorophenyl)-1H-imidazol-2-yl]-2-methylpropyl}-5-methyl-1H-pyrazole-3-carboxamide;

N-(3-aminopropyl)-N-{(1R)-1-[1-benzyl-4-(3-chlorophenyl)-1H-imidazol-2-yl]-2-methylpropyl}-2,4-dimethyl-1,3-thiazole-5-carboxamide;

N-(3-aminopropyl)-N-{(1R)-1-[1-benzyl-4-(3-chlorophenyl)-1H-imidazol-2-yl]-2-methylpropyl}tetrahydrofuran-3-carboxamide;

N-(3-aminopropyl)-N-{(1R)-1-[1-benzyl-4-(3-chlorophenyl)-1H-imidazol-2-yl]-2-methylpropyl}piperidine-4-carboxamide;

2-amino-N-(3-aminopropyl)-N-{(1R)-1-[1-benzyl-4-(3-chlorophenyl)-1H-imidazol-2-yl]-2-methylpropyl}-1,3-thiazole-4-carboxamide;

N-[(1R)-1-(1-benzyl-4-phenyl-1H-imidazol-2-yl)-2,2-dimethylpropyl]-N-(1H-imidazol-4-ylmethyl)benzamide;

N-[(1R)-1-(1-benzyl-4-phenyl-1H-imidazol-2-yl)-2,2-dimethylpropyl]-N-[(2-hydroxypyridin-4-yl)methyl]benzamide;

N-[(1R)-1-(1-benzyl-4-phenyl-1H-imidazol-2-yl)-2,2-dimethylpropyl]-N-[(6-hydroxypyridin-3-yl)methyl]benzamide;

N-[(1R)-1-(1-benzyl-4-phenyl-1H-imidazol-2-yl)-2,2-dimethylpropyl]-N-(pyridin-3-ylmethyl)benzamide;

N-[(1R)-1-(1-benzyl-4-phenyl-1H-imidazol-2-yl)-2,2-dimethylpropyl]-N-[3-(cyclobutylamino)propyl]benzamide;

N-[(1R)-1-(1-benzyl-4-phenyl-1H-imidazol-2-yl)-2,2-dimethylpropyl]-N-(pyrrolidin-3-ylmethyl)benzamide;

N-(3-aminopropyl)-N-[(1R)-1-(1-benzyl-4-phenyl-1H-imidazol-2-yl)-2,2-dimethylpropyl]-6-methylnicotinamide;

N-[(1R)-1-(1-benzyl-4-phenyl-1H-imidazol-2-yl)-2,2-dimethylpropyl]-N-{3-[(cyclopropylmethyl)amino]propyl}benzamide;

N-[(1R)-1-(1-benzyl-4-phenyl-1H-imidazol-2-yl)-2,2-dimethylpropyl]-N-[3-({[5-(pyridin-3-yloxy)-1H-indazol-3-yl]methyl}amino)propyl]benzamide;

N-[(1R)-1-(1-benzyl-4-phenyl-1H-imidazol-2-yl)-2,2-dimethylpropyl]-N-[(5-methoxy-1H-indazol-3-yl)methyl]benzamide;

N-[(1R)-1-(1-benzyl-4-phenyl-1H-imidazol-2-yl)-2,2-dimethylpropyl]-N-(3-{[(6-fluoro-1H-indazol-3-yl)methyl]amino}propyl)benzamide;

N-[(1R)-1-(1-benzyl-4-phenyl-1H-imidazol-2-yl)-2,2-dimethylpropyl]-N-{[5-(pyridin-3-yloxy)-1H-indazol-3-yl]methyl}benzamide;

N-[(1R)-1-(1-benzyl-4-phenyl-1H-imidazol-2-yl)-2,2-dimethylpropyl]-N-(3-hydroxypropyl)benzamide;

N-(3-aminopropyl)-N-[(1R)-1-(1-benzyl-4-phenyl-1H-imidazol-2-yl)-2,2-dimethylpropyl]-1,5-dimethyl-1H-pyrazole-3-carboxamide;

N-[(1R)-1-(1-benzyl-4-phenyl-1H-imidazol-2-yl)-2,2-dimethylpropyl]-N-[(3R)-3,5-diamino-5-oxopentyl]benzamide;

N-{3-[(aminoacetyl)amino]propyl}-N-[(1R)-1-(1-benzyl-4-phenyl-1H-imidazol-2-yl)-2,2-dimethylpropyl]benzamide;

N-{2-[(aminoacetyl)amino]ethyl}-N-[(1R)-1-(1-benzyl-4-phenyl-1H-imidazol-2-yl)-2,2-dimethylpropyl]benzamide;
N-[(1R)-1-(1-benzyl-4-phenyl-1H-imidazol-2-yl)-2-methylpropyl]-1,5-dimethyl-N-(piperidin-3-ylmethyl)-1H-pyrazole-3-carboxamide;
(2R)—N-(3-aminopropyl)-N-{(1R)-1-[1-benzyl-4-(3-chlorophenyl)-1H-imidazol-2-yl]-2-methylpropyl}tetrahydrofuran-2-carboxamide;
(2S)—N-(3-aminopropyl)-N-{(1R)-1-[1-benzyl-4-(3-chlorophenyl)-1H-imidazol-2-yl]-2-methylpropyl}tetrahydrofuran-2-carboxamide;
N-(3-aminopropyl)-N-{(1R)-1-[1-benzyl-4-(3-chlorophenyl)-1H-imidazol-2-yl]-2-methylpropyl}pyrazine-2-carboxamide;
3-{benzoyl[(1R)-1-(1-benzyl-4-phenyl-1H-imidazol-2-yl)-2,2-dimethylpropyl]amino}propyl benzoate;
N-{(1R)-1-[4-(3-chlorophenyl)-1-(3,5-difluorobenzyl)-1H-imidazol-2-yl]-2,2-dimethylpropyl}-1,5-dimethyl-N-[(3R)-pyrrolidin-3-ylmethyl]-1H-pyrazole-3-carboxamide;
N-{(1R)-1-[4-(3-chlorophenyl)-1-(3,5-difluorobenzyl)-1H-imidazol-2-yl]-2,2-dimethylpropyl}-1,5-dimethyl-N-[(3S)-pyrrolidin-3-ylmethyl]-1H-pyrazole-3-carboxamide;
N-(3-aminopropyl)-N-{(1R)-1-[1-benzyl-4-(3-chlorophenyl)-1H-imidazol-2-yl]-2-methylpropyl}-1-methyl-3-(trifluoromethyl)-1H-pyrazole-4-carboxamide;
N-(3-aminopropyl)-N-{(1R)-1-[1-benzyl-4-(3-chlorophenyl)-1H-imidazol-2-yl]-2-methylpropyl}-5-chloro-1-methyl-1H-pyrazole-4-carboxamide;
N-(3-aminopropyl)-N-{(1R)-1-[1-benzyl-4-(3-chlorophenyl)-1H-imidazol-2-yl]-2-methylpropyl}-2-(dimethylamino)acetamide;
N-[(1R)-1-(1-benzyl-4-phenyl-1H-imidazol-2-yl)-2,2-dimethylpropyl]-N-[3-(1H-imidazol-2-yl)propyl]benzamide;
1-benzyl-6-(1-benzyl-4-phenyl-1H-imidazol-2-yl)piperidin-2-one;
1-benzyl-6-[1-(3-chlorobenzyl)-4-phenyl-1H-imidazol-2-yl]piperidin-2-one;
N-(3-aminopropyl)-N-[(1R)-1-(1-benzyl-4-phenyl-1H-imidazol-2-yl)-2-methylpropyl]-1,5-dimethyl-1H-pyrazole-3-carboxamide;
N-[(1R)-1-(1-benzyl-4-phenyl-1H-imidazol-2-yl)-2,2-dimethylpropyl]-N-{3-[(2-hydroxyethyl)amino]propyl}benzamide;
N-[(1R)-1-(1-benzyl-4-phenyl-1H-imidazol-2-yl)-2,2-dimethylpropyl]-N-[3-(cyclopropylamino)propyl]benzamide;
N-(3-aminopropyl)-N-{(1R)-2-methyl-1-[4-phenyl-1-(1,3-thiazol-4-ylmethyl)-1H-imidazol-2-yl]propyl}benzamide;
N-(3-aminopropyl)-4-methyl-N-{(1R)-2-methyl-1-[4-phenyl-1-(1,3-thiazol-4-ylmethyl)-1H-imidazol-2-yl]propyl}benzamide;
N-(3-aminopropyl)-2,4-difluoro-N-{(1R)-2-methyl-1-[4-phenyl-1-(1,3-thiazol-4-ylmethyl)-1H-imidazol-2-yl]propyl}benzamide;
N-(3-aminopropyl)-6-chloro-N-{(1R)-2-methyl-1-[4-phenyl-1-(1,3-thiazol-4-ylmethyl)-1H-imidazol-2-yl]propyl}nicotinamide;
N-(3-aminopropyl)-N-[(1R)-1-(1-benzyl-4-pyridin-2-yl-1H-imidazol-2-yl)-2,2-dimethylpropyl]benzamide;
N-(3-aminopropyl)-N-[(1R)-1-(1-benzyl-4-pyridin-2-yl-1H-imidazol-2-yl)-2,2-dimethylpropyl]-4-methylbenzamide;
N-(3-aminopropyl)-N-[(1R)-1-(1-benzyl-4-pyridin-2-yl-1H-imidazol-2-yl)-2,2-dimethylpropyl]-2,4-difluorobenzamide;
N-(3-aminopropyl)-N-[(1R)-1-(1-benzyl-4-pyridin-2-yl-1H-imidazol-2-yl)-2,2-dimethylpropyl]-6-chloronicotinamide;
N-(2-amino-3-hydroxypropyl)-N-[(1R)-1-(1-benzyl-4-phenyl-1H-imidazol-2-yl)-2-methylpropyl]benzamide;
N-(3-aminopropyl)-N-[(1R)-1-(1-benzyl-4-phenyl-1H-imidazol-2-yl)-3-methylbutyl]benzamide;
N-(3-aminopropyl)-N-[(1R)-1-(1-benzyl-4-phenyl-1H-imidazol-2-yl)-3-methylbutyl]-4-methylbenzamide;
N-(3-aminopropyl)-N-[(1R,2R)-1-(1-benzyl-4-phenyl-1H-imidazol-2-yl)-2-methylbutyl]benzamide;
N-(3-aminopropyl)-N-[(1R,2R)-1-(1-benzyl-4-phenyl-1H-imidazol-2-yl)-2-methylbutyl]-4-methylbenzamide;
N-(3-aminopropyl)-N-[(1R,2S)-1-(1-benzyl-4-phenyl-1H-imidazol-2-yl)-2-methylbutyl]benzamide;
N-(3-aminopropyl)-N-[(1R,2S)-1-(1-benzyl-4-phenyl-1H-imidazol-2-yl)-2-methylbutyl]-4-methylbenzamide;
N-(3-aminopropyl)-N-{(1R)-1-[1-benzyl-4-(3-chlorophenyl)-1H-imidazol-2-yl]-2-methylpropyl}-5-methylisoxazole-4-carboxamide;
N-(3-aminopropyl)-N-{(1R)-1-[1-benzyl-4-(3-chlorophenyl)-1H-imidazol-2-yl]-2-methylpropyl}acetamide;
N-(3-aminopropyl)-N-{(1R)-1-[1-benzyl-4-(3-chlorophenyl)-1H-imidazol-2-yl]-2-methylpropyl}-2-(4-fluorophenoxy)acetamide;
N-(3-aminopropyl)-N-{(1R)-1-[1-benzyl-4-(3-chlorophenyl)-1H-imidazol-2-yl]-2-methylpropyl}-2-(1H-imidazol-1-yl)acetamide;
N-(3-aminopropyl)-N-{(1R)-1-[1-benzyl-4-(3-chlorophenyl)-1H-imidazol-2-yl]-2-methylpropyl}-2-morpholin-4-ylacetamide;
[(3-{benzoyl[(1R)-1-(1-benzyl-4-phenyl-1H-imidazol-2-yl)-2,2-dimethylpropyl]amino}propyl)amino]acetic acid;
N-(3-aminopropyl)-N-{(1R)-1-[1-benzyl-4-(3-chlorophenyl)-1H-imidazol-2-yl]-2-methylpropyl}-2-hydroxyacetamide;
N-(3-aminopropyl)-N-{(1R)-1-[1-benzyl-4-(3-chlorophenyl)-1H-imidazol-2-yl]-2-methylpropyl}-2-methoxyacetamide;
N-(3-aminopropyl)-N-[(1R)-1-(1-benzyl-4-phenyl-1H-imidazol-2-yl)-2,2-dimethylpropyl]-2-hydroxyacetamide;
N-(3-aminopropyl)-N-[(1R)-1-(1-benzyl-4-phenyl-1H-imidazol-2-yl)-2,2-dimethylpropyl]-2-methoxyacetamide;
N-(3-aminopropyl)-N-{(1R)-1-[1-benzyl-4-(3-chlorophenyl)-1H-imidazol-2-yl]-2-methylpropyl}-1-ethyl-3-methyl-1H-pyrazole-5-carboxamide;
ethyl [(3-{benzoyl[(1R)-1-(1-benzyl-4-phenyl-1H-imidazol-2-yl)-2,2-dimethylpropyl]amino}propyl)amino]acetate;
N-{3-[(2-amino-3-methylbutanoyl)amino]propyl}-N-[(1R)-1-(1-benzyl-4-phenyl-1H-imidazol-2-yl)-2,2-dimethylpropyl]benzamide;
N-(3-aminopropyl)-N-{(1R)-1-[1-benzyl-4-(3-chlorophenyl)-1H-imidazol-2-yl]-2-methylpropyl}tetrahydro-2H-pyran-4-carboxamide;
N-(3-aminopropyl)-N-{(1R)-1-[1-benzyl-4-(3-chlorophenyl)-1H-imidazol-2-yl]-2-methylpropyl}-2-(methylamino)acetamide;
N-[(1R)-1-(1-benzyl-4-phenyl-1H-imidazol-2-yl)-2,2-dimethylpropyl]-N-propylbenzamide;
N-[(1R)-1-(1-benzyl-4-phenyl-1H-imidazol-2-yl)-2,2-dimethylpropyl]-N-butylbenzamide;

N-[(1R)-1-(1-benzyl-4-phenyl-1H-imidazol-2-yl)-2,2-dimethylpropyl]-N-butyl-1,5-dimethyl-1H-pyrazole-3-carboxamide;
[[(1R)-1-(1-benzyl-4-phenyl-1H-imidazol-2-yl)-2,2-dimethylpropyl](butyl)amino](oxo)acetic acid;
[[(1R)-1-(1-benzyl-4-phenyl-1H-imidazol-2-yl)-2,2-dimethylpropyl](propyl)amino](oxo)acetic acid;
N-[(1R)-1-(1-benzyl-4-phenyl-1H-imidazol-2-yl)-2,2-dimethylpropyl]-N-{3-[2-(hydroxymethyl)piperidin-1-yl]propyl}benzamide;
N-[(1R)-1-(1-benzyl-4-phenyl-1H-imidazol-2-yl)-2,2-dimethylpropyl]-N-{3-[bis(2-hydroxyethyl)amino]propyl}benzamide;
1-(2-amino-1-phenylethyl)-6-(1-benzyl-4-phenyl-1H-imidazol-2-yl)piperidin-2-one;
6-(1-benzyl-4-phenyl-1H-imidazol-2-yl)piperidin-2-one;
N-[(2S)-3-amino-2-fluoropropyl]-N-[(1R)-1-(1-benzyl-4-phenyl-1H-imidazol-2-yl)-2,2-dimethylpropyl]benzamide;
N-[(1R)-1-(1-benzyl-4-phenyl-1H-imidazol-2-yl)-2,2-dimethylpropyl]-N-(3-{[2-hydroxy-1-(hydroxymethyl)ethyl]amino}propyl)benzamide;
N-[(1R)-1-(1-benzyl-4-phenyl-1H-imidazol-2-yl)-2,2-dimethylpropyl]-N-(3-{[2-(hydroxymethyl)phenyl]amino}propyl)benzamide;
N-{(1R)-1-[1-benzyl-4-(3-chlorophenyl)-1H-imidazol-2-yl]-2-methylpropyl}-N-piperidin-4-ylbenzamide;
N-{(1R)-1-[1-benzyl-4-(3-chlorophenyl)-1H-imidazol-2-yl]-2-methylpropyl}-N-(piperidin-3-ylmethyl)benzamide;
2-(3-amino-2-oxopyridin-1(2H)-yl)-N-[(1R)-1-(1-benzyl-4-phenyl-1H-imidazol-2-yl)-2,2-dimethylpropyl]acetamide;
N-{(1R)-1-[1-benzyl-4-(3-chlorophenyl)-1H-imidazol-2-yl]-2-methylpropyl}-2-pyrrolidin-3-ylbenzamide;
(1R,3S)-3-{[(2-aminoethyl)sulfonyl]amino}-N-[(1R)-1-(1-benzyl-4-phenyl-1H-imidazol-2-yl)-2,2-dimethylpropyl]cyclohexanecarboxamide;
(1R,3S)-3-[(aminoacetyl)amino]-N-[(1R)-1-(1-benzyl-4-phenyl-1H-imidazol-2-yl)-2,2-dimethylpropyl]cyclohexanecarboxamide;
N-(3-aminopropyl)-N-{(1R)-1-[1-benzyl-4-(3-chlorophenyl)-1H-imidazol-2-yl]-2-methylpropyl}-6-(trifluoromethyl)nicotinamide;
N-[(2R)-3-amino-2-fluoropropyl]-N-[(1R)-1-(1-benzyl-4-phenyl-1H-imidazol-2-yl)-2,2-dimethylpropyl]benzamide;
(3R)—N-(3-aminopropyl)-N-{(1R)-1-[1-benzyl-4-(3-chlorophenyl)-1H-imidazol-2-yl]-2-methylpropyl}piperidine-3-carboxamide;
(3S)—N-(3-aminopropyl)-N-{(1R)-1-[1-benzyl-4-(3-chlorophenyl)-1H-imidazol-2-yl]-2-methylpropyl}piperidine-3-carboxamide;
N-(3-aminopropyl)-N-{(1R)-1-[1-benzyl-4-(3-chlorophenyl)-1H-imidazol-2-yl]-2-methylpropyl}-2-(1H-1,2,4-triazol-1-yl)acetamide;
[(5R)-1-benzoyl-5-(1-benzyl-4-phenyl-1H-imidazol-2-yl)pyrrolidin-2-yl]methylamine;
N-(3-aminopropyl)-N-{(1R)-1-[1-benzyl-4-(3-chlorophenyl)-1H-imidazol-2-yl]-2-methylpropyl}-2-(4H-1,2,4-triazol-4-yl)acetamide;
N-(3-aminopropyl)-N-{(1R)-1-[1-benzyl-4-(3-chlorophenyl)-1H-imidazol-2-yl]-2-methylpropyl}-2,1,3-benzothiadiazole-4-carboxamide;
N-[(2S)-3-amino-2-hydroxypropyl]-N-[(1R)-1-(1-benzyl-4-phenyl-1H-imidazol-2-yl)-2,2-dimethylpropyl]benzamide;
N-[(2S)-3-amino-2-fluoropropyl]-N-[(1R)-1-(1-benzyl-4-phenyl-1H-imidazol-2-yl)-2,2-dimethylpropyl]-1,5-dimethyl-1H-pyrazole-3-carboxamide;
N-[(1R)-1-(1-benzyl-4-phenyl-1H-imidazol-2-yl)-2,2-dimethylpropyl]-1,5-dimethyl-N-[(2S)-morpholin-2-ylmethyl]-1H-pyrazole-3-carboxamide;
N-[(1R)-1-(1-benzyl-4-phenyl-1H-imidazol-2-yl)-2,2-dimethylpropyl]-1,5-dimethyl-N-[(2R)-morpholin-2-ylmethyl]-1H-pyrazole-3-carboxamide;
N-[(2S)-3-amino-2-hydroxypropyl]-N-[(1R)-1-(1-benzyl-4-phenyl-1H-imidazol-2-yl)-2,2-dimethylpropyl]-1,5-dimethyl-1H-pyrazole-3-carboxamide;
N-[(2S)-3-amino-2-hydroxypropyl]-N-[(1R)-1-(1-benzyl-4-phenyl-1H-imidazol-2-yl)-2,2-dimethylpropyl]-2-methoxyacetamide;
N-[(1R)-1-(1-benzyl-4-phenyl-1H-imidazol-2-yl)-2,2-dimethylpropyl]-2-pyrrolidin-3-ylbenzamide;
N-(3-aminopropyl)-N-{(1R)-1-[1-benzyl-4-(3-chlorophenyl)-1H-imidazol-2-yl]-2-methylpropyl}-2-(1H-pyrazol-1-yl)acetamide;
N-[(2R)-3-amino-2-fluoropropyl]-N-[(1R)-1-(1-benzyl-4-phenyl-1H-imidazol-2-yl)-2,2-dimethylpropyl]-1,5-dimethyl-1H-pyrazole-3-carboxamide;
methyl 3-aminopropyl[(1R)-1-(1-benzyl-4-phenyl-1H-imidazol-2-yl)-2,2-dimethylpropyl]carbamate;
N-(3-aminopropyl)-N-[(1R)-1-(1-benzyl-4-phenyl-1H-imidazol-2-yl)-2,2-dimethylpropyl]-2-(1H-tetrazol-1-yl)acetamide;
N-(3-aminopropyl)-N-[(1R)-1-(1-benzyl-4-phenyl-1H-imidazol-2-yl)-2,2-dimethylpropyl]-2-(2H-tetrazol-2-yl)acetamide;
N-(3-aminopropyl)-N-[(1R)-1-(1-benzyl-4-phenyl-1H-imidazol-2-yl)-2,2-dimethylpropyl]-2-(1H-1,2,4-triazol-1-yl)acetamide;
N-(3-aminopropyl)-N-[(1R)-1-(1-benzyl-4-phenyl-1H-imidazol-2-yl)-2,2-dimethylpropyl]-2-(4H-1,2,4-triazol-4-yl)acetamide;
N-[(1R)-1-(1-benzyl-4-phenyl-1H-imidazol-2-yl)-2,2-dimethylpropyl]-2-methoxy-N-[(2S)-morpholin-2-ylmethyl]acetamide;
N-[(1R)-1-(1-benzyl-4-phenyl-1H-imidazol-2-yl)-2,2-dimethylpropyl]-2-methoxy-N-[(2R)-morpholin-2-ylmethyl]acetamide;
N-(3-aminopropyl)-N-[(1S)-1-(1-benzyl-4-phenyl-1H-imidazol-2-yl)-2-hydroxy-2-methylpropyl]benzamide;
N-[(1R)-1-(1-benzyl-4-phenyl-1H-imidazol-2-yl)-2,2-dimethylpropyl]-2-hydroxy-N-[(2S)-morpholin-2-ylmethyl]acetamide;
N-[(1R)-1-(1-benzyl-4-phenyl-1H-imidazol-2-yl)-2,2-dimethylpropyl]-2-hydroxy-N-[(2R)-morpholin-2-ylmethyl]acetamide;
(2S)—N-(3-aminopropyl)-N-[(1R)-1-(1-benzyl-4-phenyl-1H-imidazol-2-yl)-2,2-dimethylpropyl]tetrahydrofuran-2-carboxamide;
N-(3-aminopropyl)-N-{(1R)-1-[4-(3-chlorophenyl)-1-(3-cyanobenzyl)-1H-imidazol-2-yl]-2-methylpropyl}benzamide;
N-(3-aminopropyl)-N-{(1R)-1-[4-(3-chlorophenyl)-1-(3-cyanobenzyl)-1H-imidazol-2-yl]-2-methylpropyl}-4-methylbenzamide;
N-(3-aminopropyl)-N-{(1R)-1-[4-(3-chlorophenyl)-1-(3-methylbenzyl)-1H-imidazol-2-yl]-2-methylpropyl}-4-methylbenzamide;
N-(3-aminopropyl)-N-{(1R)-1-[4-(3-chlorophenyl)-1-(3-methylbenzyl)-1H-imidazol-2-yl]-2-methylpropyl}benzamide;

ethyl 3-aminopropyl[(1R)-1-(1-benzyl-4-phenyl-1H-imidazol-2-yl)-2,2-dimethylpropyl]carbamate;
neopentyl 3-aminopropyl[(1R)-1-(1-benzyl-4-phenyl-1H-imidazol-2-yl)-2,2-dimethylpropyl]carbamate;
isobutyl 3-aminopropyl[(1R)-1-(1-benzyl-4-phenyl-1H-imidazol-2-yl)-2,2-dimethylpropyl]carbamate;
propyl 3-aminopropyl[(1R)-1-(1-benzyl-4-phenyl-1H-imidazol-2-yl)-2,2-dimethylpropyl]carbamate;
N-(3-aminopropyl)-N-[(1R)-1-(1-benzyl-4-phenyl-1H-imidazol-2-yl)-2,2-dimethylpropyl]-2-cyanoacetamide;
N-[(1R)-1-(1-benzyl-4-phenyl-1H-imidazol-2-yl)-2,2-dimethylpropyl]-2-methoxy-N-[(3R)-pyrrolidin-3-ylmethyl]acetamide;
N-[(1R)-1-(1-benzyl-4-phenyl-1H-imidazol-2-yl)-2,2-dimethylpropyl]-2-methoxy-N-[(3S)-pyrrolidin-3-ylmethyl]acetamide;
butyl 3-aminopropyl[(1R)-1-(1-benzyl-4-phenyl-1H-imidazol-2-yl)-2,2-dimethylpropyl]carbamate;
N-[(1R)-1-(1-benzyl-4-phenyl-1H-imidazol-2-yl)-2,2-dimethylpropyl]-2-hydroxy-N-[(3R)-pyrrolidin-3-ylmethyl]acetamide;
N-[(1R)-1-(1-benzyl-4-phenyl-1H-imidazol-2-yl)-2,2-dimethylpropyl]-2-hydroxy-N-[(3S)-pyrrolidin-3-ylmethyl]acetamide;
N-[(1R)-1-(1-benzyl-4-phenyl-1H-imidazol-2-yl)-2,2-dimethylpropyl]-N-[(3S)-pyrrolidin-3-ylmethyl]benzamide;
N-[(2R)-3-amino-2-fluoropropyl]-N-[(1R)-1-(1-benzyl-4-phenyl-1H-imidazol-2-yl)-2,2-dimethylpropyl]-2-(2H-tetrazol-2-yl)acetamide;
N-[(2R)-3-amino-2-fluoropropyl]-N-[(1R)-1-(1-benzyl-4-phenyl-1H-imidazol-2-yl)-2,2-dimethylpropyl]-2-(1H-tetrazol-1-yl)acetamide;
N-[(2R)-3-amino-2-fluoropropyl]-N-[(1R)-1-(1-benzyl-4-phenyl-1H-imidazol-2-yl)-2,2-dimethylpropyl]-2-methoxyacetamide;
N-[(2S)-3-amino-2-fluoropropyl]-N-[(1R)-1-(1-benzyl-4-phenyl-1H-imidazol-2-yl)-2,2-dimethylpropyl]-2-methoxyacetamide;
N-[(1R)-1-(1-benzyl-4-phenyl-1H-imidazol-2-yl)-2,2-dimethylpropyl]-N-[(3S)-3,4-diamino-4-oxobutyl]benzamide;
N-[(1R)-1-(1-benzyl-4-phenyl-1H-imidazol-2-yl)-2,2-dimethylpropyl]-N-[(3R)-3,4-diamino-4-oxobutyl]benzamide;
N-[(3S)-3-amino-4-hydroxybutyl]-N-[(1R)-1-(1-benzyl-4-phenyl-1H-imidazol-2-yl)-2,2-dimethylpropyl]benzamide;
(2S)-2-amino-4-{benzoyl[(1R)-1-(1-benzyl-4-phenyl-1H-imidazol-2-yl)-2,2-dimethylpropyl]amino}butanoic acid;
N-[(2R)-3-amino-2-fluoropropyl]-N-[(1R)-1-(1-benzyl-4-phenyl-1H-imidazol-2-yl)-2,2-dimethylpropyl]-2-hydroxyacetamide;
N-(3-aminopropyl)-N-[(1R)-1-(1-benzyl-4-phenyl-1H-imidazol-2-yl)-2,2-dimethylpropyl]-2-(1H-tetrazol-5-yl)acetamide;
N-[(1R)-1-(1-benzyl-4-phenyl-1H-imidazol-2-yl)-2,2-dimethylpropyl]-N-[(3S)-pyrrolidin-3-ylmethyl]-2-(1H-tetrazol-1-yl)acetamide;
N-[(1R)-1-(1-benzyl-4-phenyl-1H-imidazol-2-yl)-2,2-dimethylpropyl]-N-[(3S)-pyrrolidin-3-ylmethyl]-2-(2H-tetrazol-2-yl)acetamide;
N-[(1R)-1-(1-benzyl-4-phenyl-1H-imidazol-2-yl)-2,2-dimethylpropyl]-6-methyl-N-[(3S)-pyrrolidin-3-ylmethyl]nicotinamide;
N-(azetidin-3-ylmethyl)-N-[(1R)-1-(1-benzyl-4-phenyl-1H-imidazol-2-yl)-2,2-dimethylpropyl]-2-methoxyacetamide;
N-{(1R)-1-[1-(3-cyanobenzyl)-4-phenyl-1H-imidazol-2-yl]-2,2-dimethylpropyl}-N-(pyrrolidin-3-ylmethyl)benzamide;
N-{(1R)-2,2-dimethyl-1-[1-(3-methylbenzyl)-4-phenyl-1H-imidazol-2-yl]propyl}-N-(pyrrolidin-3-ylmethyl)benzamide;
N-[(2S)-3-amino-2-hydroxypropyl]-N-[(1R)-1-(1-benzyl-4-phenyl-1H-imidazol-2-yl)-2,2-dimethylpropyl]-2-hydroxyacetamide;
N-[(1R)-1-(1-benzyl-4-phenyl-1H-imidazol-2-yl)-2,2-dimethylpropyl]-N-[3-(methoxyamino)propyl]benzamide;
N-[(2S)-3-amino-2-fluoropropyl]-N-[(1R)-1-(1-benzyl-4-phenyl-1H-imidazol-2-yl)-2,2-dimethylpropyl]-2-(1H-tetrazol-1-yl)acetamide;
N-[(2S)-3-amino-2-fluoropropyl]-N-[(1R)-1-(1-benzyl-4-phenyl-1H-imidazol-2-yl)-2,2-dimethylpropyl]-2-(2H-tetrazol-2-yl)acetamide;
N-{(1R)-1-[1-(3-cyanobenzyl)-4-phenyl-1H-imidazol-2-yl]-2,2-dimethylpropyl}-2-methoxy-N-[(3S)-pyrrolidin-3-ylmethyl]acetamide;
N-{(1R)-1-[1-(3-cyanobenzyl)-4-phenyl-1H-imidazol-2-yl]-2,2-dimethylpropyl}-2-methoxy-N-[(3R)-pyrrolidin-3-ylmethyl]acetamide;
N-(3-aminopropyl)-N-{(1R)-1-[1-(3-cyanobenzyl)-4-phenyl-1H-imidazol-2-yl]-2,2-dimethylpropyl}benzamide;
N-(3-aminopropyl)-N-{(1R)-1-[1-(3-cyanobenzyl)-4-phenyl-1H-imidazol-2-yl]-2,2-dimethylpropyl}-2-methoxyacetamide;
2-hydroxy-N-{(1R)-1-[1-(3-hydroxybenzyl)-4-phenyl-1H-imidazol-2-yl]-2,2-dimethylpropyl}-N-(pyrrolidin-3-ylmethyl)acetamide;
N-{(1R)-2,2-dimethyl-1-[1-(3-methylbenzyl)-4-phenyl-1H-imidazol-2-yl]propyl}-2-methoxy-N-[(3S)-pyrrolidin-3-ylmethyl]acetamide;
N-{(1R)-2,2-dimethyl-1-[1-(3-methylbenzyl)-4-phenyl-1H-imidazol-2-yl]propyl}-2-methoxy-N-[(3R)-pyrrolidin-3-ylmethyl]acetamide;
N-(3-aminopropyl)-N-{(1R)-2,2-dimethyl-1-[1-(3-methylbenzyl)-4-phenyl-1H-imidazol-2-yl]propyl}-2-methoxyacetamide;
N-[(3S)-3-amino-4-hydroxybutyl]-N-[(1R)-1-(1-benzyl-4-phenyl-1H-imidazol-2-yl)-2,2-dimethylpropyl]-1,5-dimethyl-1H-pyrazole-3-carboxamide;
N-(3-amino-2-hydroxypropyl)-N-[(1R)-1-(1-benzyl-4-phenyl-1H-imidazol-2-yl)-2,2-dimethylpropyl]-2-(1H-tetrazol-1-yl)acetamide;
N-(3-amino-2-hydroxypropyl)-N-[(1R)-1-(1-benzyl-4-phenyl-1H-imidazol-2-yl)-2,2-dimethylpropyl]-2-(2H-tetrazol-2-yl)acetamide;
N-[(1R)-1-(1-benzyl-4-phenyl-1H-imidazol-2-yl)-2,2-dimethylpropyl]-1,5-dimethyl-N-[(3S)-pyrrolidin-3-ylmethyl]-1H-pyrazole-3-carboxamide;
N-(3-aminopropyl)-N-{(1R)-2,2-dimethyl-1-[1-(3-methylbenzyl)-4-phenyl-1H-imidazol-2-yl]propyl}benzamide;
N-(azetidin-3-ylmethyl)-N-[(1R)-1-(1-benzyl-4-phenyl-1H-imidazol-2-yl)-2,2-dimethylpropyl]benzamide;
N-(azetidin-3-ylmethyl)-N-[(1R)-1-(1-benzyl-4-phenyl-1H-imidazol-2-yl)-2,2-dimethylpropyl]-2-hydroxyacetamide;
N-(azetidin-3-ylmethyl)-N-[(1R)-1-(1-benzyl-4-phenyl-1H-imidazol-2-yl)-2,2-dimethylpropyl]-1,5-dimethyl-1H-pyrazole-3-carboxamide;
N-[(3S)-3-amino-4-hydroxybutyl]-N-[(1R)-1-(1-benzyl-4-phenyl-1H-imidazol-2-yl)-2,2-dimethylpropyl]-2-methoxyacetamide;
N-[(2S)-3-amino-2-fluoropropyl]-N-[(1R)-1-(1-benzyl-4-phenyl-1H-imidazol-2-yl)-2,2-dimethylpropyl]-2-(1H-1,2,3-triazol-1-yl)acetamide;

N-[(2S)-3-amino-2-fluoropropyl]-N-[(1R)-1-(1-benzyl-4-phenyl-1H-imidazol-2-yl)-2,2-dimethylpropyl]-2-(2H-1,2,3-triazol-2-yl)acetamide;

N-[(3S)-3-amino-4-hydroxybutyl]-N-[(1R)-1-(1-benzyl-4-phenyl-1H-imidazol-2-yl)-2,2-dimethylpropyl]-2-(1H-tetrazol-1-yl)acetamide;

N-[(3S)-3-amino-4-hydroxybutyl]-N-[(1R)-1-(1-benzyl-4-phenyl-1H-imidazol-2-yl)-2,2-dimethylpropyl]-2-(2H-tetrazol-2-yl)acetamide;

N-[(3S)-3-amino-4-hydroxybutyl]-N-[(1R)-1-(1-benzyl-4-phenyl-1H-imidazol-2-yl)-2,2-dimethylpropyl]-2-(1H-1,2,3-triazol-1-yl)acetamide;

N-[(1R)-1-(1-benzyl-4-phenyl-1H-imidazol-2-yl)-2,2-dimethylpropyl]-N-[(3-fluoropyrrolidin-3-yl)methyl]amine;

N-[(1R)-1-(1-benzyl-4-phenyl-1H-imidazol-2-yl)-2,2-dimethylpropyl]-N-{[(3S)-3-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3R)-3-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-[(3-hydroxypyrrolidin-3-yl)methyl]-2-methoxyacetamide;

N-(azetidin-3-ylmethyl)-N-[(1R)-1-(1-benzyl-4-phenyl-1H-imidazol-2-yl)-2,2-dimethylpropyl]-6-methylnicotinamide;

N-[(1R)-1-(1-benzyl-4-phenyl-1H-imidazol-2-yl)-2,2-dimethylpropyl]-N-{[(3S)-3-fluoropyrrolidin-3-yl]methyl}-1,5-dimethyl-1H-pyrazole-3-carboxamide;

N-[(1R)-1-(1-benzyl-4-phenyl-1H-imidazol-2-yl)-2,2-dimethylpropyl]-N-{[(3R)-3-fluoropyrrolidin-3-yl]methyl}-1,5-dimethyl-1H-pyrazole-3-carboxamide;

N-[(1R)-1-(1-benzyl-4-phenyl-1H-imidazol-2-yl)-2,2-dimethylpropyl]-N-[(3-fluoropyrrolidin-3-yl)methyl]-1,5-dimethyl-1H-pyrazole-3-carboxamide;

N-[(1R)-1-(1-benzyl-4-phenyl-1H-imidazol-2-yl)-2,2-dimethylpropyl]-N-{[(3S)-3-fluoropyrrolidin-3-yl]methyl}benzamide;

N-[(1R)-1-(1-benzyl-4-phenyl-1H-imidazol-2-yl)-2,2-dimethylpropyl]-N-{[(3R)-3-fluoropyrrolidin-3-yl]methyl}benzamide;

N-[(1R)-1-(1-benzyl-4-phenyl-1H-imidazol-2-yl)-2,2-dimethylpropyl]-N-[(3-fluoropyrrolidin-3-yl)methyl]benzamide;

N-(3-aminopropyl)-2-hydroxy-N-{(1R)-1-[1-(3-hydroxybenzyl)-4-phenyl-1H-imidazol-2-yl]-2,2-dimethylpropyl}acetamide;

N-{(1R)-1-[1-(3-hydroxybenzyl)-4-phenyl-1H-imidazol-2-yl]-2,2-dimethylpropyl}-N-(pyrrolidin-3-ylmethyl)benzamide;

N-(3-aminopropyl)-N-{(1R)-2,2-dimethyl-1-[1-(3-methylbenzyl)-4-phenyl-1H-imidazol-2-yl]propyl}-1,5-dimethyl-1H-pyrazole-3-carboxamide;

N-{(1R)-2,2-dimethyl-1-[1-(3-methylbenzyl)-4-phenyl-1H-imidazol-2-yl]propyl}-1,5-dimethyl-N-(pyrrolidin-3-ylmethyl)-1H-pyrazole-3-carboxamide;

N-(3-aminopropyl)-N-{(1R)-1-[1-(3-hydroxybenzyl)-4-phenyl-1H-imidazol-2-yl]-2,2-dimethylpropyl}benzamide;

N-(3-aminopropyl)-N-{(1R)-1-[1-(3-methoxybenzyl)-4-phenyl-1H-imidazol-2-yl]-2,2-dimethylpropyl}benzamide;

N-(3-aminopropyl)-2-methoxy-N-{(1R)-1-[1-(3-methoxybenzyl)-4-phenyl-1H-imidazol-2-yl]-2,2-dimethylpropyl}acetamide;

N-(3-aminopropyl)-N-{(1R)-1-[1-(3-cyanobenzyl)-4-phenyl-1H-imidazol-2-yl]-2,2-dimethylpropyl}-2-hydroxyacetamide;

N-(3-aminopropyl)-N-{(1R)-1-[1-(3-methoxybenzyl)-4-phenyl-1H-imidazol-2-yl]-2,2-dimethylpropyl}-1,5-dimethyl-1H-pyrazole-3-carboxamide;

N-[(3S)-3-amino-4-methoxybutyl]-N-[(1R)-1-(1-benzyl-4-phenyl-1H-imidazol-2-yl)-2,2-dimethylpropyl]benzamide;

N-(3-aminopropyl)-N-{(1R)-1-[1-(3-cyanobenzyl)-4-phenyl-1H-imidazol-2-yl]-2,2-dimethylpropyl}-1,5-dimethyl-1H-pyrazole-3-carboxamide;

N-{(1R)-1-[1-(3-cyanobenzyl)-4-phenyl-1H-imidazol-2-yl]-2,2-dimethylpropyl}-1,5-dimethyl-N-(pyrrolidin-3-ylmethyl)-1H-pyrazole-3-carboxamide;

N-{(1R)-1-[1-(3-cyanobenzyl)-4-phenyl-1H-imidazol-2-yl]-2,2-dimethylpropyl}-2-hydroxy-N-[(3S)-pyrrolidin-3-ylmethyl]acetamide;

N-[(2R)-3-amino-2-fluoropropyl]-N-[(1R)-1-(1-benzyl-4-phenyl-1H-imidazol-2-yl)-2,2-dimethylpropyl]-2-(1H-1,2,3-triazol-1-yl)acetamide;

N-[(2R)-3-amino-2-fluoropropyl]-N-[(1R)-1-(1-benzyl-4-phenyl-1H-imidazol-2-yl)-2,2-dimethylpropyl]-2-(2H-1,2,3-triazol-2-yl)acetamide;

N-[(1R)-1-(1-benzyl-4-phenyl-1H-imidazol-2-yl)-2,2-dimethylpropyl]-N-{[(3S)-3-hydroxypyrrolidin-3-yl]methyl}benzamide;

N-[(1R)-1-(1-benzyl-4-phenyl-1H-imidazol-2-yl)-2,2-dimethylpropyl]-N-{[(3R)-3-hydroxypyrrolidin-3-yl]methyl}benzamide;

N-[(1R)-1-(1-benzyl-4-phenyl-1H-imidazol-2-yl)-2,2-dimethylpropyl]-N-[(3-hydroxypyrrolidin-3-yl)methyl]benzamide;

N-[(1R)-1-(1-benzyl-4-phenyl-1H-imidazol-2-yl)-2,2-dimethylpropyl]-2-ethoxy-N-[(3S)-pyrrolidin-3-ylmethyl]acetamide;

N-(3-aminopropyl)-N-[(1R)-1-(1-benzyl-4-phenyl-1H-imidazol-2-yl)-2,2-dimethylpropyl]-2-ethoxyacetamide;

N-[(1R)-1-(1-benzyl-4-phenyl-1H-imidazol-2-yl)-2,2-dimethylpropyl]-N-{[(3S)-3-hydroxypyrrolidin-3-yl]methyl}-1,5-dimethyl-1H-pyrazole-3-carboxamide;

N-[(1R)-1-(1-benzyl-4-phenyl-1H-imidazol-2-yl)-2,2-dimethylpropyl]-N-{[(3R)-3-hydroxypyrrolidin-3-yl]methyl}-1,5-dimethyl-1H-pyrazole-3-carboxamide;

N-[(1R)-1-(1-benzyl-4-phenyl-1H-imidazol-2-yl)-2,2-dimethylpropyl]-N-[(3-hydroxypyrrolidin-3-yl)methyl]-1,5-dimethyl-1H-pyrazole-3-carboxamide;

N-[(2S)-3-amino-2-fluoropropyl]-N-[(1S)-1-(1-benzyl-4-phenyl-1H-imidazol-2-yl)-2-hydroxy-2-methylpropyl]-2-(1H-tetrazol-1-yl)acetamide;

N-[(2S)-3-amino-2-fluoropropyl]-N-[(1S)-1-(1-benzyl-4-phenyl-1H-imidazol-2-yl)-2-hydroxy-2-methylpropyl]-2-(2H-tetrazol-2-yl)acetamide;

N-[(2S)-3-amino-2-fluoropropyl]-N-{(1R)-1-[1-benzyl-4-(3-fluorophenyl)-1H-imidazol-2-yl]-2,2-dimethylpropyl}-2-(1H-tetrazol-1-yl)acetamide;

N-[(2S)-3-amino-2-fluoropropyl]-N-{(1R)-1-[1-benzyl-4-(3-fluorophenyl)-1H-imidazol-2-yl]-2,2-dimethylpropyl}-2-(2H-tetrazol-2-yl)acetamide;

N-[(2S)-3-amino-2-(hydroxymethyl)propyl]-N-[(1R)-1-(1-benzyl-4-phenyl-1H-imidazol-2-yl)-2,2-dimethylpropyl]-N'-methylethanediamide;

N-[(2R)-3-amino-2-(hydroxymethyl)propyl]-N-[(1R)-1-(1-benzyl-4-phenyl-1H-imidazol-2-yl)-2,2-dimethylpropyl]-N'-methylethanediamide;

N-[(3R)-3-amino-4-hydroxybutyl]-N-[(1R)-1-(1-benzyl-4-phenyl-1H-imidazol-2-yl)-2,2-dimethylpropyl]-2-methoxyacetamide;

N-[(3R)-3-amino-4-hydroxybutyl]-N-[(1R)-1-(1-benzyl-4-phenyl-1H-imidazol-2-yl)-2,2-dimethylpropyl]-2-(1H-tetrazol-1-yl)acetamide;

N-[(3R)-3-amino-4-hydroxybutyl]-N-[(1R)-1-(1-benzyl-4-phenyl-1H-imidazol-2-yl)-2,2-dimethylpropyl]-2-(2H-tetrazol-2-yl)acetamide;

N-[(1R)-1-(1-benzyl-4-phenyl-1H-imidazol-2-yl)-2,2-dimethylpropyl]-N-{[(3S)-3-fluoropyrrolidin-3-yl]methyl}-2-methoxyacetamide;

N-[(1R)-1-(1-benzyl-4-phenyl-1H-imidazol-2-yl)-2,2-dimethylpropyl]-N-{[(3R)-3-fluoropyrrolidin-3-yl]methyl}-2-methoxyacetamide;

N-[(1R)-1-(1-benzyl-4-phenyl-1H-imidazol-2-yl)-2,2-dimethylpropyl]-N-{[(3R,4R)-4-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3S,4S)-4-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3R,4R)-4-hydroxypyrrolidin-3-yl]methyl}benzamide;

N-[(1R)-1-(1-benzyl-4-phenyl-1H-imidazol-2-yl)-2,2-dimethylpropyl]-N-{[(3S,4S)-4-hydroxypyrrolidin-3-yl]methyl}benzamide;

N-[(3S)-3-amino-4-hydroxybutyl]-N-{(1R)-1-[1-benzyl-4-(3-fluorophenyl)-1H-imidazol-2-yl]-2,2-dimethylpropyl}-2-(1H-tetrazol-1-yl)acetamide;

N-[(3S)-3-amino-4-hydroxybutyl]-N-{(1R)-1-[1-benzyl-4-(3-fluorophenyl)-1H-imidazol-2-yl]-2,2-dimethylpropyl}-2-(2H-tetrazol-2-yl)acetamide;

N-[(3S)-3-amino-4-methoxybutyl]-N-[(1R)-1-(1-benzyl-4-phenyl-1H-imidazol-2-yl)-2,2-dimethylpropyl]-2-methoxyacetamide;

N-[(3S)-3-amino-4-hydroxybutyl]-N-{(1R)-1-[1-benzyl-4-(3-fluorophenyl)-1H-imidazol-2-yl]-2,2-dimethylpropyl}-2-methoxyacetamide;

N-[(1R)-1-(1-benzyl-4-phenyl-1H-imidazol-2-yl)-2,2-dimethylpropyl]-N-{[(3S)-3-fluoropyrrolidin-3-yl]methyl}-2-(2H-tetrazol-2-yl)acetamide;

N-[(1R)-1-(1-benzyl-4-phenyl-1H-imidazol-2-yl)-2,2-dimethylpropyl]-N-{[(3R)-3-fluoropyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(3S,4S)-4-hydroxypyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(3S,4S)-4-hydroxypyrrolidin-3-yl]methyl}-2-(2H-tetrazol-2-yl)acetamide;

N-[(1R)-1-(1-benzyl-4-phenyl-1H-imidazol-2-yl)-2,2-dimethylpropyl]-N-{[(3R,4R)-4-hydroxypyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(3R,4R)-4-hydroxypyrrolidin-3-yl]methyl}-2-(2H-tetrazol-2-yl)acetamide;

N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}-2-(2H-tetrazol-2-yl)acetamide;

N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}-2-methoxyacetamide;

N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}benzamide;

N-[(2R)-3-amino-2-fluoropropyl]-N-[(1R)-1-(1-benzyl-4-phenyl-1H-imidazol-2-yl)-2,2-dimethylpropyl]-2-(5-methyl-2H-tetrazol-2-yl)acetamide;

N-[(2R)-3-amino-2-fluoropropyl]-N-[(1R)-1-(1-benzyl-4-phenyl-1H-imidazol-2-yl)-2,2-dimethylpropyl]-2-(5-methyl-1H-tetrazol-1-yl)acetamide;

N-[(1R)-1-(1-benzyl-4-phenyl-1H-imidazol-2-yl)-2,2-dimethylpropyl]-N-{[(3R)-3-hydroxypyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(3S)-3-hydroxypyrrolidin-3-yl]methyl}-2-(1H-tetrazol-1-yl)acetamide;

(5S)-3-[(1R)-1-(1-benzyl-4-phenyl-1H-imidazol-2-yl)-2,2-dimethylpropyl]-1-oxa-3,7-diazaspiro[4.4]nonan-2-one;

(5R)-3-[(1R)-1-(1-benzyl-4-phenyl-1H-imidazol-2-yl)-2,2-dimethylpropyl]-1-oxa-3,7-diazaspiro[4.4]nonan-2-one;

N-[(2S,3R)-3-amino-2-fluoro-4-hydroxybutyl]-N-[(1R)-1-(1-benzyl-4-phenyl-1H-imidazol-2-yl)-2,2-dimethylpropyl]-2-methoxyacetamide;

N-[(3S)-3-amino-4-fluorobutyl]-N-[(1R)-1-(1-benzyl-4-phenyl-1H-imidazol-2-yl)-2,2-dimethylpropyl]-2-methoxyacetamide;

N-[(3R)-3-amino-4-fluorobutyl]-N-[(1R)-1-(1-benzyl-4-phenyl-1H-imidazol-2-yl)-2,2-dimethylpropyl]-2-methoxyacetamide;

N-[(1R)-1-(1-benzyl-4-phenyl-1H-imidazol-2-yl)-2,2-dimethylpropyl]-N-{[(3R,4S)-4-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3S,4R)-4-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3R,4S)-4-fluoropyrrolidin-3-yl]methyl}-2-methoxyacetamide;

N-[(1R)-1-(1-benzyl-4-phenyl-1H-imidazol-2-yl)-2,2-dimethylpropyl]-N-(2,5-dihydro-1H-pyrrol-3-ylmethyl)-2-methoxyacetamide;

N—((R)-3-Amino-2-fluoro-propyl)-N—[(R)-1-(1-benzyl-4-pyrazin-2-yl-1H-imidazol-2-yl)-2,2-dimethyl-propyl]-2-methoxy-acetamide;

N—((R)-3-Amino-2-fluoro-propyl)-N—{(R)-1-[1-benzyl-4-(3-methoxy-phenyl)-1H-imidazol-2-yl]-2,2-dimethyl-propyl}-2-ethoxy-acetamide;

N—((R)-3-Amino-2-fluoro-propyl)-N—{(R)-1-[1-benzyl-4-(3-methoxy-phenyl)-1H-imidazol-2-yl]-2,2-dimethyl-propyl}-2-methoxy-acetamide;

(S)-Tetrahydro-furan-2-carboxylic acid ((R)-3-amino-2-fluoro-propyl)-[(R)-1-(1-benzyl-4-pyrazin-2-yl-1H-imidazol-2-yl)-2,2-dimethyl-propyl]-amide;

N—((R)-3-Amino-2-fluoro-propyl)-N—[(R)-1-(1-benzyl-4-pyrazin-2-yl-1H-imidazol-2-yl)-2,2-dimethyl-propyl]-2-ethoxy-acetamide;

N—((R)-3-Amino-2-fluoro-propyl)-N—[(R)-1-(1-benzyl-4-phenyl-1H-imidazol-2-yl)-2,2-dimethyl-propyl]-2-ethoxy-acetamide;

(S)-Tetrahydro-furan-2-carboxylic acid ((R)-3-amino-2-fluoro-propyl)-[(R)-1-(1-benzyl-4-phenyl-1H-imidazol-2-yl)-2,2-dimethyl-propyl]-amide;

N—((S)-3-Amino-4-fluoro-butyl)-N—[(R)-2,2-dimethyl-1-(4-phenyl-1-pyridin-3-ylmethyl-1H-imidazol-2-yl)-propyl]-2-methoxy-acetamide;

N—((R)-3-Amino-4-fluoro-butyl)-N—[(R)-2,2-dimethyl-1-(4-phenyl-1-pyridin-3-ylmethyl-1H-imidazol-2-yl)-propyl]-2-methoxy-acetamide;

N—((S)-3-Amino-4-methoxy-butyl)-N-{(R)-1-[1-benzyl-4-(3-fluoro-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(4-cyano-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(4-methoxy-phenyl)-1H-imidazol-2-yl]-2,2-dimethyl-propyl}-2-methoxy-acetamide;
N—((R)-3-Amino-2-fluoro-propyl)-N-{(R)-1-[1-(2-fluoro-benzyl)-4-phenyl-1H-imidazol-2-yl]-2,2-dimethyl-propyl}-2-methoxy-acetamide;
N—((R)-3-Amino-2-fluoro-propyl)-N-{(R)-1-[1-(3-fluoro-benzyl)-4-phenyl-1H-imidazol-2-yl]-2,2-dimethyl-propyl}-2-methoxy-acetamide;
N—((R)-3-Amino-2-fluoro-propyl)-N-{(R)-1-[1-(3-chloro-benzyl)-4-phenyl-1H-imidazol-2-yl]-2,2-dimethyl-propyl}-2-methoxy-acetamide;
N—((R)-3-Amino-2-fluoro-propyl)-N-{(R)-1-[1-(3-cyano-benzyl)-4-phenyl-1H-imidazol-2-yl]-2,2-dimethyl-propyl}-2-methoxy-acetamide;
N—((R)-3-Amino-2-fluoro-propyl)-N-{(R)-2,2-dimethyl-1-[4-phenyl-1-(tetrahydro-pyran-4-ylmethyl)-1H-imidazol-2-yl]-propyl}-2-methoxy-acetamide;
(S)-Tetrahydro-furan-2-carboxylic acid ((R)-3-amino-2-fluoro-propyl)-{(R)-1-[1-benzyl-4-(3-fluoro-phenyl)-1H-imidazol-2-yl]-2,2-dimethyl-propyl}-amide;
(S)-Tetrahydro-furan-2-carboxylic acid ((R)-3-amino-2-fluoro-propyl)-{(R)-1-[1-benzyl-4-(2-methoxy-phenyl)-1H-imidazol-2-yl]-2,2-dimethyl-propyl}-amide;
(S)-Tetrahydro-furan-2-carboxylic acid ((R)-3-amino-2-fluoro-propyl)-{(R)-1-[1-benzyl-4-(3-trifluoromethyl-phenyl)-1H-imidazol-2-yl]-2,2-dimethyl-propyl}-amide;
(S)-Tetrahydro-furan-2-carboxylic acid ((R)-3-amino-2-fluoro-propyl)-{(R)-1-[1-benzyl-4-(3-bromo-phenyl)-1H-imidazol-2-yl]-2,2-dimethyl-propyl}-amide;
N—((R)-3-Amino-2-fluoro-propyl)-N-{(R)-1-[1-benzyl-4-(3-fluoro-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(2-methoxy-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(3-trifluoromethyl-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(3-bromo-phenyl)-1H-imidazol-2-yl]-2,2-dimethyl-propyl}-2-methoxy-acetamide;
N—((R)-3-Amino-2-fluoro-propyl)-N—[(R)-1-(1-benzyl-4-p-tolyl-1H-imidazol-2-yl)-2,2-dimethyl-propyl]-2-methoxy-acetamide;
N—((S)-3-Amino-4-fluoro-butyl)-N—[(R)-2,2-dimethyl-1-(4-phenyl-1-pyridin-4-ylmethyl-1H-imidazol-2-yl)-propyl]-2-methoxy-acetamide;
N—((R)-3-Amino-4-fluoro-butyl)-N—[(R)-2,2-dimethyl-1-(4-phenyl-1-pyridin-4-ylmethyl-1H-imidazol-2-yl)-propyl]-2-methoxy-acetamide;
N—((S)-3-Amino-4-fluoro-butyl)-N-{(R)-2,2-dimethyl-1-[1-(5-methyl-isoxazol-3-ylmethyl)-4-phenyl-1H-imidazol-2-yl]-propyl}-2-methoxy-acetamide;
N—((R)-3-Amino-4-fluoro-butyl)-N-{(R)-2,2-dimethyl-1-[1-(5-methyl-isoxazol-3-ylmethyl)-4-phenyl-1H-imidazol-2-yl]-propyl}-2-methoxy-acetamide;
N—((S)-3-Amino-4-fluoro-butyl)-N—[(R)-2,2-dimethyl-1-(4-phenyl-1-pyridin-2-ylmethyl-1H-imidazol-2-yl)-propyl]-2-methoxy-acetamide;
N—((R)-3-Amino-4-fluoro-butyl)-N—[(R)-2,2-dimethyl-1-(4-phenyl-1-pyridin-2-ylmethyl-1H-imidazol-2-yl)-propyl]-2-methoxy-acetamide;
N—((S)-3-Amino-4-fluoro-butyl)-N-{(R)-1-[1-benzyl-4-(3-fluoro-phenyl)-1H-imidazol-2-yl]-2,2-dimethyl-propyl}-2-methoxy-acetamide;
N—((R)-3-Amino-4-fluoro-butyl)-N-{(R)-1-[1-benzyl-4-(3-fluoro-phenyl)-1H-imidazol-2-yl]-2,2-dimethyl-propyl}-2-methoxy-acetamide;
N-(3-Amino-3-methyl-butyl)-N—[(R)-1-(1-benzyl-4-phenyl-1H-imidazol-2-yl)-2,2-dimethyl-propyl]-2-methoxy-acetamide;
(S)-Tetrahydro-furan-2-carboxylic acid ((R)-3-amino-2-fluoro-propyl)-[(R)-1-(1-benzyl-5-chloro-4-phenyl-1H-imidazol-2-yl)-2,2-dimethyl-propyl]-amide;
N—((R)-3-Amino-2-fluoro-propyl)-N—[(R)-1-(1-benzyl-5-chloro-4-phenyl-1H-imidazol-2-yl)-2,2-dimethyl-propyl]-2-methoxy-acetamide;
(S)-Tetrahydro-furan-2-carboxylic acid ((R)-3-amino-2-fluoro-propyl)-[(R)-1-(1-benzyl-4-thiazol-2-yl-1H-imidazol-2-yl)-2,2-dimethyl-propyl]-amide;
N—((S)-3-Amino-2-fluoro-propyl)-N-{(R)-2,2-dimethyl-1-[4-phenyl-1-(5-trifluoromethyl-furan-2-ylmethyl)-1H-imidazol-2-yl]-propyl}-2-methoxy-acetamide;
N—((S)-3-Amino-2-fluoro-propyl)-N-{(R)-2,2-dimethyl-1-[1-(5-methyl-isoxazol-3-ylmethyl)-4-phenyl-1H-imidazol-2-yl]-propyl}-2-methoxy-acetamide;
(S)-Tetrahydro-furan-2-carboxylic acid ((S)-3-amino-2-fluoro-propyl)-{(R)-2,2-dimethyl-1-[1-(5-methyl-isoxazol-3-ylmethyl)-4-phenyl-1H-imidazol-2-yl]-propyl}-amide;
(S)-Tetrahydro-furan-2-carboxylic acid ((S)-3-amino-2-fluoro-propyl)-{(R)-2,2-dimethyl-1-[4-phenyl-1-(5-trifluoromethyl-furan-2-ylmethyl)-1H-imidazol-2-yl]-propyl}-amide;
N—((S)-3-Amino-4-methoxy-butyl)-N-{(R)-1-[1-(3-fluoro-benzyl)-4-(3-fluoro-phenyl)-1H-imidazol-2-yl]-2,2-dimethyl-propyl}-2-methoxy-acetamide;
N—((S)-3-Amino-4-hydroxy-butyl)-N-{(R)-1-[1-(3-fluoro-benzyl)-4-(3-fluoro-phenyl)-1H-imidazol-2-yl]-2,2-dimethyl-propyl}-2-methoxy-acetamide;
N—((S)-3-Amino-4-fluoro-butyl)-N-{(R)-1-[1-(2,5-difluoro-benzyl)-4-phenyl-1H-imidazol-2-yl]-2,2-dimethyl-propyl}-2-methoxy-acetamide;
N—((R)-3-Amino-4-fluoro-butyl)-N-{(R)-1-[1-(2,5-difluoro-benzyl)-4-phenyl-1H-imidazol-2-yl]-2,2-dimethyl-propyl}-2-methoxy-acetamide;
N—((R)-3-Amino-2-fluoro-propyl)-N-{(R)-1-[1-(4-fluoro-benzyl)-4-phenyl-1H-imidazol-2-yl]-2,2-dimethyl-propyl}-2-methoxy-acetamide;
N—((R)-3-Amino-2-fluoro-propyl)-2-methoxy-N-{(R)-1-[1-(3-methoxy-benzyl)-4-phenyl-1H-imidazol-2-yl]-2,2-dimethyl-propyl}-acetamide;
N—((R)-3-Amino-2-fluoro-propyl)-N-{(R)-2,2-dimethyl-1-[1-(2-methyl-benzyl)-4-phenyl-1H-imidazol-2-yl]-propyl}-2-methoxy-acetamide;
N—((R)-3-Amino-2-fluoro-propyl)-N-{(R)-2,2-dimethyl-1-[1-(3-methyl-benzyl)-4-phenyl-1H-imidazol-2-yl]-propyl}-2-methoxy-acetamide;
N—((S)-3-Amino-2-fluoro-propyl)-N-{(R)-2,2-dimethyl-1-[1-(3-methyl-benzyl)-4-phenyl-1H-imidazol-2-yl]-propyl}-2-methoxy-acetamide;
N-(3-Amino-propyl)-N—[(R)-1-(1-benzyl-4-phenyl-1H-imidazol-2-yl)-2,2-dimethyl-propyl]-acetamide;
N—((S)-3-Amino-2-fluoro-propyl)-N—[(R)-1-(1-benzyl-1H-imidazol-2-yl)-2,2-dimethyl-propyl]-2-methoxy-acetamide;

(S)-Tetrahydro-furan-2-carboxylic acid ((S)-3-amino-2-fluoro-propyl)-[(R)-1-(1-benzyl-1H-imidazol-2-yl)-2,2-dimethyl-propyl]-amide;

N—((S)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-2-methoxy-acetamide;

N—((S)-3-Amino-2-fluoro-propyl)-N—[(R)-1-(1-benzyl-4-thiazol-2-yl-1H-imidazol-2-yl)-2,2-dimethyl-propyl]-2-methoxy-acetamide;

N—((R)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-2-methoxy-acetamide;

N-[2-(1-Amino-cyclopropyl)-ethyl]-N—[(R)-1-(1-benzyl-4-phenyl-1H-imidazol-2-yl)-2,2-dimethyl-propyl]-2-methoxy-acetamide;

(S)-Tetrahydro-furan-2-carboxylic acid [2-(1-amino-cyclopropyl)-ethyl]-[(R)-1-(1-benzyl-4-phenyl-1H-imidazol-2-yl)-2,2-dimethyl-propyl]-amide;

[2-(1-Amino-cyclopropyl)-ethyl]-[(R)-1-(1-benzyl-4-phenyl-1H-imidazol-2-yl)-2,2-dimethyl-propyl]-carbamic acid methyl ester;

N-[2-(1-Amino-cyclopropyl)-ethyl]-N-{(R)-1-[1-benzyl-4-(3-fluoro-phenyl)-1H-imidazol-2-yl]-2,2-dimethyl-propyl}-2-methoxy-acetamide;

(S)-Tetrahydro-furan-2-carboxylic acid [2-(1-amino-cyclopropyl)-ethyl]-{(R)-1-[1-benzyl-4-(3-fluoro-phenyl)-1H-imidazol-2-yl]-2,2-dimethyl-propyl}-amide;

N-(3-Amino-propyl)-N-{(R)-1-[1-benzyl-4-(2,5-difluoro-phenyl)-1H-imidazol-2-yl]-2,2-dimethyl-propyl}-2-methoxy-acetamide;

N—((S)-3-Amino-4-fluoro-butyl)-N-{(R)-1-[1-benzyl-4-(2,5-difluoro-phenyl)-1H-imidazol-2-yl]-2,2-dimethyl-propyl}-2-methoxy-acetamide;

N—((R)-3-Amino-4-fluoro-butyl)-N-{(R)-1-[1-benzyl-4-(2,5-difluoro-phenyl)-1H-imidazol-2-yl]-2,2-dimethyl-propyl}-2-methoxy-acetamide;

N-(3-Amino-propyl)-N-{1-[1-(3-fluoro-benzyl)-4-(3-fluoro-phenyl)-1H-imidazol-2-yl]-1-methyl-ethyl}-2-methoxy-acetamide;

N-(3-Amino-propyl)-N-{(R)-1-[1-(3-fluoro-benzyl)-4-(3-fluoro-phenyl)-1H-imidazol-2-yl]-2,2-dimethyl-propyl}-2-methoxy-acetamide;

(S)-Tetrahydro-furan-2-carboxylic acid ((S)-3-amino-4-fluoro-butyl)-{(R)-1-[1-(3-fluoro-benzyl)-4-(3-fluoro-phenyl)-1H-imidazol-2-yl]-2,2-dimethyl-propyl}-amide;

N—((S)-3-Amino-4-fluoro-butyl)-N-{(R)-1-[1-benzyl-5-(3-fluoro-phenyl)-1H-imidazol-2-yl]-2,2-dimethyl-propyl}-2-methoxy-acetamide;

N—((S)-3-Amino-4-methoxy-butyl)-N-{(R)-1-[4-(3-chloro-phenyl)-1-(3-fluoro-benzyl)-1H-imidazol-2-yl]-2-methyl-propyl}-2-methoxy-acetamide;

N—((S)-3-Amino-4-fluoro-butyl)-N-{(R)-1-[1-benzyl-4-(3-chloro-phenyl)-1H-imidazol-2-yl]-2-methyl-propyl}-2-methoxy-acetamide;

N—((S)-3-Amino-4-fluoro-butyl)-N-{(R)-1-[4-(3-chloro-phenyl)-1-(3-fluoro-benzyl)-1H-imidazol-2-yl]-2-methyl-propyl}-2-methoxy-acetamide;

N-(3-Amino-4-fluoro-butyl)-N-{1-[1-(3-fluoro-benzyl)-4-(3-fluoro-phenyl)-1H-imidazol-2-yl]-1-methyl-ethyl}-2-methoxy-acetamide;

N—((S)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-acetamide;

N—((R)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-acetamide;

(S)-Tetrahydro-furan-2-carboxylic acid ((S)-3-amino-2-fluoro-propyl)-{(R)-1-[1-(3-fluoro-benzyl)-4-(3-fluoro-phenyl)-1H-imidazol-2-yl]-2,2-dimethyl-propyl}-amide;

(R)-9-{(R)-1-[1-(3-Fluoro-benzyl)-4-(3-fluoro-phenyl)-1H-imidazol-2-yl]-2,2-dimethyl-propyl}-6-oxa-2,9-diaza-spiro[4.5]decan-8-one;

(3-Amino-4-fluoro-butyl)-{(R)-1-[1-(3-fluoro-benzyl)-4-(3-fluoro-phenyl)-1H-imidazol-2-yl]-2,2-dimethyl-propyl}-carbamic acid methyl ester;

N—((S)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-formamide;

N—((R)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-formamide;

N-(3-Dimethylamino-propyl)-N-{(R)-1-[1-(3-fluoro-benzyl)-4-(3-fluoro-phenyl)-1H-imidazol-2-yl]-2,2-dimethyl-propyl}-2-methoxy-acetamide;

N—((S)-3-Amino-butyl)-N-{(R)-1-[1-(3-fluoro-benzyl)-4-(3-fluoro-phenyl)-1H-imidazol-2-yl]-2,2-dimethyl-propyl}-2-methoxy-acetamide;

N—((R)-3-Amino-butyl)-N-{(R)-1-[1-(3-fluoro-benzyl)-4-(3-fluoro-phenyl)-1H-imidazol-2-yl]-2,2-dimethyl-propyl}-2-methoxy-acetamide;

N—((S)-3-Amino-4-fluoro-butyl)-N-{(R)-1-[1-(6-amino-pyridin-2-ylmethyl)-4-(3-fluoro-phenyl)-1H-imidazol-2-yl]-2,2-dimethyl-propyl}-2-methoxy-acetamide;

N—((R)-3-Amino-4-fluoro-butyl)-N-{(R)-1-[1-(6-amino-pyridin-2-ylmethyl)-4-(3-fluoro-phenyl)-1H-imidazol-2-yl]-2,2-dimethyl-propyl}-2-methoxy-acetamide;

N—((S)-3-Amino-4-fluoro-butyl)-N-{(R)-1-[4-(3-fluoro-phenyl)-1-(3-hydroxy-benzyl)-1H-imidazol-2-yl]-2,2-dimethyl-propyl}-2-methoxy-acetamide;

N—((R)-3-Amino-4-fluoro-butyl)-N-{(R)-1-[4-(3-fluoro-phenyl)-1-(3-hydroxy-benzyl)-1H-imidazol-2-yl]-2,2-dimethyl-propyl}-2-methoxy-acetamide;

N—((S)-3-Amino-4-fluoro-butyl)-N—[(R)-1-(1-benzyl-4-thiazol-2-yl-1H-imidazol-2-yl)-2,2-dimethyl-propyl]-2-methoxy-acetamide;

N-{(R)-1-[1-(3-Fluoro-benzyl)-4-(3-fluoro-phenyl)-1H-imidazol-2-yl]-2,2-dimethyl-propyl}-2-methoxy-N-(3-methylamino-propyl)-acetamide;

N-(3-Amino-propyl)-N-{(R)-1-[1-benzyl-4-(2,5-difluoro-phenyl)-1H-imidazol-2-yl]-2,2-dimethyl-propyl}-acetamide;

(3-Amino-propyl)-{(R)-1-[1-benzyl-4-(2,5-difluoro-phenyl)-1H-imidazol-2-yl]-2,2-dimethyl-propyl}-carbamic acid methyl ester;

(S)-Tetrahydro-furan-2-carboxylic acid (3-amino-propyl)-{(R)-1-[1-benzyl-4-(2,5-difluoro-phenyl)-1H-imidazol-2-yl]-2,2-dimethyl-propyl}-amide;

3-[{(R)-1-[1-(3-Fluoro-benzyl)-4-(3-fluoro-phenyl)-1H-imidazol-2-yl]-2,2-dimethyl-propyl}-(2-methoxy-acetyl)-amino]-propionamide;

N-(3-Amino-propyl)-N-{(R)-1-[1-benzyl-4-(2,5-difluoro-phenyl)-1H-imidazol-2-yl]-2,2-dimethyl-propyl}-2-methanesulfonyl-acetamide;

N—((S)-3-Amino-4-methoxy-butyl)-N-{(R)-1-[1-benzyl-4-(2,5-difluoro-phenyl)-1H-imidazol-2-yl]-2,2-dimethyl-propyl}-2-methoxy-acetamide;

(S)-Tetrahydro-furan-2-carboxylic acid ((S)-3-amino-4-fluoro-butyl)-{(R)-1-[1-benzyl-4-(2,5-difluoro-phenyl)-1H-imidazol-2-yl]-2,2-dimethyl-propyl}-amide;

(R)-1-[1-Benzyl-4-(2,5-difluoro-phenyl)-1H-imidazol-2-yl]-2,2-dimethyl-propylamine;

(S)-Tetrahydro-furan-2-carboxylic acid ((S)-3-amino-4-methoxy-butyl)-{(R)-1-[1-benzyl-4-(2,5-difluoro-phenyl)-1H-imidazol-2-yl]-2,2-dimethyl-propyl}-amide;
N—((R)-3-Amino-butyl)-N-{(R)-1-[1-benzyl-4-(2,5-difluoro-phenyl)-1H-imidazol-2-yl]-2,2-dimethyl-propyl}-2-methoxy-acetamide;
N—((S)-3-Amino-butyl)-N-{(R)-1-[1-benzyl-4-(2,5-difluoro-phenyl)-1H-imidazol-2-yl]-2,2-dimethyl-propyl}-2-methoxy-acetamide;
N-{(R)-1-[1-Benzyl-4-(2,5-difluoro-phenyl)-1H-imidazol-2-yl]-2,2-dimethyl-propyl}-2-methoxy-N-(1H-[1,2,3]triazol-4-ylmethyl)-acetamide;
N—((S)-3-Amino-4-fluoro-butyl)-N-{(R)-1-[1-benzyl-4-(2,5-difluoro-phenyl)-1H-imidazol-2-yl]-2,2-dimethyl-propyl}-acetamide;
((S)-3-Amino-4-fluoro-butyl)-{(R)-1-[1-benzyl-4-(2,5-difluoro-phenyl)-1H-imidazol-2-yl]-2,2-dimethyl-propyl}-carbamic acid methyl ester;
{(R)-1-[1-Benzyl-4-(2,5-difluoro-phenyl)-1H-imidazol-2-yl]-2,2-dimethyl-propyl}-carbamic acid tert-butyl ester;
N-[(1R)-1-(1-benzyl-4-phenyl-1H-imidazol-2-yl)-2-methylpropyl]-4-methylbenzamide;
N-(3-aminopropyl)-N-[(1R)-1-(1-benzyl-4-phenyl-1H-imidazol-2-yl)-2-methylpropyl]-2-(4-fluorophenoxy)acetamide; and pharmaceutically acceptable salts thereof.

23. A pharmaceutical composition comprising a therapeutically effective amount of a compound of claim 1 and a pharmaceutically acceptable carrier.

24. The composition of claim 23 further comprising at least one additional agent for the treatment of cancer.

25. The composition of claim 23, wherein the additional agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

26. A method of treating a disorder mediated, at least in part, by KSP in a mammalian patient comprising administering to a mammalian patient in need of such treatment a therapeutically effective amount of a composition of claim 23.

27. The method of claim 26, wherein the disorder is a cellular proliferative disease.

28. The method of claim 27, wherein the cellular proliferative disease is cancer.

29. The method of claim 28, wherein the cancer is selected from the group consisting of lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

30. The method of claim 29 further comprising administering to the mammalian patient one additional agent for the treatment of cancer.

31. The method of claim 30, wherein the additional agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

32. A method for inhibiting KSP kinesin in a mammalian patient, wherein said method comprises administering to the patient an effective KSP-inhibiting amount of a compound of claim 1.

33. Use of the composition of claim 23 in the manufacture of a medicament for the treatment of cancer.

Alternate Embodiments

In an alternate embodiment, the invention is directed to compounds represented by the following formula:

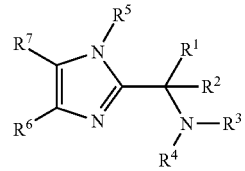

VII wherein:
$R^1$ is aminoacyl, acylamino, carboxyl, carboxyl ester, aryl, $C_1$ to $C_6$ alkyl, optionally substituted with hydroxy or halo;
$R^2$ is selected from the group consisting of hydrogen, $C_1$ to $C_6$ alkyl, and aryl;
$R^3$ is —X-A, wherein A is selected from the group consisting of alkyl, substituted alkyl, aryl, heteroaryl, heterocyclic, and cycloalkyl, all of which may be optionally substituted with 1 to 4 substituents selected from the group consisting of $C_1$ to $C_6$ alkyl, $C_1$ to $C_6$ substituted alkyl, $C_1$ to $C_6$ alkoxy, $C_1$ to $C_6$ substituted alkoxy, amino, substituted amino, heterocyclic, substituted heterocyclic, heterocyclyloxy, substituted heterocyclyloxy, acyl, carboxyl, carboxyl ester, oxo (except when A is optionally substituted aryl or optionally substituted heteroaryl), halo, hydroxy, and nitro and X is selected from the group consisting of —C(O)—, —C(S)—, —S(O)—, —S(O)$_2$—, and —S(O)$_2$—NR, where R is hydrogen or $C_1$ to $C_6$ alkyl;
$R^1$ and $R^3$, together with the carbon atom attached to $R^1$ and the nitrogen atom attached to $R^3$ form a heterocyclic or substituted heterocyclic group;
$R^4$ is selected from the group consisting of -alkylene-aminoacyl, -alkylene-oxyacyl, -alkylene-hydroxy, -[alkylene]$_p$-nitrogen-containing heterocyclic, -[alkylene]$_p$-nitrogen-containing substituted heterocyclic, -[alkylene]$_p$-nitrogen-containing aryl, -[alkylene]$_p$-nitrogen-containing substituted aryl, -[alkylene]$_p$-nitrogen-containing heteroaryl, -[alkylene]$_p$-nitrogen-containing substituted heteroaryl and -[alkylene]$_p$—NR$^a$R$^b$ wherein p is an integer from 0 to 1, alkylene is a $C_1$ to $C_6$ straight chained alkylene optionally mono- or disubstituted with one of the foregoing substituents selected from the group consisting of amino, substituted amino, hydroxy, alkyl, substituted alkyl, carboxyl, carboxyl ester, oxo and halo; R$^a$ and R$^b$ are independently selected from the group consisting of hydrogen, $C_1$ to $C_6$ alkyl, $C_1$ to $C_6$ substituted alkyl, —S(O)-alkyl, —S(O)-substituted alkyl, —S(O)$_2$-alkyl, —S(O)$_2$-substituted alkyl, heterocyclic, substituted heterocyclic, acyl, aryl, substituted aryl, heteroaryl, substituted heteroaryl, cycloalkyl and substituted cycloalkyl or when R$^a$ is hydrogen, R$^b$ is hydroxy, alkoxy or substituted alkoxy;
$R^5$ is selected from the group consisting of L-A', wherein L is selected from the group consisting of —S(O)$_q$— where q is one or two, and $C_1$ to $C_5$ alkylene, optionally substituted with hydroxy, halo, or acylamino; and A' is selected from the group consisting of aryl, substituted aryl, heteroaryl, substituted heteroaryl, heterocyclic, substituted heterocyclic, cycloalkyl and substituted cycloalkyl; and one of either $R^6$ or $R^7$ is selected from the group consisting of aryl and heteroaryl, wherein aryl and heteroaryl may be optionally substituted with $—(R)_m$ where $R^8$ is as defined herein and m is an integer from 0 to 3, and the other of $R^6$ and $R^7$ is hydrogen or $C_1$ to $C_6$ alkyl;

$R^8$ is selected from the group consisting of $C_1$ to $C_6$ alkyl, $C_2$ to $C_6$ alkenyl, $C_2$ to $C_6$ alkynyl, —$CF_3$, $C_1$ to $C_6$ alkoxy, halo, and hydroxy;

or pharmaceutically acceptable salts, esters or prodrugs thereof.

Representative Compounds of the Invention

Specific compounds within the scope of this invention are exemplified in Tables 1, 2, and 3 in the experimental section.

Methods and Compositions of the Invention

Also provided is a composition comprising a compound of formulae I-VII (including mixtures thereof) and a pharmaceutically acceptable excipient or carrier.

In another aspect, the present invention provides methods of treating a mammalian patient suffering from a disorder mediated, at least in part, by KSP. Thus, the present invention provides methods of treating a mammalian patient in need of such treatment comprising administering to the patient a therapeutically effective amount of a compound of formulae I-VII (including mixtures thereof) either alone or in combination with other anticancer agents.

DETAILED DESCRIPTION OF INVENTION

A. Definitions and Overview

As discussed above, the present invention is directed to new substituted imidazole compounds.

It is to be understood that the terminology used herein is for the purpose of describing particular embodiments only and is not intended to limit the scope of the present invention. It must be noted that as used herein and in the claims, the singular forms "a," "and" and "the" include plural referents unless the context clearly dictates otherwise. In this specification and in the claims which follow, reference will be made to a number of terms which shall be defined to have the following meanings:

As used herein, "alkyl" refers to monovalent saturated aliphatic hydrocarbyl groups having from 1 to 6 carbon atoms and more preferably 1 to 3 carbon atoms. This term is exemplified by groups such as methyl, ethyl, n-propyl, iso-propyl, n-butyl, t-butyl, n-pentyl and the like.

The term "linear alkyl" refers to an alkyl group that is not branched.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, spirocycloalkyl, heteroaryl, substituted heteroaryl, heterocyclic, substituted heterocyclic, —$SO_2$-alkyl, —$SO_2$-substituted alkyl wherein said substituents are defined herein.

"Alkylene" refers to divalent saturated aliphatic hydrocarbyl groups preferably having from 1 to 5 and more preferably 1 to 3 carbon atoms which are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) and the like.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxyacyl" or "carboxyl ester" refers to the groups —C(O)O-alkyl, substituted —C(O)O-alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to an acetylenic carbon atom.

"Amino" refers to the group —NH$_2$.

"Cyano" refers to the group —CN.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO$_2$-alkyl, —SO$_2$-substituted alkyl, and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' or R" is hydrogen.

"Acylamino" refers to the groups —NRC(O)alkyl, —NRC(O) substituted alkyl, —NRC(O)cycloalkyl, —NRC(O) substituted cycloalkyl, —NRC(O)alkenyl, —NRC(O) substituted alkenyl, —NRC(O)alkynyl, —NRC(O) substituted alkynyl, —NRC(O)aryl, —NRC(O) substituted aryl, —NRC(O)heteroaryl, —NRC(O) substituted heteroaryl, —NRC(O) heterocyclic, and —NRC(O) substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Nitro" refers to the group —NO$_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl (NH$_2$—SO$_2$-), and substituted amino sulfonyl.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Spirocycloalkyl" refers to cyclic groups from 3 to 10 carbon atoms having a cycloalkyl ring with a spiro union (the union formed by a single atom which is the only common member of the rings) as exemplified by the following structure:

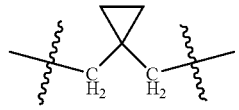

"Substituted cycloalkyl" refers to a cycloalkyl group, having from 1 to 5 substituents selected from the group consisting of alkyl, substituted alkyl, oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Halo" or "halogen" refers to fluoro, chloro, bromo and iodo and preferably is fluoro or chloro.

"Hydroxy" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O) sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 3 substituents selected from the same group of substituents defined for substituted aryl.

"Nitrogen-containing heteroaryl" and "nitrogen-containing substituted heteroaryl" refers to heteroaryl groups and substituted heteroaryl groups comprising at least one nitrogen ring atom and optionally comprising other non-nitrogen hetero ring atoms such as sulfur, oxygen and the like.

"Heteroaryloxy" refers to the group —O-heteroaryl and "substituted heteroaryloxy" refers to the group —O-substituted heteroaryl wherein heteroaryl and substituted heteroaryl are as defined herein.

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring. In one embodiment, the nitrogen and/or sulfur atom(s) of the heterocycylic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 3 of the same substituents as defined for substituted cycloalkyl.

Examples of heterocyclyls and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitrogen-containing heterocyclic" and "nitrogen-containing substituted heterocyclic" refers to heterocyclic groups and substituted heterocyclic groups comprising at least one nitrogen ring atom and optionally comprising other non-nitrogen hetero ring atoms such as sulfur, oxygen and the like.

"Thiol" refers to the group —SH.

"Alkylthio" or "thioalkoxy" refers to the group —S-alkyl.

"Substituted alkylthio" or "substituted thioalkoxy" refers to the group —S-substituted alkyl.

"Arylthio" refers to the group —S-aryl, where aryl is defined above.

"Substituted arylthio" refers to the group —S-substituted aryl, where substituted aryl is defined above.

"Heteroarylthio" refers to the group —S-heteroaryl, where heteroaryl is as defined above.

"Substituted heteroarylthio" refers to the group —S-substituted heteroaryl, where substituted heteroaryl is defined above.

"Heterocyclicthio" refers to the group —S-heterocyclic and "substituted heterocyclicthio" refers to the group —S-substituted heterocyclic, where heterocyclic and substituted heterocyclic are as defined above.

"Heterocyclyloxy" refers to the group heterocyclyl-O— and "substituted heterocycyloxy refers to the group substituted heterocyclyl-O— where heterocyclyl and substituted heterocyclyl are as defined above.

"Cycloalkylthio" refers to the group —S-cycloalkyl and "substituted cycloalkylthio" refers to the group —S-substituted cycloalkyl, where cycloalkyl and substituted cycloalkyl are as defined above.

"Biological activity" as used herein refers to an inhibition concentration when tested in at least one of the assays outlined in Example 20-27.

As used herein, the term "pharmaceutically acceptable salts" refers to the nontoxic acid or alkaline earth metal salts of the compounds of formulae I-VII. These salts can be prepared in situ during the final isolation and purification of the compounds of formulae I-VII, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formulae I-VII, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which hydrolyze in vivo and include those that break down in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein "anticancer agents" or "agent for the treatment of cancer" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

Compounds of this invention may exhibit stereoisomerism by virtue of the presence of one or more asymmetric or chiral centers in the compounds. The present invention contemplates the various stereoisomers and mixtures thereof. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," *Pure Appl. Chem.* 45:13-30, 1976. Desired enantiomers can be obtained by chiral synthesis from commercially available chiral starting materials by methods well known in the art, or may be obtained from mixtures of the enantiomers by separating the desired enantiomer by using known techniques.

Compounds of this invention may also exhibit geometrical isomerism. Geometrical isomers include the cis and trans forms of compounds of the invention having alkenyl or alkenylenyl moieties. The present invention comprises the individual geometrical isomers and stereoisomers and mixtures thereof.

B. Compound Preparation

The compounds of this invention can be prepared from readily available starting materials using the following general methods and procedures. Unless otherwise indicated, the starting materials are commercially available and well known in the art. It will be appreciated that where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Compounds in the present invention may be better understood by the following synthetic Scheme that illustrate methods for the synthesis of compounds of the invention. Unless otherwise indicated, the reagents used in the following examples are commercially available and may be purchased from vendors such as Sigma-Aldrich Company, Inc. (Milwaukee, Wis., USA).

Arylimidazole compounds may be synthesized by Scheme 1 below:

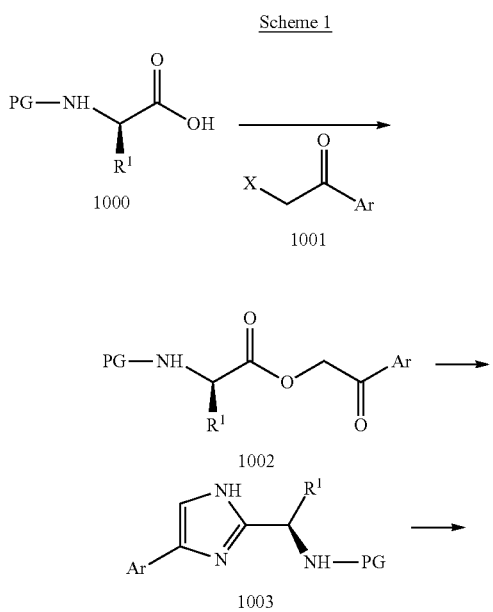

Scheme 1

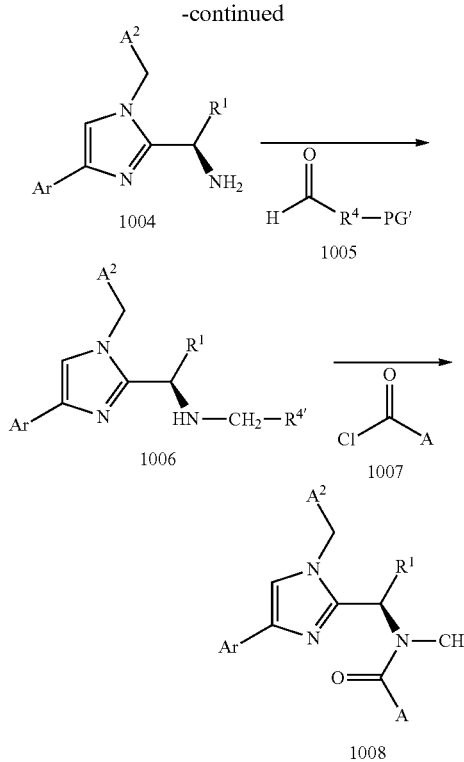

R¹, Ar, A², and A are as defined herein.
—CH₂—R⁴' is R⁴, where R⁴ is as defined herein.
PG refers to a protecting group, such as BOC.
PG' refers to a protecting group, such as phthalimide.
X refers to a halide, such as bromo.

Specifically, in Scheme 1, an appropriately protected (PG) amino acid 1000, is dissolved in a suitable amount of an inert solvent, such as methanol or ethanol. It should be noted amino acid 1000 is typically commercially available as are α,α-disubstituted amino acids (PG-NH—C(R¹)(R²)—COOH). To that is added about a stoichiometric amount of a monovalent cation, such as cesium carbonate (Cs₂CO₃), to form the carboxylate salt (not shown). Upon substantial completion of the reaction, typically about 15 minutes to about 2 hours, excess solvent is removed under reduced pressure. The remaining salt is then re-dissolved in a suitable solvent, such as DMF, and then treated with 1 to 4 equivalents of the appropriate α-halo ketone 1001, for example 2-bromoacetophenone and then stirred at room temperature until the reaction is substantially complete.

The resulting β-ketoester 1002 can be recovered and optionally purified by conventional methods, such as precipitation, filtration, evaporation, crystallization and the like. Alternatively, β-ketoester 1002 can be used directly in the next step without purification or isolation.

Next, to a stirred solution of β-ketoester 1002 in a suitable inert solvent, such as toluene, xylenes, and the like is added an excess of ammonium acetate, typically from about 2 to about 20 equivalents and preferably about 5 equivalents. In one embodiment, a Dean-Stark trap is added and the resulting mixture is heated at elevated temperatures of from about 120 to about 160° C. until the reaction is complete. Once complete, the mixture is allowed to cool to room temperature. The resulting arylimidazole 1003 is then recovered and optionally purified by conventional methods such as precipitation, filtration, evaporation, crystallization, chromatography and the like. Alternatively, arylimidazole 1003 may be used in the next step without purification and/or isolation.

The arylimidazole 1003 is then reacted with an appropriate aryl or heteroaryl-substituted alkyl halide, such as benzyl bromide. Typically, this can be accomplished by stirring the arylimidazole 1003 with an excess of potassium carbonate and DMF and then adding at least an equimolar amount of the aryl or heteroaryl-substituted alkyl halide.

Compounds of the invention when R⁵ is L-A¹ and L is —S(O)$_q$—, may be synthesized using a suitable sulfonyl chloride. Descriptions of various sulfonyl chlorides may be found, for example, in U.S. Pat. No. 6,489,300, which is hereby incorporated by reference.

The protecting group, PG is then removed by conventional techniques to provide amine 1004, which is then optionally purified by conventional means such as precipitation, filtration, evaporation, crystallization, chromatography and the like. Alternatively, amine 1004 can be used directly in the next step without purification and/or isolation.

Amine 1004 is reacted under conventional reductive amination conditions with aldehyde 1005 to provide for substituted amine 1006 which is then recovered and optionally purified by conventional methods such as precipitation, filtration, evaporation, crystallization, chromatography and the like. Alternatively, substituted amine 1006 can be used directly in the next step without purification and/or isolation.

Substituted amine 1006 is then reacted under conventional amidation conditions with acyl chloride 1007. Any protecting groups, such as PG', remaining on the resulting amide product, 1008, can be removed by conventional methods and the product can be recovered and purified by conventional methods such as precipitation, filtration, evaporation, crystallization, chromatography and the like.

It will be well within the skill of the art to further modify the above preparation to synthesize other compounds of this invention.

C. Pharmaceutical Formulations

When employed as pharmaceuticals, the compounds of the subject invention are usually administered in the form of pharmaceutical compositions. These compositions can be administered by a variety of routes including oral, parenteral, transdermal, topical, rectal, and intranasal. These compounds are effective, for example, as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 1 to about 500 mg, usually about 5 to about 100 mg, occasionally about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the condition being treated, the chosen route of administration, the actual compound administered, the age, weight, and response of the individual patient, the severity of the patient's symptoms, and the like.

In therapeutic use for treating, or combating, cancer in mammals, the compounds or pharmaceutical compositions thereof will be administered by any appropriate route, such as orally, topically, transdermally, and/or parenterally at a dosage to obtain and maintain a concentration, that is, an amount, or blood-level of active component in the mammal undergoing treatment that will be therapeutically effective. Generally, such therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water.

The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
| --- | --- |
| Active Ingredient | 5.0 mg |
| Corn Oil | 1.0 ml |

Formulation Example 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

An intravenous formulation may be prepared as follows:

| Ingredient | Quantity |
| --- | --- |
| Active Ingredient | 250 mg |
| Isotonic saline | 1000 ml |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mack Publishing Company, Philadelphia, Pa., 17th ed. (1985).

D. Dosage and Administration

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Compounds of the instant invention are useful for inhibiting or treating a disorder mediated, at least in part, by the activity of KSP. In one aspect, the disorder that is mediated, at least in part by KSP, is a cellular proliferative disorder. The term "cellular proliferative disorder" or "cell proliferative disorder" refers to diseases including, for example, cancer, tumor, hyperplasia, restenosis, cardiac hypertrophy, immune disorder and inflammation. The present invention provides methods of treating a human or mammalian subject in need of such treatment, comprising administering to the subject a therapeutically effective amount of a compound of formulae I-VII, either alone or in combination with other anticancer agents.

The compounds of the invention are useful in vitro or in vivo in inhibiting the growth of cancer cells. The term "cancer" refers to cancer diseases including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

Cancer also includes tumors or neoplasms selected from the group consisting of carcinomas, adenocarcinomas, sarcomas, and hematological malignancies.

Additionally, the type of cancer can be selected from the group consisting of growth of solid tumors/malignancies, myxoid and round cell carcinoma, locally advanced tumors, human soft tissue carcinoma, cancer metastases, squamous cell carcinoma, esophageal squamous cell carcinoma, oral carcinoma, cutaneous T cell lymphoma, Hodgkin's lymphoma, non-Hodgkin's lymphoma, cancer of the adrenal cortex, ACTH-producing tumors, nonsmall cell cancers, breast cancer, gastrointestinal cancers, urological cancers, malignancies of the female genital tract, malignancies of the male genital tract, kidney cancer, brain cancer, bone cancers, skin cancers, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

A compound or composition of this invention may be administered to the mammal by a suitable route, such as orally, intravenously, parenterally, transdermally, topically, rectally, or intranasally.

Mammals include, for example, humans and other primates, pet or companion animals, such as dogs and cats, laboratory animals, such as rats, mice and rabbits, and farm animals, such as horses, pigs, sheep, and cattle.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and organization relative to one another and to surrounding tissues. This property is called "anaplasia."

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the compounds during incubation with peptidases or human plasma or serum.

For diagnostic purposes, a wide variety of labels may be linked to the compounds, which may provide, directly or indirectly, a detectable signal. Thus, the compounds and/or compositions of the subject invention may be modified in a variety of ways for a variety of end purposes while still retaining biological activity. In addition, various reactive sites may be introduced for linking to particles, solid substrates, macromolecules, and the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the progression or symptoms of the disease and its complications. An amount adequate to accomplish this is defined as "therapeutically effective dose." Amounts effective for this use will depend on the disease condition being treated as well as by the judgment of the attending clinician depending upon factors such as the severity of the disease, disorder or condition, the age, weight and general condition of the patient, and the like.

The compounds administered to a patient are typically in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between about 3 and 11, more preferably from about 5 to 9 and most preferably from about 7 to 8. It will be understood that use of certain of the foregoing excipients, carriers, or stabilizers will result in the formation of pharmaceutical salts.

The therapeutic dosage of the compounds and/or compositions of the present invention will vary according to, for example, the particular use for which the treatment is made, the manner of administration of the compound, the health and condition of the patient, and the judgment of the prescribing physician. For example, for oral administration, the dose will typically be in the range of about 5 μg to about 50 mg per kilogram body weight per day, preferably about 1 mg to about 10 mg per kilogram body weight per day. In the alternative, for intravenous administration, the dose will typically be in the range of about 5 μg to about 50 mg per kilogram body weight, preferably about 500 μg to about 5000 μg per kilogram body weight. Alternative routes of administration contemplated include, but are not limited to, intranasal, transdermal, inhaled, subcutaneous and intramuscular. Effective doses can be extrapolated from dose-response curves derived from in vitro or animal model test systems.

In general, the compounds and/or compositions of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound and/or composition used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of activity) as determined in cell culture. Such information can be used to more accurately determine useful doses in humans. Levels in plasma may be measured, for example, by high performance liquid chromatography.

The following synthetic and biological examples are offered to illustrate this invention and are not to be construed in any way as limiting the scope of this invention.

EXAMPLES

Referring to the examples that follow, compounds of the present invention were synthesized using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 ml/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 ml/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 ml; initial column temperature: 50° C.; final column temperature: 250° C.; ramp time: 20 minutes; gas flow rate: 1 ml/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.).

Melting points are determined on a Laboratory Devices MeI-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

Unless otherwise stated all temperatures are in degrees Celsius. Also, in these examples and elsewhere, abbreviations have the following meanings:

μg=micrograms
μl=microliter
μM=micromolar
AcOH=acetic acid
aq=aqueous
ATP=adenosine 5'-triphosphate
Boc=t-butoxycarbonyl
BSA=bovine serum albumin
cbz=benzyloxycarbonyl
DCM=dichloromethane
DIAD=diisopropyl azodicarboxylate
DIBAL=diisobutylaluminum hydride
DIPEA=diisopropylethylamine
DMAP=dimethylaminopyridine
DMF=dimethyl formamide
DMSO=dimethylsulfoxide
DTT=dithiothreitol
EDC=ethylene dichloride
eq.=equivalents
ES/MS=electrospray mass spectroscopy
Et=ethyl
$Et_2O$=diethyl ether
$Et_3N$=triethyl amine
EtOAc=ethyl acetate
EtOH=ethanol
g=gram
GCMS=gas chromatography mass spectroscopy
h=hour
HOAT=1-Hydroxy-7-azabenzotriazole
HPLC=high performance liquid chromatography
kg=kilogram
L=liter
LCMS=liquid chromatography mass spectroscopy
LiHMDS=lithium hexamethyldisilazide
M=molar
m=meter
m/z=mass/charge ratio
MeOH=methanol
mg=milligram
min=minute
ml=milliliter
mM=millimolar
mm=millimeter
mM=millimolar
mmol=millimole
mol=mole
N=normal
nm=nanometer
NMR=nuclear magnetic resonance
PTFE=Teflon tetrafluoroethylene
PyBOP=Benzotriazole-1-yl-oxy-trispyrrolidinophosphonium hexafluorophosphate
room temperature or r.t.=room temperature
sat.=saturated
TEA=triethylamine
TFA=trifluoroacetic acid
THF=tetrahydrofuran
TMS=tetramethylsilane
TMSCl=trimethylsilyl chloride

Example 1

Preparation of Compounds of the Invention of the Following Formula

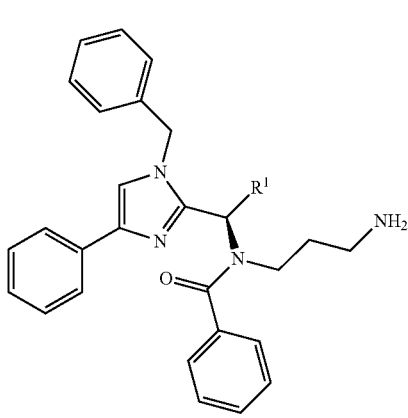

wherein R¹ is as defined herein

Step A: Keto-Ester Synthesis

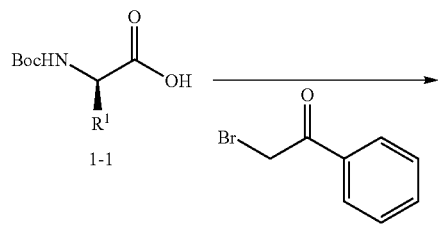

where R¹ is as defined herein

A stirred solution of the appropriate N-Boc-acid 1-1 (4.0 mmol) in EtOH (10 ml) was treated with $Cs_2CO_3$ (2.0 mmol). After 45 min, the EtOH was removed by evaporation under reduced pressure. The residual cesium salt was re-dissolved in DMF (15 ml) and the treated with the appropriate α-halo-ketone 1-2, e.g., 2-bromoacetophenone (4.0 mmol) and stirred at room temperature until the reaction was complete. The reaction mixture was then partitioned between EtOAc and $H_2O$, and the organics separated, then washed with $H_2O$ (×3), brine (×3), then dried ($Na_2SO_4$), filtered, and evaporated under reduced pressure to give the keto-ester 1-3 which was pure enough to use directly in the next step.

Step B: Phenyl-Imidazole Formation

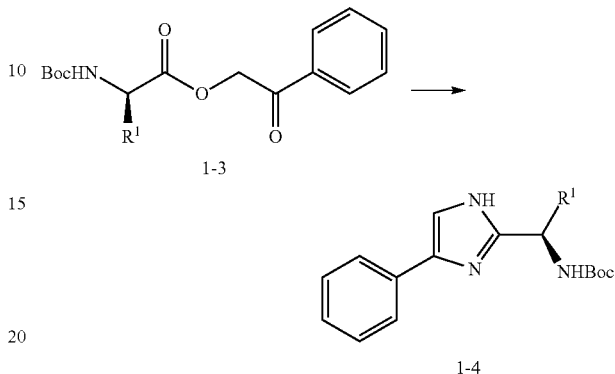

To a stirred solution of keto-ester 1-3 (4.0 mmol) in xylenes (40 ml) was added ammonium acetate (20 mmol). A Dean-Stark trap was added and the reaction heated to 140° C. Once the reaction was complete, the mixture was allowed to cool to room temperature, then partitioned between EtOAc and sat. aq. $NaHCO_3$. The organics were separated, then washed with sat. aq. $NaHCO_3$ (×2), $H_2O$ (×3), brine (×3), then dried ($Na_2SO_4$), filtered, and evaporated under reduced pressure to give the phenyl imidazole 1-4 which was pure enough to use directly in the next step.

Step C: Benzylation of the Phenyl Imidazole

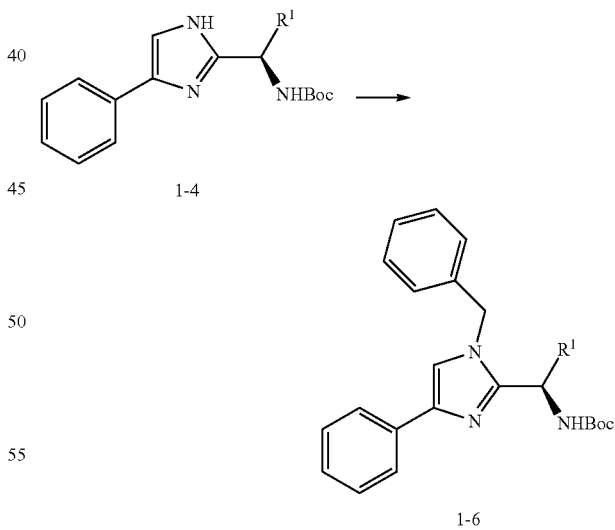

To a stirred solution/suspension of imidazole 1-4 (4.0 mmol) and $K_2CO_3$ (8.0 mmol) in DMF (10 ml) was added the benzylating agent, e.g., benzyl bromide (4.40 mmol). Once the reaction was complete, the mixture was partitioned between EtOAc and $H_2O$. The organic layer was separated and washed with $H_2O$ (×3), brine (×3), then dried ($Na_2SO_4$), filtered, and evaporated under reduced pressure to give the crude benzylated phenyl imidazole 1-6. The crude reaction material was then crystallized (EtOAc, hexanes) to give pure product. The regiochemical outcome was verified by ¹H NMR.

Step D: Deprotection to the Free Amine

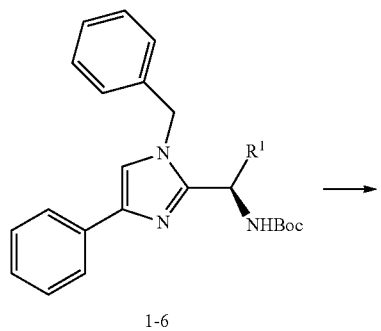

1-6

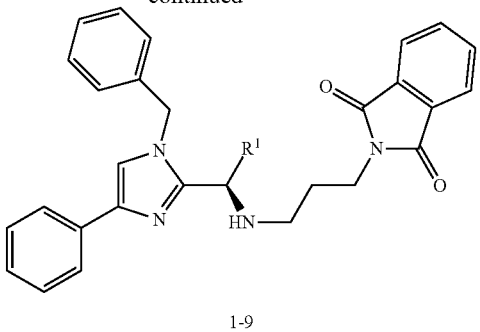

1-9

To a stirred solution of amine 1-7 (1.0 mmol) and appropriate aldehyde 1-8, e.g., 2-(3-oxopropyl)benzo[c]azoline-1,3-dione (1.0 mmol) in CH$_2$Cl$_2$ (7 ml) was added AcOH (1.0 mmol). The mixture was allowed to stir for 5 min before the addition of sodium tris-acetoxyborohydride (1.10 mmol). Once the reaction was complete, the mixture was concentrated in vacuo, partitioned between EtOAc and 2 M aq. Na$_2$CO$_3$. The organics were separated, then washed with 2 M aq. Na$_2$CO$_3$ (×2), H$_2$O (×2), brine (×2), then dried (Na$_2$SO$_4$), filtered, and evaporated under reduced pressure to give product 1-9 which was either purified by reverse phase prep. HPLC, or more usually was pure enough to use directly in the next step.

Step F: Acylation 1-7

Boc-protected amine 1-6 (1.0 mmol) was treated with 10% TFA in CH$_2$Cl$_2$ (5 ml). Once reaction was complete, the reaction was concentrated in vacuo and then partitioned between EtOAc and sat. aq. NaHCO$_3$. The organics were separated, then washed with sat. aq. NaHCO$_3$ (×2), H$_2$O (×2), brine (×2), then dried (Na$_2$SO$_4$), filtered, and evaporated under reduced pressure to give the phenyl imidazole free amine 1-7 which was pure enough to use directly in the next step.

Step E: Reductive Amination

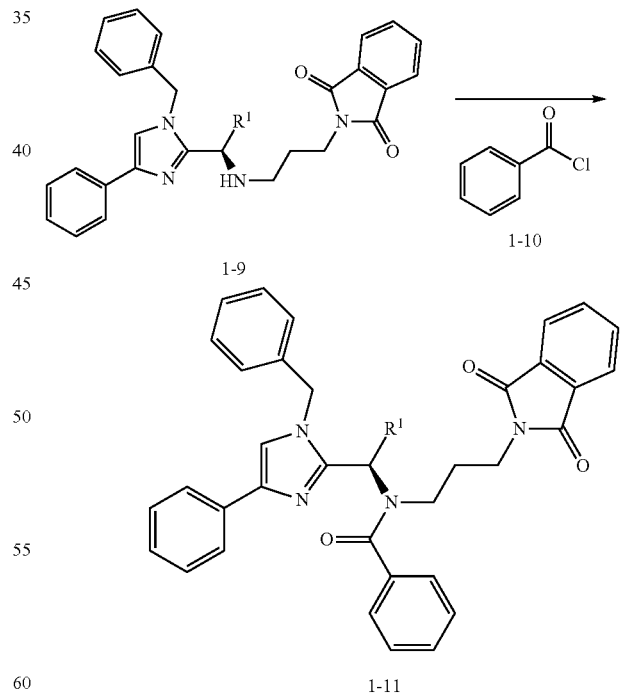

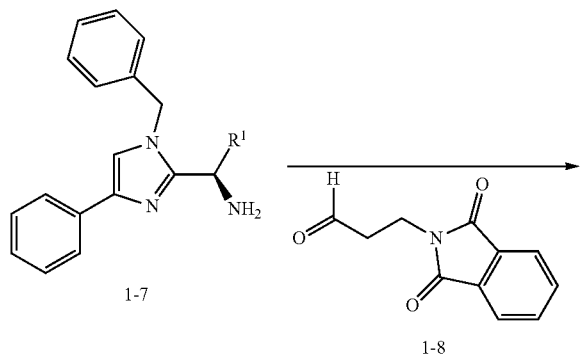

To a stirred solution of amine 1-9 (1.0 mmol) in CH$_2$Cl$_2$ (6 ml) was added Et$_3$N (2.0 mmol) followed by the appropriate acid chloride 1-10, e.g., benzoyl chloride (1.0 mmol). Once the reaction was complete, the mixture was partitioned between CH$_2$Cl$_2$ and sat. aq. NaHCO$_3$. The organics were separated and washed with H₂O (×2), brine (×2), then dried (Na₂SO₄), filtered, and evaporated under reduced pressure to give product 1-11.

Step G: Final Deprotection

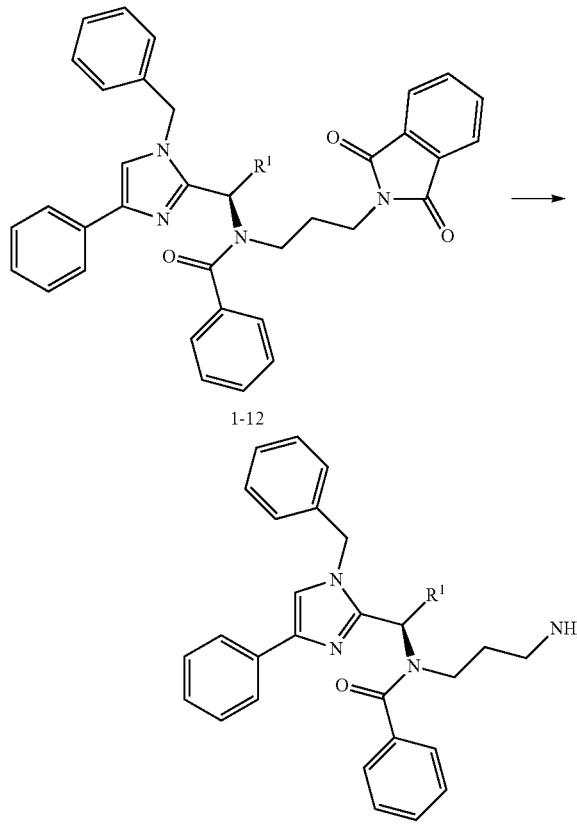

1-12

To a non-stirred solution of phthalimido compound 1-12 (0.3 mmol) in EtOH (1.5 ml) was added anhydrous hydrazine (1.5 mmol). Once the reaction was complete, the reaction was filtered, and the filtrate evaporated under reduced pressure to give the title compound which was purified by reverse phase prep. HPLC to give the pure product 1-13.

Example 2

Preparation of N-[(2S)-3-amino-2-hydroxypropyl]-N-[(1R)-1-(1-benzyl-4-phenyl-1H-imidazol-2-yl)-2,2-dimethylpropyl]benzamide (Compound 175)

Step A: Keto-Ester Synthesis

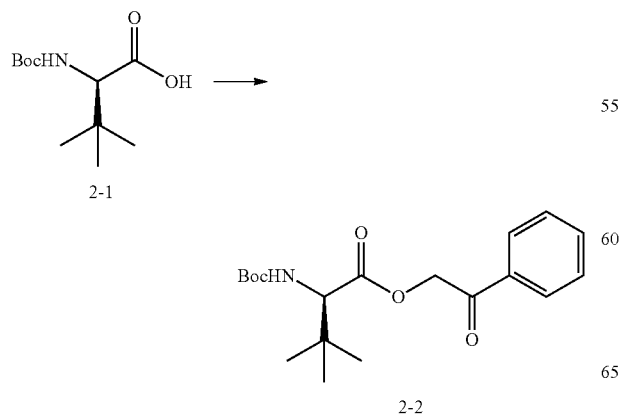

A stirred solution of the appropriate N-Boc-acid (4.0 mmol), compound 2-1, tert-butyl glycine, in EtOH (10 ml) was treated with Cs₂CO₃ (2.0 mmol). After 45 min, the EtOH was removed by evaporation under reduced pressure. The residual cesium salt was re-dissolved in DMF (15 ml) and the treated with the appropriate α-halo-ketone, eg, 2-bromoacetophenone (4.0 mmol) and stirred at r.t. until the reaction was complete. The reaction mixture was then partitioned between EtOAc and H₂O, and the organics separated, then washed with H₂O (×3), brine (×3), then dried (Na₂SO₄), filtered, and evaporated under reduced pressure to give the keto-ester 2-2 which was pure enough to use directly in the next step.

Step B: Phenyl-Imidazole Formation

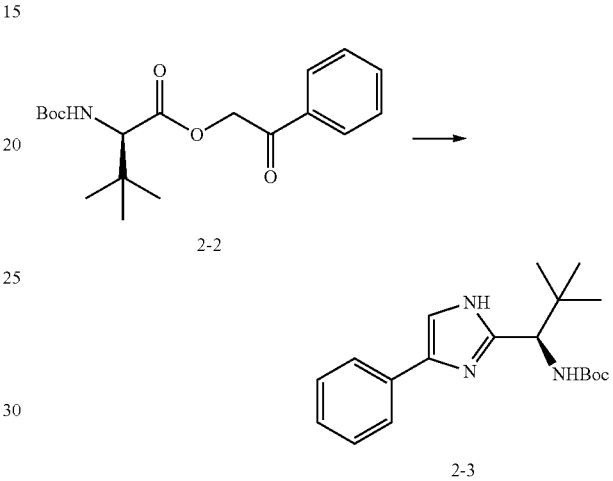

To a stirred solution of keto-ester 2-2 (4.0 mmol) in xylenes (40 ml) was added ammonium acetate (20 mmol). A Dean-Stark trap was added and the reaction heated to 140° C. Once the reaction was complete, the mixture was allowed to cool to r.t., then partitioned between EtOAc and sat. aq. NaHCO₃. The organics were separated, then washed with sat. aq. NaHCO₃ (×2), H₂O (×3), brine (×3), then dried (Na₂SO₄), filtered, and evaporated under reduced pressure to give the phenyl imidazole 2-3 which was pure enough to use directly in the next step.

Step C: Benzylation of the Phenyl Imidazole

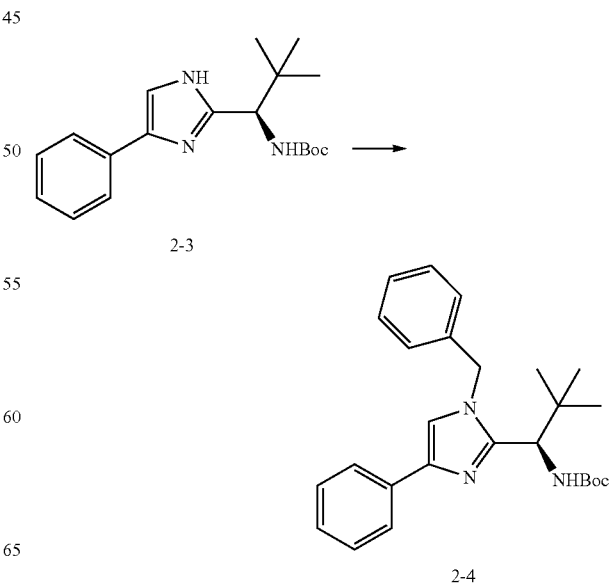

To a stirred solution/suspension of imidazole 2-3 (4.0 mmol) and K$_2$CO$_3$ (8.0 mmol) in DMF (10 ml) was added the benzylating agent, eg, benzyl bromide (4.40 mmol). Once the reaction was complete, the mixture was partitioned between EtOAc and H$_2$O. The organic layer was separated and washed with H$_2$O (×3), brine (×3), then dried (Na$_2$SO$_4$), filtered, and evaporated under reduced pressure to give the crude benzylated phenyl imidazole. The crude reaction material was then crystallized (EtOAc, hexanes) to give pure product 2-4.

Step D: Deprotection to the Free Amine

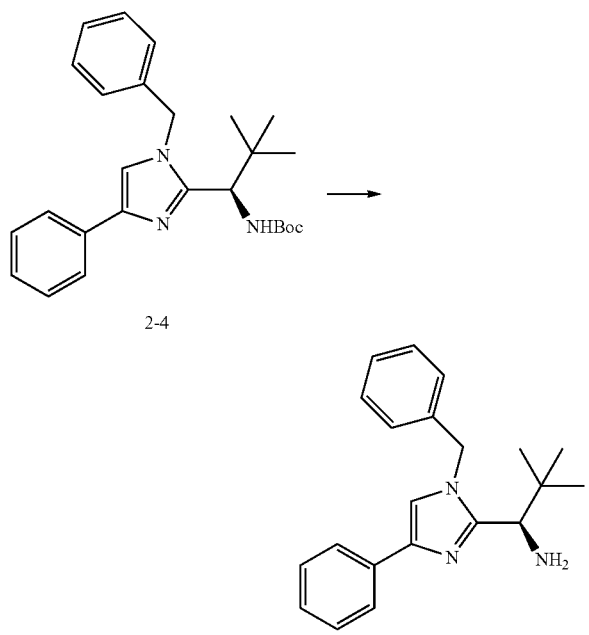

Boc-protected amine 2-4 (1.0 mmol) was treated with 10% TFA in CH$_2$Cl$_2$ (5 ml). Once reaction was complete, the reaction was concentrated in vacuo and then partitioned between EtOAc and sat. aq. NaHCO$_3$. The organics were separated, then washed with sat. aq. NaHCO$_3$ (×2), H$_2$O (×2), brine (×2), then dried (Na$_2$SO$_4$), filtered, and evaporated under reduced pressure to give the phenyl imidazole free amine 2-5 which was pure enough to use directly in the next step.

Step E: Synthesis of Aldehyde

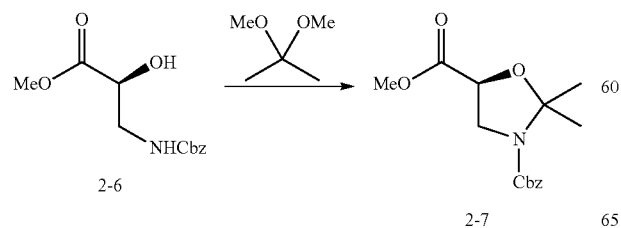

To a stirred solution of Cbz protected amino alcohol 2-6 (12.25 mmol) in acetone (50 ml) was added dimethoxypropane (24.5 mmol) followed by BF$_3$ etherate (20 μL, catalytic amount). After 16 h, further dimethoxypropane (80.6 mmol) was added and stirring continued for a further 16 h. The mixture was then concentrated under reduced pressure, then partitioned between EtOAc and sat. aqueous NaHCO$_3$. The organics were separated, then washed with sat. aq. NaHCO$_3$ (×2), H$_2$O (×2), brine (×2), then dried (Na$_2$SO$_4$), filtered, and evaporated under reduced pressure to give the crude compound. Purification by silica gel chromatography afforded the ester product 2-7.

Step F: DIBAL Reduction to the Aldehyde

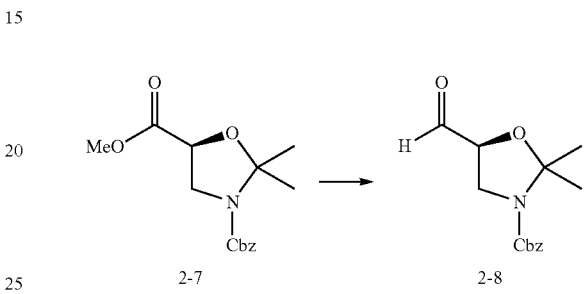

To a cooled (−78° C.), stirred solution of ester 2-7 (5.11 mmol) in toluene (25 ml) was added DIBAL-H (6.64 mmol) dropwise. After 3 h, the reaction was quenched by cautious addition of sat. aqueous NH$_4$Cl (40 ml). The mixture was diluted with EtOAc, the organic phase was separated, the aqueous extracted with EtOAc (×2). The organics were combined, then washed with 10% Rochelle's Salt (×3), H$_2$O (×1), brine (×3) then dried (Na$_2$SO$_4$), filtered, and evaporated under reduced pressure to give the crude aldehyde 2-8 which was used directly in the reductive amination.

Step G: Reductive Amination to Install Sidechain

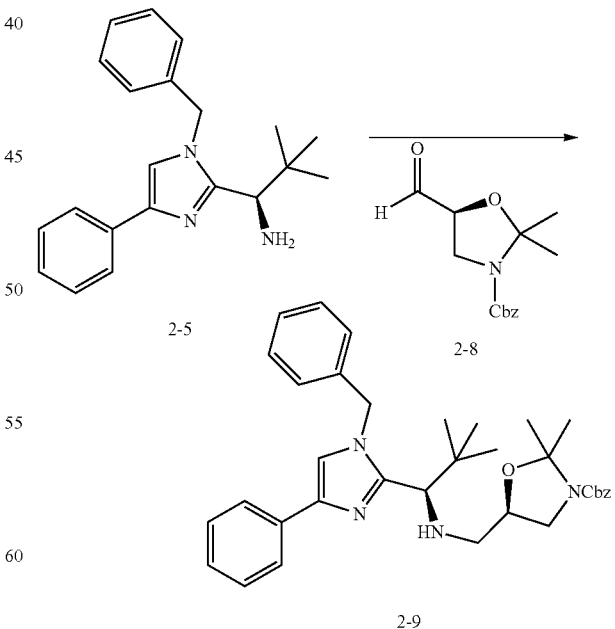

To a stirred solution of (R)-amine 2-5 from step D (1.15 mmol) and aldehyde 2-8, (1.0 mmol) in CH$_2$Cl$_2$ (10 ml) was added AcOH (1.15 mmol) followed by the addition of sodium tris-acetoxyborohydride (1.28 mmol). Once the reaction was complete, the mixture was concentrated in vacuo, partitioned between EtOAc and 1M NaOH. The organics were separated, then washed with 1M NaOH (×2), H₂O (×1), brine (×2), then dried (Na₂SO₄), filtered, and evaporated under reduced pressure to give crude product 2-9 which was used directly in the next step.

Step H: Acylation

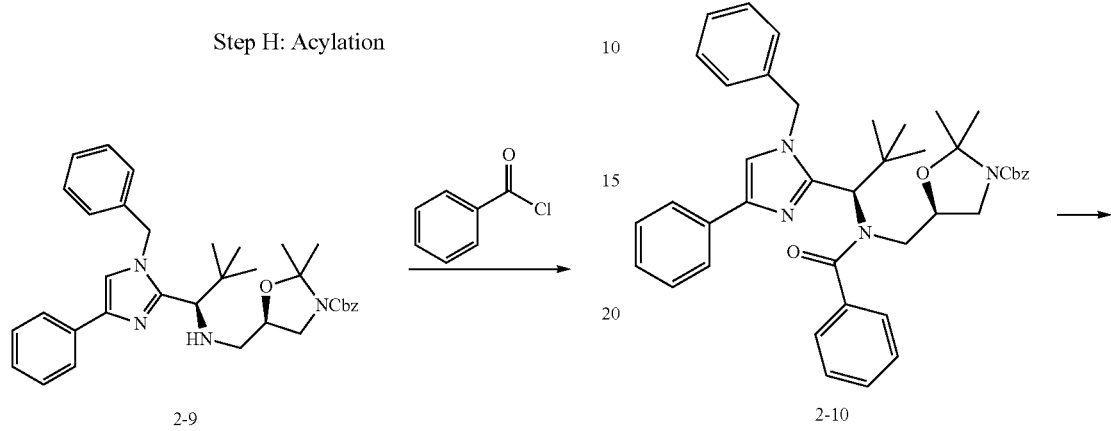

2-9

2-10

Step I: Final Deprotection

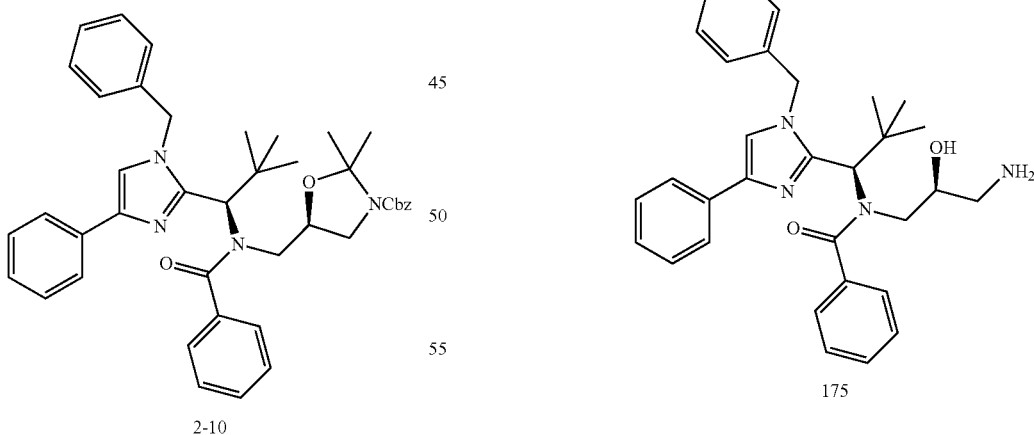

2-10

175

To a stirred solution of amine 2-9 (0.25 mmol) in CH₂Cl₂ (2 ml) was added DIPEA (0.5 mmol) followed by the appropriate acid chloride, e.g., benzoyl chloride (0.27 mmol). Once the reaction was complete, the mixture was partitioned between CH₂Cl₂ and sat. aq. NaHCO₃. The organics were separated and washed with H₂O (×2), brine (×2), then dried (Na₂SO₄), filtered, and evaporated under reduced pressure to give product 2-10 which was used directly in the next step.

A solution of Cbz-protected amine 2-10 from step H (0.25 mmol) in MeOH was hydrogenated in the presence of a catalytic amount of 10% Pd/C under an atmosphere of hydrogen. After 2 h, the solution was filtered (Celite) then concentrated under reduced pressure. The residue was treated with 10% TFA/CH₂Cl₂ (5 ml). Once reaction was complete, the reaction was evaporated under reduced pressure to give the title compound which was purified by reverse phase prep. HPLC to give the pure Compound 175 in Table 2.

Example 3

Preparation of (R)-9-{(R)-1-[1-(3-Fluoro-benzyl)-4-(3-fluoro-phenyl)-1H-imidazol-2-yl]-2,2-dimethyl-propyl}-6-oxa-2,9-diaza-spiro[4.5]decan-8-one (Compound 404)

Step A: Formation of Enol Ethers

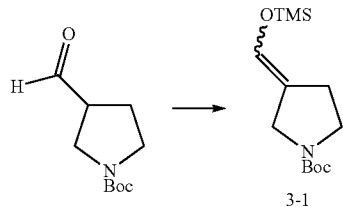

3-1

A mixture of N-Boc-3-formyl pyrrolidine (50 mmol), TMSCl (125 mmol) and Et₃N (250 mmol) in DMF (60 ml) were heated for 6 h. The mixture was then diluted with hexanes and filtered (Celite). The filtrate was then evaporated under reduced pressure to give the TMS enol ethers 3-1 as a mixture of E and Z isomers that were used directly in the next step.

Step B: Formation of the Aldehyde

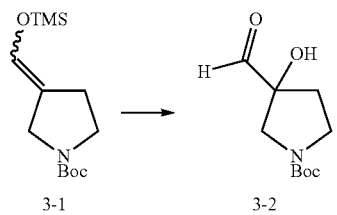

3-1                  3-2

To a solution of TMS enol ether 3-1 (3.7 mmol) in acetone (8 ml) was added a solution of N-methyl morpholine N-oxide (5.5 mmol) in H₂O (1.2 ml). To this rapidly stirred solution was added OsO₄ (0.074 mmol). After 3 h, the mixture was evaporated to dryness under reduced pressure azeotroping with benzene (3×5 ml) to give the crude hydroxy aldehyde. Purification by silica gel chromatography afforded pure hydroxy aldehyde 3-2.

Step C: Reductive Amination

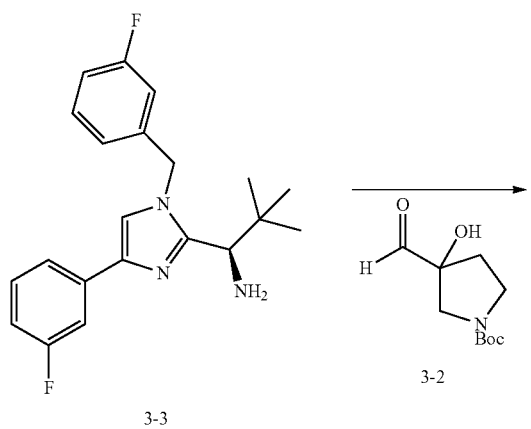

3-3                  3-2

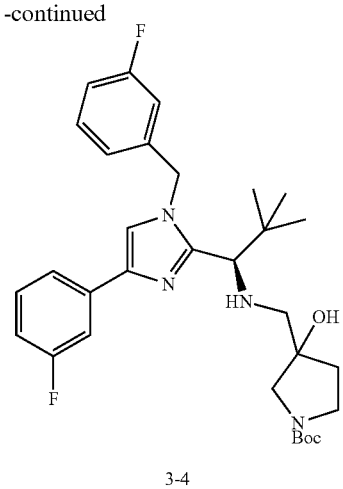

3-4

To a stirred solution of (R)-amine 3-3 (0.282 mmol) and aldehyde 3-2, (0.3 mmol) in CH₂Cl₂ (3 ml) was added AcOH (0.31 mmol) followed by the addition of sodium tris-acetoxyborohydride (0.31 mmol). Compound 3-3 was synthesized in a manner similar to Example 1, utilizing the appropriately fluoro-substituted starting materials. After 18 h, further sodium tris-acetoxyborohydride (0.157 mmol) was added. Once the reaction was complete, the mixture was concentrated in vacuo, partitioned between EtOAc and 1M NaOH. The organics were separated, then washed with 1M NaOH (×2), H₂O (×1), brine (×2), then dried (Na₂SO₄), filtered, and evaporated under reduced pressure to give crude product. Purification by silica gel chromatography afforded a single diastereomer 3-4, though it was unknown whether it was the R,R or R,S diastereomer.

Step D: Cyclization to 5,6-spiro compound

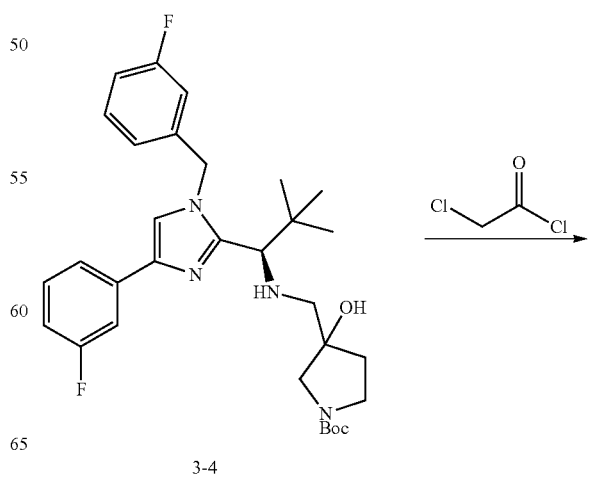

3-4

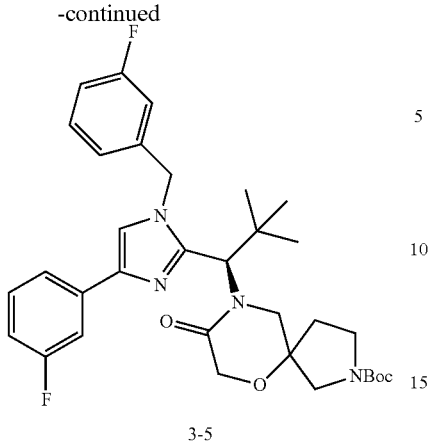

3-5

To a stirred solution of amino alcohol 3-4 (0.115 mmol) in CH₂Cl₂ (1.0 ml) was added DIPEA (0.575 mmol) followed by chloroacetyl chloride (0.127 mmol). After 1 h, further chloroacetyl chloride (0.075 mmol) followed by DIPEA (0.287 mmol). Once the reaction was complete, the mixture was evaporated under reduced pressure to give the spiro compound 3-5 which was used directly in the next step.

Step E: Final Deprotection

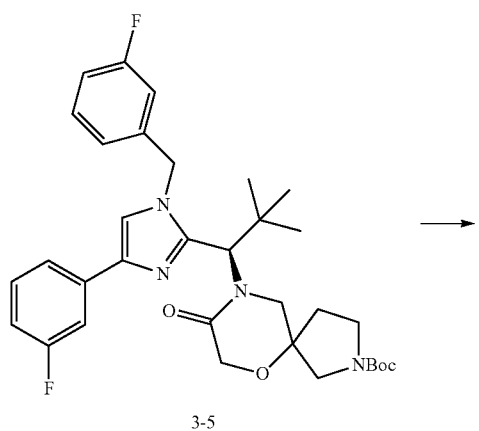

3-5

↓

404

Boc-protected amine 3-5 (0.115 mmol) was treated with 10% TFA/CH₂Cl₂ (3 ml). Once reaction was complete, the reaction was evaporated under reduced pressure to give the title compound which was purified by reverse phase prep. HPLC to give the pure compound 404 in Table 3.

Example 4

Preparation of N-[(1R)-1-(1-benzyl-4-phenyl-1H-imidazol-2-yl)-2,2-dimethylpropyl]-N-{[(3S)-3-fluoropyrrolidin-3-yl]methyl}-1,5-dimethyl-1H-pyrazole-3-carboxamide (Compound 257) and N-[(1R)-1-(1-benzyl-4-phenyl-1H-imidazol-2-yl)-2,2-dimethylpropyl]-N-{[(3R)-3-fluoropyrrolidin-3-yl]methyl}-1,5-dimethyl-1H-pyrazole-3-carboxamide (Compound 258)

Step A

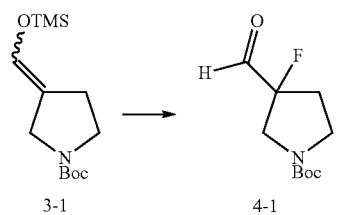

3-1          4-1

To a solution of TMS enol ether 3-1 from Step A of Example 3 (42 mmol) in CH₃CN (400 ml) was added Select-Fluor® (available from Air Products and Chemicals, Inc.) (43.2 mmol). Once the reaction was complete, the mixture was evaporated under reduced pressure and the remaining solid/oil was extracted with Et₂O (×5). The ether extracts were evaporated under reduced pressure to give the crude aldehyde. Purification by silica gel chromatography afforded the desired aldehyde 4-1.

Step B: Reductive Amination

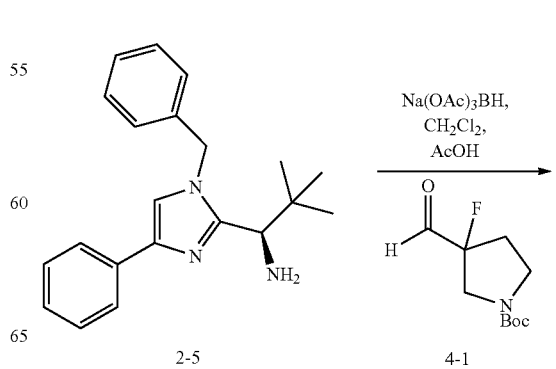

2-5          4-1

69

-continued

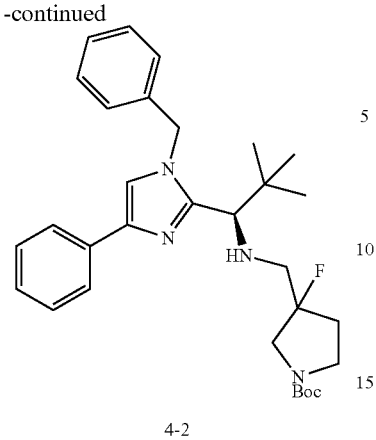

4-2

To a stirred solution of (R)-amine 2-5 (2.0 mmol) and aldehyde 4-1, (2.2 mmol) in CH₂Cl₂ (20 ml) was added AcOH (2.0 mmol) followed by the addition of sodium tris-acetoxyborohydride (3.0 mmol). After 19 h, further sodium tris-acetoxyborohydride (1.0 mmol) was added. Once the reaction was complete, the mixture was concentrated in vacuo, partitioned between EtOAc and 1M NaOH. The organics were separated, then washed with 1M NaOH (×2), H₂O (×1), brine (×2), then dried (Na₂SO₄), filtered, and evaporated under reduced pressure to give crude product. Purification by silica gel chromatography afforded the amine 4-2 as a mixture of (R,R) and (R,S) diastereomers.

Step C: Acylation

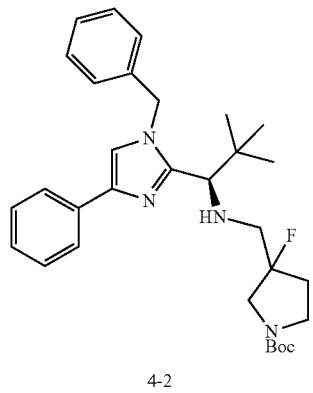

4-2

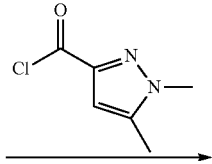

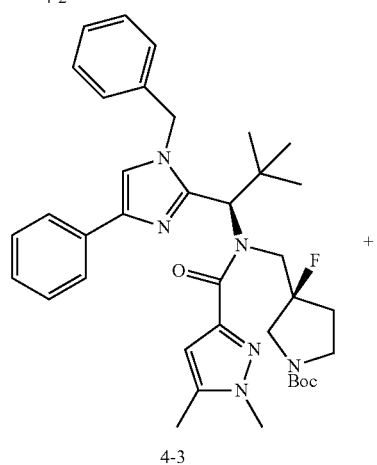

4-3

70

-continued

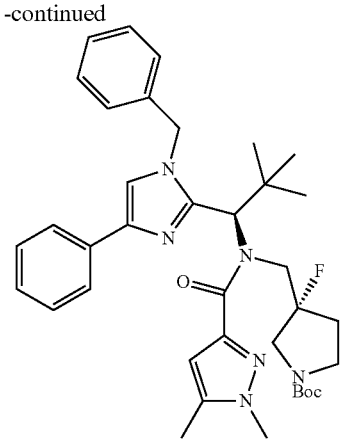

4-4

To a solution of (R) amine 4-2 (0.069 mmol) in THF (0.5 ml) was added DIPEA (0.138 mmol) followed by 1,5-dimethyl-1H-pyrazole-3-carbonyl chloride (0.076 mmol). The mixture was heated at 50° C. Once the reaction was complete, the mixture was concentrated in vacuo, and then purified by reverse phase prep. HPLC which separated the (R,R) 4-4 and the (R,S) 4-3 diastereomers.

Step D: Final Deprotection

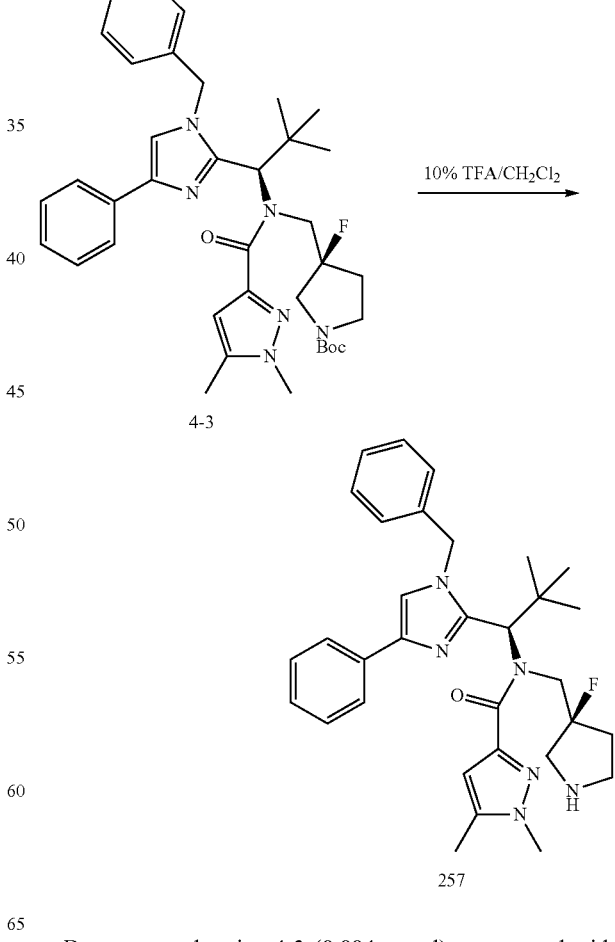

4-3

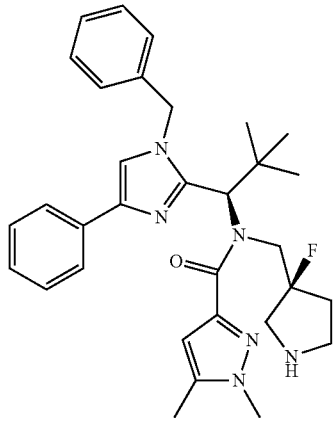

257

Boc-protected amine 4-3 (0.004 mmol) was treated with 10% TFA/CH₂Cl₂ (1 ml). Once the reaction was complete, the reaction was evaporated under reduced pressure and purified by reverse phase prep. HPLC to give the pure Compound 257 in Table 2. Compound 258 (not shown) in Table 2 was synthesized using similar procedures using 47 as starting material in Step D.

Example 5

Preparation of (5S)-3-[(1R)-1-(1-benzyl-4-phenyl-1H-imidazol-2-yl)-2,2-dimethylpropyl]-1-oxa-3,7-diazaspiro[4.4]nonan-2-one (Compound 319) and (5R)-3-[(1R)-1-(1-benzyl-4-phenyl-1H-imidazol-2-yl)-2,2-dimethylpropyl]-1-oxa-3,7-diazaspiro[4.4]nonan-2-one (Compound 320)

Step A

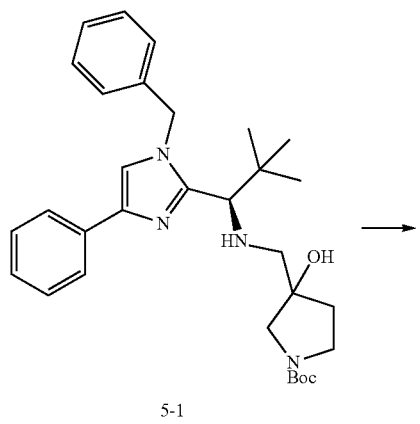

5-1

To a stirred solution of amino alcohol 5-1 (0.96 mmol) in DMF (0.4 ml) was added imidazole (0.482 mmol), DMAP (catalytic amount) and TMSCl. Once the reaction was complete, the mixture was partitioned between EtOAc and sat. aqueous NaHCO₃. The organics were separated, then washed with sat. aqueous NaHCO₃ (×2), H₂O (×1), brine (×2), then dried (Na₂SO₄), filtered, and evaporated under reduced pressure to give crude product. Purification by silica gel chromatography afforded the silyl ether 5-2.

Step B: Cyclization to the 5,5-spiro compound

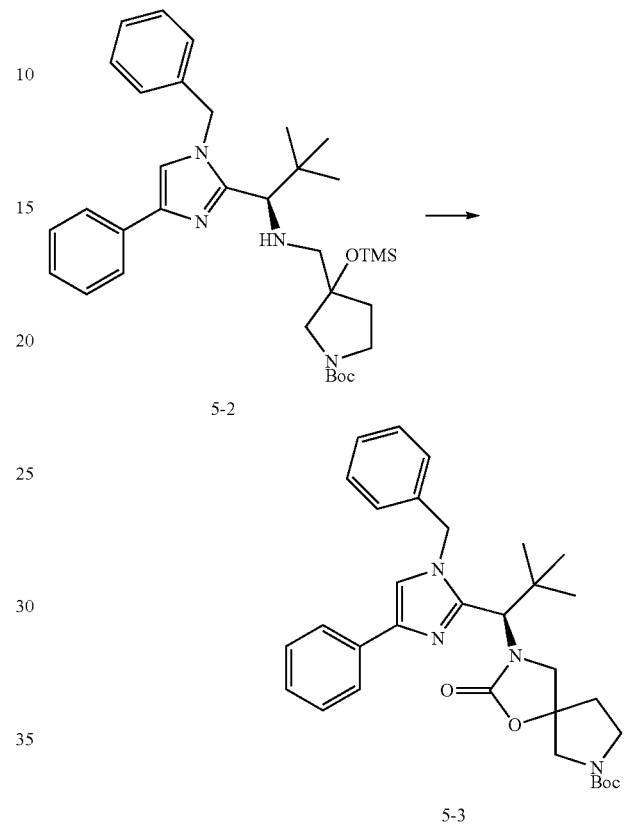

To a solution of silyl ether 5-2 (0.073 mmol) in CH₂Cl₂ (0.8 ml) was added DIPEA (0.876 mmol) followed by phosgene (0.584 mmol). Once the reaction was complete, the mixture was concentrated in vacuo, and then purified by reverse phase prep. HPLC to give the pure spiro compound 5-3 as a mixture of (R,R) and (R,S) diastereomers.

Step C: Final Deprotection

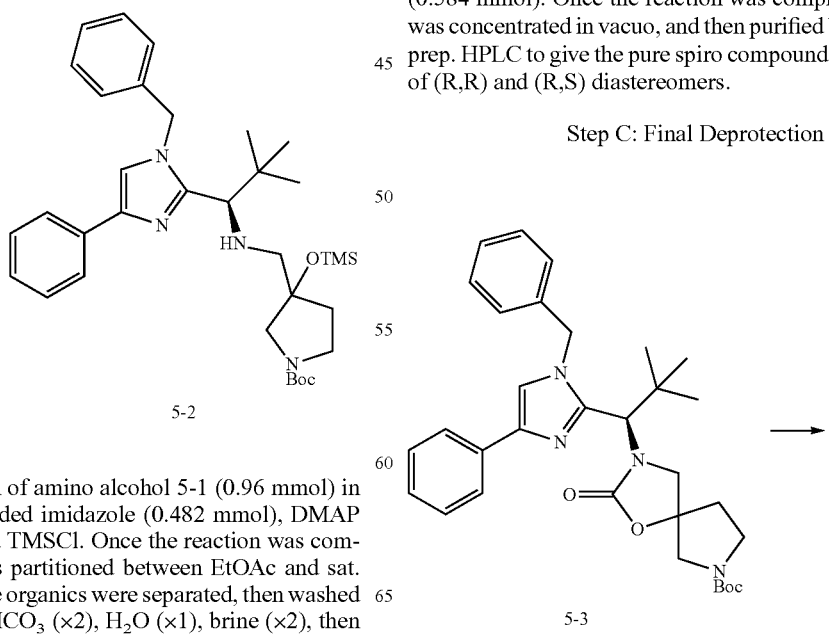

5-3

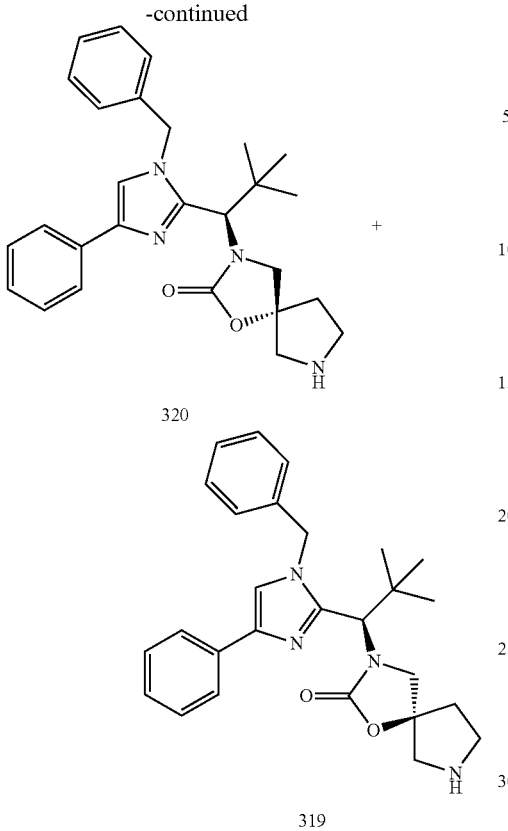

320

319

Boc-amine 5-3 (0.0135 mmol) was treated with 10% TFA/CH₂Cl₂ (0.3 ml). Once reaction was complete, the reaction was evaporated under reduced pressure and purified by reverse phase prep. HPLC to give the separated 320 (R,R) and 319 (R,S) diastereomers.

Example 6

Preparation of N-(3-aminopropyl)-N-[(1R)-1-(1-benzyl-4-phenyl-1H-imidazol-2-yl)-2-methylpropyl]-4-methylbenzamide (Compound 1)

Step A: Keto Ester Synthesis 6-1

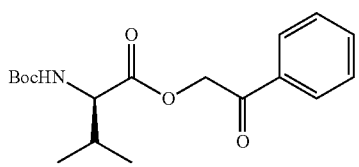

A stirred solution of D-Boc-Valine (4.605 mmol) in EtOH (10 ml) was treated with Cs₂CO₃ (0.75 g, 2.30 mmol). After 45 min, the EtOH was removed by evaporation under reduced pressure. The residual cesium salt was re-dissolved in DMF (15 ml) and the treated with 2-bromoacetophenone (0.916 g, 4.605 mmol) and stirred at room temperature until the reaction was complete. The reaction mixture was then partitioned between EtOAc and H₂O, and the organics separated, then washed with H₂O (×3), brine (×3), then dried (Na₂SO₄), filtered, and evaporated under reduced pressure to give the keto-ester 6-1 which was pure enough to use directly in the next step.

Step B: Synthesis of Phenyl-Imidazole 6-2

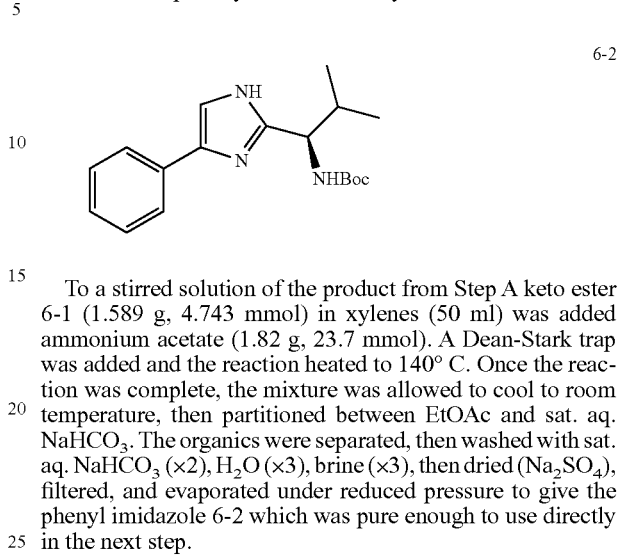

To a stirred solution of the product from Step A keto ester 6-1 (1.589 g, 4.743 mmol) in xylenes (50 ml) was added ammonium acetate (1.82 g, 23.7 mmol). A Dean-Stark trap was added and the reaction heated to 140° C. Once the reaction was complete, the mixture was allowed to cool to room temperature, then partitioned between EtOAc and sat. aq. NaHCO₃. The organics were separated, then washed with sat. aq. NaHCO₃ (×2), H₂O (×3), brine (×3), then dried (Na₂SO₄), filtered, and evaporated under reduced pressure to give the phenyl imidazole 6-2 which was pure enough to use directly in the next step.

Step C: Benzylation of the Phenyl Imidazole 6-3

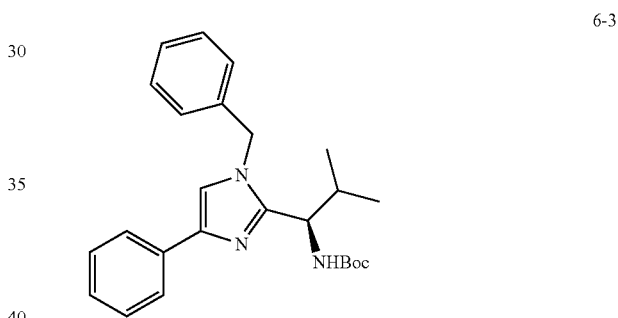

To a stirred solution/suspension of the product from Step B compound 6-2 (1.00 g, 3.17 mmol) and K₂CO₃ (0.876 g, 6.34 mmol) in DMF (10 ml) was added benzyl bromide (0.415 ml, 3.49 mmol). Once the reaction was complete, the mixture was partitioned between EtOAc and H₂O. The organic layer was separated and washed with H₂O (×3), brine (×3), then dried (Na₂SO₄), filtered, and evaporated under reduced pressure to give the crude benzylated phenyl imidazole. The crude reaction material was then crystallized (EtOAc, hexanes) to give pure product compound 6-3. The regiochemical outcome was verified by ¹H nOe NMR.

Step D: Deprotection to the Free Amine 6-4

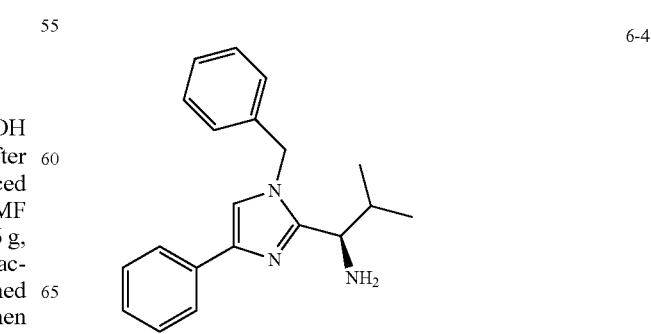

Boc-protected amine compound 6-3 from Step C (0.406 g, 1.0 mmol) was treated with 10% TFA in CH$_2$Cl$_2$ (5 ml). Once reaction was complete, the reaction was concentrated in vacuo and then partitioned between EtOAc and sat. aq. NaHCO$_3$. The organics were separated, then washed with sat. aq. NaHCO$_3$ (×2), H$_2$O (×2), brine (×2), then dried (Na$_2$SO$_4$), filtered, and evaporated under reduced pressure to give the phenyl imidazole free amine compound 6-4 which was pure enough to use directly in the next step.

Step E: Reductive Amination

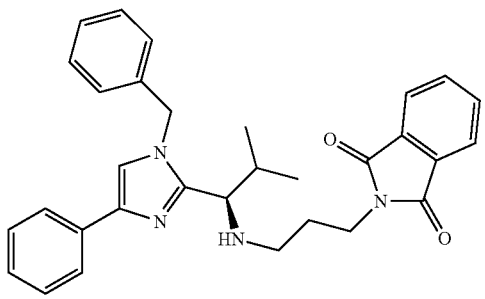

6-5

To a stirred solution of amine 6-4 from Step D (59 mg, 0.193 mmol) and 2-(3-oxopropyl)benzo[c]azoline-1,3-dione (39 mg, 0.193 mmol) in CH$_2$Cl$_2$ (1.5 ml) was added AcOH (11 μL, 0.193 mmol). The mixture was allowed to stir for 5 min before the addition of sodium tris-acetoxyborohydride (45 mg, 0.212 mmol). After 1 h, the mixture was concentrated in vacuo, partitioned between EtOAc and 2 M aq. Na$_2$CO$_3$. The organics were separated, then washed with 2 M aq. Na$_2$CO$_3$ (×2), H$_2$O (×2), brine (×2), then dried (Na$_2$SO$_4$), filtered, and evaporated under reduced pressure to give product 6-5 which was pure enough to use directly in the next step.

Step F: Acylation

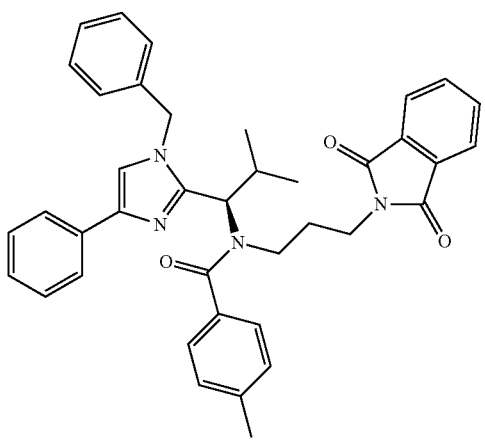

6-6

To a stirred solution of amine 6-5 from Step E (42 mg, 0.085 mmol) in CH$_2$Cl$_2$ (1.2 ml) was added DIPEA (30 μL, 0.170 mmol) followed by p-toluoyl chloride (12.4 L, 1.0 mmol). Once the reaction was complete, the mixture was partitioned between CH$_2$Cl$_2$ and sat. aq. NaHCO$_3$. The organics were separated and washed with H$_2$O (×2), brine (×2), then dried (Na$_2$SO$_4$), filtered, and evaporated under reduced pressure to give product 6-6 which was pure enough to use directly in the next step.

Step G: Final Deprotection

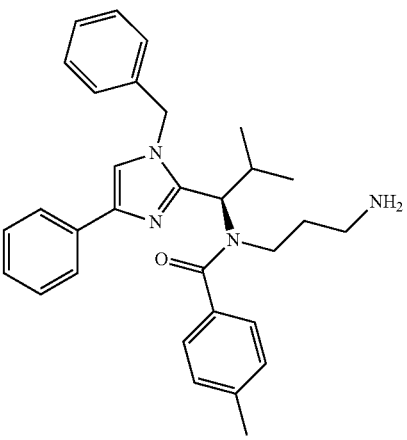

1

To a non-stirred solution of phthalimido compound 6-6 from step F, (52 mg, 0.085 mmol) in EtOH (1.5 ml) was added anhydrous hydrazine (26 μL, 0.85 mmol). Once the reaction was complete, the reaction was filtered, and the filtrate evaporated under reduced pressure to give the title compound which was purified by reverse phase prep. HPLC to give the pure product 1 in Table 1.

Example 7

Preparation of N-(3-aminopropyl)-N-[(1R)-1-(1-benzyl-4-phenyl-1H-imidazol-2-yl)-2,2-dimethylpropyl]-1,5-dimethyl-1H-pyrazole-3-carboxamide (Compound 99)

Step A: Keto Ester Synthesis

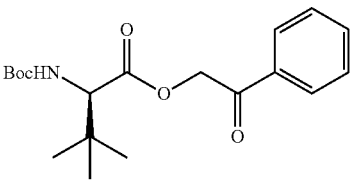

2-2

A stirred solution of the N-Boc-acid (10.0 g, 43.2 mmol 1.0 eq.) in EtOH (150 ml) was treated with Cs$_2$CO$_3$ (7.04 g, 21.6 mmol, 0.5 eq.). After 45 min, the EtOH was removed by evaporation under reduced pressure. The residual cesium salt was re-dissolved in DMF (150 ml) and the treated with 2-bromoacetophenone (8.60 g, 43.2 mmol, 1.0 eq.) and stirred at room temperature for 1 hour. The reaction mixture was then partitioned between EtOAc and H$_2$O, and the organics separated, then washed with H$_2$O (×3), brine (×3), then dried (Na$_2$SO$_4$), filtered, and evaporated under reduced pressure to give the keto-ester 2-2 which was pure enough to use directly in the next step.

Step B: Phenyl Imidazole Formation

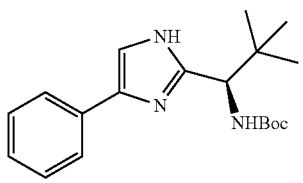

2-3

To a stirred solution of keto-ester 2-2 from Step A (15.1 g, 43.2 mmol, 1.0 eq.) in xylenes (500 ml) was added ammonium acetate (16.6 g, 216.2 mmol, 5.0 eq.). A Dean-Stark trap was added and the reaction heated to 140° C. for 1 hour. Once the reaction was complete, the mixture was allowed to cool to room temperature, then partitioned between EtOAc and sat. aq. NaHCO$_3$. The organics were separated, then washed with sat. aq. NaHCO$_3$ (×2), H$_2$O (×3), brine (×3), then dried (Na$_2$SO$_4$), filtered, and evaporated under reduced pressure to give the phenyl imidazole 2-3 which was pure enough to use directly in the next step.

Step C: Benzylation

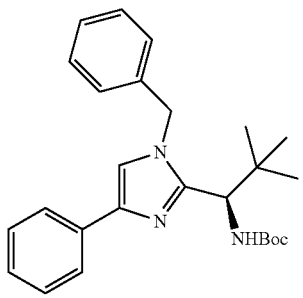

2-4

To a stirred solution/suspension of imidazole 2-3 from Step B (14.26 g, 43.2 mmol, 1.0 eq.) and K$_2$CO$_3$ (12.00 g, 86.4 mmol, 2.0 eq.) in DMF (150 ml) was added the benzyl bromide (5.65 ml, 47.53 mmol, 1.1 eq.). The reaction was stirred at room temperature for 12 hours. Once the reaction was complete, the mixture was partitioned between EtOAc and H$_2$O. The organic layer was separated and washed with H$_2$O (×3), brine (×3), then dried (Na$_2$SO$_4$), filtered, and evaporated under reduced pressure to give the crude benzylated phenyl imidazole 2-4, which was pure enough to move directly onto the next step.

Step D: Deprotection of the Free Amine

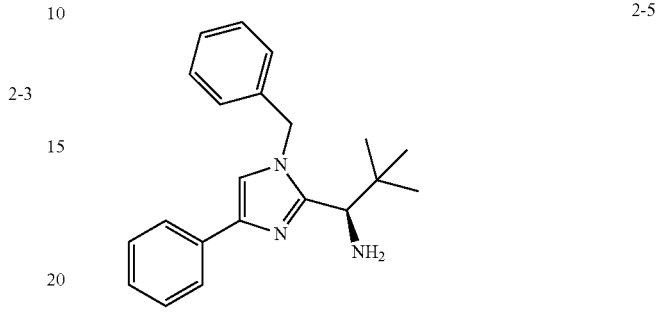

2-5

Boc-protected amine 2-4 from Step C (5.0 g, 11.93 mmol) was treated with 15% TFA in CH$_2$Cl$_2$ (35 ml). Once reaction was complete, the reaction was concentrated in vacuo and then partitioned between EtOAc and sat. aq. NaHCO$_3$. The organics were separated, then washed with sat. aq. NaHCO$_3$ (×2), H$_2$O (×2), brine (×2), then dried (Na$_2$SO$_4$), filtered, and evaporated under reduced pressure to give the phenyl imidazole free amine 2-5 which was pure enough to use directly in the next step.

Step E: Reductive Amination

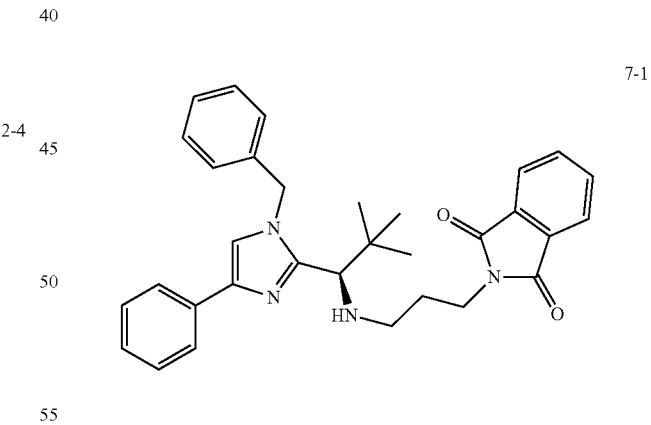

7-1

To a stirred solution of amine 2-5 from Step D (1.00 g, 3.13 mmol, 1.0 eq.) and the 2-(3-oxopropyl)benzo[c]azoline-1,3-dione 25 (0.51 g, 2.51 mmol, 1.0 eq.) in CH$_2$Cl$_2$ (10 ml) was added AcOH (0.18 ml, 3.13 mmol, 1.0 eq.). The mixture was allowed to stir for 5 min before the addition of sodium tris-acetoxyborohydride (0.73 g, 3.44 mmol, 1.1 eq.). Once the reaction was complete, the mixture was concentrated in vacuo, partitioned between EtOAc and 2 M aq. Na$_2$CO$_3$. The organics were separated, then washed with 2 M aq. Na$_2$CO$_3$ (×2), H$_2$O (×2), brine (×2), then dried (Na$_2$SO$_4$), filtered, and evaporated under reduced pressure to give product 7-1 which was pure enough to use directly in the next step.

Step F: Acylation

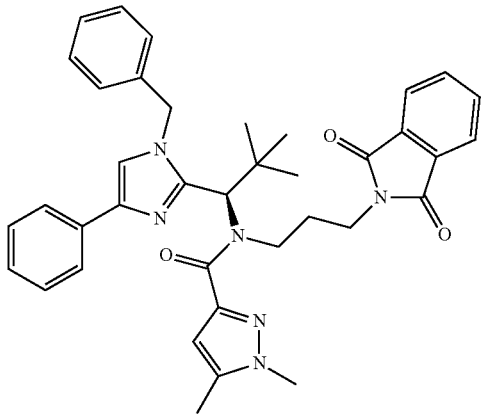

7-2

To a stirred solution of amine 7-1 from Step E (0.04 g, 0.08 mmol, 1.0 eq.) in CH₂Cl₂ (0.3 ml) was added the acid (0.024 g, 0.17 mmol, 2.2 eq.), HOAT (0.24 g, 0.17 mmol, 2.2 eq.), and TEA (0.05 ml, 0.33 mmol, 4.2 eq.). After 5 minutes EDC (0.04 g, 0.18 mmol, 2.3 eq.) was added, and the reaction was heated to 55° C. for 24 hours. The mixture was then partitioned between CH₂Cl₂ and sat. aq. NaHCO₃. The organics were separated and washed with H₂O (×2), brine (×2), then dried (Na₂SO₄), filtered, and evaporated under reduced pressure to give product 7-2.

Step G: Synthesis of 99

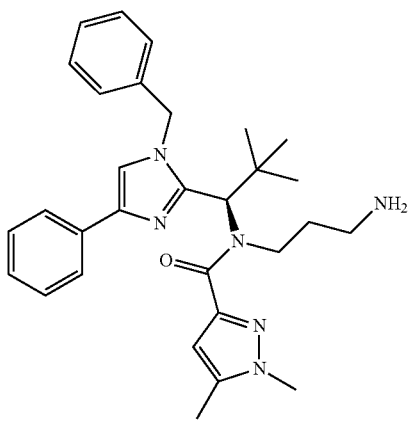

99

To a non-stirred solution of phthalimido compound 7-2 from Step F (0.02 g, 0.03 mmol, 1.0 eq.) in EtOH (0.1 ml) was added anhydrous hydrazine (0.005 g, 0.15 mmol, 5.0 eq.). Once the reaction was complete, the reaction was filtered, and the filtrate evaporated under reduced pressure to give the title compound which was purified by reverse phase prep. HPLC to give the pure product 99.

Example 8

Preparation of N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide (Compound 71)

Step A: Keto Ester Synthesis

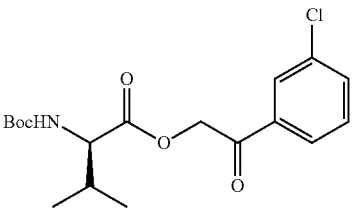

8-1

A stirred solution of the N-Boc-acid (8.0 g, 36.8 mmol 1.0 eq.) in EtOH (130 ml) was treated with Cs₂CO₃ (6.0 g, 18.4 mmol, 0.5 eq.). After 45 min, the EtOH was removed by evaporation under reduced pressure. The residual cesium salt was redissolved in DMF (130 ml) and the treated with chloro-substituted 2-bromoacetophenone (8.60 g, 36.84 mmol, 1.0 eq.) and stirred at room temperature for 1 hour. The reaction mixture was then partitioned between EtOAc and H₂O, and the organics separated, then washed with H₂O (×3), brine (×3), then dried (Na₂SO₄), filtered, and evaporated under reduced pressure to give the keto-ester 8-1 which was pure enough to use directly in the next step.

Step B: Formation of Phenyl-Imidazole

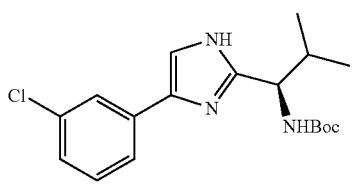

8-2

To a stirred solution of keto-ester 8-1 from Step A (13.5 g, 36.8 mmol, 1.0 eq.) in xylenes (450 ml) was added ammonium acetate (14.2 g, 185.0 mmol, 5.0 eq.). A Dean-Stark trap was added and the reaction heated to 140° C. for 1 hour. Once the reaction was complete, the mixture was allowed to cool to room temperature, then partitioned between EtOAc and sat. aq. NaHCO₃. The organics were separated, then washed with sat. aq. NaHCO₃ (×2), H₂O (×3), brine (×3), then dried (Na₂SO₄), filtered, and evaporated under reduced pressure to give the phenyl imidazole 8-2 which was pure enough to use directly in the next step.

Step C: Benzylation

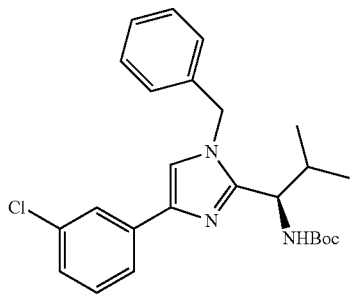

8-3

To a stirred solution/suspension of imidazole 8-2 from Step B (12.85 g, 36.8 mmol, 1.0 eq.) and K₂CO₃ (10.17 g, 73.6 mmol, 2.0 eq.) in DMF (122 ml) was added the benzyl bromide (5.20 ml, 40.49 mmol, 1.1 eq.). Reaction was stirred at room temperature for 12 hours. Once the reaction was complete, the mixture was partitioned between EtOAc and H₂O. The organic layer was separated and washed with H₂O (×3), brine (×3), then dried (Na₂SO₄), filtered, and evaporated under reduced pressure to give the crude benzylated phenyl imidazole 8-3, which was pure enough to move directly onto the next step.

Step D: Deprotection of the Amine

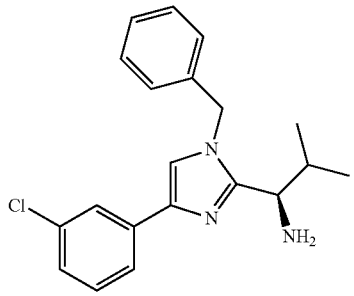

8-4

Boc-protected amine 8-3 from Step C (5.0 g, 11.40 mmol) was treated with 15% TFA in CH₂Cl₂ (35 ml). Once reaction was complete, the reaction was concentrated in vacuo and then partitioned between EtOAc and sat. aq. NaHCO₃. The organics were separated, then washed with sat. aq. NaHCO₃ (×2), H₂O (×2), brine (×2), then dried (Na₂SO₄), filtered, and evaporated under reduced pressure to give the phenyl imidazole free amine 8-4 which was pure enough to use directly in the next step.

Step E: Reductive Amination

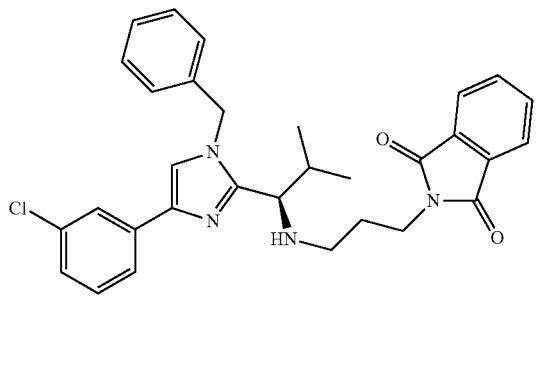

8-5

To a stirred solution of amine 8-4 from Step D (3.86 g, 11.40 mmol, 1.0 eq.) and 2-(3-oxopropyl)benzo[c]azoline-1,3-dione (2.31 g, 11.40 mmol, 1.0 eq.) in CH₂Cl₂ (40 ml) was added AcOH (0.65 ml, 11.40 mmol, 1.0 eq.). The mixture was allowed to stir for 5 min before the addition of sodium tris-acetoxyborohydride (2.65 g, 12.52 mmol, 1.1 eq.). Once the reaction was complete, the mixture was concentrated in vacuo, partitioned between EtOAc and 2 M aq. Na₂CO₃. The organics were separated, then washed with 2 M aq. Na₂CO₃ (×2), H₂O (×2), brine (×2), then dried (Na₂SO₄), filtered, and evaporated under reduced pressure to give product 8-5 which was pure enough to use directly in the next step.

Step F: Acylation

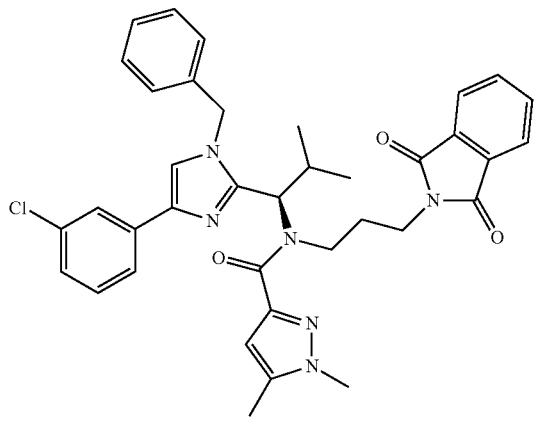

8-6

To a stirred solution of amine 8-5 from Step E (0.05 g, 0.10 mmol, 1.0 eq.) in CH₂Cl₂ (0.3 ml) was added the acid (0.02 g, 0.11 mmol, 1.0 eq.), HOAT (0.15 g, 0.10 mmol, 1.0 eq.), and TEA (0.03 ml, 0.20 mmol, 2.1 eq.). After 5 minutes EDC was added (0.22 g, 0.20 mmol, 2.0 eq.), and the reaction was heated to 55° C. for 24 hours. The mixture was then partitioned between CH₂Cl₂ and sat. aq. NaHCO₃. The organics were separated and washed with $H_2O$ (×2), brine (×2), then dried ($Na_2SO_4$), filtered, and evaporated under reduced pressure to give product 8-6.

Step G: Deprotection of the Amine

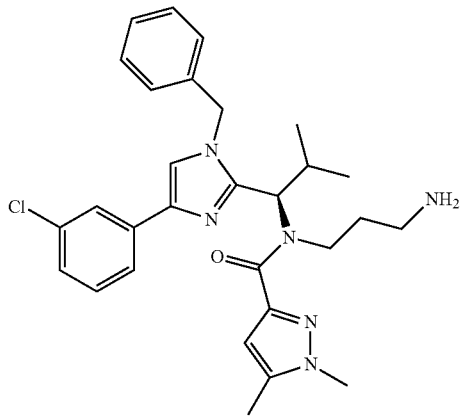

71

To a non-stirred solution of phthalimido compound 8-6 from Step F (0.01 g, 0.02 mmol, 1.0 eq.) in EtOH (0.6 ml) was added anhydrous hydrazine (0.003 g, 0.10 mmol, 5.0 eq.). Once the reaction was complete, the reaction was filtered, and the filtrate evaporated under reduced pressure to give the title compound which was purified by reverse phase prep. HPLC to give the pure product 71.

Example 9

Synthesis of intermediate (3R,4S)-tert-butyl 3-formyl-4-hydroxypyrrolidin-1-carboxylate The title compound is useful as an intermediate in synthesizing compounds of the invention.

Step A

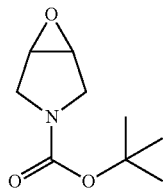

9-1

5.0 g (29.5 mmol) of tert-Butyl 2,5-dihydro-1H-pyrrole-1-carboxylate and 11.7 g (67.9 mmol) 3-chloroperoxybenzoic acid were stirred in 70 ml of DCM under nitrogen at ambient temperature for 20 hours. Excess 1N NaOH was added to the reaction mixture and the resulting solution was extracted using DCM (3×). The organic layers were combined, dried over $MgSO_4$, and the solvent was removed in vacuo yielding 5.2 g (28.1 mmol, 95%) of 9-1 as a yellow oil.

Step B

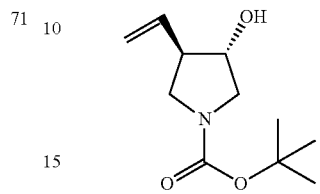

9-2

4.3 g (23.3 mmol) of compound 9-1 and 0.21 g (2.33 mmol) CuCN in 50 ml anhydrous THF were cooled to −78° C. Vinyl magnesium bromide (73.3 mmol) was added drop wise and the resulting solution was allowed to warm to ambient temperature during the course of 7 hours. The reaction was monitored by thin-layer chromatography and the product was eluted using 1:2 ethyl acetate and hexanes and staining with ninhydrin. The reaction was quenched with saturated $NH_4Cl$ and extracted with ethyl acetate (3×). The combined organic layers were dried over $MgSO_4$ and the solvent was removed in vacuo yielding 4.75 g (22.3 mmol, 96%) of 9-2 as a tan oil.

Step C

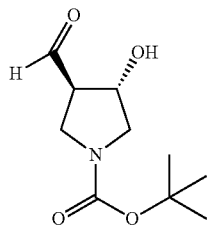

9-3

2.0 g (9.4 mmol) of 9-2 was dissolved in 20 ml THF and 10 ml $H_2O$ followed by the addition of 3.51 g (16.4 mmol) $NaIO_4$ and 0.23 ml osmium tetroxide. The reaction was stirred at ambient temperature under nitrogen yielding a white precipitate after 30 minutes. The reaction was monitored by thin-layer chromatography and the product was eluted using 1:1 ethyl acetate and hexanes and staining with ninhydrin. The reaction was complete after approximately 8 hours. Excess $H_2O$ was added to the reaction mixture and the resulting solution was extracted using ethyl acetate (3×). The combined organic layers were washed with saturated $NaHCO_3$ and brine, dried over $MgSO_4$, and the solvent was removed in vacuo yielding 1.35 g (6.3 mmol, 67%) of 9-3 as a tan foam.

Compound 297, 298, 299, 300, 307, 308, 309, 310, 326, and 327 were synthesized using similar procedures as in Example 6, 7, and 8 using intermediate 9-3 as intermediate in reductive amination step.

Example 10

Preparation of N-[(1R)-1-(1-benzyl-4-phenyl-1H-imidazol-2-yl)-2,2-dimethylpropyl]-N-[(3R)-3,5-diamino-5-oxopentyl]benzamide (Compound 100)

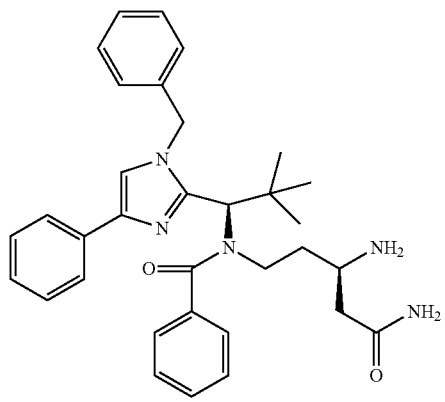 [SMILES: CC(C)(C)[C@H](c1nc(-c2ccccc2)cn1Cc1ccccc1)N(CC[C@@H](N)CC(N)=O)C(=O)c1ccccc1]

Step A: Thio-Ester Synthesis

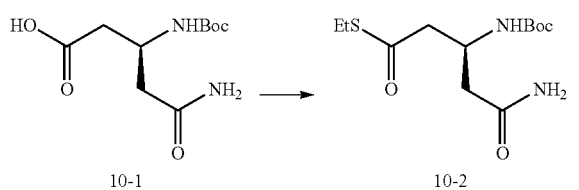

To a stirred solution of Boc-L-β-homoasparagine 10-1 (8.0 mmol) and ethane thiol (16 mmol) in DMF (10 ml) was added 1,3-dicyclohexylcarbodimide (8.8 mmol) and DMAP (0.8 mmol). The reaction was stirred at room temperature until the reaction was complete. The precipitate was filtered and washed with ethyl acetate. The organics were combined and concentrated. Separation on a silica gel column with ethyl acetate gave the desired thioester 10-2.

Step B: Aldehyde Synthesis

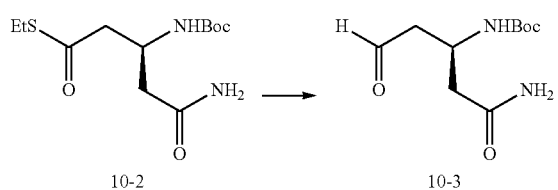

To a stirred mixture of ethyl thio ester 10-2 (0.1 mmol) and 10% Pd on carbon (20 mol %) in acetone (1 ml) was added Et$_3$SiH (4.4 mmol) at room temperature under an argon atmosphere. Stirring was continued at room temperature until the reduction was complete in about 30 min. The catalyst was filtered off through Celite and washed with acetone. Evaporation under reduced pressure produced aldehyde 10-3, which was use directly in the next step.

Step C: Reductive Amination to Install Sidechain

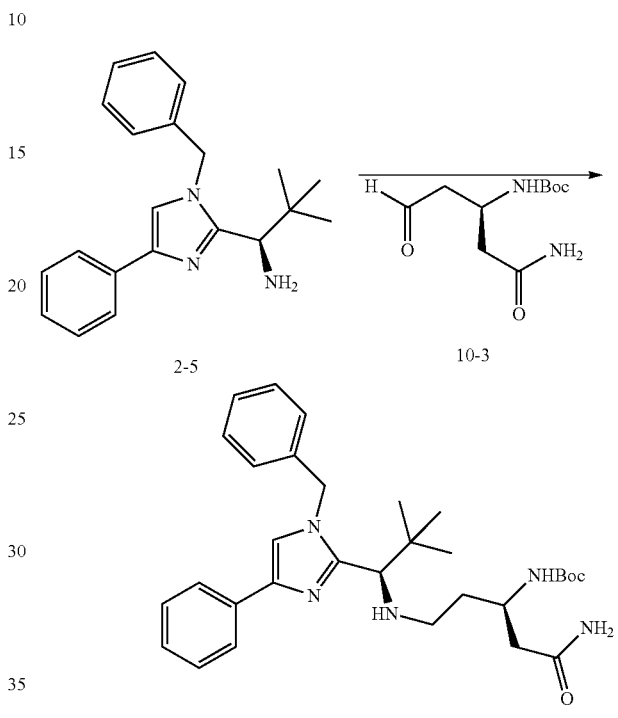

To a stirred solution of amine 2-5, from Example 2 above (1.0 mmol) in CH$_2$Cl$_2$ was added appropriate aldehyde 10-3 (1.0 mmol) (7 ml). The mixture was allowed to stir for 5 min before the addition of sodium tris-acetoxyborohydride (1.0 mmol). Once the reaction was complete, the mixture was concentrated in vacuo, partitioned between EtOAc and 2M aq. Na$_2$CO$_3$. The organics were separated, then washed with 2M aq. Na$_2$CO$_3$ (×2), H$_2$O (×2), brine (×2), then dried (Na$_2$SO$_4$), filtered, and evaporated under reduced pressure to give product 10-4 which was used directly in the next step.

Step D: Acylation

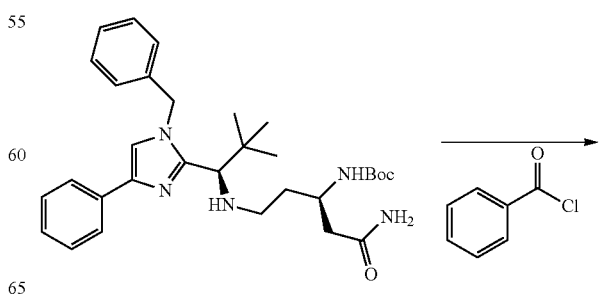

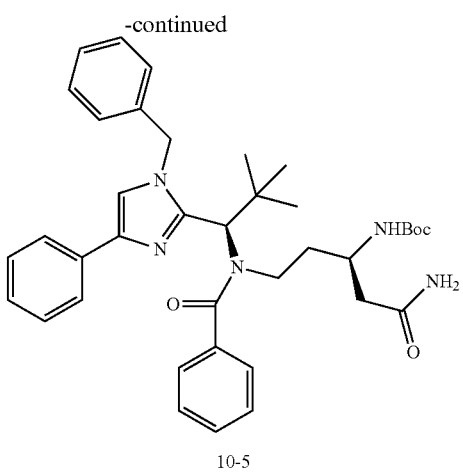

10-5

To a stirred solution of amine 10-4 (1.0 mmol) in CH₂Cl₂ (6 ml) was added Et₃N (2.0 mmol), DMAP (10.1 mmol) followed by benzoyl chloride (1.0 mmol). Once the reaction was complete, the mixture was partitioned between CH₂Cl₂ and sat. aq. NaHCO₃. The organics were separated and washed with H₂O (×2), brine (×2), then dried (Na₂SO₄), filtered, and evaporated under reduced pressure to give product 10-5, which was further purified by reverse phase HPLC.

E: Final Deprotection

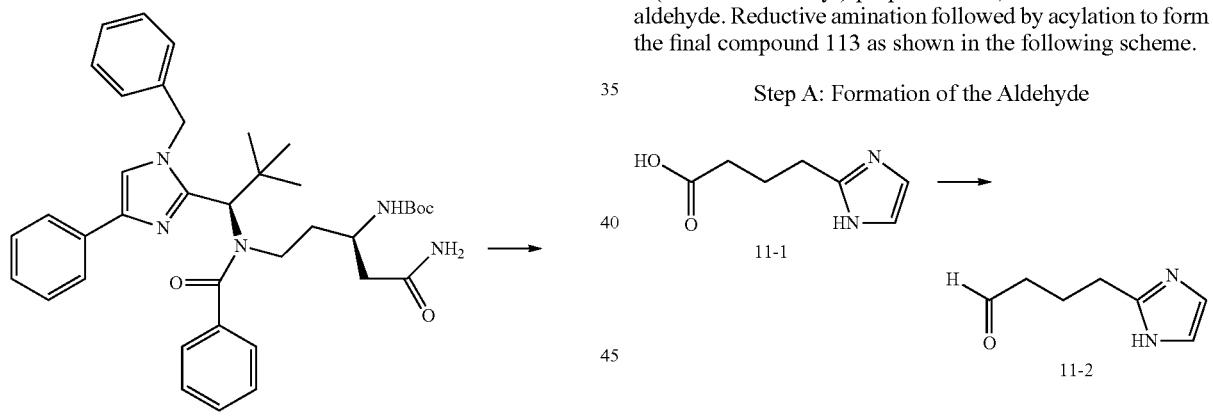

The Boc protected compound 10-5 was treated with HCl in dioxane (4N, 10 eq.) for 30 min, and the solvent was removed to give the final product 100 as HCl salt.

Example 11

Preparation of N-[(1R)-1-(1-benzyl-4-phenyl-1H-imidazol-2-yl)-2,2-dimethylpropyl]-N-[3-(1H-imidazol-2-yl)propyl]benzamide (Compound 113)

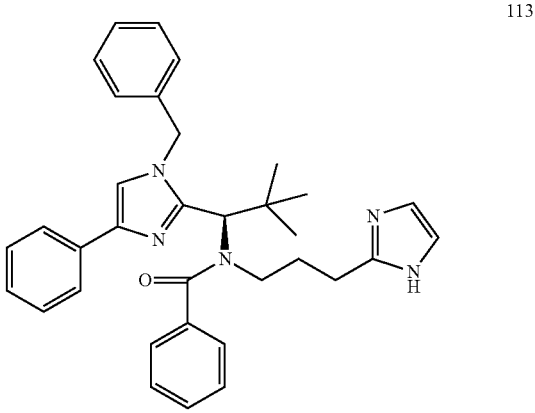 [SMILES: CC(C)(C)[C@H](c1nc(-c2ccccc2)cn1Cc1ccccc1)N(CCCc1ncc[nH]1)C(=O)c1ccccc1]

Using the similar procedures to make the thiol ester from 3-(1H-imidazole-2-yl)-propionic acid, then reduced to the aldehyde. Reductive amination followed by acylation to form the final compound 113 as shown in the following scheme.

Step A: Formation of the Aldehyde

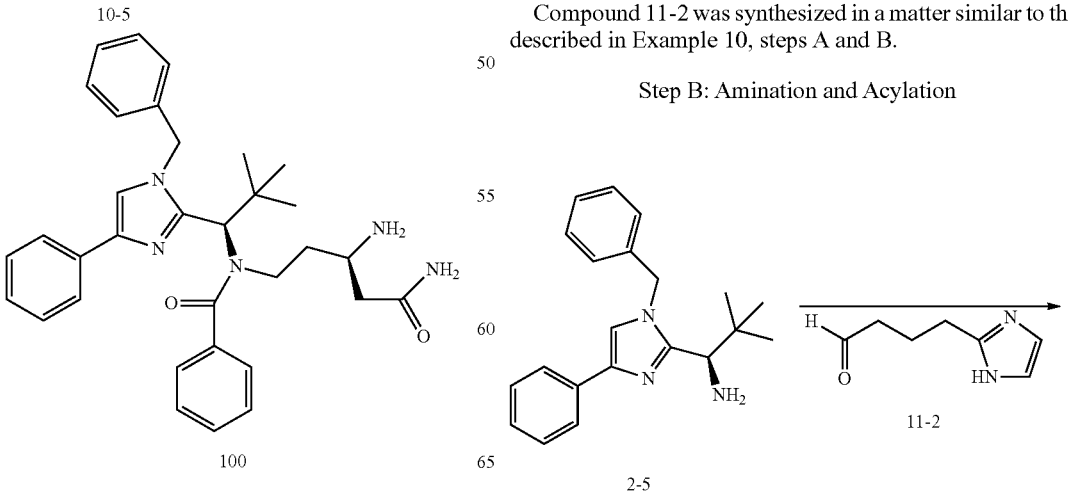

Compound 11-2 was synthesized in a matter similar to that described in Example 10, steps A and B.

Step B: Amination and Acylation

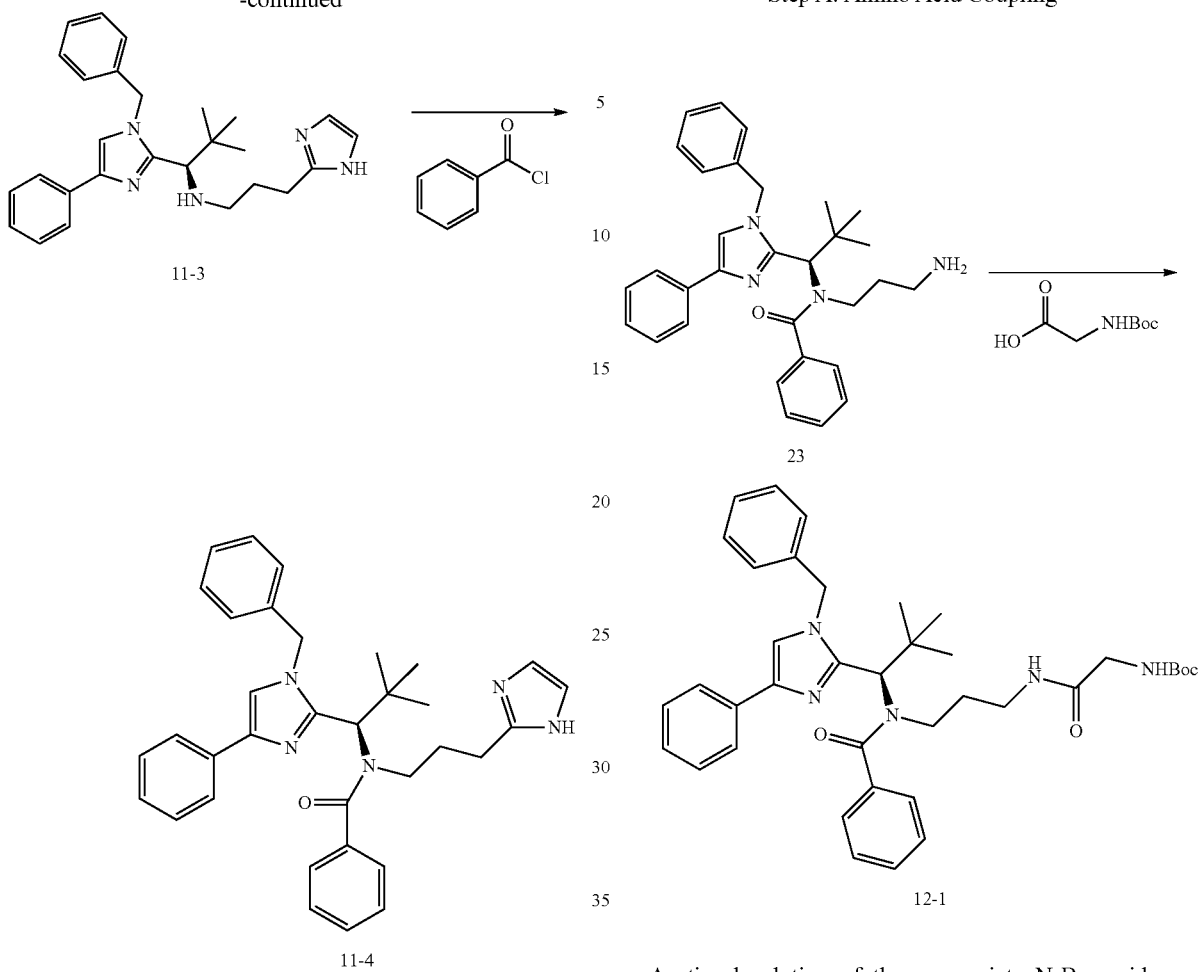

Compound 11-4 was synthesized using procedures similar to that in Example 10, steps C, D, and E.

Example 12

Preparation of N-{3-[(aminoacetyl)amino]propyl}-N-[(1R)-1-(1-benzyl-4-phenyl-1H-imidazol-2-yl)-2,2-dimethylpropyl]benzamide (Compound 101)

Step A: Amino Acid Coupling

A stirred solution of the appropriate N-Boc-acid, e.g. N-Boc-Glycine (0.15 mmol) and phenylimidazole amine compound 23 (0.1 mmol) in THF (3 ml) was treated with PyBOP (0.15 mmol) and Et₃N (0.3 mmol). Compound 23 was prepared using the method described in Example 1. The reaction was stirred at room temperature until the completion, and was evaporated under reduced pressure. Purification by silica gel column to give the protected amine 12-1.

Step B: Final Deprotection

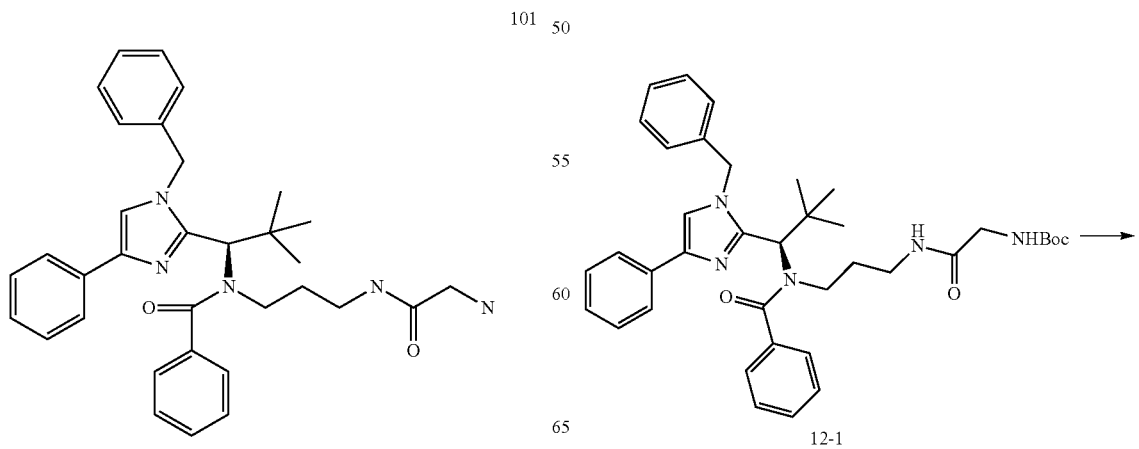

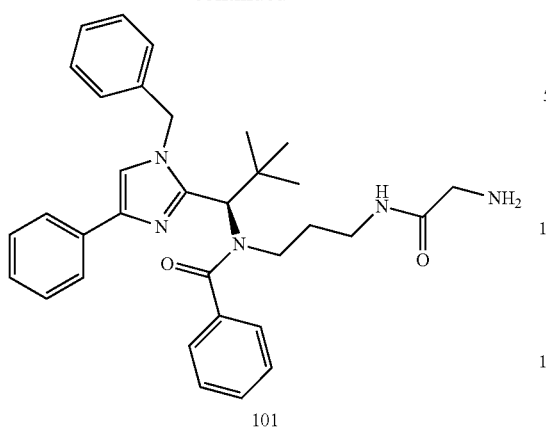

101

The Boc protected compound 12-1 was treated with HCl in dioxane (4N, 10 eq.). Once the reaction was complete, the solvent was removed to give the final product, compound 101, which was purified by reverse phase prep. HPLC.

The following compounds were synthesized using the similar procedures:

Compound 102

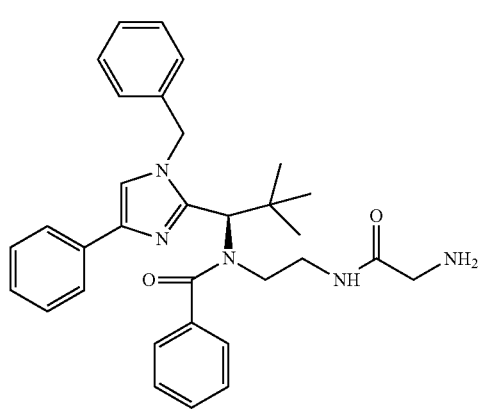

Compound 146

Chiral

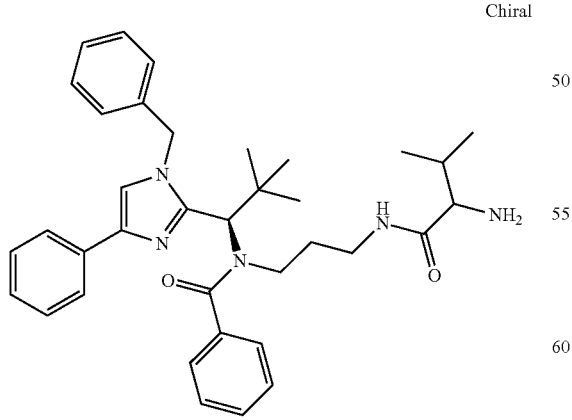

Example 13

Preparation of Carboxyl and Carboxyl Ester-Containing Compounds of the Invention

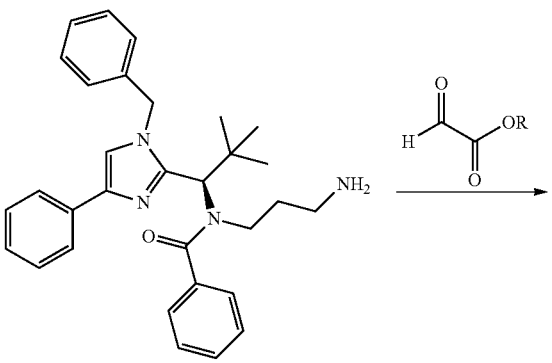

23

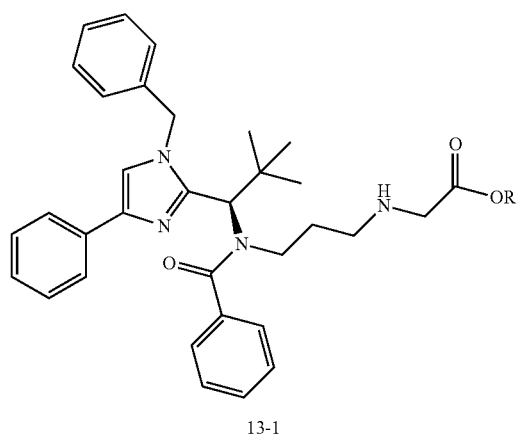

13-1

To a stirred solution of amine 23 (0.1 mmol) was added appropriate aldehyde, e.g., glyoxylic acid (0.1 mmol) in $CH_2Cl_2$ (1 ml). The mixture was allowed to stir for min before the addition of sodium tris-acetoxyborohydride (0.1 mmol). Once the reaction was complete, the mixture was concentrated and purified by reverse phase prep. HPLC to get the title compound 13-1 as TFA salt.

The following compounds were prepared by this procedure:

Compound 139

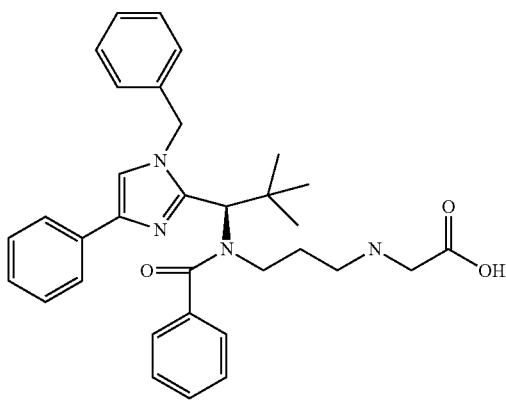

Compound 145

Chiral

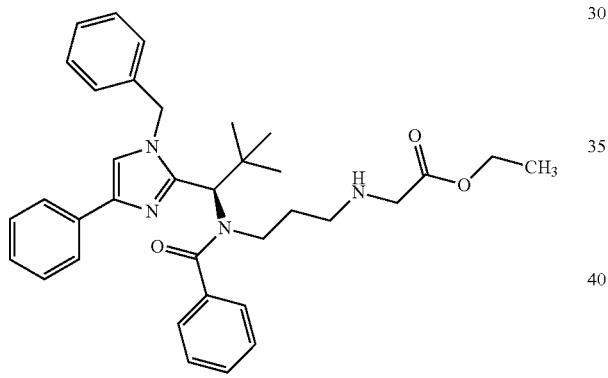

Example 14

Preparation of 1-benzyl-6-(1-benzyl-4-phenyl-1H-imidazol-2-yl)piperidin-2-one (Compound 114)

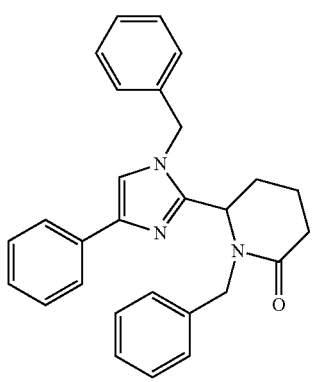 [SMILES: O=C1CCCC(c2nc(-c3ccccc3)cn2Cc2ccccc2)N1Cc1ccccc1]

Step A: Lactam formation

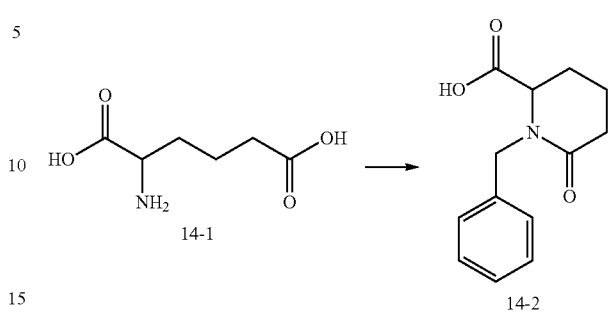

DL-α-Aminoadipic acid hydrate 14-1 (2 g, 11 mmol) was dissolved in 2 M NaOH (11 ml, 22 mmol). Benzaldehyde (1.4 ml, 11 mmol) was dissolved in 3.0 ml of ethanol and this solution was added to the first solution. After 10 minutes the mixture was cooled to 0° C. and sodium borohydride (0.13 g, 3.3 mmol) was added. After 1 hour, the reaction was complete as monitored by LCMS. The solution was extracted 3 times with 20 ml portions of ether, cooled to 0° C., acidified to pH 2 with concentrated HCl and the resulting precipitate was filtered to afford a white solid. The solid was washed once with a minimum amount of acetonitrile (1 ml) and three times with ether. The crude solid was dissolved in 55 ml ethanol and the solution was refluxed overnight. The solution was evaporated to provide the lactam product 14-2.

Step B: Keto Ester Formation

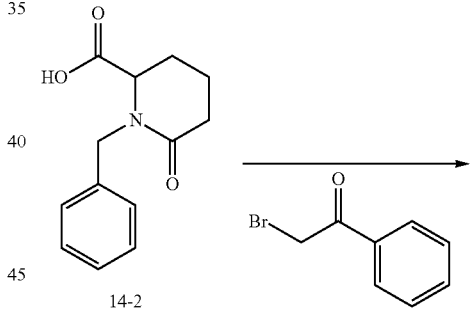

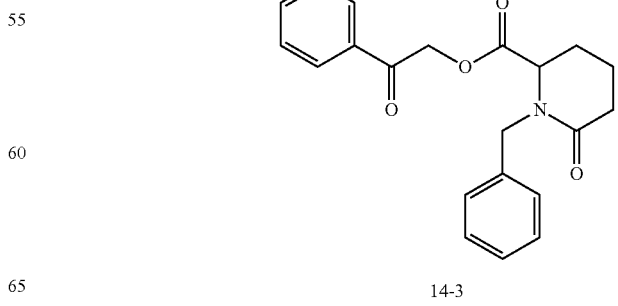

A stirred solution of the lactam acid 14-2 (4.0 mmol) in EtOH (10 ml) was treated with Cs$_2$CO$_3$ (2.0 mmol). After 45 min, the EtOH was removed by evaporation under reduced pressure. The residual cesium salt was re-dissolved in DMF (15 ml) and the treated with 2-bromoacetophenone (4.0 mmol) and stirred at r.t. until the reaction was complete. The reaction mixture was then partitioned between EtOAc and H$_2$O, and the organics separated, washed with H$_2$O (×3), brine (×3), then dried (Na$_2$SO$_4$), filtered, and evaporated under reduced pressure. The residue was purified by silica gel column to afford the keto ester 14-3.

Step C: Formation of the Phenyl-Imidazole

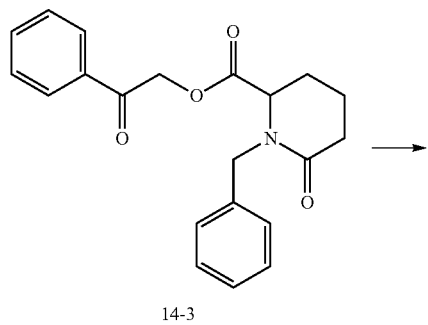

14-3

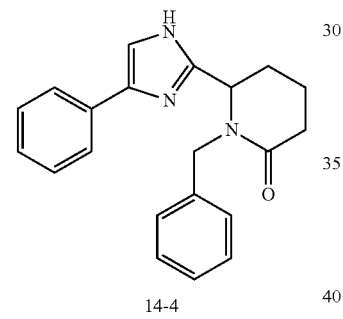

14-4

To a stirred solution of keto-ester 14-3 (4.0 mmol) in xylenes (40 ml) was added ammonium acetate (20 mmol). A Dean-Stark trap was added and the reaction heated to 140° C. Once the reaction was complete, the mixture was allowed to cool to r.t., then partitioned between EtOAc and sat. aq. NaHCO$_3$. The organics were separated, then washed with sat. aq. NaHCO$_3$ (×2), H$_2$O (×3), brine (×3), then dried (Na$_2$SO$_4$), filtered, and evaporated under reduced pressure to give the phenyl imidazole which was purified on a silica gel column to get the title compound 14-4.

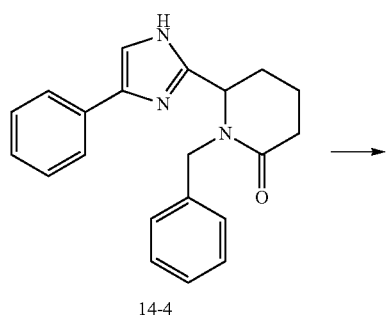

14-4

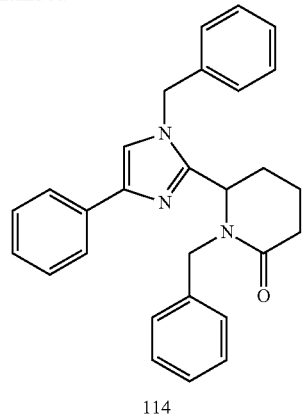

114

To a stirred suspension of imidazole 14-4 (4.0 mmol) and K$_2$CO$_3$ (8.0 mmol) in DMF (10 ml) was added the benzylating agent, benzyl bromide (4.40 mmol). Once the reaction was complete, the mixture was partitioned between EtOAc and H$_2$O. The organic layer was separated and washed with H$_2$O (×3), brine (×3), then dried (Na$_2$SO$_4$), filtered, and evaporated under reduced pressure to give the crude benzylated phenyl imidazole 114. The crude reaction material was then purified by silica gel column or reverse phase HPLC. The following compound was also prepared by using a similar procedure.

Compound 115

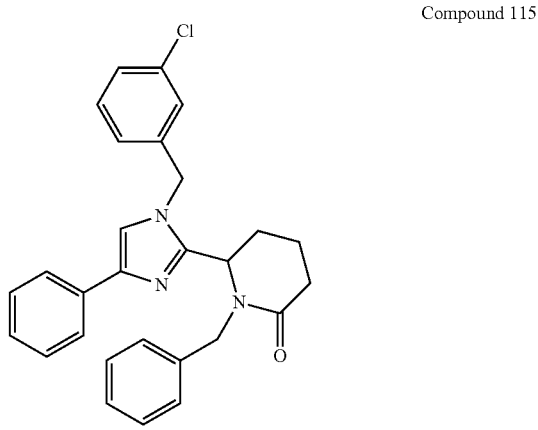 [SMILES: O=C1CCCC(c2nc(-c3ccccc3)cn2Cc2cccc(Cl)c2)N1Cc1ccccc1]

Example 15

Preparation of N-(3-Amino-propyl)-N-{1-[1-(3-fluoro-benzyl)-4-(3-fluoro-phenyl)-1H-imidazol-2-yl]-1-methyl-ethyl}-2-methoxy-acetamide (compound 393)

Step A: Synthesis of (tert-butoxy)-N-{1-[4-(3-fluorophenyl)-imidazol-2-yl]-isopropyl}carboxamide To 2-[(tert-butoxy)carbonylamino]-2-methylpropanoic acid (1 eq.) in N,N-dimethylformamide was added ammonium carbonate (1 eq.) and the mixture was heated to 110° C. for 10 min. The reaction mixture was cooled to 60° C. and to it was added 2-bromo-1-(3-fluorophenyl)ethan-1-one (0.2 eq.) and the mixture was heated to 125° C. for 3 h. LCMS showed the formation of (tert-butoxy)-N-{1-[4-(3-fluorophenyl-imidazol-2-yl]-isopropyl}carboxamide. The reaction mixture was concentrated and partitioned between ethyl acetate and water. The organic layer was separated and washed with saturated sodium chloride solution and dried with sodium sulfate. The resulting crude was purified by silica gel chromatography to give (tert-butoxy)-N-{1-[4-(3-fluorophenyl-imidazol-2-yl]-isopropyl}carboxamide.
MS: $MH^+$=320.

Step B: Synthesis of (tert-butoxy)-N{1-[4-(3-fluorophenyl-1-[(3-fluorophenyl)methyl]imidazol-2-yl]-isopropyl}carboxamide To a stirred solution/suspension of (tert-butoxy)-N-{1-[4-(3-fluorophenyl-imidazol-2-yl]-isopropyl}carboxamide (1 eq.) and potassium carbonate (2 eq.) in N,N-dimethylformamide was added 1-(bromomethyl)-3-fluorobenzene (1.1 eq.). Once the reaction was complete, the mixture was partitioned between ethyl acetate and water. The organic layer was separated and washed with water, saturated sodium chloride solution, then dried with sodium sulfate, filtered, and evaporated under reduced pressure to give the crude benzylated phenyl imidazole. The crude reaction material was purified by silica gel chromatography.
MS: $MH^+$=428.

Step C: Synthesis of 2-{4-(3-fluorophenyl}-1-[(3-fluorophenyl)methyl]imidazol-2-yl}prop-2-yl-amine To (tert-butoxy)-N {1-[4-(3-fluorophenyl-imidazol-2-yl]-isopropyl}carboxaimide (1 eq.) was added 10% trifluoroacetic acid in methylene chloride. Once the reaction was complete the mixture was concentrated and partitioned between saturated sodium carbonate and ethyl acetate. The organic layer was separated and washed with water saturated sodium chloride solution, then dried with sodium sulfate, filtered, and evaporated under reduced pressure to give 2-{4-(3-fluorophenyl}-1-[(3-fluorophenyl)methyl]imidazol-2-yl}prop-2-yl-amine.
MS: $MH^+$=328.

Step D: Synthesis of 2-{3-[(1-{4-(3-fluorophenyl)-1-[(3-fluorophenyl)methyl]imidazol-2-yl}-isopropyl)amino]propyl}benzo[C]azoline-1,3-dione To a stirred solution of 2-{4-(3-fluorophenyl}-1-[(3-fluorophenyl)methyl]imidazol-2-yl}prop-2-yl-amine amine (1 eq.) and 2-(3-oxopropyl)benzo[C]azoline-1,3-dione (1 eq.) in methylene chloride at 0° C. was added acetic acid (1 eq.) followed by the addition of sodium tris-acetoxyborohydride (1.5 eq.). Once the reaction was complete, the mixture was concentrated in vacuo, partitioned between ethyl acetate and saturated sodium bicarbonate solution. The organic layer was separated and washed with saturated bicarbonate and water followed by saturated sodium chloride solution, then dried with sodium sulfate, filtered, and evaporated under reduced pressure to give crude product which was purified by silica gel chromatography.
MS: $MH^+$=515.

Step E: Synthesis of N-[3-(1,3-dioxobenzo[C]azoline-2-yl)propyl]-N-(1-{4-(3-fluorophenyl}-1-[3-fluorophenyl)methyl]imidazol-2-yl}-isopropyl)-2-methoxyacetamide To a stirred solution of 2-{(1S)-1-(fluoromethyl)-3-[(1-{4-(3-fluorophenyl)-1-[(3-fluorophenyl)methyl]imidazol-2-yl}-isopropyl)amino]propyl}benzo {C}azoline-1,3-dione) (1 eq.) in methylene chloride was added methoxy acetylchloride (3 eq.) and triethylamine (3 eq.). Once the reaction was complete, the mixture was concentrated in vacuo, partitioned between ethyl acetate and saturated sodium bicarbonate solution. The organic layer was separated and washed with saturated bicarbonate and water followed by saturated sodium chloride solution, then dried with sodium sulfate, filtered, and evaporated under reduced pressure to give N-[3-(1,3-dioxobenzo[C]azline-2-yl)propyl]-N-(1-{4-(3-fluorophenyl}-1-[3-fluorophenyl)methyl]imidazol-2-yl}-isopropyl)-2-methoxyacetamide
MS: $MH^+$=587.

Step F: Synthesis of N-(3-Amino-propyl)-N-{1-[1-(3-fluoro-benzyl)-4-(3-fluoro-phenyl)-1H-imidazol-2-yl]-1-methyl-ethyl}-2-methoxy-acetamide To a stirred solution of 2-{(1S)-1-(fluoromethyl)-3-[(1-{4-(3-fluorophenyl)-1-[(3-fluorophenyl)methyl]imidazol-2-yl}-isopropyl)amino]propyl}benzo {C}azoline-1,3-dione) in ethanol was added hydrazine (1.5 eq.). Once the reaction was complete it was filtered and the filtrate was evaporated under reduced pressure. It was purified on preparative HPLC to give N-(3-Amino-propyl)-N-{1-[1-(3-fluoro-benzyl)-4-(3-fluoro-phenyl)-1H-imidazol-2-yl]-1-methyl-ethyl}-2-methoxy-acetamide
MS: $MH^+$=457.

Example 16

Alternate Preparation of N—((S)-3-amino-4-methoxybutyl)-N—((R)-1-(1-benzyl-4-(2,5-difluorophenyl)-1H-imidazol-2-yl)-2,2-dimethylpropyl)-2-methoxyacetamide (Compound 422)

Step A: Synthesis of tert-butyl (S)-1-((benzyloxy)carbonyl)-3-methoxypropan-2-ylcarbamate To tert-butyl (S)-1-((benzyloxy)carbonyl)-3-hydroxypropan-2-ylcarbamate (1 eq.) in dichloromethane was added 2,6-di-t-butyl 4-methylpyridine (2.5 eq.) and trimethyloxonium tetrafluoroborate (1.25 eq.) at 0° C. The reaction mixture was gradually warm to room temperature and stirred overnight. The reaction mixture was diluted with dichloromethane and washed with cold satd. sodium bicarbonate, water, and brine and dried over sodium sulfate. Purification by silica gel chromatography (25% EtOAc/Hexane) provide pure product as a colorless viscous liquid.
MS: $MH^+$=324.1

Step B: Synthesis of tert-butyl (S)-1-formyl-3-methoxypropan-2-ylcarbamate

Azeotrope tert-butyl (S)-1-((benzyloxy)carbonyl)-3-methoxy propan-2-ylcarbamate (1 eq.) with toluene (x=3). Dissolved in dichloromethane and cooled to −78° C. To then was added drop wise 1 M solution of DIBAL in toluene (2 eq.) under $N_2$ atmosphere and stirred at −78° C. for 2 h. The reaction was quenched with methanol and concentrated. To concentrated residue was added 2 M potassium sodium tartrate solution at 0° C. and stirred vigorously at room temperature for 30 min. Partitioned between ethyl acetate and water. The organic layer was washed with brine and dried over sodium sulfate. Filtered, evaporated and dried under high-pressure vacuum to provide product as a colorless viscous liquid.
MS: $MH^+$=218.2

Step C: Synthesis of tert-butyl (S)-4-((R)-1-(1-benzyl-4-(2,5-difluorophenyl)-1H-imidazol-2-yl)-2,2-dimethylpropylamino)-1-methoxybutan-2-ylcarbamate To (R)-1-(1-benzyl-4-(2,5-difluorophenyl)-1H-imidazol-2-yl)-2,2-dimethylpropan-1-amine (1 eq) in dichloromethane was added tert-butyl (S)-1-formyl-3-methoxypropan-2-ylcarbamate (1.5 eq) and acetic acid (1 eq). The reaction mixture was stirred at room temperature for 1 h. Sodium triacetoxy borohydride (2 eq) was added at 0° C. The reaction mixture was warmed to room temperature and stirred overnight. Solvent was concentrated and crude was partitioned between ethyl acetate and satd. sodium bicarbonate. The organic layer was washed with water, brine and dried over sodium sulfate. Purification by silica gel chromatography (25% EtOAc/Hexane) provide pure product as a white foamy solid.
MS: MH+=557.2

Step D: Synthesis of tert-butyl (S)-4-((R)-1-(1-benzyl-4-(2,5-difluorophenyl)-1H-imidazol-2-yl)-2,2-dimethylpropyl)-2-methoxyacetamido)-1-methoxybutan-2-ylcarbamate To tert-butyl (S)-4-((R)-1-(1-benzyl-4-(2,5-difluorophenyl)-1H-imidazol-2-yl)-2,2-dimethylpropylamino)-1-methoxybutan-2-ylcarbamate (1 eq.) in THF was added triethylamine (2 eq.) and methoxyacetalchloride (10 eq.). Stirred at room temperature for 30 min. The reaction mixture was diluted with ethyl acetate and washed with water and brine. Dried over sodium sulfate. Filtered, evaporated and dried under reduced pressure to provide product as a colorless semi solid.
MS: MH+=629.2

Step E: Synthesis of N—((S)-3-amino-4-methoxybutyl)-N—((R)-1-(1-benzyl-4-(2,5-difluorophenyl)-1H-imidazol-2-yl)-2,2-dimethylpropyl)-2-methoxyacetamide To tert-butyl (S)-4-((R)-1-(1-benzyl-4-(2,5-difluorophenyl)-1H-imidazol-2-yl)-2,2-dimethylpropyl)-2-methoxyacetamido)-1-methoxybutan-2-ylcarbamate was added 30% TFA/DCM. Stirred at room temperature for 1 h. Solvent was evaporated. Purification by preparative chromatography provide product as a white solid.
MS: MH+=529.1

Example 17

Preparation of Intermediate (R)-1-(1-benzyl-4-(pyrazin-2-yl)-1H-imidazol-2-yl)-2,2-dimethylpropan-1-amine This intermediate is useful in preparing compounds of the invention which have pyrazine substituent, such as Compound 328, 331 and the like.

Step A: TMS-Enol Ether Synthesis

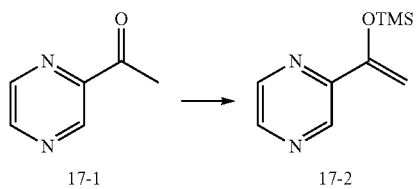

To a stirred solution of acetylpyrazine 17-1 (24.6 mmol) and TMSCl (24.6 mmol) in THF (12.3 ml) in a −78° C. acetone/dry ice bath was added LiHMDS (24.6 mmol, 1.0 M solution in THF) dropwise via an addition funnel. After 90 min, the reaction was allowed to warm to r.t. To the reaction was added cold EtOAc and the organics were washed with sat. aq. NaHCO₃ (×3) and cold brine (×1), then dried (Na₂SO₄), filtered, and concentrated in vacuo to provide a yellow liquid. The liquid was purified via flash chromatography (5% EtOAc/hexanes) to give 85% pure product 17-2 (remaining 15% as starting pyrazine).

Step B: α-Bromo Ketone Synthesis

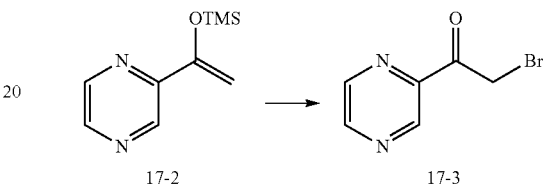

To a stirred solution of TMS enol ether 17-2 (6.5 mmol) in cold pentane (15.2 ml), was added a solution of bromine (6.8 mmol) in pentane (5.3 ml) dropwise. After 1 h, the reaction was diluted with EtOAc. The organics were washed with sat. aq. NaHCO₃ (×3) and brine (×1), dried (Na₂SO₄), filtered, and evaporated under reduced pressure to give a brown solid.

Step C: Keto-Ester Synthesis

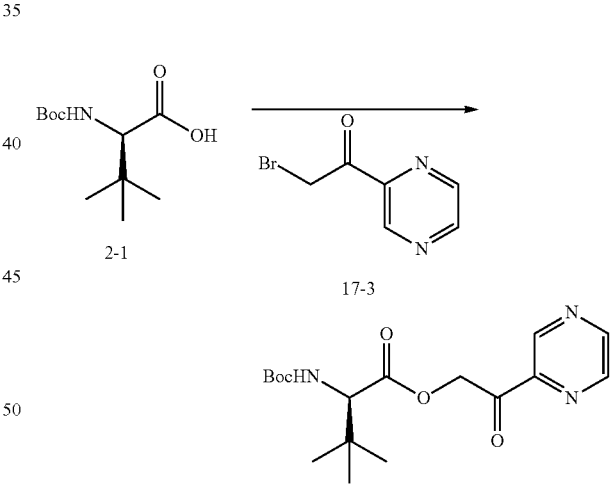

A stirred solution of tert-butyl leucine 2-1 (4.5 mmol), in EtOH (15 ml) was treated with Cs₂CO₃ (2.25 mmol). After 45 min, the EtOH was removed by evaporation under reduced pressure. The residual cesium salt was re-dissolved in DMF (15 ml) and the treated with the α-bromo ketone 17-3 (4.5 mmol) and stirred at room temperature until the reaction was complete. The reaction mixture was then partitioned between EtOAc and H₂O, and the organics separated, then washed with H₂O (×3), brine (×3), then dried (Na₂SO₄), filtered, and evaporated under reduced pressure to give the keto-ester 17-4 which was pure enough to use directly in the next step.

Step D: Pyrazine-Imidazole Formation

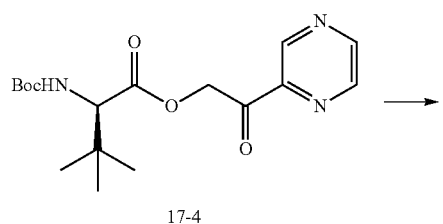

17-4

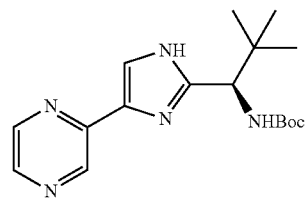

17-5

To a stirred solution of keto-ester 17-4 (4.4 mmol) in xylenes (44 ml) was added ammonium acetate (22 mmol). A Dean-Stark trap was added and the reaction heated to 140° C. Once the reaction was complete, the mixture was allowed to cool to r.t., then partitioned between EtOAc and sat. aq. NaHCO$_3$. The organics were separated, then washed with sat. aq. NaHCO$_3$ (×2), H$_2$O (×3), brine (×3), then dried (Na$_2$SO$_4$), filtered, and evaporated under reduced pressure to give the pyrazine-imidazole 17-5 which was pure enough to use directly in the next step.

Step E: Benzylation of the Pyrazine-Imidazole

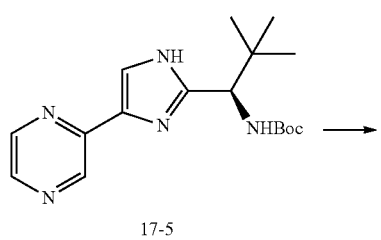

17-5

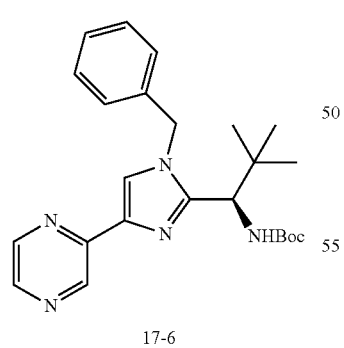

17-6

To a stirred solution/suspension of imidazole 17-5 (0.9 mmol) and K$_2$CO$_3$ (1.8 mmol) in DMF (3 ml) was added benzyl bromide (0.95 mmol). Once the reaction was complete, the mixture was partitioned between EtOAc and H$_2$O. The organic layer was separated and washed with H$_2$O (×3), brine (×3), then dried (Na$_2$SO$_4$), filtered, and evaporated under reduced pressure to give the crude benzylated imida- zole. The crude reaction material was then purified via flash chromatography (15% EtOAc/hexanes) to give pure product 17-6.

Step F: Deprotection to the Free Amine

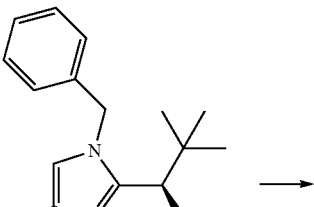

17-6

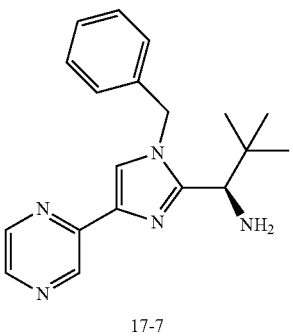

17-7

Boc-protected amine 17-6 (0.5 mmol) was treated with 20% TFA in CH$_2$Cl$_2$ (5 ml). Once reaction was complete, the reaction was concentrated in vacuo and then partitioned between EtOAc and sat. aq. NaHCO$_3$. The organics were separated, then washed with sat. aq. NaHCO$_3$ (×2), H$_2$O (×2), brine (×2), then dried (Na$_2$SO$_4$), filtered, and evaporated under reduced pressure to give the imidazole free amine 17-7 which was pure enough to use as an intermediate in synthe- sizing compounds of the invention with the pyrazine substi- tution.

Example 18

Preparation for Intermediate of β-Fluoro Aldehyde Side Chain

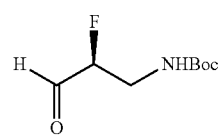 [SMILES: CC(C)(C)OC(=O)NC[C@H](F)C=O]

Step A: Amine Protection

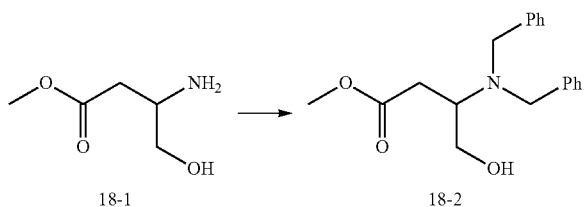

To a stirred solution of anhydrous K₂CO₃ (46.53 g, 0.3371 mol) in N,N-dimethylformamide (500 ml), D-serine methyl ester hydrochloride (35.0 g, 0.2250 mol), KI (18.66 g, 0.1124 mol) and benzyl bromide (96.18 g, 0.5623 mol) were added in one shot. The reaction mixture was stirred vigorously for 5 h at room temperature. After completion of reaction, contents were poured into ice water and extracted with ethyl acetate. The combined organic layer was washed with water, brine, dried over Na₂SO₄ and concentrated to give a crude product 18-2. Purification was carried out by column chromatography to yield pure (61.7 g, 91.7%) as pale yellow oil.

Step B: Fluorination

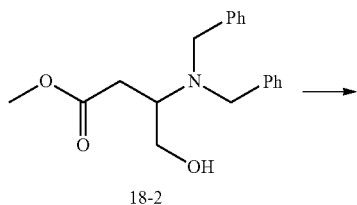

To a stirred solution of diethylamine sulphur trifluoride (32.3 ml, 0.2006 mol) in THF (400 ml), alcohol (100.0 g, 0.3344 mol) in THF (400 ml) was added dropwise compound 18-2 during the span of 3 h at room temperature. After completion of addition, stirring was continued for further 1 h. The mixture was extracted with ethylacetate and combined organic phase was washed with saturated solution of NaHCO₃. Removal of solvent under vacuum lead to a crude product, which was purified by column chromatography using hexane grading to 3% EtOAc in hexane afforded product 18-3 (70.4 g, 69.9%) as pale yellow oil.

Step C: Reduction

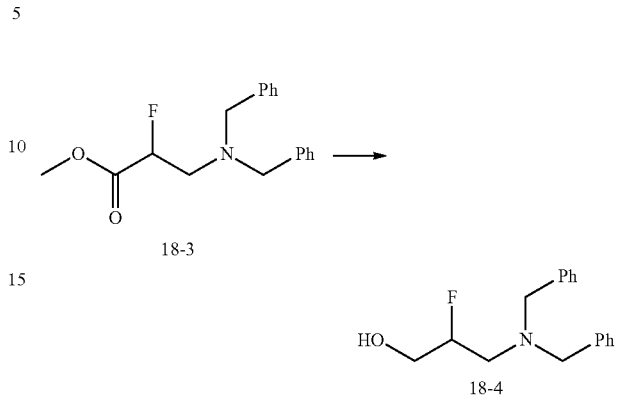

To a mechanically stirred solution of LiBH₄ (230.8 ml, 0.4651 mol) in THF (2.0 L), methyl ester (100.0 g, 0.3322 mol) in THF (1.0 L) was added dropwise 18-3 through addition funnel during the span of 3 h at −15° C. under N₂. After the completion of addition, stirring was continued for 4 h at room temperature. Saturated solution of NH₄Cl (500 ml) was added dropwise to the above mixture and extracted with EtOAc. The combined organic phase was washed with water, brine, dried over Na₂SO₄ and concentrated under vacuum. Residual oil was dissolved in 1N HCl (200 ml), extracted with diethylether and pH of the aqueous layer was adjusted to 10 with the help of NH₄OH (50%, 300 ml). The resultant was extracted with EtOAc and combined extracts were concentrated under vacuum to give product (86.2 g, 95.0%) as pale brown oil.

Step D: Deprotection

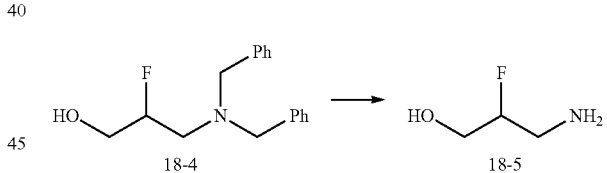

A mixture of alcohol 18-4 (50 g, 0.18315 mol) and Pd(OH)₂ on carbon (20%, 6.26 g, 0.04395 mol) in absolute ethanol (500 ml) was stirred for 7 h under the pressure of hydrogen at 50-60 psi. After the reaction, charcoal was removed by filtration and residue was concentrated on rota evaporator to get product 18-5 (15.8 g, 92.7%) as pale brown oil.

Step E: Boc-Protection

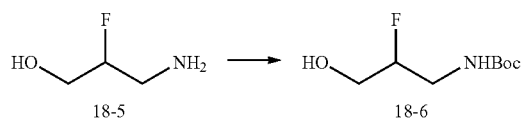 [SMILES: NCC(F)CO ; CC(C)(C)OC(=O)NCC(F)CO]

To a stirred mixture of amino alcohol 18-5 (15.0 g, 0.16129 mol) and K₂CO₃ (33.39 g, 0.24195 mol) in aqueous dioxane (~25%, 375 ml dioxane in 125 ml water), (Boc)₂O (38.66 g, 0.17733 mol) was added drop wise at 0° C. The reaction mixture was stirred overnight at room temperature after the addition. Saturated solution of KHSO₄ was added to the above mixture to adjust the pH 3-4 and extracted with EtOAc. The organic phase was concentrated under vacuum to give pure product (27.7 g, 89.0%) as a pale brown oil.

Step F: Oxidation to Aldehyde

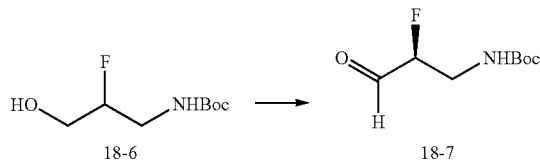 [SMILES: CC(C)(C)OC(=O)NCC(F)CO ; CC(C)(C)OC(=O)NC[C@H](F)C=O]

To a cooled (−78° C.), stirred solution of oxalyl chloride (84 mmol) in CH₂Cl₂ (180 ml) was added a solution of DMSO (168 mmol) in CH₂Cl₂ (90 ml). After 1 h, a solution of alcohol 18-6 (56 mmol) in CH₂Cl₂ (90 ml) was added. After 1 h, triethyl amine (281 mmol) was added and stirred for a further hour. Then a solution of saturated aqueous NH₄Cl was added and allowed to warm to room temperature. The organics were separated, washed with H₂O (×2), saturated brine (×2), then dried, filtered and evaporated under reduced pressure to give the crude aldehyde. Purification by column chromatography afforded the pure (S)-aldehyde.

Starting from the other enantiomer, (L)-serine methyl ester leads to the (R) enantiomer.

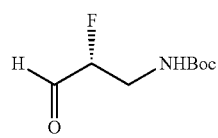

Example 19

Preparation for Intermediate of β-Fluoromethyl Aldehyde Side Chain

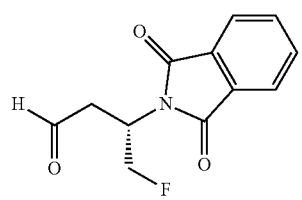 [SMILES: O=CC[C@@H](CF)N1C(=O)c2ccccc2C1=O]

Step A: (S)-3-((benzyloxy)carbonyl)-2-(1,3-dioxoisoindolin-2-yl)propanoic acid

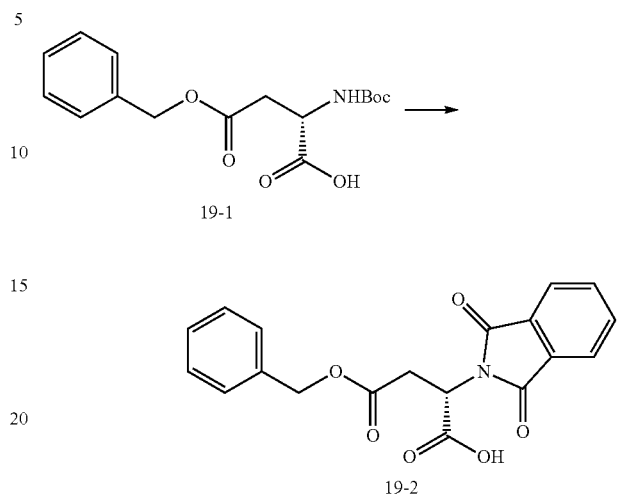

To a stirred solution of Boc-Asp(Obzl)-OH 19-1 (10.0 mmol) in 20 ml of DCM was added 10 ml of trifluoroacetic acid. The mixture was stirred at room temperature for 24 h. The reaction progress was followed by LCMS. After completion, the solvent and TFA were removed by evaporation under reduced pressure and lypholization to get white solid as TFA salts. The crude solid was suspended in 50 ml of THF and N-carboethoxy phthalimide (10.5 mmol), Et₃N (10 mmol) were added. The mixture was refluxed under N₂ for 18 hr. Then the reaction was cooled down and the solvents were evaporated off. DCM was added and washed with water, brine, dried over sodium sulfate, filter and concentrated. Purification by chromatography on silica gel column (Hexan/Ethylacetate) to give 2.68 g of colorless oil 19-2, yield 76%.

Step B: (S)-benzyl 4-hydroxy-3-(1,3-dioxoisoindolin-2-yl)butanoate

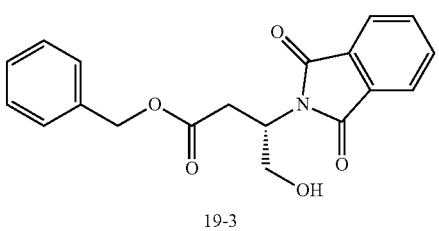

To a stirred solution of (S)-3-((benzyloxy)carbonyl)-2-(1,3-dioxoisoindolin-2-yl)propanoic acid (19-2, 6.07 mmol) in 30 ml of dry THF at −15° C. were successively added N-methylmorpholine (6.07 mmol), iso-butylchloroformate (6.07 mmol). After stirring for 5 min at −15° C., a solution of NaBH₄ (689 mg, 18.21 mmol) in 2.73 ml of water were added at once. The reaction was stirred at −15° C. for 2 min, then hydrolyzed with water (30 ml). Extracted with EtOAc (×3), washed with water (×3), brine (×1), dried over sodium sulfate, filtered, concentrated. Purification by chromatography on silica gel column (Hexan/Ethylacetate) to give 1.9 g of colorless oil 19-3, yield 92%.

Step C: (S)-benzyl 4-fluoro-3-(1,3-dioxoisoindolin-2-yl)butanoate

To a stirred solution of (S)-benzyl 4-hydroxy-3-(1,3-dioxoisoindolin-2-yl)butanoate (19-3, 5.6 mmol) in acetonitrile (28 ml) were added perfluoro-1-butane sulfonyl fluoride (44.8 mmol), diisopropylethylamine (44.8 mmol), and diisopropylethylamine trihydrofluoride (134 mmol). The mixture was stirred at 50° C. overnight. The reaction progress was followed by LCMS. After completion, the reaction was cooled down to room temperature, evaporated under reduced pressure. The mixture was then partitioned into DCM, washed with water (×3), brine (×2), dried over sodium sulfate, filtered, concentrated. Purification by chromatography on silica gel column (Hexan/Ethylacetate) to give light yellow oil 19-4, yield 40%.

Step D: (S)-4-fluoro-3-(1,3-dioxoisoindolin-2-yl)butanal

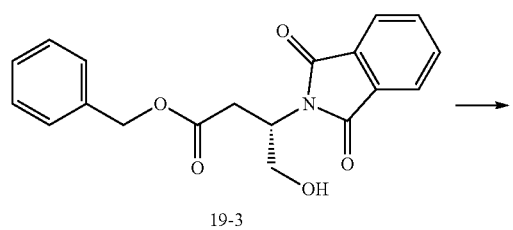

19-3

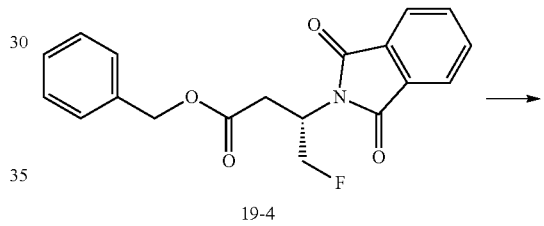

19-4

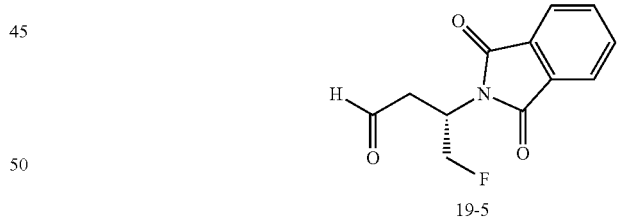

19-5

To a stirred solution of (S)-benzyl 4-fluoro-3-(1,3-dioxoisoindolin-2-yl)butanoate (19-4, 0.5 mmol) in dry ether (5 ml) was added dropwise diisobutylaluminum hydride (1.0 M in toluene, 1.5 mmol) at −78° C. The reaction was stirred at −78° C. for approximately 30 min as monitored by LC-MS. After completion, the reaction was quenched by adding water (10 ml) at −78° C. Extracted with ethyl acetate, washed with water (×3), brine (×2), dried over sodium sulfate, filtered and

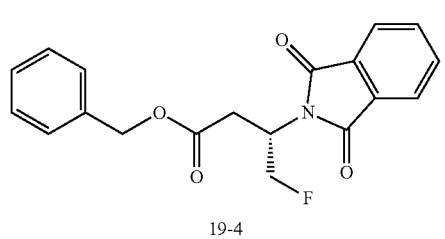

19-4 concentrated. The crude product 19-5 was used in the next reaction step.

An alternate route for preparing 19-5 is presented below.

Step A-1: (S)-4-fluoro-3-(1,3-dioxoisoindolin-2-yl) butanoic acid

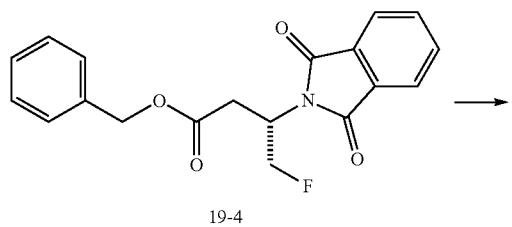

19-4

(S)-4-fluoro-3-(1,3-dioxoisoindolin-2-yl)butanoic acid 19-4 (0.20 mmol) was dissolved in ethanol (5 ml). This solution was purged with nitrogen for 10 minutes, then 10% palladium on carbon was added (0.02 mmol of palladium) under an atmosphere of nitrogen. Hydrogen was then bubbled rapidly through the solution, while stirring, for approximately 1 h. The reaction progress was followed with LCMS. The reaction mixture was filtered through celite to remove the palladium. The celite was rinsed twice with methylene chloride. The filtrate was then concentrated to give the crude product. The crude product 19-6 was used for the next reaction step.

Step A-2: (S)—S-ethyl 4-fluoro-3-(1,3-dioxoisoindolin-2-yl)butanethioate

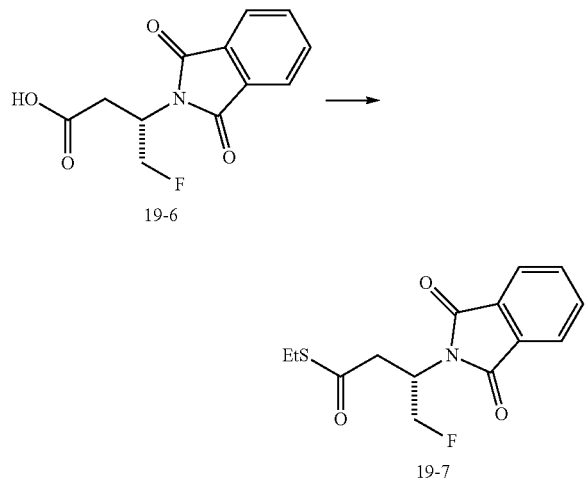

19-6 (0.20 mmol), 1,3 dicyclohexyl carbodiimid (0.30 mmol), ethanethiol (0.6 mmol), and 4-dimethylaminopyridine (0.10 mmol) were dissolved in DMF (5 ml). The mixture was stirred overnight at room temperature. The reaction completion was determined with LCMS.EtOAc was added to the reaction mixture. This was then washed with water (2×) and brine (2×). The EtOAc layer was then dried over sodium sulfate, filtered, and concentrated. The crude product was then purified using flash chromatography.

Step A-3: (S)-4-fluoro-3-(1,3-dioxoisoindolin-2-yl) butanal

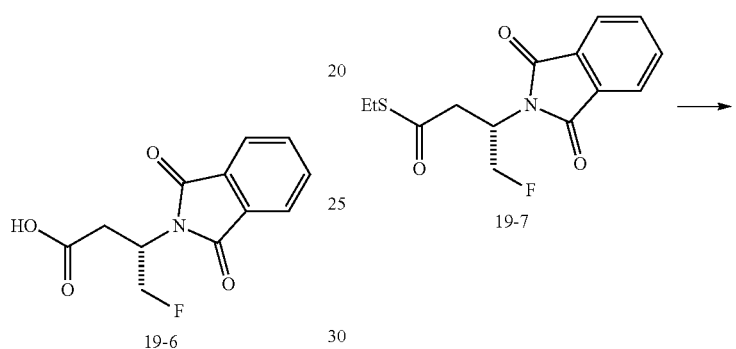

19-7 (0.20 mmol) was dissolved in dry acetone (10 ml). 10% Palladium (0.02 mmol) on carbon was then added under an atmosphere of nitrogen. Triethyl silane (0.5 mmol) was then added. Bubbling occurred after about 10 seconds, and the reaction was allowed to continue until the bubbling ceased (30 min). The reaction completion was determined using LCMS. The reaction mixture was filtered through a celite plug. The plug was washed twice with methylene chloride, and the filtrate was then concentrated to give the crude product. The crude product was used in the next reaction.

Starting from the other (R) enantiomer, (R)-3-((benzyloxy) carbonyl)-2-(1,3-dioxoisoindolin-2-yl)propanoic acid, leads to the other enantiomer.

The compounds in the table below were prepared using the methodology described in the previous Examples and Methods. The following tables also include compounds described in the experimentals. The starting materials used in the synthesis are recognizable to one of skill in the art and are commercially available or may be prepared using known methods. The compounds were named using ACD/Name Batch Version 5.04 (Advanced Chemistry Development Inc.; Toronto, Ontario; wwy.acdlabs.com).

| No. | Compound | | MH+ | Name |
|---|---|---|---|---|
| 1. | | Chiral | 481.3 | N-(3-aminopropyl)-N-[(1R)-1-(1-benzyl-4-phenyl-1H-imidazol-2-yl)-2-methylpropyl]-4-methylbenzamide |
| 2. | | Chiral | 467.3 | N-(3-aminopropyl)-N-[(1R)-1-(1-benzyl-4-phenyl-1H-imidazol-2-yl)-2-methylpropyl]benzamide |
| 3. | | Chiral | 515.3 | N-(3-aminopropyl)-N-[(R)-(1-benzyl-4-phenyl-1H-imidazol-2-yl)(phenyl)methyl]-4-methylbenzamide |

-continued

| No. | Compound | | MH+ | Name |
|---|---|---|---|---|
| 4. | | Chiral | 501.3 | N-(3-aminopropyl)-N-[(R)-(1-benzyl-4-phenyl-1H-imidazol-2-yl)(phenyl)methyl]benzamide |
| 5. | | Chiral | 545.2 | N-(3-aminopropyl)-N-{(1R)-1-[1-benzyl-4-(3-bromophenyl)-1H-imidazol-2-yl]-2-methylpropyl}benzamide |
| 6. | | Chiral | 559.2 | N-(3-aminopropyl)-N-{(1R)-1-[1-benzyl-4-(3-bromophenyl)-1H-imidazol-2-yl]-2-methylpropyl}-4-methylbenzamide |

-continued

| No. | Compound | MH+ | Name |
|---|---|---|---|
| 7. | Chiral | 613.2 | N-(3-aminopropyl)-N-{(1R)-1-[1-benzyl-4-(3-bromophenyl)-1H-imidazol-2-yl]-2-methylpropyl}-4-(trifluoromethyl)benzamide |
| 8. | Chiral | 581.2 | N-(3-aminopropyl)-N-{(1R)-1-[1-benzyl-4-(3-bromophenyl)-1H-imidazol-2-yl]-2-methylpropyl}-2,4-difluorobenzamide |
| 9. | | 495.3 | N-(3-aminopropyl)-4-methyl-N-{2-methyl-1-[1-(3-methylbenzyl)-4-phenyl-1H-imidazol-2-yl]propyl}benzamide |

-continued
| No. | Compound | | MH+ | Name |
|---|---|---|---|---|
| 10. | 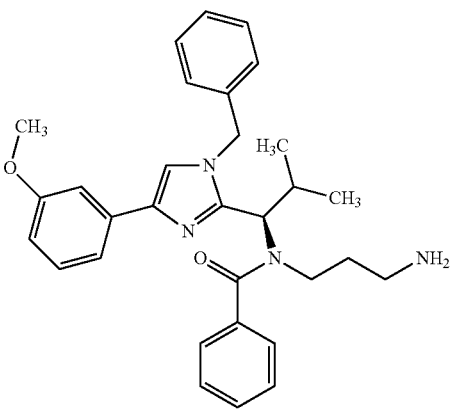 | Chiral | 497.3 | N-(3-aminopropyl)-N-{(1R)-1-[1-benzyl-4-(3-methoxyphenyl)-1H-imidazol-2-yl]-2-methylpropyl}benzamide |
| 11. | 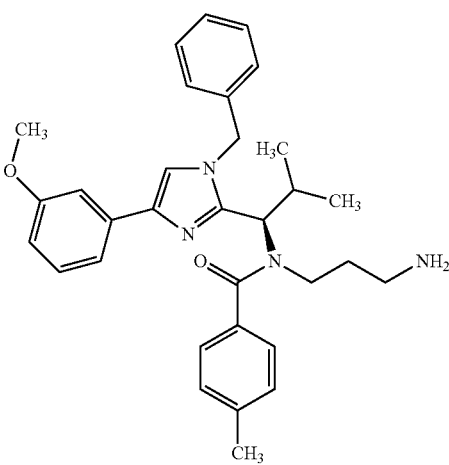 | Chiral | 511.3 | N-(3-aminopropyl)-N-{(1R)-1-[1-benzyl-4-(3-methoxyphenyl)-1H-imidazol-2-yl]-2-methylpropyl}-4-methylbenzamide |
| 12. | 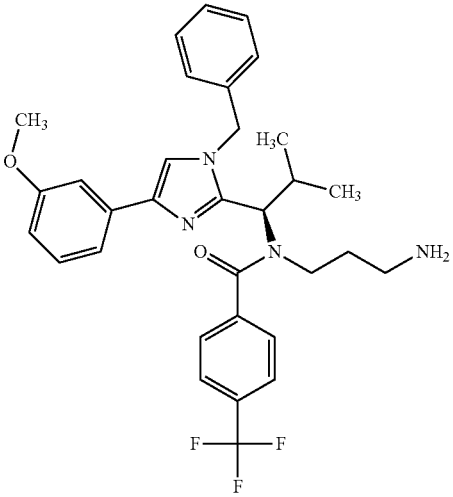 | Chiral | 565.3 | N-(3-aminopropyl)-N-{(1R)-1-[1-benzyl-4-(3-methoxyphenyl)-1H-imidazol-2-yl]-2-methylpropyl}-4-(trifluoromethyl)benzamide |

-continued

| No. | Compound | | MH+ | Name |
|---|---|---|---|---|
| 13. | | Chiral | 533.3 | N-(3-aminopropyl)-N-{(1R)-1-[1-benzyl-4-(3-methoxyphenyl)-1H-imidazol-2-yl]-2-methylpropyl}-2,4-difluorobenzamide |
| 14. | | Chiral | 501.2 | N-(3-aminopropyl)-N-{(1R)-1-[1-benzyl-4-(3-chlorophenyl)-1H-imidazol-2-yl]-2-methylpropyl}benzamide |
| 15. | | Chiral | 515.2 | N-(3-aminopropyl)-N-{(1R)-1-[1-benzyl-4-(3-chlorophenyl)-1H-imidazol-2-yl]-2-methylpropyl}-4-methylbenzamide |

-continued

| No. | Compound | | MH+ | Name |
|---|---|---|---|---|
| 16. | | Chiral | 569.2 | N-(3-aminopropyl)-N-{(1R)-1-[1-benzyl-4-(3-chlorophenyl)-1H-imidazol-2-yl]-2-methylpropyl}-4-(trifluoromethyl)benzamide |
| 17. | | Chiral | 537.2 | N-(3-aminopropyl)-N-{(1R)-1-[1-benzyl-4-(3-chlorophenyl)-1H-imidazol-2-yl]-2-methylpropyl}-2,4-difluorobenzamide |
| 18. | | Chiral | 481.3 | N-(3-aminopropyl)-N-{(1R)-1-[1-benzyl-4-(4-methylphenyl)-1H-imidazol-2-yl]-2-methylpropyl}benzamide |

-continued

| No. | Compound | | MH+ | Name |
|---|---|---|---|---|
| 19. | (structure) | Chiral | 495.3 | N-(3-aminopropyl)-N-{(1R)-1-[1-benzyl-4-(4-methylphenyl)-1H-imidazol-2-yl]-2-methylpropyl}-4-methylbenzamide |
| 20. | (structure) | Chiral | 549.3 | N-(3-aminopropyl)-N-{(1R)-1-[1-benzyl-4-(4-methylphenyl)-1H-imidazol-2-yl]-2-methylpropyl}-4-(trifluoromethyl)benzamide |
| 21. | (structure) | Chiral | 517.3 | N-(3-aminopropyl)-N-{(1R)-1-[1-benzyl-4-(4-methylphenyl)-1H-imidazol-2-yl]-2-methylpropyl}-2,4-difluorobenzamide |

| No. | Compound | MH+ | Name |
|---|---|---|---|
| 22. | Chiral | 495.3 | N-(3-aminopropyl)-N-[(1R)-1-(1-benzyl-4-phenyl-1H-imidazol-2-yl)-2,2-dimethylpropyl]-4-methylbenzamide |
| 23. | Chiral | 481.3 | N-(3-aminopropyl)-N-[(1R)-1-(1-benzyl-4-phenyl-1H-imidazol-2-yl)-2,2-dimethylpropyl]benzamide |
| 24. | Chiral | 517.3 | N-(3-aminopropyl)-N-{(1R)-1-[1-(3,5-difluorobenzyl)-4-phenyl-1H-imidazol-2-yl]-2-methylpropyl}-4-methylbenzamide |

-continued

| No. | Compound | MH+ | Name |
|-----|----------|-----|------|
| 25. | | 503.2 | N-(3-aminopropyl)-N-{(1R)-1-[1-(3,5-difluorobenzyl)-4-phenyl-1H-imidazol-2-yl]-2-methylpropyl}benzamide |
| 26. | | 637.2 | N-{(1R)-1-[1-benzyl-4-(3-bromophenyl)-1H-imidazol-2-yl]-2-methylpropyl}-4-methyl-N-{3-[(methylsulfonyl)amino]propyl}benzamide |
| 27. | | 507.3 | N-[(1R)-1-(1-benzyl-4-phenyl-1H-imidazol-2-yl)-2-methylpropyl]-N-[(3R)-piperidin-3-ylmethyl]benzamide |

| No. | Compound | | MH+ | Name |
|---|---|---|---|---|
| 28. | 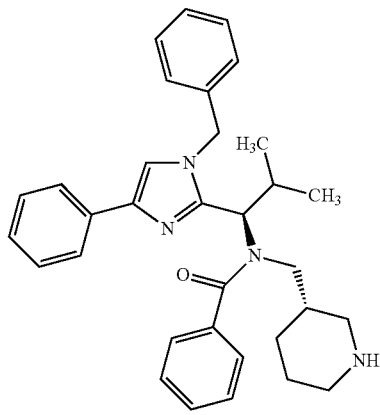 | Chiral | 507.3 | N-[(1R)-1-(1-benzyl-4-phenyl-1H-imidazol-2-yl)-2-methylpropyl]-N-[(3S)-piperidin-3-ylmethyl]benzamide |
| 29. | 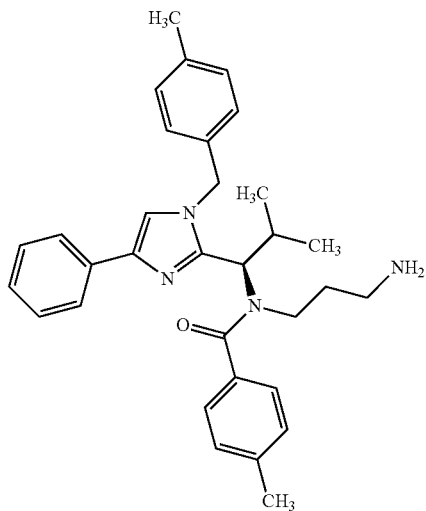 | Chiral | 495.3 | N-(3-aminopropyl)-4-methyl-N-{(1R)-2-methyl-1-[1-(4-methylbenzyl)-4-phenyl-1H-imidazol-2-yl]propyl}benzamide |
| 30. | 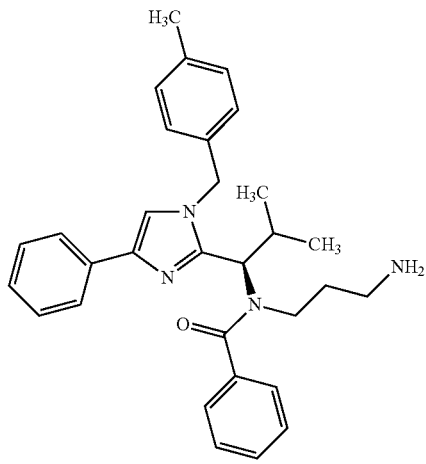 | Chiral | 481.3 | N-(3-aminopropyl)-N-{(1R)-2-methyl-1-[1-(4-methylbenzyl)-4-phenyl-1H-imidazol-2-yl]propyl}benzamide |

-continued

| No. | Compound | MH+ | Name |
|---|---|---|---|
| 31. | Chiral | 495.3 | N-(3-aminopropyl)-4-methyl-N-{(1R)-2-methyl-1-[1-(2-methylbenzyl)-4-phenyl-1H-imidazol-2-yl]propyl}benzamide |
| 32. | Chiral | 480.65 | N-(3-aminopropyl)-N-{(1R)-2-methyl-1-[1-(2-methylbenzyl)-4-phenyl-1H-imidazol-2-yl]propyl}benzamide |
| 33. | Chiral | 578.4 | N-[(1R)-1-(1-benzyl-4-phenyl-1H-imidazol-2-yl)-2-methylpropyl]-N-[2,2-dimethyl-3-(4-methylpiperazin-1-yl)propyl]benzamide |

-continued
| No. | Compound | MH+ | Name |
|---|---|---|---|
| 34. | 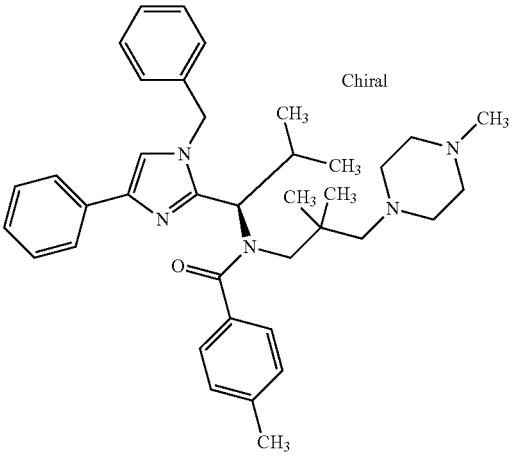 [SMILES: Cc1ccc(C(=O)N(CC(C)(C)CN2CCN(C)CC2)[C@@H](c2nc(-c3ccccc3)cn2Cc2ccccc2)C(C)C)cc1] | 592.4 | N-[(1R)-1-(1-benzyl-4-phenyl-1H-imidazol-2-yl)-2-methylpropyl]-N-[2,2-dimethyl-3-(4-methylpiperazin-1-yl)propyl]-4-methylbenzamide |
| 35. | 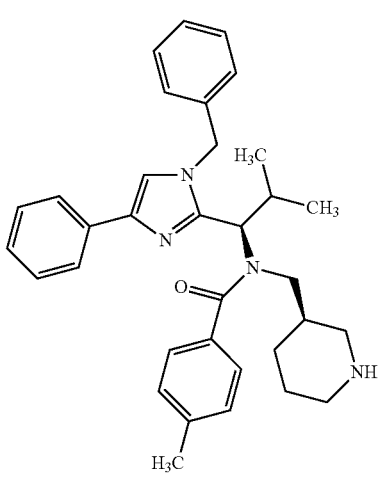 | 521.3 | N-[(1R)-1-(1-benzyl-4-phenyl-1H-imidazol-2-yl)-2-methylpropyl]-4-methyl-N-[(3R)-piperidin-3-ylmethyl]benzamide |
| 36. | 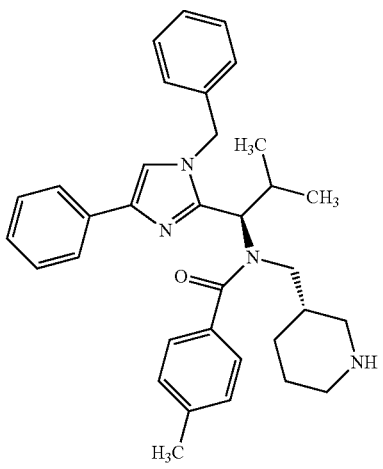 | 521.3 | N-[(1R)-1-(1-benzyl-4-phenyl-1H-imidazol-2-yl)-2-methylpropyl]-4-methyl-N-[(3S)-piperidin-3-ylmethyl]benzamide |

-continued

| No. | Compound | | MH+ | Name |
|---|---|---|---|---|
| 37. | (structure) | Chiral | 535.3 | N-(3-aminopropyl)-N-((1R)-1-{1-benzyl-4-[2-(trifluoromethyl)phenyl]-1H-imidazol-2-yl}-2-methylpropyl)benzamide |
| 38. | (structure) | Chiral | 549.3 | N-(3-aminopropyl)-N-((1R)-1-{1-benzyl-4-[2-(trifluoromethyl)phenyl]-1H-imidazol-2-yl}-2-methylpropyl)-4-methylbenzamide |
| 39. | (structure) | Chiral | 571.2 | N-(3-aminopropyl)-N-((1R)-1-{1-benzyl-4-[2-(trifluoromethyl)phenyl]-1H-imidazol-2-yl}-2-methylpropyl)-2,4-difluorobenzamide |

-continued

| No. | Compound | | MH+ | Name |
|---|---|---|---|---|
| 40. | | Chiral | 531.2 | N-(3-aminopropyl)-N-{(1R)-1-[1-benzyl-4-(3-chlorophenyl)-1H-imidazol-2-yl]-2-methylpropyl}-4-methoxybenzamide |
| 41. | | Chiral | 535.2 | N-(3-aminopropyl)-N-{(1R)-1-[1-benzyl-4-(3-chlorophenyl)-1H-imidazol-2-yl]-2-methylpropyl}-3-chlorobenzamide |
| 42. | | Chiral | 535.2 | N-(3-aminopropyl)-N-{(1R)-1-[1-benzyl-4-(3-chlorophenyl)-1H-imidazol-2-yl]-2-methylpropyl}-4-chlorobenzamide |

-continued
| No. | Compound | MH+ | Name |
|---|---|---|---|
| 43. | 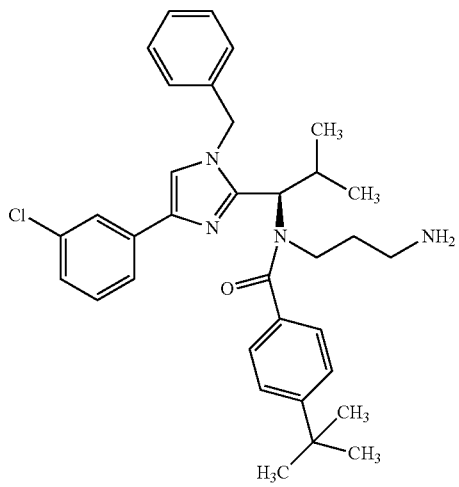 Chiral | 557.3 | N-(3-aminopropyl)-N-{(1R)-1-[1-benzyl-4-(3-chlorophenyl)-1H-imidazol-2-yl]-2-methylpropyl}-4-tert-butylbenzamide |
| 44. | 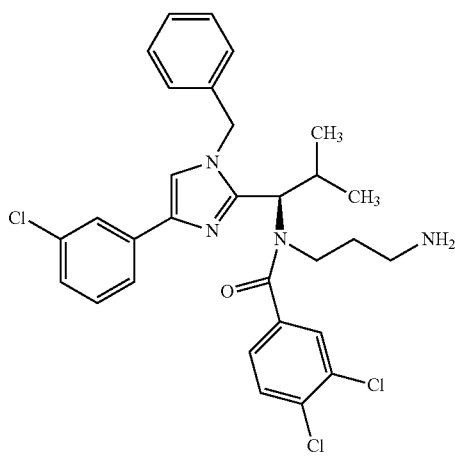 Chiral | 569.2 | N-(3-aminopropyl)-N-{(1R)-1-[1-benzyl-4-(3-chlorophenyl)-1H-imidazol-2-yl]-2-methylpropyl}-3,4-dichlorobenzamide |
| 45. | 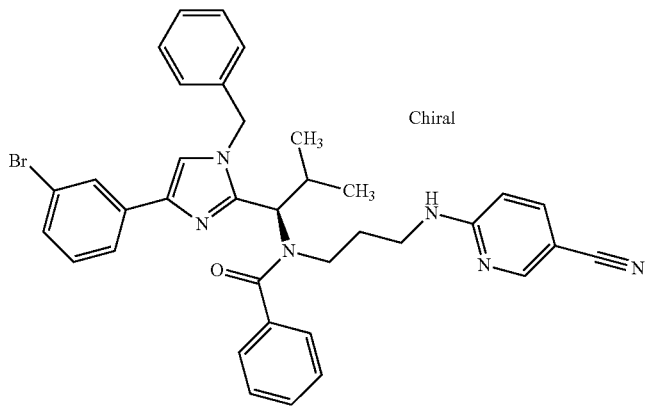 [SMILES: CC(C)[C@H](c1nc(-c2cccc(Br)c2)cn1Cc1ccccc1)N(CCCNc1ccc(C#N)cn1)C(=O)c1ccccc1] Chiral | 647.2 | N-{(1R)-1-[1-benzyl-4-(3-bromophenyl)-1H-imidazol-2-yl]-2-methylpropyl}-N-{3-[(5-cyanopyridin-2-yl)amino]propyl}benzamide |

| No. | Compound | MH+ | Name |
|---|---|---|---|
| 46. | 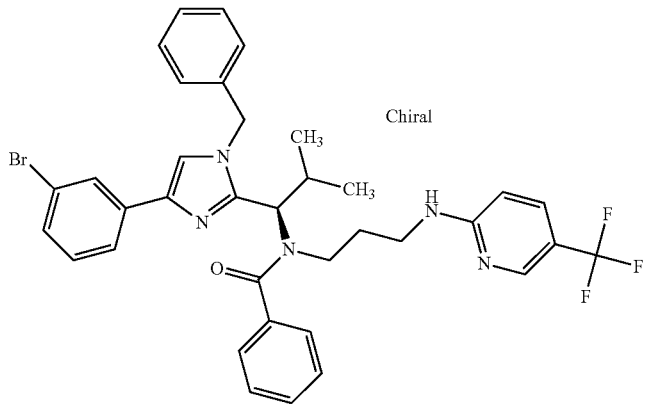 [SMILES: CC(C)[C@H](c1nc(-c2cccc(Br)c2)cn1Cc1ccccc1)N(CCCNc1ccc(C(F)(F)F)cn1)C(=O)c1ccccc1] | 690.2 | N-{(1R)-1-[1-benzyl-4-(3-bromophenyl)-1H-imidazol-2-yl]-2-methylpropyl}-N-(3-{[5-(trifluoromethyl)pyridin-2-yl]amino}propyl)benzamide |
| 47. | 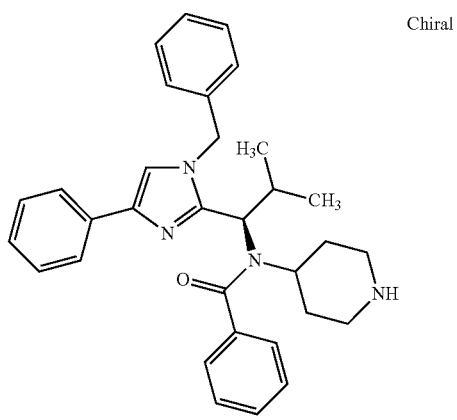 [SMILES: CC(C)[C@H](c1nc(-c2ccccc2)cn1Cc1ccccc1)N(C(=O)c1ccccc1)C1CCNCC1] | 493.3 | N-[(1R)-1-(1-benzyl-4-phenyl-1H-imidazol-2-yl)-2-methylpropyl]-N-piperidin-4-ylbenzamide |
| 48. | 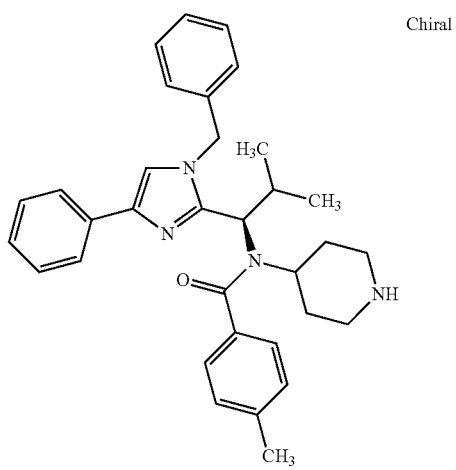 [SMILES: Cc1ccc(C(=O)N(C2CCNCC2)[C@@H](c2nc(-c3ccccc3)cn2Cc2ccccc2)C(C)C)cc1] | 507.3 | N-[(1R)-1-(1-benzyl-4-phenyl-1H-imidazol-2-yl)-2-methylpropyl]-4-methyl-N-piperidin-4-ylbenzamide |

| No. | Compound | MH+ | Name |
|---|---|---|---|
| 49. | 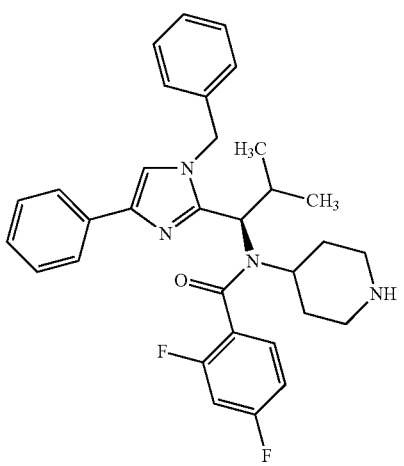 Chiral | 529.3 | N-[(1R)-1-(1-benzyl-4-phenyl-1H-imidazol-2-yl)-2-methylpropyl]-2,4-difluoro-N-piperidin-4-ylbenzamide |
| 50. | 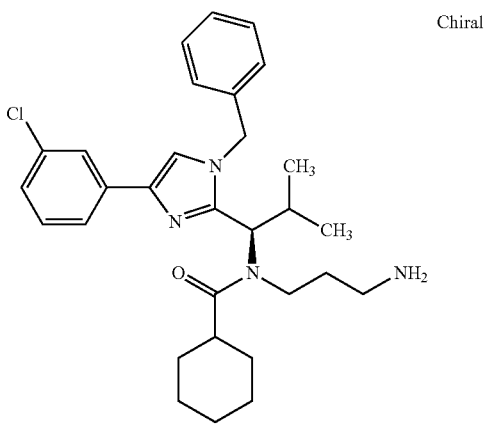 [SMILES: CC(C)[C@H](c1nc(-c2cccc(Cl)c2)cn1Cc1ccccc1)N(CCCN)C(=O)C1CCCCC1] Chiral | 507.3 | N-(3-aminopropyl)-N-{(1R)-1-[1-benzyl-4-(3-chlorophenyl)-1H-imidazol-2-yl]-2-methylpropyl}cyclohexanecarboxamide |
| 51. | 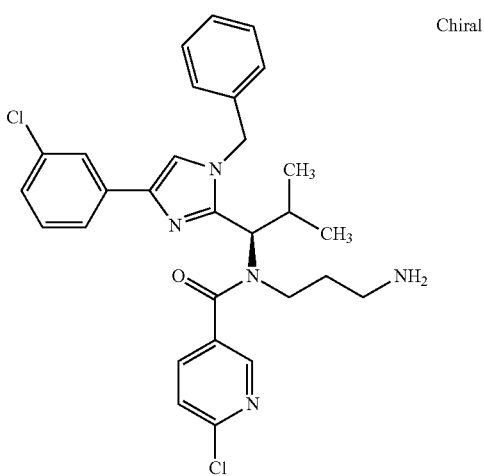 [SMILES: CC(C)[C@H](c1nc(-c2cccc(Cl)c2)cn1Cc1ccccc1)N(CCCN)C(=O)c1ccc(Cl)nc1] Chiral | 536.2 | N-(3-aminopropyl)-N-{(1R)-1-[1-benzyl-4-(3-chlorophenyl)-1H-imidazol-2-yl]-2-methylpropyl}-6-chloronicotinamide |

-continued

| No. | Compound | MH+ | Name |
|---|---|---|---|
| 52. | Chiral | 515.2 | N-(3-aminopropyl)-N-{(1R)-1-[1-benzyl-4-(3-chlorophenyl)-1H-imidazol-2-yl]-2,2-dimethylpropyl}benzamide |
| 53. | Chiral | 529.3 | N-(3-aminopropyl)-N-{(1R)-1-[1-benzyl-4-(3-chlorophenyl)-1H-imidazol-2-yl]-2,2-dimethylpropyl}-4-methylbenzamide |
| 54. | Chiral | 551.2 | N-(3-aminopropyl)-N-{(1R)-1-[4-(3-chlorophenyl)-1-(2,4-difluorobenzyl)-1H-imidazol-2-yl]-2,2-dimethylpropyl}benzamide |

-continued
| No. | Compound | MH+ | Name |
|---|---|---|---|
| 55. | 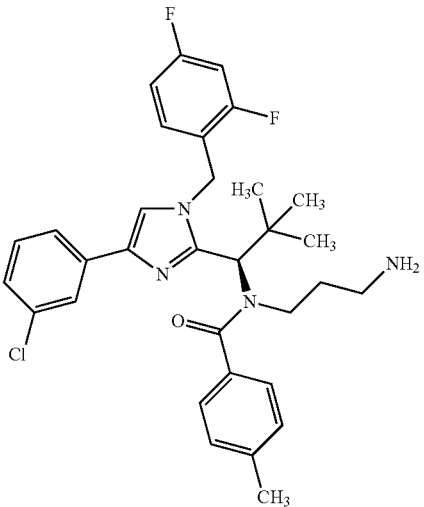 | 565.2 | N-(3-aminopropyl)-N-{(1R)-1-[4-(3-chlorophenyl)-1-(2,4-difluorobenzyl)-1H-imidazol-2-yl]-2,2-dimethylpropyl}-4-methylbenzamide |
| 56. | 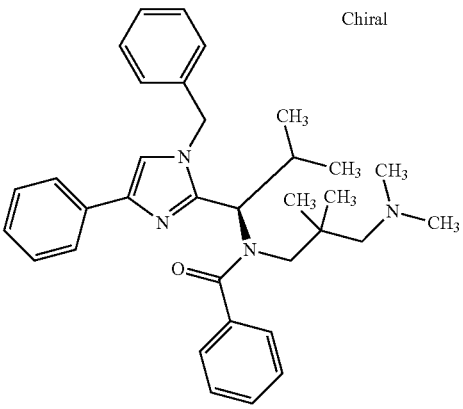 [SMILES: CC(C)[C@H](c1nc(-c2ccccc2)cn1Cc1ccccc1)N(CC(C)(C)CN(C)C)C(=O)c1ccccc1] | 523.3 | N-[(1R)-1-(1-benzyl-4-phenyl-1H-imidazol-2-yl)-2-methylpropyl]-N-[3-(dimethylamino)-2,2-dimethylpropyl]benzamide |
| 57. | 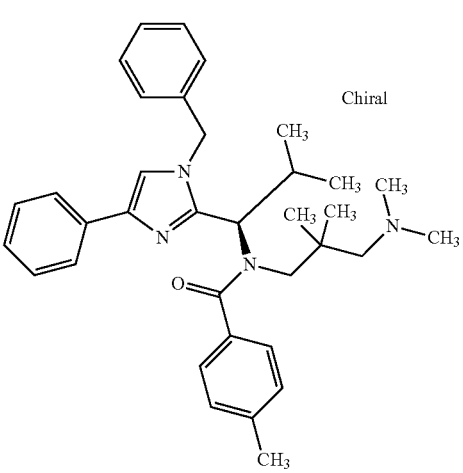 [SMILES: Cc1ccc(C(=O)N(CC(C)(C)CN(C)C)[C@@H](c2nc(-c3ccccc3)cn2Cc2ccccc2)C(C)C)cc1] | 537.4 | N-[(1R)-1-(1-benzyl-4-phenyl-1H-imidazol-2-yl)-2-methylpropyl]-N-[3-(dimethylamino)-2,2-dimethylpropyl]-4-methylbenzamide |

-continued
| No. | Compound | MH+ | Name |
|---|---|---|---|
| 58. | 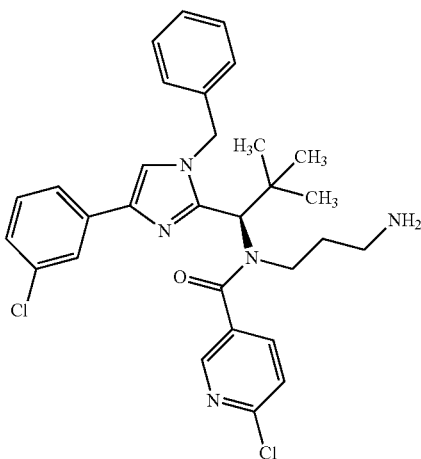 Chiral | 550.2 | N-(3-aminopropyl)-N-{(1R)-1-[1-benzyl-4-(3-chlorophenyl)-1H-imidazol-2-yl]-2,2-dimethylpropyl}-6-chloronicotinamide |
| 59. | 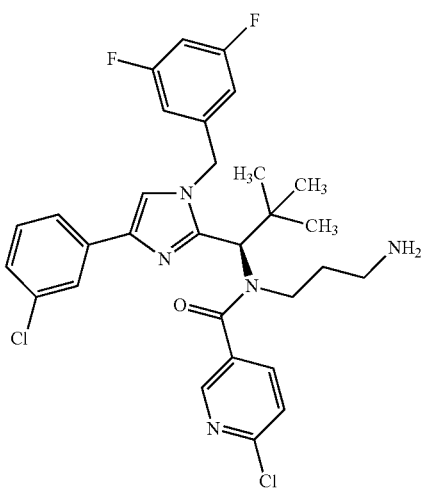 Chiral | 586.2 | N-(3-aminopropyl)-6-chloro-N-{(1R)-1-[4-(3-chlorophenyl)-1-(3,5-difluorobenzyl)-1H-imidazol-2-yl]-2,2-dimethylpropyl}nicotinamide |
| 60. | 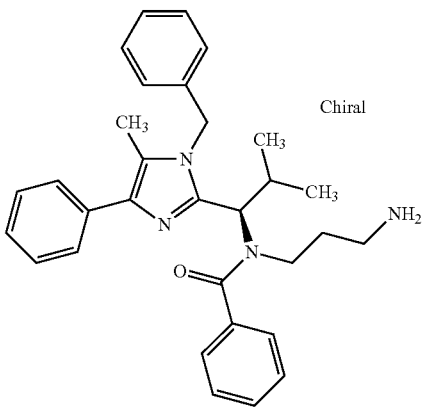 [SMILES: Cc1c(-c2ccccc2)nc([C@@H](C(C)C)N(CCCN)C(=O)c2ccccc2)n1Cc1ccccc1] Chiral | 481.3 | N-(3-aminopropyl)-N-[(1R)-1-(1-benzyl-5-methyl-4-phenyl-1H-imidazol-2-yl)-2-methylpropyl]benzamide |

-continued

| No. | Compound | MH+ | Name |
|---|---|---|---|
| 61. | | 495.3 | N-(3-aminopropyl)-N-[(1R)-1-(1-benzyl-5-methyl-4-phenyl-1H-imidazol-2-yl)-2-methylpropyl]-4-methylbenzamide |
| 62. | | 517.3 | N-(3-aminopropyl)-N-[(1R)-1-(1-benzyl-5-methyl-4-phenyl-1H-imidazol-2-yl)-2-methylpropyl]-2,4-difluorobenzamide |
| 63. | | 516.2 | N-(3-aminopropyl)-N-[(1R)-1-(1-benzyl-5-methyl-4-phenyl-1H-imidazol-2-yl)-2-methylpropyl]-6-chloronicotinamide |

-continued

| No. | Compound | | MH+ | Name |
|---|---|---|---|---|
| 64. | | Chiral | 535.2 | N-(3-aminopropyl)-N-{(1R)-1-[1-benzyl-4-(3-chlorophenyl)-1H-imidazol-2-yl]-2-methylpropyl}-2-chlorobenzamide |
| 65. | | Chiral | 550.2 | N-(3-aminopropyl)-N-{(1R)-1-[1-benzyl-4-(3-chlorophenyl)-1H-imidazol-2-yl]-2-methylpropyl}-2-chloro-6-methylisonicotinamide |
| 66. | | Chiral | 491.2 | N-(3-aminopropyl)-N-{(1R)-1-[1-benzyl-4-(3-chlorophenyl)-1H-imidazol-2-yl]-2-methylpropyl}-3-furamide |

-continued

| No. | Compound | | MH+ | Name |
|---|---|---|---|---|
| 67. | | Chiral | 505.2 | N-(3-aminopropyl)-N-{(1R)-1-[1-benzyl-4-(3-chlorophenyl)-1H-imidazol-2-yl]-2-methylpropyl}-5-methyl-2H-imidazole-4-carboxamide |
| 68. | | Chiral | 531.2 | N-(3-aminopropyl)-N-{(1R)-1-[1-benzyl-4-(3-chlorophenyl)-1H-imidazol-2-yl]-2-methylpropyl}-2-methoxybenzamide |
| 69. | | Chiral | 502.2 | N-(3-aminopropyl)-N-{(1R)-1-[1-benzyl-4-(3-chlorophenyl)-1H-imidazol-2-yl]-2-methylpropyl}pyridine-2-carboxamide |

-continued

| No. | Compound | MH+ | Name |
|---|---|---|---|
| 70. | Chiral | 519.3 | N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide |
| 71. | Chiral | 481.3 | N-(3-aminopropyl)-N-[(1R)-1-(1-benzyl-4-phenyl-1H-imidazol-2-yl)-1,2-dimethylpropyl]benzamide |
| 72. | Chiral | 495.3 | N-(3-aminopropyl)-N-[(1R)-1-(1-benzyl-4-phenyl-1H-imidazol-2-yl)-1,2-dimethylpropyl]-4-methylbenzamide |

-continued
| No. | Compound | MH+ | Name |
|---|---|---|---|
| 73. | 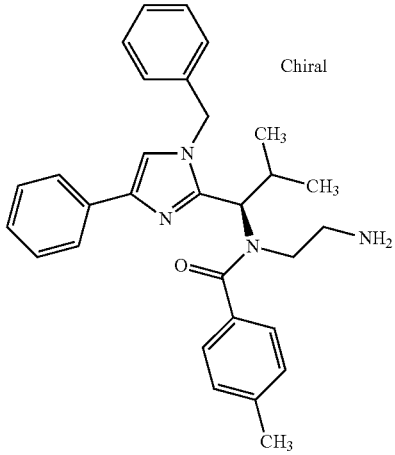 [SMILES: Cc1ccc(C(=O)N(CCN)[C@@H](c2nc(-c3ccccc3)cn2Cc2ccccc2)C(C)C)cc1] | 467.3 | N-(2-amino ethyl)-N-[(1R)-1-(1-benzyl-4-phenyl-1H-imidazol-2-yl)-2-methylpropyl]-4-methylbenzamide |
| 74. | 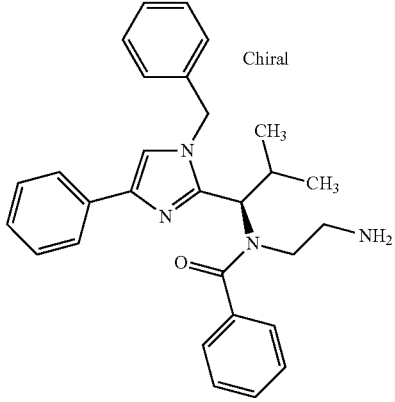 [SMILES: CC(C)[C@H](c1nc(-c2ccccc2)cn1Cc1ccccc1)N(CCN)C(=O)c1ccccc1] | 453.3 | N-(2-amino ethyl)-N-[(1R)-1-(1-benzyl-4-phenyl-1H-imidazol-2-yl)-2-methylpropyl]benzamide |
| 75. | 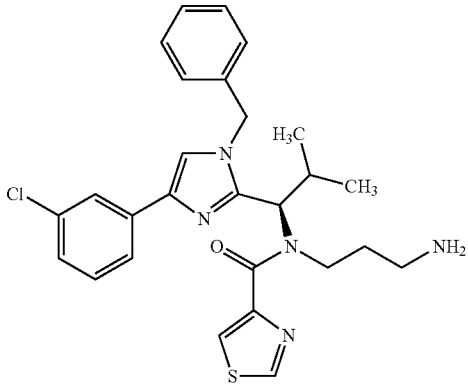 | 508.2 | N-(3-aminopropyl)-N-{(1R)-1-[1-benzyl-4-(3-chlorophenyl)-1H-imidazol-2-yl]-2-methylpropyl}-1,3-thiazole-4-carboxamide |

-continued
| No. | Compound | | MH+ | Name |
|---|---|---|---|---|
| 76. | 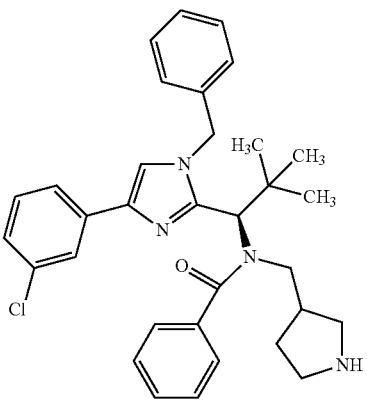 | Chiral | 541.3 | N-{(1R)-1-[1-benzyl-4-(3-chlorophenyl)-1H-imidazol-2-yl]-2,2-dimethylpropyl}-N-(pyrrolidin-3-ylmethyl)benzamide |
| 77. | 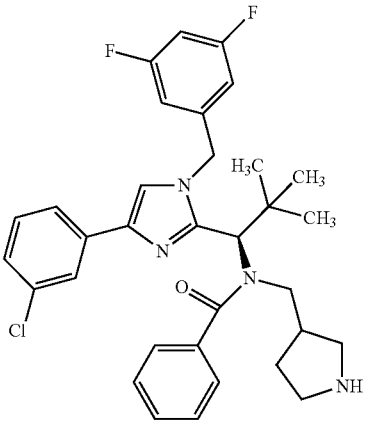 | Chiral | 577.2 | N-{(1R)-1-[4-(3-chlorophenyl)-1-(3,5-difluorobenzyl)-1H-imidazol-2-yl]-2,2-dimethylpropyl}-N-(pyrrolidin-3-ylmethyl)benzamide |
| 78. | 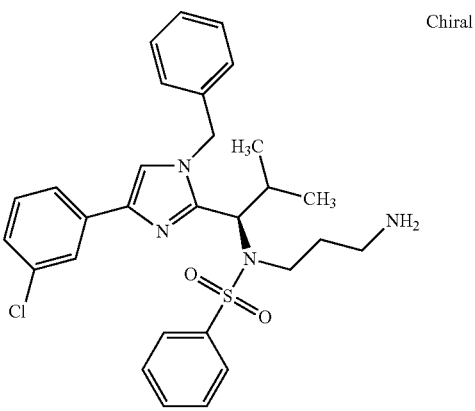 [SMILES: CC(C)[C@H](c1nc(-c2cccc(Cl)c2)cn1Cc1ccccc1)N(CCCN)S(=O)(=O)c1ccccc1] | Chiral | 537.2 | N-(3-aminopropyl)-N-{(1R)-1-[1-benzyl-4-(3-chlorophenyl)-1H-imidazol-2-yl]-2-methylpropyl}benzenesulfonamide |

-continued

| No. | Compound | | MH+ | Name |
|---|---|---|---|---|
| 79. | | Chiral | 506.2 | N-(3-aminopropyl)-N-{(1R)-1-[1-benzyl-4-(3-chlorophenyl)-1H-imidazol-2-yl]-2-methylpropyl}-4-methylisoxazole-3-carboxamide |
| 80. | | Chiral | 492.2 | N-(3-aminopropyl)-N-{(1R)-1-[1-benzyl-4-(3-chlorophenyl)-1H-imidazol-2-yl]-2-methylpropyl}isoxazole-3-carboxamide |
| 81. | | Chiral | 505.2 | N-(3-aminopropyl)-N-{(1R)-1-[1-benzyl-4-(3-chlorophenyl)-1H-imidazol-2-yl]-2-methylpropyl}-5-methyl-1H-pyrazole-3-carboxamide |

-continued
| No. | Compound | MH+ | Name |
|---|---|---|---|
| 82. | 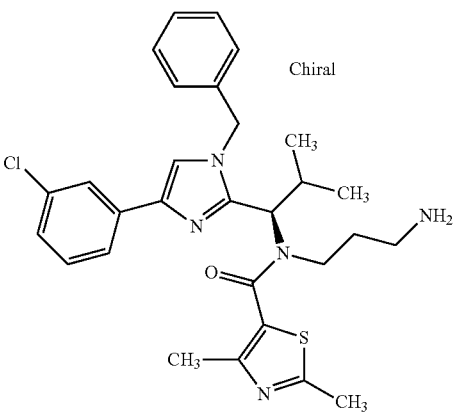 [SMILES: Cc1nc(C)c(C(=O)N(CCCN)[C@@H](c2nc(-c3cccc(Cl)c3)cn2Cc2ccccc2)C(C)C)s1] | 536.2 | N-(3-aminopropyl)-N-{(1R)-1-[1-benzyl-4-(3-chlorophenyl)-1H-imidazol-2-yl]-2-methylpropyl}-2,4-dimethyl-1,3-thiazole-5-carboxamide |
| 83. | 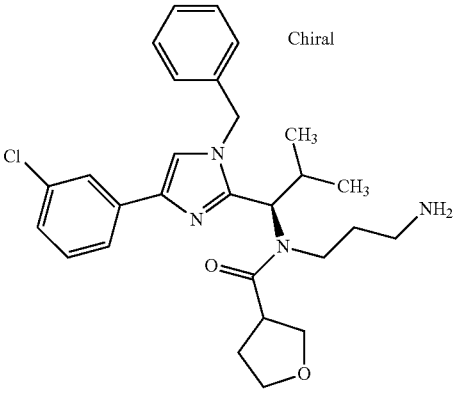 [SMILES: CC(C)[C@H](c1nc(-c2cccc(Cl)c2)cn1Cc1ccccc1)N(CCCN)C(=O)C1CCOC1] | 495.2 | N-(3-aminopropyl)-N-{(1R)-1-[1-benzyl-4-(3-chlorophenyl)-1H-imidazol-2-yl]-2-methylpropyl}tetrahydro-furan-3-carboxamide |
| 84. | 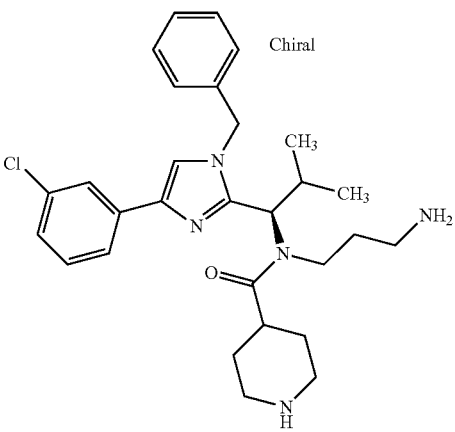 [SMILES: CC(C)[C@H](c1nc(-c2cccc(Cl)c2)cn1Cc1ccccc1)N(CCCN)C(=O)C1CCNCC1] | 508.3 | N-(3-aminopropyl)-N-{(1R)-1-[1-benzyl-4-(3-chlorophenyl)-1H-imidazol-2-yl]-2-methylpropyl}piperidine-4-carboxamide |

| No. | Compound | MH+ | Name |
|---|---|---|---|
| 85. | | 523.2 | 2-amino-N-(3-aminopropyl)-N-{(1R)-1-[1-benzyl-4-(3-chlorophenyl)-1H-imidazol-2-yl]-2-methylpropyl}-1,3-thiazole-4-carboxamide |
| 86. | | 504.3 | N-[(1R)-1-(1-benzyl-4-phenyl-1H-imidazol-2-yl)-2,2-dimethylpropyl]-N-(1H-imidazol-4-ylmethyl)benzamide |
| 87. | | 531.3 | N-[(1R)-1-(1-benzyl-4-phenyl-1H-imidazol-2-yl)-2,2-dimethylpropyl]-N-[(2-hydroxypyridin-4-yl)methyl]benzamide |
| 88. | | 531.3 | N-[(1R)-1-(1-benzyl-4-phenyl-1H-imidazol-2-yl)-2,2-dimethylpropyl]-N-[(6-hydroxypyridin-3-yl)methyl]benzamide |

| No. | Compound | MH+ | Name |
|---|---|---|---|
| 89. | 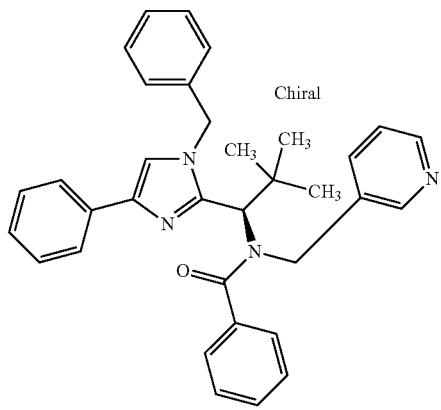 [SMILES: CC(C)(C)[C@H](c1nc(-c2ccccc2)cn1Cc1ccccc1)N(Cc1cccnc1)C(=O)c1ccccc1] | 515.3 | N-[(1R)-1-(1-benzyl-4-phenyl-1H-imidazol-2-yl)-2,2-dimethylpropyl]-N-(pyridin-3-ylmethyl)benzamide |
| 90. | 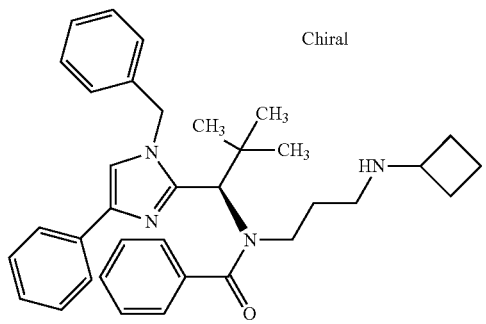 [SMILES: CC(C)(C)[C@H](c1nc(-c2ccccc2)cn1Cc1ccccc1)N(CCCNC1CCC1)C(=O)c1ccccc1] | 535.3 | N-[(1R)-1-(1-benzyl-4-phenyl-1H-imidazol-2-yl)-2,2-dimethylpropyl]-N-[3-(cyclobutylamino)propyl]benzamide |
| 91. | 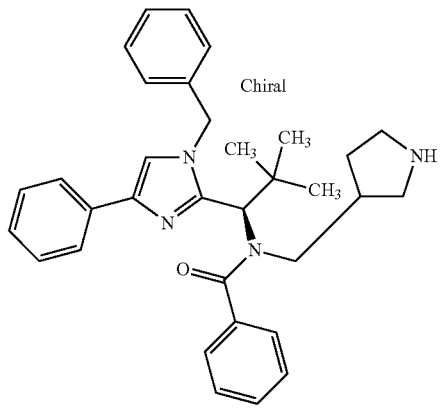 [SMILES: CC(C)(C)[C@H](c1nc(-c2ccccc2)cn1Cc1ccccc1)N(CC1CCNC1)C(=O)c1ccccc1] | 507.3 | N-[(1R)-1-(1-benzyl-4-phenyl-1H-imidazol-2-yl)-2,2-dimethylpropyl]-N-(pyrrolidin-3-ylmethyl)benzamide |

| No. | Compound | MH+ | Name |
|---|---|---|---|
| 92. | | 496.3 | N-(3-aminopropyl)-N-[(1R)-1-(1-benzyl-4-phenyl-1H-imidazol-2-yl)-2,2-dimethylpropyl]-6-methylnicotinamide |
| 93. | | 535.3 | N-[(1R)-1-(1-benzyl-4-phenyl-1H-imidazol-2-yl)-2,2-dimethylpropyl]-N-{3-[(cyclopropylmethyl)amino]propyl}benzamide |
| 94. | | 704.4 | N-[(1R)-1-(1-benzyl-4-phenyl-1H-imidazol-2-yl)-2,2-dimethylpropyl]-N-[3-({[5-(pyridin-3-yloxy)-1H-indazol-3-yl]methyl}amino)propyl]benzamide |
| 95. | | 584.3 | N-[(1R)-1-(1-benzyl-4-phenyl-1H-imidazol-2-yl)-2,2-dimethylpropyl]-N-[(5-methoxy-1H-indazol-3-yl)methyl]benzamide |

-continued

| No. | Compound | MH+ | Name |
|---|---|---|---|
| 96. | 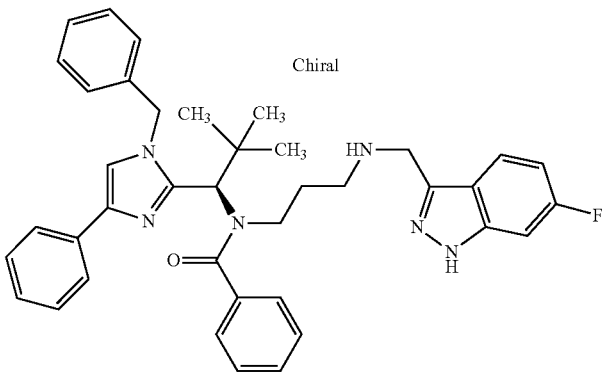 [SMILES: CC(C)(C)[C@H](c1nc(-c2ccccc2)cn1Cc1ccccc1)N(CCCNCc1n[nH]c2cc(F)ccc12)C(=O)c1ccccc1] | 629.3 | N-[(1R)-1-(1-benzyl-4-phenyl-1H-imidazol-2-yl)-2,2-dimethylpropyl]-N-(3-{[(6-fluoro-1H-indazol-3-yl)methyl]amino}propyl)benzamide |
| 97. | 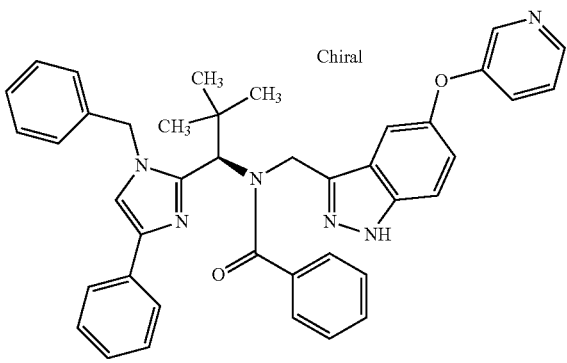 [SMILES: CC(C)(C)[C@H](c1nc(-c2ccccc2)cn1Cc1ccccc1)N(Cc1n[nH]c2ccc(Oc3cccnc3)cc12)C(=O)c1ccccc1] | 647.3 | N-[(1R)-1-(1-benzyl-4-phenyl-1H-imidazol-2-yl)-2,2-dimethylpropyl]-N-{[5-(pyridin-3-yloxy)-1H-indazol-3-yl]methyl}benzamide |
| 98. | 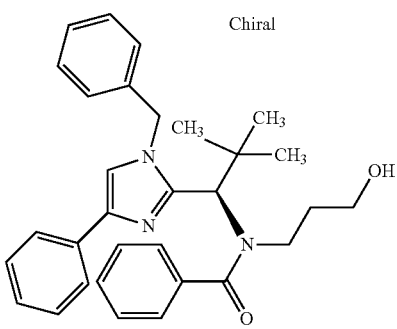 [SMILES: CC(C)(C)[C@H](c1nc(-c2ccccc2)cn1Cc1ccccc1)N(CCCO)C(=O)c1ccccc1] | 482.3 | N-[(1R)-1-(1-benzyl-4-phenyl-1H-imidazol-2-yl)-2,2-dimethylpropyl]-N-(3-hydroxypropyl)benzamide |
| 99. | 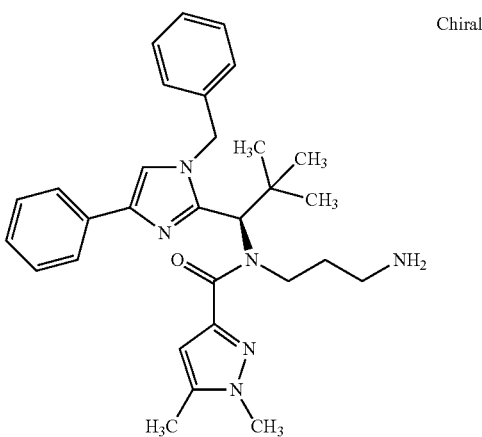 [SMILES: Cc1cc(C(=O)N(CCCN)[C@@H](c2nc(-c3ccccc3)cn2Cc2ccccc2)C(C)(C)C)nn1C] | 499.3 | N-(3-aminopropyl)-N-[(1R)-1-(1-benzyl-4-phenyl-1H-imidazol-2-yl)-2,2-dimethylpropyl]-1,5-dimethyl-1H-pyrazole-3-carboxamide |

-continued

| No. | Compound | | MH+ | Name |
|---|---|---|---|---|
| 100. | 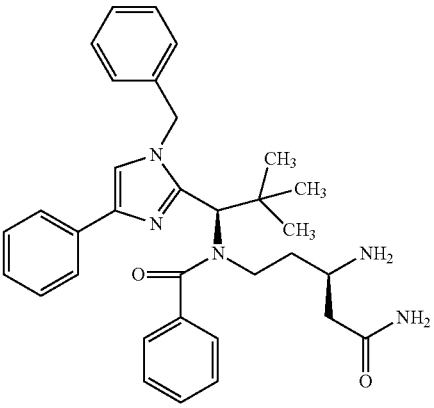 | Chiral | 538.3 | N-[(1R)-1-(1-benzyl-4-phenyl-1H-imidazol-2-yl)-2,2-dimethylpropyl]-N-[(3R)-3,5-diamino-5-oxopentyl]benzamide |
| 101. | 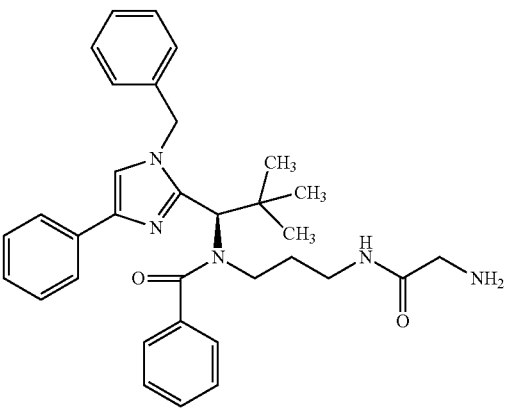 | Chiral | 538.3 | N-{3-[(aminoacetyl)amino]propyl}-N-[(1R)-1-(1-benzyl-4-phenyl-1H-imidazol-2-yl)-2,2-dimethylpropyl]benzamide |
| 102. | 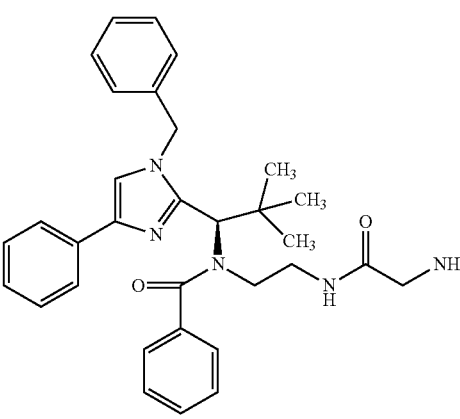 | Chiral | 524.3 | N-{2-[(aminoacetyl)amino]ethyl}-N-[(1R)-1-(1-benzyl-4-phenyl-1H-imidazol-2-yl)-2,2-dimethylpropyl]benzamide |
| 103. | 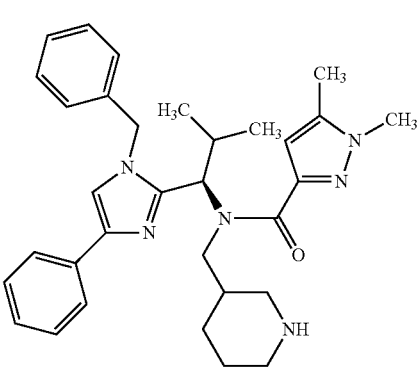 | Chiral | 525.3 | N-[(1R)-1-(1-benzyl-4-phenyl-1H-imidazol-2-yl)-2-methylpropyl]-1,5-dimethyl-N-(piperidin-3-ylmethyl)-1H-pyrazole-3-carboxamide |

| No. | Compound | | MH+ | Name |
|---|---|---|---|---|
| 104. | | Chiral | 495.2 | (2R)-N-(3-aminopropyl)-N-{(1R)-1-[1-benzyl-4-(3-chlorophenyl)-1H-imidazol-2-yl]-2-methylpropyl}tetrahydro-furan-2-carboxamide |
| 105. | | Chiral | 495.2 | (2S)-N-(3-aminopropyl)-N-{(1R)-1-[1-benzyl-4-(3-chlorophenyl)-1H-imidazol-2-yl]-2-methylpropyl}tetrahydro-furan-2-carboxamide |
| 106. | | Chiral | 503.2 | N-(3-aminopropyl)-N-{(1R)-1-[1-benzyl-4-(3-chlorophenyl)-1H-imidazol-2-yl]-2-methylpropyl}pyrazine-2-carboxamide |

| No. | Compound | MH+ | Name |
|---|---|---|---|
| 107. | 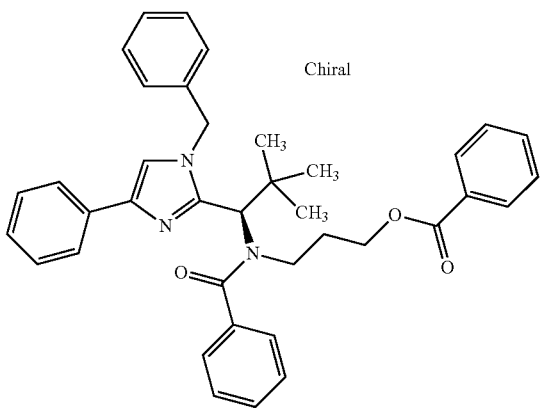 [SMILES: CC(C)(C)[C@H](c1nc(-c2ccccc2)cn1Cc1ccccc1)N(CCCOC(=O)c1ccccc1)C(=O)c1ccccc1] Chiral | 586.3 | 3-{benzoyl[(1R)-1-(1-benzyl-4-phenyl-1H-imidazol-2-yl)-2,2-dimethylpropyl]amino}propyl benzoate |
| 108. | 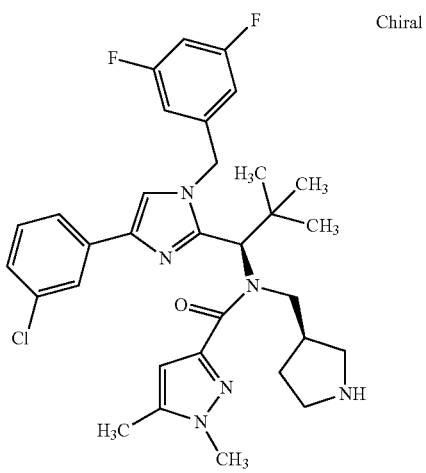 [SMILES: Cc1cc(C(=O)N(C[C@@H]2CCNC2)[C@@H](c2nc(-c3cccc(Cl)c3)cn2Cc2cc(F)cc(F)c2)C(C)(C)C)nn1C] Chiral | 595.3 | N-{(1R)-1-[4-(3-chlorophenyl)-1-(3,5-difluorobenzyl)-1H-imidazol-2-yl]-2,2-dimethylpropyl}-1,5-dimethyl-N-[(3R)-pyrrolidin-3-ylmethyl]-1H-pyrazole-3-carboxamide |
| 109. | 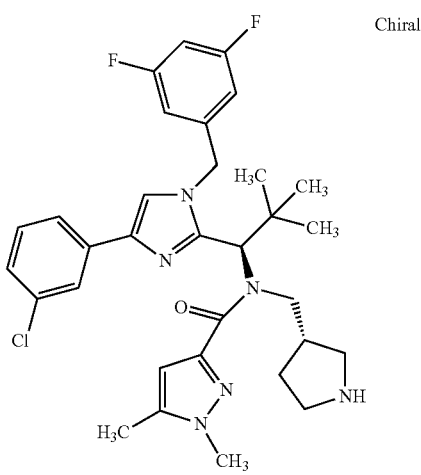 [SMILES: Cc1cc(C(=O)N(C[C@H]2CCNC2)[C@@H](c2nc(-c3cccc(Cl)c3)cn2Cc2cc(F)cc(F)c2)C(C)(C)C)nn1C] Chiral | 595.3 | N-{(1R)-1-[4-(3-chlorophenyl)-1-(3,5-difluorobenzyl)-1H-imidazol-2-yl]-2,2-dimethylpropyl}-1,5-dimethyl-N-[(3S)-pyrrolidin-3-ylmethyl]-1H-pyrazole-3-carboxamide |

-continued

| No. | Compound | MH+ | Name |
|---|---|---|---|
| 110. | Chiral | 573.2 | N-(3-aminopropyl)-N-{(1R)-1-[1-benzyl-4-(3-chlorophenyl)-1H-imidazol-2-yl]-2-methylpropyl}-1-methyl-3-(trifluoromethyl)-1H-pyrazole-4-carboxamide |
| 111. | Chiral | 539.2 | N-(3-aminopropyl)-N-{(1R)-1-[1-benzyl-4-(3-chlorophenyl)-1H-imidazol-2-yl]-2-methylpropyl}-5-chloro-1-methyl-1H-pyrazole-4-carboxamide |
| 112. | Chiral | 482.3 | N-(3-aminopropyl)-N-{(1R)-1-[1-benzyl-4-(3-chlorophenyl)-1H-imidazol-2-yl]-2-methylpropyl}-2-(dimethylamino)acetamide |

| No. | Compound | | MH+ | Name |
|---|---|---|---|---|
| 113. | 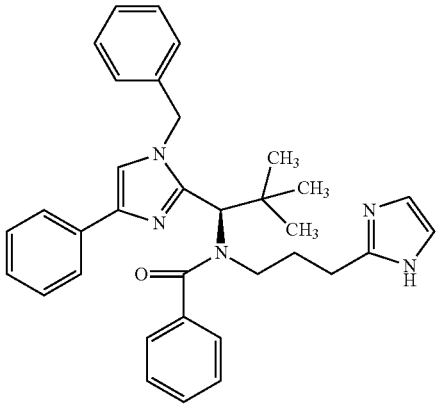 | Chiral | 532.3 | N-[(1R)-1-(1-benzyl-4-phenyl-1H-imidazol-2-yl)-2,2-dimethylpropyl]-N-[3-(1H-imidazol-2-yl)propyl]benzamide |
| 114. | 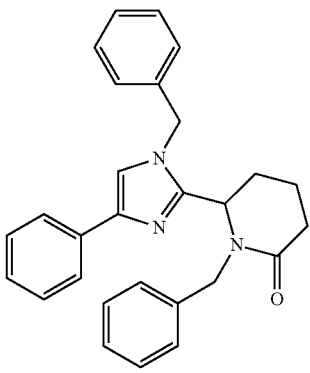 [SMILES: O=C1CCCC(c2nc(-c3ccccc3)cn2Cc2ccccc2)N1Cc1ccccc1] | | 422.2 | 1-benzyl-6-(1-benzyl-4-phenyl-1H-imidazol-2-yl)piperidin-2-one |
| 115. | 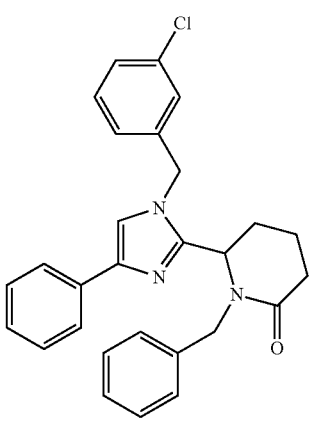 [SMILES: O=C1CCCC(c2nc(-c3ccccc3)cn2Cc2cccc(Cl)c2)N1Cc1ccccc1] | | 456.2 | 1-benzyl-6-[1-(3-chlorobenzyl)-4-phenyl-1H-imidazol-2-yl]piperidin-2-one |

-continued

| No. | Compound | | MH+ | Name |
|---|---|---|---|---|
| 116. | | Chiral | 485.3 | N-(3-aminopropyl)-N-[(1R)-1-(1-benzyl-4-phenyl-1H-imidazol-2-yl)-2-methylpropyl]-1,5-dimethyl-1H-pyrazole-3-carboxamide |
| 117. | | Chiral | 525.3 | N-[(1R)-1-(1-benzyl-4-phenyl-1H-imidazol-2-yl)-2,2-dimethylpropyl]-N-{3-[(2-hydroxyethyl)amino]propyl}benzamide |
| 118. | | Chiral | 521.3 | N-[(1R)-1-(1-benzyl-4-phenyl-1H-imidazol-2-yl)-2,2-dimethylpropyl]-N-[3-(cyclopropylamino)propyl]benzamide |
| 119. | | Chiral | 474.2 | N-(3-aminopropyl)-N-{(1R)-2-methyl-1-[4-phenyl-1-(1,3-thiazol-4-ylmethyl)-1H-imidazol-2-yl]propyl}benzamide |

-continued

| No. | Compound | | MH+ | Name |
|---|---|---|---|---|
| 120. | (structure) | Chiral | 488.2 | N-(3-aminopropyl)-4-methyl-N-{(1R)-2-methyl-1-[4-phenyl-1-(1,3-thiazol-4-ylmethyl)-1H-imidazol-2-yl]propyl}benzamide |
| 121. | (structure) | Chiral | 510.2 | N-(3-aminopropyl)-2,4-difluoro-N-{(1R)-2-methyl-1-[4-phenyl-1-(1,3-thiazol-4-ylmethyl)-1H-imidazol-2-yl]propyl}benzamide |
| 122. | (structure) | Chiral | 509.2 | N-(3-aminopropyl)-6-chloro-N-{(1R)-2-methyl-1-[4-phenyl-1-(1,3-thiazol-4-ylmethyl)-1H-imidazol-2-yl]propyl}nicotinamide |

| No. | Compound | | MH+ | Name |
|---|---|---|---|---|
| 123. | | Chiral | 482.3 | N-(3-aminopropyl)-N-[(1R)-1-(1-benzyl-4-pyridin-2-yl-1H-imidazol-2-yl)-2,2-dimethylpropyl]benzamide |
| 124. | | Chiral | 496.3 | N-(3-aminopropyl)-N-[(1R)-1-(1-benzyl-4-pyridin-2-yl-1H-imidazol-2-yl)-2,2-dimethylpropyl]-4-methylbenzamide |
| 125. | | Chiral | 518.3 | N-(3-aminopropyl)-N-[(1R)-1-(1-benzyl-4-pyridin-2-yl-1H-imidazol-2-yl)-2,2-dimethylpropyl]-2,4-difluorobenzamide |

-continued
| No. | Compound | | MH+ | Name |
|---|---|---|---|---|
| 126. | 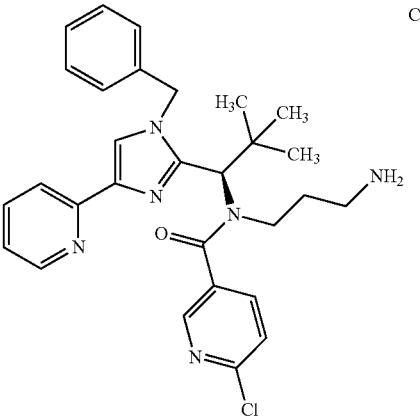 | Chiral | 517.3 | N-(3-aminopropyl)-N-[(1R)-1-(1-benzyl-4-pyridin-2-yl-1H-imidazol-2-yl)-2,2-dimethylpropyl]-6-chloronicotinamide |
TABLE 2
| No. | Compound | | MH+ | Name |
|---|---|---|---|---|
| 127 | 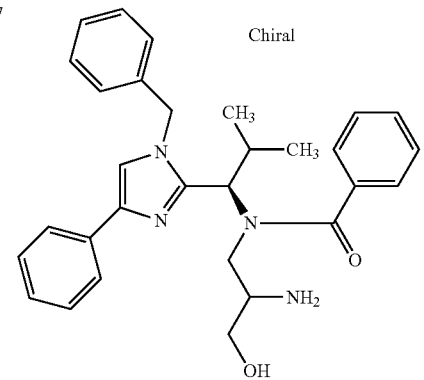 | Chiral | 483.2 | N-(2-amino-3-hydroxypropyl)-N-[(1R)-1-(1-benzyl-4-phenyl-1H-imidazol-2-yl)-2-methylpropyl]benzamide |
| 128 | 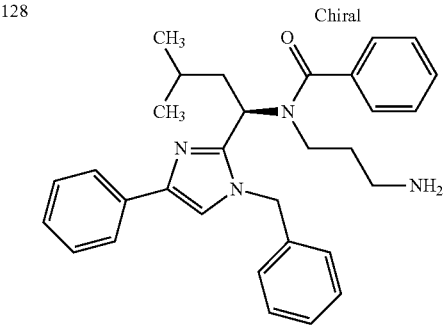 | Chiral | 481.2 | N-(3-aminopropyl)-N-[(1R)-1-(1-benzyl-4-phenyl-1H-imidazol-2-yl)-3-methylbutyl]benzamide |

TABLE 2-continued

| No. | Compound | MH+ | Name |
|---|---|---|---|
| 129 | Chiral | 495.3 | N-(3-aminopropyl)-N-[(1R)-1-(1-benzyl-4-phenyl-1H-imidazol-2-yl)-3-methylbutyl]-4-methylbenzamide |
| 130 | Chiral | 481.3 | N-(3-aminopropyl)-N-[(1R,2R)-1-(1-benzyl-4-phenyl-1H-imidazol-2-yl)-2-methylbutyl]benzamide |
| 131 | Chiral | 495.3 | N-(3-aminopropyl)-N-[(1R,2R)-1-(1-benzyl-4-phenyl-1H-imidazol-2-yl)-2-methylbutyl]-4-methylbenzamide |
| 132 | Chiral | 481.3 | N-(3-aminopropyl)-N-[(1R,2S)-1-(1-benzyl-4-phenyl-1H-imidazol-2-yl)-2-methylbutyl]benzamide |

TABLE 2-continued

| No. | Compound | MH+ | Name |
|---|---|---|---|
| 133 | Chiral | 495.2 | N-(3-aminopropyl)-N-[(1R,2S)-1-(1-benzyl-4-phenyl-1H-imidazol-2-yl)-2-methylbutyl]-4-methylbenzamide |
| 134 | Chiral | 506.2 | N-(3-aminopropyl)-N-{(1R)-1-[1-benzyl-4-(3-chlorophenyl)-1H-imidazol-2-yl]-2-methylpropyl}-5-methylisoxazole-4-carboxamide |
| 135 | Chiral | 439.2 | N-(3-aminopropyl)-N-{(1R)-1-[1-benzyl-4-(3-chlorophenyl)-1H-imidazol-2-yl]-2-methylpropyl}acetamide |

TABLE 2-continued

| No. | Compound | MH+ | Name |
|---|---|---|---|
| 136 | | 519.2 | N-(3-aminopropyl)-N-{(1R)-1-[1-benzyl-4-(3-chlorophenyl)-1H-imidazol-2-yl]-2-methylpropyl}-2-(4-fluorophenoxy)acetamide |
| 137 | | 506.2 | N-(3-aminopropyl)-N-{(1R)-1-[1-benzyl-4-(3-chlorophenyl)-1H-imidazol-2-yl]-2-methylpropyl}-2-(1H-imidazol-1-yl)acetamide |
| 138 | | 525.3 | N-(3-aminopropyl)-N-{(1R)-1-[1-benzyl-4-(3-chlorophenyl)-1H-imidazol-2-yl]-2-methylpropyl}-2-morpholin-4-ylacetamide |

TABLE 2-continued

| No. | Compound | MH+ | Name |
|---|---|---|---|
| 139 | 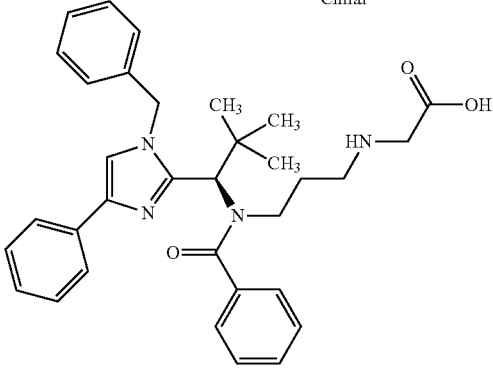 Chiral | 539.3 | [(3-{benzoyl[(1R)-1-(1-benzyl-4-phenyl-1H-imidazol-2-yl)-2,2-dimethylpropyl]amino}propyl)amino]acetic acid |
| 140 | 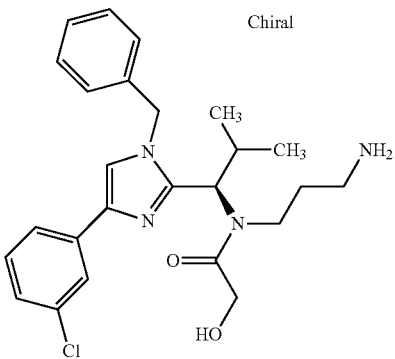 [SMILES: CC(C)[C@H](c1nc(-c2cccc(Cl)c2)cn1Cc1ccccc1)N(CCCN)C(=O)CO] Chiral | 455.2 | N-(3-aminopropyl)-N-{(1R)-1-[1-benzyl-4-(3-chlorophenyl)-1H-imidazol-2-yl]-2-methylpropyl}-2-hydroxyacetamide |
| 141 | 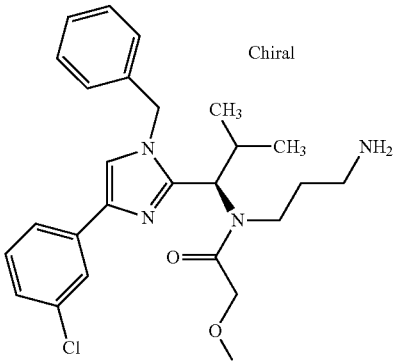 Chiral | 469.2 | N-(3-aminopropyl)-N-{(1R)-1-[1-benzyl-4-(3-chlorophenyl)-1H-imidazol-2-yl]-2-methylpropyl}-2-methoxyacetamide |
| 142 | 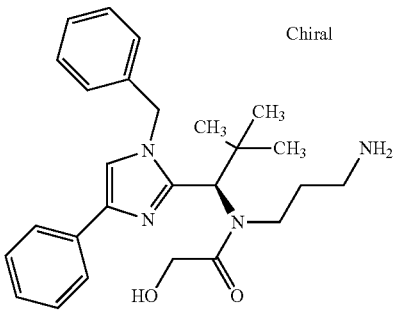 [SMILES: CC(C)(C)[C@H](c1nc(-c2ccccc2)cn1Cc1ccccc1)N(CCCN)C(=O)CO] Chiral | 435.3 | N-(3-aminopropyl)-N-[(1R)-1-(1-benzyl-4-phenyl-1H-imidazol-2-yl)-2,2-dimethylpropyl]-2-hydroxyacetamide |

TABLE 2-continued

| No. | Compound | MH+ | Name |
|---|---|---|---|
| 143 | (structure) | 449.3 | N-(3-aminopropyl)-N-[(1R)-1-(1-benzyl-4-phenyl-1H-imidazol-2-yl)-2,2-dimethylpropyl]-2-methoxyacetamide |
| 144 | (structure) | 533.3 | N-(3-aminopropyl)-N-{(1R)-1-[1-benzyl-4-(3-chlorophenyl)-1H-imidazol-2-yl]-2-methylpropyl}-1-ethyl-3-methyl-1H-pyrazole-5-carboxamide |
| 145 | (structure) | 567.3 | ethyl [(3-{benzoyl[(1R)-1-(1-benzyl-4-phenyl-1H-imidazol-2-yl)-2,2-dimethylpropyl]amino}propyl)amino]acetate |
| 146 | (structure) | 580.2 | N-{3-[(2-amino-3-methylbutanoyl)amino]propyl}-N-[(1R)-1-(1-benzyl-4-phenyl-1H-imidazol-2-yl)-2,2-dimethylpropyl]benzamide |

TABLE 2-continued

| No. | Compound | MH+ | Name |
|---|---|---|---|
| 147 | 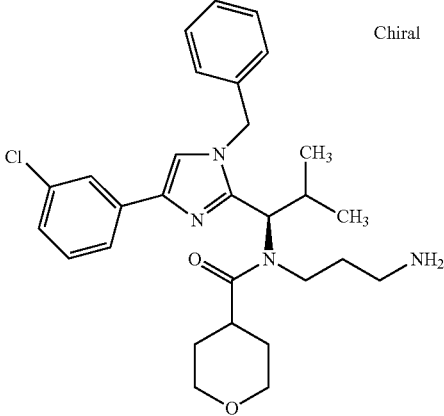 [SMILES: CC(C)[C@H](c1nc(-c2cccc(Cl)c2)cn1Cc1ccccc1)N(CCCN)C(=O)C1CCOCC1] Chiral | 509.3 | N-(3-aminopropyl)-N-{(1R)-1-[1-benzyl-4-(3-chlorophenyl)-1H-imidazol-2-yl]-2-methylpropyl}tetrahydro-2H-pyran-4-carboxamide |
| 148 | 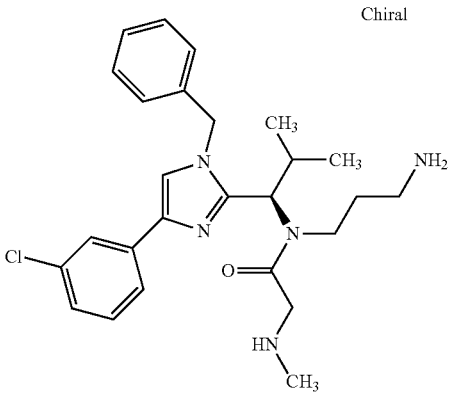 [SMILES: CNCC(=O)N(CCCN)[C@@H](c1nc(-c2cccc(Cl)c2)cn1Cc1ccccc1)C(C)C] Chiral | 469.2 | N-(3-aminopropyl)-N-{(1R)-1-[1-benzyl-4-(3-chlorophenyl)-1H-imidazol-2-yl]-2-methylpropyl}-2-(methylamino)acetamide |
| 149 | 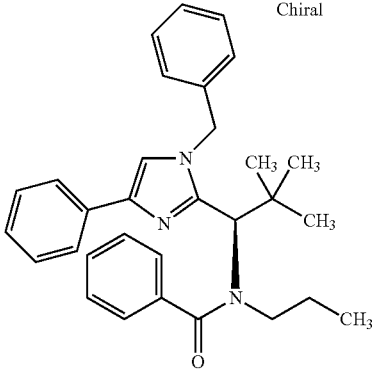 [SMILES: CCCN(C(=O)c1ccccc1)[C@@H](c1nc(-c2ccccc2)cn1Cc1ccccc1)C(C)(C)C] Chiral | 466.2 | N-[(1R)-1-(1-benzyl-4-phenyl-1H-imidazol-2-yl)-2,2-dimethylpropyl]-N-propylbenzamide |
| 150 | 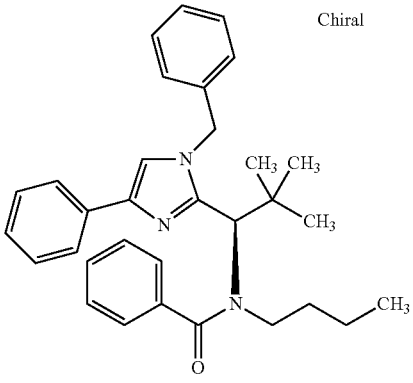 [SMILES: CCCCN(C(=O)c1ccccc1)[C@@H](c1nc(-c2ccccc2)cn1Cc1ccccc1)C(C)(C)C] Chiral | 480.3 | N-[(1R)-1-(1-benzyl-4-phenyl-1H-imidazol-2-yl)-2,2-dimethylpropyl]-N-butylbenzamide |

TABLE 2-continued

| No. | Compound | MH+ | Name |
|---|---|---|---|
| 151 | 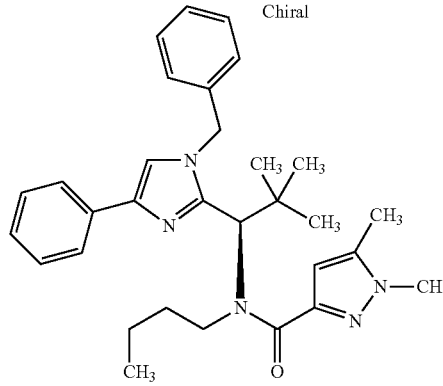 | 498.3 | N-[(1R)-1-(1-benzyl-4-phenyl-1H-imidazol-2-yl)-2,2-dimethylpropyl]-N-butyl-1,5-dimethyl-1H-pyrazole-3-carboxamide |
| 152 | 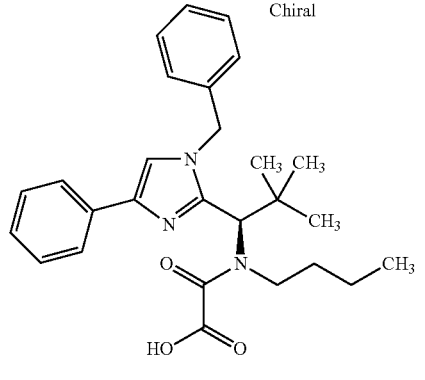 [SMILES: CCCCN(C(=O)C(=O)O)[C@@H](c1nc(-c2ccccc2)cn1Cc1ccccc1)C(C)(C)C] | 448.2 | [[(1R)-1-(1-benzyl-4-phenyl-1-imidazol-2-yl)-2,2-dimethylpropyl](butyl)amino](oxo)acetic acid |
| 153 | 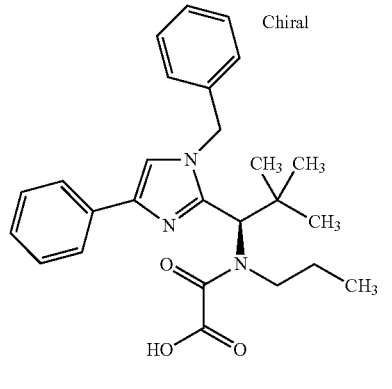 [SMILES: CCCN(C(=O)C(=O)O)[C@@H](c1nc(-c2ccccc2)cn1Cc1ccccc1)C(C)(C)C] | 434.2 | [[(1R)-1-(1-benzyl-4-phenyl-1-imidazol-2-yl)-2,2-dimethylpropyl](propyl)amino](oxo)acetic acid |
| 154 | 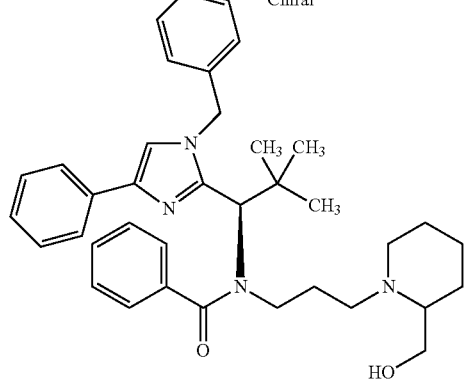 | 579.3 | N-[(1R)-1-(1-benzyl-4-phenyl-1H-imidazol-2-yl)-2,2-dimethylpropyl]-N-{3-[2-(hydroxymethyl)piperidin-1-yl]propyl}benzamide |

TABLE 2-continued
| No. | Compound | MH+ | Name |
|---|---|---|---|
| 155 | 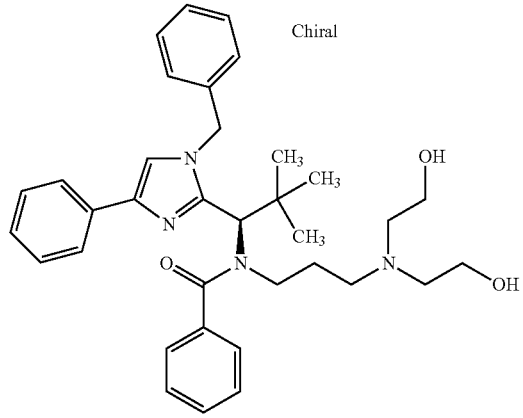 [SMILES: CC(C)(C)[C@H](c1nc(-c2ccccc2)cn1Cc1ccccc1)N(CCCN(CCO)CCO)C(=O)c1ccccc1] | 569.3 | N-[(1R)-1-(1-benzyl-4-phenyl-1H-imidazol-2-yl)-2,2-dimethylpropyl]-N-{3-[bis(2-hydroxyethyl)amino]propyl}benzamide |
| 156 | 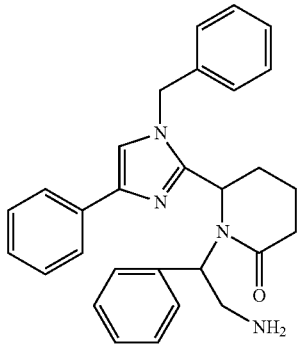 [SMILES: NCC(c1ccccc1)N1C(=O)CCCC1c1nc(-c2ccccc2)cn1Cc1ccccc1] | 451.2 | 1-(2-amino-1-phenylethyl)-6-(1-benzyl-4-phenyl-1H-imidazol-2-yl)piperidin-2-one |
| 157 | 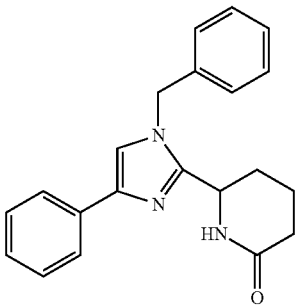 [SMILES: O=C1CCCC(c2nc(-c3ccccc3)cn2Cc2ccccc2)N1] | 332.2 | 6-(1-benzyl-4-phenyl-1H-imidazol-2-yl)piperidin-2-one |
| 158 | 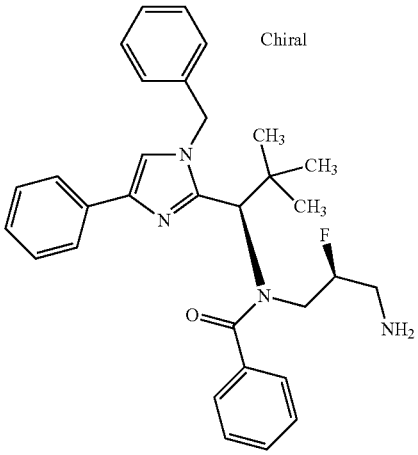 [SMILES: CC(C)(C)[C@H](c1nc(-c2ccccc2)cn1Cc1ccccc1)N(C[C@@H](F)CN)C(=O)c1ccccc1] | 499.2 | N-[(2S)-3-amino-2-fluoropropyl]-N-[(1R)-1-(1-benzyl-4-phenyl-1H-imidazol-2-yl)-2,2-dimethylpropyl]benzamide |

TABLE 2-continued
| No. | Compound | MH+ | Name |
|---|---|---|---|
| 159 | 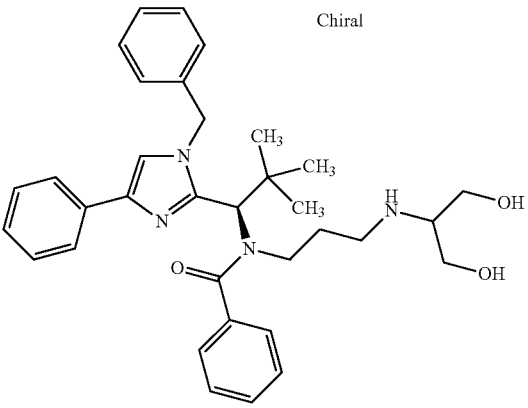 [SMILES: CC(C)(C)[C@H](c1nc(-c2ccccc2)cn1Cc1ccccc1)N(CCCNC(CO)CO)C(=O)c1ccccc1] Chiral | 555.3 | N-[(1R)-1-(1-benzyl-4-phenyl-1H-imidazol-2-yl)-2,2-dimethylpropyl]-N-(3-{[2-hydroxy-1-(hydroxymethyl)ethyl]amino}propyl)benzamide |
| 160 | 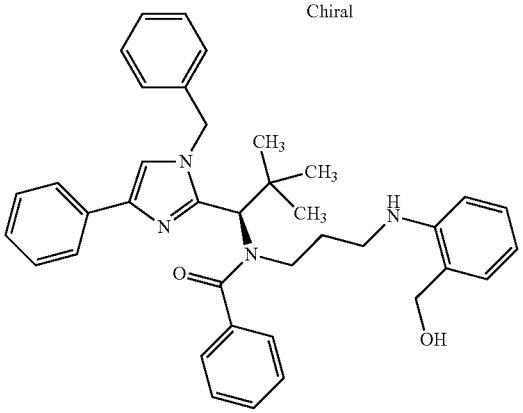 [SMILES: CC(C)(C)[C@H](c1nc(-c2ccccc2)cn1Cc1ccccc1)N(CCCNc1ccccc1CO)C(=O)c1ccccc1] Chiral | 587.3 | N-[(1R)-1-(1-benzyl-4-phenyl-1H-imidazol-2-yl)-2,2-dimethylpropyl]-N-(3-{[2-(hydroxymethyl)phenyl]amino}propyl)benzamide |
| 161 | 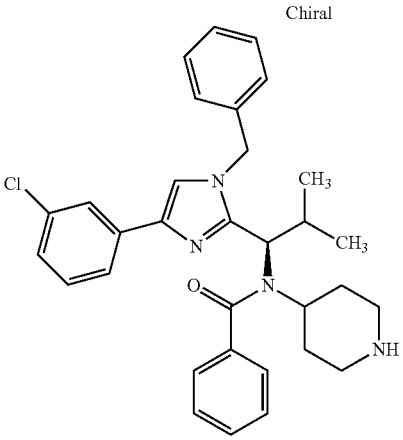 [SMILES: CC(C)[C@H](c1nc(-c2cccc(Cl)c2)cn1Cc1ccccc1)N(C(=O)c1ccccc1)C1CCNCC1] Chiral | 527.3 | N-{(1R)-1-[1-benzyl-4-(3-chlorophenyl)-1H-imidazol-2-yl]-2-methylpropyl}-N-piperidin-4-ylbenzamide |

TABLE 2-continued
| No. | Compound | MH+ | Name |
|---|---|---|---|
| 162 | 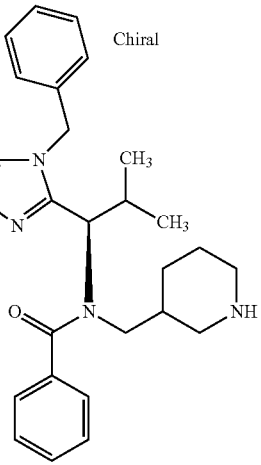 | 527.3 | N-{(1R)-1-[1-benzyl-4-(3-chlorophenyl)-1H-imidazol-2-yl]-2-methylpropyl}-N-(piperidin-3-ylmethyl)benzamide |
| 163 | 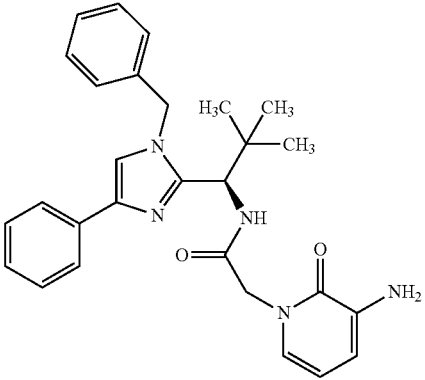 [SMILES: CC(C)(C)[C@@H](NC(=O)Cn1cccc(N)c1=O)c1nc(-c2ccccc2)cn1Cc1ccccc1] | 470.2 | 2-(3-amino-2-oxopyridin-1(2H)-yl)-N-[(1R)-1-(1-benzyl-4-phenyl-1H-imidazol-2-yl)-2,2-dimethylpropyl]acetamide |
| 164 | 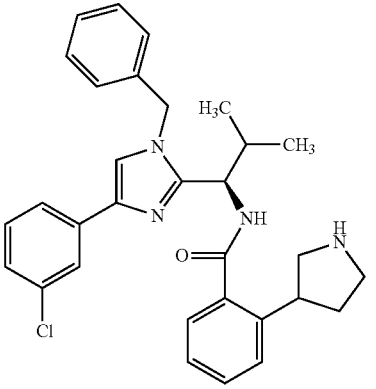 [SMILES: CC(C)[C@@H](NC(=O)c1ccccc1C1CCNC1)c1nc(-c2cccc(Cl)c2)cn1Cc1ccccc1] | 513.2 | N-{(1R)-1-[1-benzyl-4-(3-chlorophenyl)-1H-imidazol-2-yl]-2-methylpropyl}-2-pyrrolidin-3-ylbenzamide |

TABLE 2-continued

| No. | Compound | MH+ | Name |
|---|---|---|---|
| 165 | | 552.3 | (1R,3S)-3-{[(2-aminoethyl)sulfonyl]amino}-N-[(1R)-1-(1-benzyl-4-phenyl-1H-imidazol-2-yl)-2,2-dimethylpropyl]cyclohexane carboxamide |
| 166 | | 502.3 | (1R,3S)-3-[(aminoacetyl)amino]-N-[(1R)-1-(1-benzyl-4-phenyl-1H-imidazol-2-yl)-2,2-dimethylpropyl]cyclohexane carboxamide |
| 167 | | 570.2 | N-(3-aminopropyl)-N-{(1R)-1-[1-benzyl-4-(3-chlorophenyl)-1H-imidazol-2-yl]-2-methylpropyl}-6-(trifluoromethyl)nicotinamide |
| 168 | | 499.2 | N-[(2R)-3-amino-2-fluoropropyl]-N-[(1R)-1-(1-benzyl-4-phenyl-1H-imidazol-2-yl)-2,2-dimethylpropyl]benzamide |

TABLE 2-continued

| No. | Compound | MH+ | Name |
|---|---|---|---|
| 169 | | 508.2 | (3R)-N-(3-aminopropyl)-N-{(1R)-1-[1-benzyl-4-(3-chlorophenyl)-1H-imidazol-2-yl]-2-methylpropyl}piperidine-3-carboxamide |
| 170 | | 508.2 | (3S)-N-(3-aminopropyl)-N-{(1R)-1-[1-benzyl-4-(3-chlorophenyl)-1H-imidazol-2-yl]-2-methylpropyl}piperidine-3-carboxamide |
| 171 | | 506.2 | N-(3-aminopropyl)-N-{(1R)-1-[1-benzyl-4-(3-chlorophenyl)-1H-imidazol-2-yl]-2-methylpropyl}-2-(1H-1,2,4-triazol-1-yl)acetamide |
| 172 | | 437.2 | [(5R)-1-benzoyl-5-(1-benzyl-4-phenyl-1H-imidazol-2-yl)pyrrolidin-2-yl]methylamine |

TABLE 2-continued

| No. | Compound | MH+ | Name |
|---|---|---|---|
| 173 | | 506.05 | N-(3-aminopropyl)-N-{(1R)-1-[1-benzyl-4-(3-chlorophenyl)-1H-imidazol-2-yl]-2-methylpropyl}-2-(4H-1,2,4-triazol-4-yl)acetamide |
| 174 | | 559.2 | N-(3-aminopropyl)-N-{(1R)-1-[1-benzyl-4-(3-chlorophenyl)-1H-imidazol-2-yl]-2-methylpropyl}-2,1,3-benzothiadiazole-4-carboxamide |
| 175 | | 497.3 | N-[(2S)-3-amino-2-hydroxypropyl]-N-[(1R)-1-(1-benzyl-4-phenyl-1H-imidazol-2-yl)-2,2-dimethylpropyl]benzamide |

TABLE 2-continued

| No. | Compound | MH+ | Name |
|---|---|---|---|
| 176 | | 517.3 | N-[(2S)-3-amino-2-fluoropropyl]-N-[(1R)-1-(1-benzyl-4-phenyl-1H-imidazol-2-yl)-2,2-dimethylpropyl]-1,5-dimethyl-1H-pyrazole-3-carboxamide |
| 177 | | 541.3 | N-[(1R)-1-(1-benzyl-4-phenyl-1H-imidazol-2-yl)-2,2-dimethylpropyl]-1,5-dimethyl-N-[(2S)-morpholin-2-ylmethyl]-1H-pyrazole-3-carboxamide |
| 178 | | 541.3 | N-[(1R)-1-(1-benzyl-4-phenyl-1H-imidazol-2-yl)-2,2-dimethylpropyl]-1,5-dimethyl-N-[(2R)-morpholin-2-ylmethyl]-1H-pyrazole-3-carboxamide |

TABLE 2-continued

| No. | Compound | MH+ | Name |
|---|---|---|---|
| 179 | | 515.3 | N-[(2S)-3-amino-2-hydroxypropyl]-N-[(1R)-1-(1-benzyl-4-phenyl-1H-imidazol-2-yl)-2,2-dimethylpropyl]-1,5-dimethyl-1H-pyrazole-3-carboxamide |
| 180 | | 465.3 | N-[(2S)-3-amino-2-hydroxypropyl]-N-[(1R)-1-(1-benzyl-4-phenyl-1H-imidazol-2-yl)-2,2-dimethylpropyl]-2-methoxyacetamide |
| 181 | | 493.3 | N-[(1R)-1-(1-benzyl-4-phenyl-1H-imidazol-2-yl)-2,2-dimethylpropyl]-2-pyrrolidin-3-ylbenzamide |
| 182 | | 505.2 | N-(3-aminopropyl)-N-{(1R)-1-[1-benzyl-4-(3-chlorophenyl)-1H-imidazol-2-yl]-2-methylpropyl}-2-(1H-pyrazol-1-yl)acetamide |

TABLE 2-continued

| No. | Compound | MH+ | Name |
|---|---|---|---|
| 183 | | 517.2 | N-[(2R)-3-amino-2-fluoropropyl]-N-[(1R)-1-(1-benzyl-4-phenyl-1H-imidazol-2-yl)-2,2-dimethylpropyl]-1,5-dimethyl-1H-pyrazole-3-carboxamide |
| 184 | | 435.2 | methyl 3-aminopropyl[(1R)-1-(1-benzyl-4-phenyl-1H-imidazol-2-yl)-2,2-dimethylpropyl]carbamate |
| 185 | | 487.3 | N-(3-aminopropyl)-N-[(1R)-1-(1-benzyl-4-phenyl-1H-imidazol-2-yl)-2,2-dimethylpropyl]-2-(1H-tetrazol-1-yl)acetamide |
| 186 | | 487.3 | N-(3-aminopropyl)-N-[(1R)-1-(1-benzyl-4-phenyl-1H-imidazol-2-yl)-2,2-dimethylpropyl]-2-(2H-tetrazol-2-yl)acetamide |

TABLE 2-continued

| No. | Compound | MH+ | Name |
|---|---|---|---|
| 187 | | 486.3 | N-(3-aminopropyl)-N-[(1R)-1-(1-benzyl-4-phenyl-1H-imidazol-2-yl)-2,2-dimethylpropyl]-2-(1H-1,2,4-triazol-1-yl)acetamide |
| 188 | | 486.3 | N-(3-aminopropyl)-N-[(1R)-1-(1-benzyl-4-phenyl-1H-imidazol-2-yl)-2,2-dimethylpropyl]-2-(4H-1,2,4-triazol-4-yl)acetamide |
| 189 | | 491.3 | N-[(1R)-1-(1-benzyl-4-phenyl-1H-imidazol-2-yl)-2,2-dimethylpropyl]-2-methoxy-N-[(2S)-morpholin-2-ylmethyl]acetamide |
| 190 | | 491.3 | N-[(1R)-1-(1-benzyl-4-phenyl-1H-imidazol-2-yl)-2,2-dimethylpropyl]-2-methoxy-N-[(2R)-morpholin-2-ylmethyl]acetamide |

TABLE 2-continued

| No. | Compound | MH+ | Name |
|---|---|---|---|
| 191 | | 483.2 | N-(3-aminopropyl)-N-[(1S)-1-(1-benzyl-4-phenyl-1H-imidazol-2-yl)-2-hydroxy-2-methylpropyl]benzamide |
| 192 | | 477.3 | N-[(1R)-1-(1-benzyl-4-phenyl-1H-imidazol-2-yl)-2,2-dimethylpropyl]-2-hydroxy-N-[(2S)-morpholin-2-ylmethyl]acetamide |
| 193 | | 477.3 | N-[(1R)-1-(1-benzyl-4-phenyl-1H-imidazol-2-yl)-2,2-dimethylpropyl]-2-hydroxy-N-[(2R)-morpholin-2-ylmethyl]acetamide |
| 194 | | 475.3 | (2S)-N-(3-aminopropyl)-N-[(1R)-1-(1-benzyl-4-phenyl-1H-imidazol-2-yl)-2,2-dimethylpropyl]tetrahydrofuran-2-carboxamide |

TABLE 2-continued

| No. | Compound | MH+ | Name |
|---|---|---|---|
| 195 | | 526.3 | N-(3-aminopropyl)-N-{(1R)-1-[4-(3-chlorophenyl)-1-(3-cyanobenzyl)-1H-imidazol-2-yl]-2-methylpropyl}benzamide |
| 196 | | 540.3 | N-(3-aminopropyl)-N-{(1R)-1-[4-(3-chlorophenyl)-1-(3-cyanobenzyl)-1H-imidazol-2-yl]-2-methylpropyl}-4-methylbenzamide |
| 197 | | 529.3 | N-(3-aminopropyl)-N-{(1R)-1-[4-(3-chlorophenyl)-1-(3-methylbenzyl)-1H-imidazol-2-yl]-2-methylpropyl}-4-methylbenzamide |

TABLE 2-continued

| No. | Compound | MH+ | Name |
|---|---|---|---|
| 198 | | 514.3 | N-(3-aminopropyl)-N-{(1R)-1-[4-(3-chlorophenyl)-1-(3-methylbenzyl)-1H-imidazol-2-yl]-2-methylpropyl}benzamide |
| 199 | | 449.3 | ethyl 3-aminopropyl[(1R)-1-(1-benzyl-4-phenyl-1H-imidazol-2-yl)-2,2-dimethylpropyl]carbamate |
| 200 | | 491.4 | neopentyl 3-aminopropyl[(1R)-1-(1-benzyl-4-phenyl-1H-imidazol-2-yl)-2,2-dimethylpropyl]carbamate |
| 201 | | 477.3 | isobutyl 3-aminopropyl[(1R)-1-(1-benzyl-4-phenyl-1H-imidazol-2-yl)-2,2-dimethylpropyl]carbamate |

TABLE 2-continued

| No. | Compound | MH+ | Name |
|---|---|---|---|
| 202 | | 444.2 | propyl 3-aminopropyl[(1R)-1-(1-benzyl-4-phenyl-1H-imidazol-2-yl)-2,2-dimethylpropyl]carbamate |
| 203 | | 444.3 | N-(3-aminopropyl)-N-[(1R)-1-(1-benzyl-4-phenyl-1H-imidazol-2-yl)-2,2-dimethylpropyl]-2-cyanoacetamide |
| 204 | | 475.3 | N-[(1R)-1-(1-benzyl-4-phenyl-1H-imidazol-2-yl)-2,2-dimethylpropyl]-2-methoxy-N-[(3R)-pyrrolidin-3-ylmethyl]acetamide |
| 205 | | 475.3 | N-[(1R)-1-(1-benzyl-4-phenyl-1H-imidazol-2-yl)-2,2-dimethylpropyl]-2-methoxy-N-[(3S)-pyrrolidin-3-ylmethyl]acetamide |

TABLE 2-continued

| No. | Compound | MH+ | Name |
|-----|----------|-----|------|
| 206 | 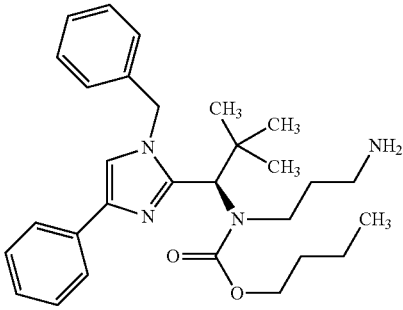 [SMILES: CCCCOC(=O)N(CCCN)[C@@H](c1nc(-c2ccccc2)cn1Cc1ccccc1)C(C)(C)C] | 477.3 | butyl 3-aminopropyl[(1R)-1-(1-benzyl-4-phenyl-1H-imidazol-2-yl)-2,2-dimethylpropyl]carbamate |
| 207 | 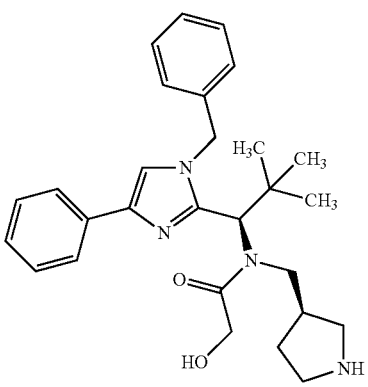 [SMILES: CC(C)(C)[C@H](c1nc(-c2ccccc2)cn1Cc1ccccc1)N(C[C@@H]1CCNC1)C(=O)CO] | 461.3 | N-[(1R)-1-(1-benzyl-4-phenyl-1H-imidazol-2-yl)-2,2-dimethylpropyl]-2-hydroxy-N-[(3R)-pyrrolidin-3-ylmethyl]acetamide |
| 208 | 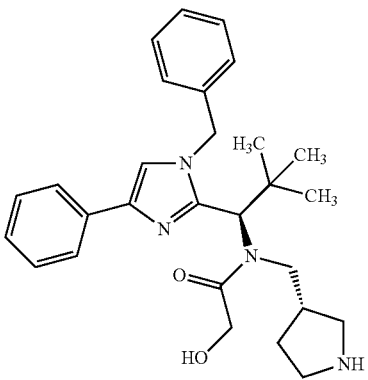 [SMILES: CC(C)(C)[C@H](c1nc(-c2ccccc2)cn1Cc1ccccc1)N(C[C@H]1CCNC1)C(=O)CO] | 461.3 | N-[(1R)-1-(1-benzyl-4-phenyl-1H-imidazol-2-yl)-2,2-dimethylpropyl]-2-hydroxy-N-[(3S)-pyrrolidin-3-ylmethyl]acetamide |
| 209 | 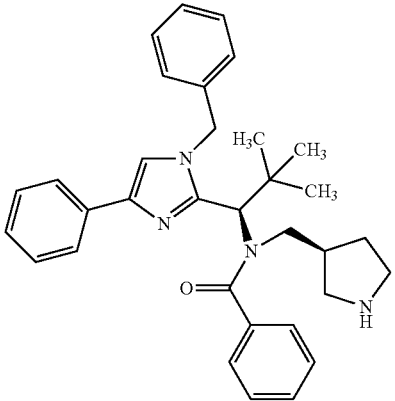 [SMILES: CC(C)(C)[C@H](c1nc(-c2ccccc2)cn1Cc1ccccc1)N(C[C@H]1CCNC1)C(=O)c1ccccc1] | 507.3 | N-[(1R)-1-(1-benzyl-4-phenyl-1H-imidazol-2-yl)-2,2-dimethylpropyl]-N-[(3S)-pyrrolidin-3-ylmethyl]benzamide |

TABLE 2-continued

| No. | Compound | MH+ | Name |
|---|---|---|---|
| 210 | | 505.2 | N-[(2R)-3-amino-2-fluoropropyl]-N-[(1R)-1-(1-benzyl-4-phenyl-1H-imidazol-2-yl)-2,2-dimethylpropyl]-2-(2H-tetrazol-2-yl)acetamide |
| 211 | | 505.3 | N-[(2R)-3-amino-2-fluoropropyl]-N-[(1R)-1-(1-benzyl-4-phenyl-1H-imidazol-2-yl)-2,2-dimethylpropyl]-2-(1H-tetrazol-1-yl)acetamide |
| 212 | | 467.2 | N-[(2R)-3-amino-2-fluoropropyl]-N-[(1R)-1-(1-benzyl-4-phenyl-1H-imidazol-2-yl)-2,2-dimethylpropyl]-2-methoxyacetamide |
| 213 | | 467.2 | N-[(2S)-3-amino-2-fluoropropyl]-N-[(1R)-1-(1-benzyl-4-phenyl-1H-imidazol-2-yl)-2,2-dimethylpropyl]-2-methoxyacetamide |

TABLE 2-continued

| No. | Compound | MH+ | Name |
|---|---|---|---|
| 214 | | 524.3 | N-[(1R)-1-(1-benzyl-4-phenyl-1H-imidazol-2-yl)-2,2-dimethylpropyl]-N-[(3S)-3,4-diamino-4-oxobutyl]benzamide |
| 215 | | 524.3 | N-[(1R)-1-(1-benzyl-4-phenyl-1H-imidazol-2-yl)-2,2-dimethylpropyl]-N-[(3R)-3,4-diamino-4-oxobutyl]benzamide |
| 216 | | 511.3 | N-[(3S)-3-amino-4-hydroxybutyl]-N-[(1R)-1-(1-benzyl-4-phenyl-1H-imidazol-2-yl)-2,2-dimethylpropyl]benzamide |

TABLE 2-continued

| No. | Compound | MH+ | Name |
|---|---|---|---|
| 217 | | 525.3 | (2S)-2-amino-4-{benzoyl[(1R)-1-(1-benzyl-4-phenyl-1H-imidazol-2-yl)-2,2-dimethylpropyl]amino}butanoic acid |
| 218 | | 453.2 | N-[(2R)-3-amino-2-fluoropropyl]-N-[(1R)-1-(1-benzyl-4-phenyl-1H-imidazol-2-yl)-2,2-dimethylpropyl]-2-hydroxyacetamide |
| 219 | | 487.3 | N-(3-aminopropyl)-N-[(1R)-1-(1-benzyl-4-phenyl-1H-imidazol-2-yl)-2,2-dimethylpropyl]-2-(1H-tetrazol-5-yl)acetamide |
| 220 | | 513.3 | N-[(1R)-1-(1-benzyl-4-phenyl-1H-imidazol-2-yl)-2,2-dimethylpropyl]-N-[(3S)-pyrrolidin-3-ylmethyl]-2-(1H-tetrazol-1-yl)acetamide |

TABLE 2-continued

| No. | Compound | MH+ | Name |
|---|---|---|---|
| 221 | | 513.3 | N-[(1R)-1-(1-benzyl-4-phenyl-1H-imidazol-2-yl)-2,2-dimethylpropyl]-N-[(3S)-pyrrolidin-3-ylmethyl]-2-(2H-tetrazol-2-yl)acetamide |
| 222 | | 522.3 | N-[(1R)-1-(1-benzyl-4-phenyl-1H-imidazol-2-yl)-2,2-dimethylpropyl]-6-methyl-N-[(3S)-pyrrolidin-3-ylmethyl]nicotinamide |
| 223 | | 461.3 | N-(azetidin-3-ylmethyl)-N-[(1R)-1-(1-benzyl-4-phenyl-1H-imidazol-2-yl)-2,2-dimethylpropyl]-2-methoxyacetamide |

TABLE 2-continued

| No. | Compound | MH+ | Name |
|---|---|---|---|
| 224 | | 532.3 | N-{(1R)-1-[1-(3-cyanobenzyl)-4-phenyl-1H-imidazol-2-yl]-2,2-dimethylpropyl}-N-(pyrrolidin-3-ylmethyl)benzamide |
| 225 | | 521.3 | N-{(1R)-2,2-dimethyl-1-[1-(3-methylbenzyl)-4-phenyl-1H-imidazol-2-yl]propyl}-N-(pyrrolidin-3-ylmethyl)benzamide |
| 226 | | 451.3 | N-[(2S)-3-amino-2-hydroxypropyl]-N-[(1R)-1-(1-benzyl-4-phenyl-1H-imidazol-2-yl)-2,2-dimethylpropyl]-2-hydroxyacetamide |

TABLE 2-continued

| No. | Compound | MH+ | Name |
|---|---|---|---|
| 227 | | 511.2 | N-[(1R)-1-(1-benzyl-4-phenyl-1H-imidazol-2-yl)-2,2-dimethylpropyl]-N-[3-(methoxyamino)propyl]benzamide |
| 228 | | 505.2 | N-[(2S)-3-amino-2-fluoropropyl]-N-[(1R)-1-(1-benzyl-4-phenyl-1H-imidazol-2-yl)-2,2-dimethylpropyl]-2-(1H-tetrazol-1-yl)acetamide |
| 229 | | 505.2 | N-[(2S)-3-amino-2-fluoropropyl]-N-[(1R)-1-(1-benzyl-4-phenyl-1H-imidazol-2-yl)-2,2-dimethylpropyl]-2-(2H-tetrazol-2-yl)acetamide |
| 230 | | 500.3 | N-{(1R)-1-[1-(3-cyanobenzyl)-4-phenyl-1H-imidazol-2-yl]-2,2-dimethylpropyl}-2-methoxy-N-[(3S)-pyrrolidin-3-ylmethyl]acetamide |

TABLE 2-continued

| No. | Compound | MH+ | Name |
|---|---|---|---|
| 231 | | 500.3 | N-{(1R)-1-[1-(3-cyanobenzyl)-4-phenyl-1H-imidazol-2-yl]-2,2-dimethylpropyl}-2-methoxy-N-[(3R)-pyrrolidin-3-ylmethyl]acetamide |
| 232 | | 506.3 | N-(3-aminopropyl)-N-{(1R)-1-[1-(3-cyanobenzyl)-4-phenyl-1H-imidazol-2-yl]-2,2-dimethylpropyl}benzamide |
| 233 | | 474.3 | N-(3-aminopropyl)-N-{(1R)-1-[1-(3-cyanobenzyl)-4-phenyl-1H-imidazol-2-yl]-2,2-dimethylpropyl}-2-methoxyacetamide |

TABLE 2-continued

| No. | Compound | MH+ | Name |
|-----|----------|-----|------|
| 234 | | 477.3 | 2-hydroxy-N-{(1R)-1-[1-(3-hydroxybenzyl)-4-phenyl-1H-imidazol-2-yl]-2,2-dimethylpropyl}-N-(pyrrolidin-3-ylmethyl)acetamide |
| 235 | | 489.3 | N-{(1R)-2,2-dimethyl-1-[1-(3-methylbenzyl)-4-phenyl-1H-imidazol-2-yl]propyl}-2-methoxy-N-[(3S)-pyrrolidin-3-ylmethyl]acetamide |
| 236 | | 489.3 | N-{(1R)-2,2-dimethyl-1-[1-(3-methylbenzyl)-4-phenyl-1H-imidazol-2-yl]propyl}-2-methoxy-N-[(3R)-pyrrolidin-3-ylmethyl]acetamide |
| 237 | | 463.3 | N-(3-aminopropyl)-N-{(1R)-2,2-dimethyl-1-[1-(3-methylbenzyl)-4-phenyl-1H-imidazol-2-yl]propyl}-2-methoxyacetamide |

TABLE 2-continued

| No. | Compound | MH+ | Name |
|---|---|---|---|
| 238 | | 529.3 | N-[(3S)-3-amino-4-hydroxybutyl]-N-[(1R)-1-(1-benzyl-4-phenyl-1H-imidazol-2-yl)-2,2-dimethylpropyl]-1,5-dimethyl-1H-pyrazole-3-carboxamide |
| 239 | | 503.2 | N-(3-amino-2-hydroxypropyl)-N-[(1R)-1-(1-benzyl-4-phenyl-1H-imidazol-2-yl)-2,2-dimethylpropyl]-2-(1H-tetrazol-1-yl)acetamide |
| 240 | | 503.2 | N-(3-amino-2-hydroxypropyl)-N-[(1R)-1-(1-benzyl-4-phenyl-1H-imidazol-2-yl)-2,2-dimethylpropyl]-2-(2H-tetrazol-2-yl)acetamide |

TABLE 2-continued

| No. | Compound | MH+ | Name |
|---|---|---|---|
| 241 | | 525.3 | N-[(1R)-1-(1-benzyl-4-phenyl-1H-imidazol-2-yl)-2,2-dimethylpropyl]-1,5-dimethyl-N-[(3S)-pyrrolidin-3-ylmethyl]-1H-pyrazole-3-carboxamide |
| 242 | | 495.3 | N-(3-aminopropyl)-N-{(1R)-2,2-dimethyl-1-[1-(3-methylbenzyl)-4-phenyl-1H-imidazol-2-yl]propyl}benzamide |
| 243 | | 493.3 | N-(azetidin-3-ylmethyl)-N-[(1R)-1-(1-benzyl-4-phenyl-1H-imidazol-2-yl)-2,2-dimethylpropyl]benzamide |

TABLE 2-continued

| No. | Compound | MH+ | Name |
|---|---|---|---|
| 244 | | 447.3 | N-(azetidin-3-ylmethyl)-N-[(1R)-1-(1-benzyl-4-phenyl-1H-imidazol-2-yl)-2,2-dimethylpropyl]-2-hydroxyacetamide |
| 245 | | 511.3 | N-(azetidin-3-ylmethyl)-N-[(1R)-1-(1-benzyl-4-phenyl-1H-imidazol-2-yl)-2,2-dimethylpropyl]-1,5-dimethyl-1H-pyrazole-3-carboxamide |
| 246 | | 479.3 | N-[(3S)-3-amino-4-hydroxybutyl]-N-[(1R)-1-(1-benzyl-4-phenyl-1H-imidazol-2-yl)-2,2-dimethylpropyl]-2-methoxyacetamide |

TABLE 2-continued

| No. | Compound | MH+ | Name |
|---|---|---|---|
| 247 | | 504.3 | N-[(2S)-3-amino-2-fluoropropyl]-N-[(1R)-1-(1-benzyl-4-phenyl-1H-imidazol-2-yl)-2,2-dimethylpropyl]-2-(1H-1,2,3-triazol-1-yl)acetamide |
| 248 | | 504.3 | N-[(2S)-3-amino-2-fluoropropyl]-N-[(1R)-1-(1-benzyl-4-phenyl-1H-imidazol-2-yl)-2,2-dimethylpropyl]-2-(2H-1,2,3-triazol-2-yl)acetamide |
| 249 | | 517.3 | N-[(3S)-3-amino-4-hydroxybutyl]-N-[(1R)-1-(1-benzyl-4-phenyl-1H-imidazol-2-yl)-2,2-dimethylpropyl]-2-(1H-tetrazol-1-yl)acetamide |
| 250 | | 517.3 | N-[(3S)-3-amino-4-hydroxybutyl]-N-[(1R)-1-(1-benzyl-4-phenyl-1H-imidazol-2-yl)-2,2-dimethylpropyl]-2-(2H-tetrazol-2-yl)acetamide |

TABLE 2-continued

| No. | Compound | MH+ | Name |
|---|---|---|---|
| 251 | | 516.3 | N-[(3S)-3-amino-4-hydroxybutyl]-N-[(1R)-1-(1-benzyl-4-phenyl-1H-imidazol-2-yl)-2,2-dimethylpropyl]-2-(1H-1,2,3-triazol-1-yl)acetamide |
| 252 | | 421.3 | N-[(1R)-1-(1-benzyl-4-phenyl-1H-imidazol-2-yl)-2,2-dimethylpropyl]-N-[(3-fluoropyrrolidin-3-yl)methyl]amine |
| 253 | | 491.3 | N-[(1R)-1-(1-benzyl-4-phenyl-1H-imidazol-2-yl)-2,2-dimethylpropyl]-N-{[(3S)-3-hydroxypyrrolidin-3-yl]methyl}-2-methoxyacetamide |
| 254 | | 491.3 | N-[(1R)-1-(1-benzyl-4-phenyl-1H-imidazol-2-yl)-2,2-dimethylpropyl]-N-{[(3R)-3-hydroxypyrrolidin-3-yl]methyl}-2-methoxyacetamide |

TABLE 2-continued

| No. | Compound | MH+ | Name |
|---|---|---|---|
| 255 | | 491.3 | N-[(1R)-1-(1-benzyl-4-phenyl-1H-imidazol-2-yl)-2,2-dimethylpropyl]-N-[(3-hydroxypyrrolidin-3-yl)methyl]-2-methoxyacetamide |
| 256 | | 508.3 | N-(azetidin-3-ylmethyl)-N-[(1R)-1-(1-benzyl-4-phenyl-1H-imidazol-2-yl)-2,2-dimethylpropyl]-6-methylnicotinamide |
| 257 | | 529.3 | N-[(1R)-1-(1-benzyl-4-phenyl-1H-imidazol-2-yl)-2,2-dimethylpropyl]-N-{[(3S)-3-fluoropyrrolidin-3-yl]methyl}-1,5-dimethyl-1H-pyrazole-3-carboxamide |

TABLE 2-continued

| No. | Compound | MH+ | Name |
|-----|----------|-----|------|
| 258 | | 529.3 | N-[(1R)-1-(1-benzyl-4-phenyl-1H-imidazol-2-yl)-2,2-dimethylpropyl]-N-{[(3R)-3-fluoropyrrolidin-3-yl]methyl}-1,5-dimethyl-1H-pyrazole-3-carboxamide |
| 259 | | 529.3 | N-[(1R)-1-(1-benzyl-4-phenyl-1H-imidazol-2-yl)-2,2-dimethylpropyl]-N-[(3-fluoropyrrolidin-3-yl)methyl]-1,5-dimethyl-1H-pyrazole-3-carboxamide |
| 260 | | 525.3 | N-[(1R)-1-(1-benzyl-4-phenyl-1H-imidazol-2-yl)-2,2-dimethylpropyl]-N-{[(3S)-3-fluoropyrrolidin-3-yl]methyl}benzamide |
| 261 | | 525.3 | N-[(1R)-1-(1-benzyl-4-phenyl-1H-imidazol-2-yl)-2,2-dimethylpropyl]-N-{[(3R)-3-fluoropyrrolidin-3-yl]methyl}benzamide |

TABLE 2-continued

| No. | Compound | MH+ | Name |
|---|---|---|---|
| 262 | | 525.3 | N-[(1R)-1-(1-benzyl-4-phenyl-1H-imidazol-2-yl)-2,2-dimethylpropyl]-N-[(3-fluoropyrrolidin-3-yl)methyl]benzamide |
| 263 | | 451.3 | N-(3-aminopropyl)-2-hydroxy-N-{(1R)-1-[1-(3-hydroxybenzyl)-4-phenyl-1H-imidazol-2-yl]-2,2-dimethylpropyl}acetamide |
| 264 | | 523.3 | N-{(1R)-1-[1-(3-hydroxybenzyl)-4-phenyl-1H-imidazol-2-yl]-2,2-dimethylpropyl}-N-(pyrrolidin-3-ylmethyl)benzamide |

TABLE 2-continued

| No. | Compound | MH+ | Name |
|---|---|---|---|
| 265 | | 513.3 | N-(3-aminopropyl)-N-{(1R)-2,2-dimethyl-1-[1-(3-methylbenzyl)-4-phenyl-1H-imidazol-2-yl]propyl}-1,5-dimethyl-1H-pyrazole-3-carboxamide |
| 266 | | 539.3 | N-{(1R)-2,2-dimethyl-1-[1-(3-methylbenzyl)-4-phenyl-1H-imidazol-2-yl]propyl}-1,5-dimethyl-N-(pyrrolidin-3-ylmethyl)-1H-pyrazole-3-carboxamide |
| 267 | | 497.3 | N-(3-aminopropyl)-N-{(1R)-1-[1-(3-hydroxybenzyl)-4-phenyl-1H-imidazol-2-yl]-2,2-dimethylpropyl}benzamide |

TABLE 2-continued

| No. | Compound | MH+ | Name |
|---|---|---|---|
| 268 | | 511.3 | N-(3-aminopropyl)-N-{(1R)-1-[1-(3-methoxybenzyl)-4-phenyl-1H-imidazol-2-yl]-2,2-dimethylpropyl}benzamide |
| 269 | | 479.3 | N-(3-aminopropyl)-2-methoxy-N-{(1R)-1-[1-(3-methoxybenzyl)-4-phenyl-1H-imidazol-2-yl]-2,2-dimethylpropyl}acetamide |
| 270 | | 460.3 | N-(3-aminopropyl)-N-{(1R)-1-[1-(3-cyanobenzyl)-4-phenyl-1H-imidazol-2-yl]-2,2-dimethylpropyl}-2-hydroxyacetamide |

TABLE 2-continued

| No. | Compound | MH+ | Name |
|---|---|---|---|
| 271 | | 529.3 | N-(3-aminopropyl)-N-{(1R)-1-[1-(3-methoxybenzyl)-4-phenyl-1H-imidazol-2-yl]-2,2-dimethylpropyl}-1,5-dimethyl-1H-pyrazole-3-carboxamide |
| 272 | | 525.3 | N-[(3S)-3-amino-4-methoxybutyl]-N-[(1R)-1-(1-benzyl-4-phenyl-1H-imidazol-2-yl)-2,2-dimethylpropyl]benzamide |
| 273 | | 524.3 | N-(3-aminopropyl)-N-{(1R)-1-[1-(3-cyanobenzyl)-4-phenyl-1H-imidazol-2-yl]-2,2-dimethylpropyl}-1,5-dimethyl-1H-pyrazole-3-carboxamide |

TABLE 2-continued

| No. | Compound | MH+ | Name |
|---|---|---|---|
| 274 | | 550.3 | N-{(1R)-1-[1-(3-cyanobenzyl)-4-phenyl-1H-imidazol-2-yl]-2,2-dimethylpropyl}-1,5-dimethyl-N-(pyrrolidin-3-ylmethyl)-1H-pyrazole-3-carboxamide |
| 275 | | 486.3 | N-{(1R)-1-[1-(3-cyanobenzyl)-4-phenyl-1H-imidazol-2-yl]-2,2-dimethylpropyl}-2-hydroxy-N-[(3S)-pyrrolidin-3-ylmethyl]acetamide |
| 276 | | 504.3 | N-[(2R)-3-amino-2-fluoropropyl]-N-[(1R)-1-(1-benzyl-4-phenyl-1H-imidazol-2-yl)-2,2-dimethylpropyl]-2-(1H-1,2,3-triazol-1-yl)acetamide |

TABLE 2-continued

| No. | Compound | MH+ | Name |
|---|---|---|---|
| 277 | | 504.3 | N-[(2R)-3-amino-2-fluoropropyl]-N-[(1R)-1-(1-benzyl-4-phenyl-1H-imidazol-2-yl)-2,2-dimethylpropyl]-2-(2H-1,2,3-triazol-2-yl)acetamide |
| 278 | | 523.3 | N-[(1R)-1-(1-benzyl-4-phenyl-1H-imidazol-2-yl)-2,2-dimethylpropyl]-N-{[(3S)-3-hydroxypyrrolidin-3-yl]methyl}benzamide |
| 279 | | 523.3 | N-[(1R)-1-(1-benzyl-4-phenyl-1H-imidazol-2-yl)-2,2-dimethylpropyl]-N-{[(3R)-3-hydroxypyrrolidin-3-yl]methyl}benzamide |
| 280 | | 523.3 | N-[(1R)-1-(1-benzyl-4-phenyl-1H-imidazol-2-yl)-2,2-dimethylpropyl]-N-[(3-hydroxypyrrolidin-3-yl)methyl]benzamide |

TABLE 2-continued

| No. | Compound | MH+ | Name |
|---|---|---|---|
| 281 | | 489.3 | N-[(1R)-1-(1-benzyl-4-phenyl-1H-imidazol-2-yl)-2,2-dimethylpropyl]-2-ethoxy-N-[(3S)-pyrrolidin-3-ylmethyl]acetamide |
| 282 | | 463.3 | N-(3-aminopropyl)-N-[(1R)-1-(1-benzyl-4-phenyl-1H-imidazol-2-yl)-2,2-dimethylpropyl]-2-ethoxyacetamide |
| 283 | | 527.3 | N-[(1R)-1-(1-benzyl-4-phenyl-1H-imidazol-2-yl)-2,2-dimethylpropyl]-N-{[(3S)-3-hydroxypyrrolidin-3-yl]methyl}-1,5-dimethyl-1H-pyrazole-3-carboxamide |
| 284 | | 527.3 | N-[(1R)-1-(1-benzyl-4-phenyl-1H-imidazol-2-yl)-2,2-dimethylpropyl]-N-{[(3R)-3-hydroxypyrrolidin-3-yl]methyl}-1,5-dimethyl-1H-pyrazole-3-carboxamide |

TABLE 2-continued

| No. | Compound | MH+ | Name |
|---|---|---|---|
| 285 | | 527.3 | N-[(1R)-1-(1-benzyl-4-phenyl-1H-imidazol-2-yl)-2,2-dimethylpropyl]-N-[(3-hydroxypyrrolidin-3-yl)methyl]-1,5-dimethyl-1H-pyrazole-3-carboxamide |
| 286 | | 507.3 | N-[(2S)-3-amino-2-fluoropropyl]-N-[(1S)-1-(1-benzyl-4-phenyl-1H-imidazol-2-yl)-2-hydroxy-2-methylpropyl]-2-(1H-tetrazol-1-yl)acetamide |
| 287 | | 507.3 | N-[(2S)-3-amino-2-fluoropropyl]-N-[(1S)-1-(1-benzyl-4-phenyl-1H-imidazol-2-yl)-2-hydroxy-2-methylpropyl]-2-(2H-tetrazol-2-yl)acetamide |

TABLE 2-continued

| No. | Compound | MH+ | Name |
|---|---|---|---|
| 288 | | 523.2 | N-[(2S)-3-amino-2-fluoropropyl]-N-{(1R)-1-[1-benzyl-4-(3-fluorophenyl)-1H-imidazol-2-yl]-2,2-dimethylpropyl}-2-(1H-tetrazol-1-yl)acetamide |
| 289 | | 523.2 | N-[(2S)-3-amino-2-fluoropropyl]-N-{(1R)-1-[1-benzyl-4-(3-fluorophenyl)-1H-imidazol-2-yl]-2,2-dimethylpropyl}-2-(2H-tetrazol-2-yl)acetamide |
| 290 | | 492.3 | N-[(2S)-3-amino-2-(hydroxymethyl)propyl]-N-[(1R)-1-(1-benzyl-4-phenyl-1H-imidazol-2-yl)-2,2-dimethylpropyl]-N'-methylethanediamide |
| 291 | | 492.3 | N-[(2R)-3-amino-2-(hydroxymethyl)propyl]-N-[(1R)-1-(1-benzyl-4-phenyl-dimethylpropyl]-N'-methylethanediamide |

TABLE 2-continued

| No. | Compound | MH+ | Name |
|---|---|---|---|
| 292 | | 479.3 | N-[(3R)-3-amino-4-hydroxybutyl]-N-[(1R)-1-(1-benzyl-4-phenyl-1H-imidazol-2-yl)-2,2-dimethylpropyl]-2-methoxyacetamide |
| 293 | | 517.2 | N-[(3R)-3-amino-4-hydroxybutyl]-N-[(1R)-1-(1-benzyl-4-phenyl-1H-imidazol-2-yl)-2,2-dimethylpropyl]-2-(1H-tetrazol-1-yl)acetamide |
| 294 | | 517.2 | N-[(3R)-3-amino-4-hydroxybutyl]-N-[(1R)-1-(1-benzyl-4-phenyl-1H-imidazol-2-yl)-2,2-dimethylpropyl]-2-(2H-tetrazol-2-yl)acetamide |
| 295 | | 493.3 | N-[(1R)-1-(1-benzyl-4-phenyl-1H-imidazol-2-yl)-2,2-dimethylpropyl]-N-{[(3S)-3-fluoropyrrolidin-3-yl]methyl}-2-methoxyacetamide |

TABLE 2-continued

| No. | Compound | MH+ | Name |
|---|---|---|---|
| 296 | | 493.3 | N-[(1R)-1-(1-benzyl-4-phenyl-1H-imidazol-2-yl)-2,2-dimethylpropyl]-N-{[(3R)-3-fluoropyrrolidin-3-yl]methyl}-2-methoxyacetamide |
| 297 | | 491.3 | N-[(1R)-1-(1-benzyl-4-phenyl-1H-imidazol-2-yl)-2,2-dimethylpropyl]-N-{[(3R,4R)-4-hydroxypyrrolidin-3-yl]methyl}-2-methoxyacetamide |
| 298 | | 491.3 | N-[(1R)-1-(1-benzyl-4-phenyl-1H-imidazol-2-yl)-2,2-dimethylpropyl]-N-{[(3S,4S)-4-hydroxypyrrolidin-3-yl]methyl}-2-methoxyacetamide |
| 299 | | 523.3 | N-[(1R)-1-(1-benzyl-4-phenyl-1H-imidazol-2-yl)-2,2-dimethylpropyl]-N-{[(3R,4R)-4-hydroxypyrrolidin-3-yl]methyl}benzamide |

TABLE 2-continued

| No. | Compound | MH+ | Name |
|---|---|---|---|
| 300 | | 523.3 | N-[(1R)-1-(1-benzyl-4-phenyl-1H-imidazol-2-yl)-2,2-dimethylpropyl]-N-{[(3S,4S)-4-hydroxypyrrolidin-3-yl]methyl}benzamide |
| 301 | | 535.3 | N-[(3S)-3-amino-4-hydroxybutyl]-N-{(1R)-1-[1-benzyl-4-(3-fluorophenyl)-1H-imidazol-2-yl]-2,2-dimethylpropyl}-2-(1H-tetrazol-1-yl)acetamide |
| 302 | | 535.3 | N-[(3S)-3-amino-4-hydroxybutyl]-N-{(1R)-1-[1-benzyl-4-(3-fluorophenyl)-1H-imidazol-2-yl]-2,2-dimethylpropyl}-2-(2H-tetrazol-2-yl)acetamide |
| 303 | | 497.3 | N-[(3S)-3-amino-4-methoxybutyl]-N-[(1R)-1-(1-benzyl-4-phenyl-1H-imidazol-2-yl)-2,2-dimethylpropyl]-2-methoxyacetamide |

TABLE 2-continued

| No. | Compound | MH+ | Name |
|---|---|---|---|
| 304 | | 497.3 | N-[(3S)-3-amino-4-hydroxybutyl]-N-{(1R)-1-[1-benzyl-4-(3-fluorophenyl)-1H-imidazol-2-yl]-2,2-dimethylpropyl}-2-methoxyacetamide |
| 305 | | 531.3 | N-[(1R)-1-(1-benzyl-4-phenyl-1H-imidazol-2-yl)-2,2-dimethylpropyl]-N-{[(3S)-3-fluoropyrrolidin-3-yl]methyl}-2-(2H-tetrazol-2-yl)acetamide |
| 306 | | 531.2 | N-[(1R)-1-(1-benzyl-4-phenyl-1H-imidazol-2-yl)-2,2-dimethylpropyl]-N-{[(3R)-3-fluoropyrrolidin-3-yl]methyl}-2-(1H-tetrazol-1-yl)acetamide |

TABLE 2-continued

| No. | Compound | MH+ | Name |
|---|---|---|---|
| 307 | | 529.2 | N-[(1R)-1-(1-benzyl-4-phenyl-1H-imidazol-2-yl)-2,2-dimethylpropyl]-N-{[(3S,4S)-4-hydroxypyrrolidin-3-yl]methyl}-2-(1H-tetrazol-1-yl)acetamide |
| 308 | | 529.2 | N-[(1R)-1-(1-benzyl-4-phenyl-1H-imidazol-2-yl)-2,2-dimethylpropyl]-N-{[(3S,4S)-4-hydroxypyrrolidin-3-yl]methyl}-2-(2H-tetrazol-2-yl)acetamide |
| 309 | | 529.3 | N-[(1R)-1-(1-benzyl-4-phenyl-1H-imidazol-2-yl)-2,2-dimethylpropyl]-N-{[(3R,4R)-4-hydroxypyrrolidin-3-yl]methyl}-2-(1H-tetrazol-1-yl)acetamide |

TABLE 2-continued

| No. | Compound | MH+ | Name |
|---|---|---|---|
| 310 | | 529.3 | N-[(1R)-1-(1-benzyl-4-phenyl-1H-imidazol-2-yl)-2,2-dimethylpropyl]-N-{[(3R,4R)-4-hydroxypyrrolidin-3-yl]methyl}-2-(2H-tetrazol-2-yl)acetamide |
| 311 | | 543.3 | N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}-2-(2H-tetrazol-2-yl)acetamide |
| 312 | | 543.3 | N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}-2-(1H-tetrazol-1-yl)acetamide |
| 313 | | 505.3 | N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}-2-methoxyacetamide |

TABLE 2-continued

| No. | Compound | MH+ | Name |
|-----|----------|-----|------|
| 314 | | 537.3 | N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}benzamide |
| 315 | | 519.3 | N-[(2R)-3-amino-2-fluoropropyl]-N-[(1R)-1-(1-benzyl-4-phenyl-1H-imidazol-2-yl)-2,2-dimethylpropyl]-2-(5-methyl-2H-tetrazol-2-yl)acetamide |
| 316 | | 519.2 | N-[(2R)-3-amino-2-fluoropropyl]-N-[(1R)-1-(1-benzyl-4-phenyl-1H-imidazol-2-yl)-2,2-dimethylpropyl]-2-(5-methyl-1H-tetrazol-1-yl)acetamide |
| 317 | | 529.3 | N-[(1R)-1-(1-benzyl-4-phenyl-1H-imidazol-2-yl)-2,2-dimethylpropyl]-N-{[(3R)-3-hydroxypyrrolidin-3-yl]methyl}-2-(1H-tetrazol-1-yl)acetamide |

TABLE 2-continued

| No. | Compound | MH+ | Name |
|---|---|---|---|
| 318 | | 529.2 | N-[(1R)-1-(1-benzyl-4-phenyl-1H-imidazol-2-yl)-2,2-dimethylpropyl]-N-{[(3S)-3-hydroxypyrrolidin-3-yl]methyl}-2-(1H-tetrazol-1-yl)acetamide |
| 319 | | 445.2 | (5S)-3-[(1R)-1-(1-benzyl-4-phenyl-1H-imidazol-2-yl)-2,2-dimethylpropyl]-1-oxa-3,7-diazaspiro[4.4]nonan-2-one |
| 320 | | 445.2 | (5R)-3-[(1R)-1-(1-benzyl-4-phenyl-1H-imidazol-2-yl)-2,2-dimethylpropyl]-1-oxa-3,7-diazaspiro[4.4]nonan-2-one |
| 321 | | 497.3 | N-[(2S,3R)-3-amino-2-fluoro-4-hydroxybutyl]-N-[(1R)-1-(1-benzyl-4-phenyl-1H-imidazol-2-yl)-2,2-dimethylpropyl]-2-methoxyacetamide |

TABLE 2-continued

| No. | Compound | MH+ | Name |
|---|---|---|---|
| 322 | 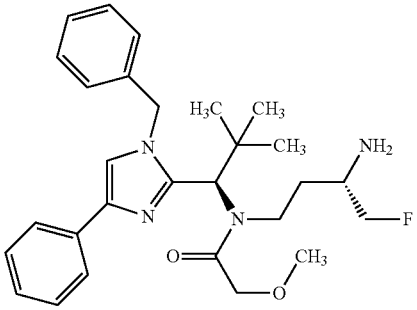 [SMILES: COCC(=O)N(CC[C@H](N)CF)[C@@H](c1nc(-c2ccccc2)cn1Cc1ccccc1)C(C)(C)C] | 481.2 | N-[(3S)-3-amino-4-fluorobutyl]-N-[(1R)-1-(1-benzyl-4-phenyl-1H-imidazol-2-yl)-2,2-dimethylpropyl]-2-methoxyacetamide |
| 323 | 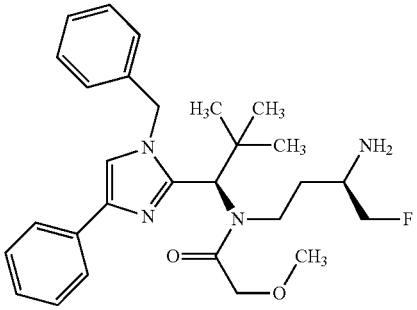 [SMILES: COCC(=O)N(CC[C@@H](N)CF)[C@@H](c1nc(-c2ccccc2)cn1Cc1ccccc1)C(C)(C)C] | 481.2 | N-[(3R)-3-amino-4-fluorobutyl]-N-[(1R)-1-(1-benzyl-4-phenyl-1H-imidazol-2-yl)-2,2-dimethylpropyl]-2-methoxyacetamide |
| 324 | 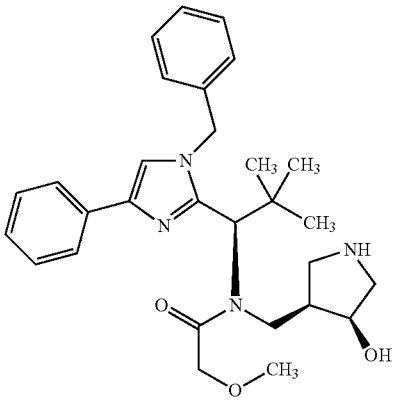 [SMILES: COCC(=O)N(C[C@H]1CNC[C@H]1O)[C@@H](c1nc(-c2ccccc2)cn1Cc1ccccc1)C(C)(C)C] | 491.2 | N-[(1R)-1-(1-benzyl-4-phenyl-1H-imidazol-2-yl)-2,2-dimethylpropyl]-N-{[(3R,4S)-4-hydroxypyrrolidin-3-yl]methyl}-2-methoxyacetamide |
| 325 | 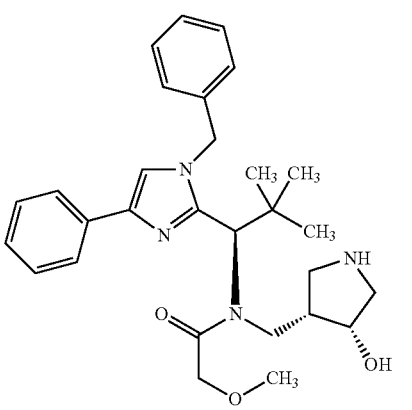 [SMILES: COCC(=O)N(C[C@@H]1CNC[C@@H]1O)[C@@H](c1nc(-c2ccccc2)cn1Cc1ccccc1)C(C)(C)C] | 491.2 | N-[(1R)-1-(1-benzyl-4-phenyl-1H-imidazol-2-yl)-2,2-dimethylpropyl]-N-{[(3S,4R)-4-hydroxypyrrolidin-3-yl]methyl}-2-methoxyacetamide |

TABLE 2-continued

| No. | Compound | MH+ | Name |
|---|---|---|---|
| 326 | | 493.2 | N-[(1R)-1-(1-benzyl-4-phenyl-1H-imidazol-2-yl)-2,2-dimethylpropyl]-N-{[(3R,4S)-4-fluoropyrrolidin-3-yl]methyl}-2-methoxyacetamide |
| 327 | | 473.2 | N-[(1R)-1-(1-benzyl-4-phenyl-1H-imidazol-2-yl)-2,2-dimethylpropyl]-N-(2,5-dihydro-1H-pyrrol-3-ylmethyl)-2-methoxyacetamide |

TABLE 3

| No. | Compound | MH+ | Name |
|---|---|---|---|
| 328 | | 469.3 | N-((R)-3-Amino-2-fluoro-propyl)-N-[(R)-1-(1-benzyl-4-pyrazin-2-yl-1H-imidazol-2-yl)-2,2-dimethyl-propyl]-2-methoxy-acetamide |

TABLE 3-continued
| No. | Compound | MH+ | Name |
|---|---|---|---|
| 329 | 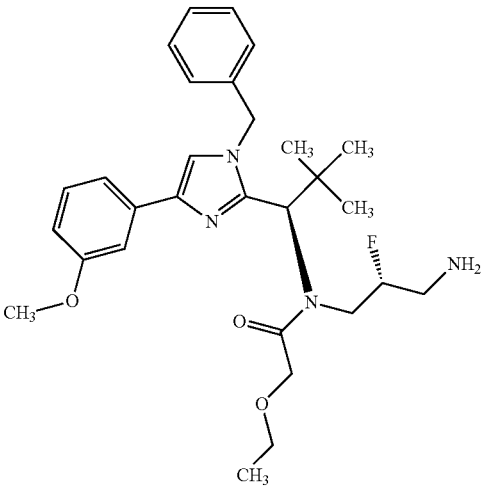 [SMILES: CCOCC(=O)N(C[C@H](F)CN)[C@@H](c1nc(-c2cccc(OC)c2)cn1Cc1ccccc1)C(C)(C)C] | 511.3 | N-((R)-3-Amino-2-fluoro-propyl)-N-{(R)-1-[1-benzyl-4-(3-methoxy-phenyl)-1H-imidazol-2-yl]-2,2-dimethyl-propyl}-2-ethoxy-acetamide |
| 330 | 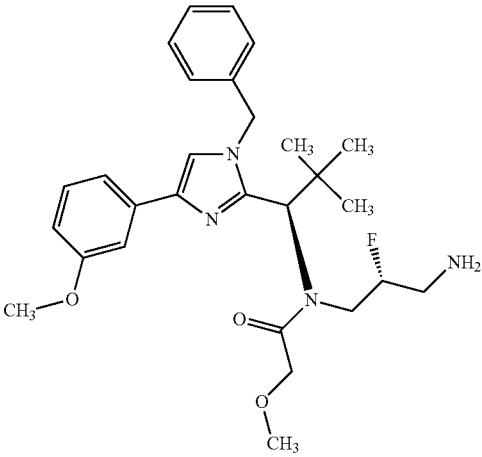 [SMILES: COCC(=O)N(C[C@H](F)CN)[C@@H](c1nc(-c2cccc(OC)c2)cn1Cc1ccccc1)C(C)(C)C] | 497.3 | N-((R)-3-Amino-2-fluoro-propyl)-N-{(R)-1-[1-benzyl-4-(3-methoxy-phenyl)-1H-imidazol-2-yl]-2,2-dimethyl-propyl}-2-methoxy-acetamide |
| 331 | 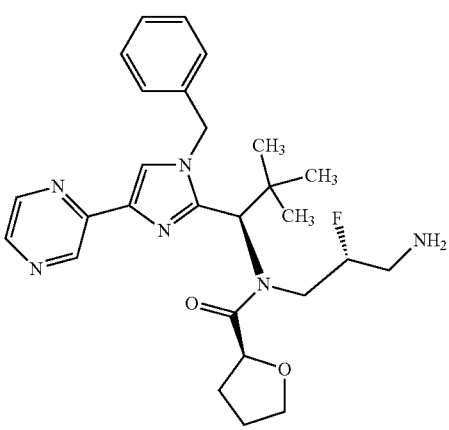 [SMILES: CC(C)(C)[C@H](c1nc(-c2cnccn2)cn1Cc1ccccc1)N(C[C@H](F)CN)C(=O)[C@@H]1CCCO1] | 495.3 | (S)-Tetrahydro-furan-2-carboxylic acid ((R)-3-amino-2-fluoro-propyl)-[(R)-1-(1-benzyl-4-pyrazin-2-yl-1H-imidazol-2-yl)-2,2-dimethyl-propyl]-amide |

TABLE 3-continued

| No. | Compound | MH+ | Name |
|---|---|---|---|
| 332 | | 483.3 | N-((R)-3-Amino-2-fluoro-propyl)-N-[(R)-1-(1-benzyl-4-pyrazin-2-yl-1H-imidazol-2-yl)-2,2-dimethyl-propyl]-2-ethoxy-acetamide |
| 333 | | 481.3 | N-((R)-3-Amino-2-fluoro-propyl)-N-[(R)-1-(1-benzyl-4-phenyl-1H-imidazol-2-yl)-2,2-dimethyl-propyl]-2-ethoxy-acetamide |
| 334 | | 493.3 | (S)-Tetrahydro-furan-2-carboxylic acid ((R)-3-amino-2-fluoro-propyl)-[(R)-1-(1-benzyl-4-phenyl-1H-imidazol-2-yl)-2,2-dimethyl-propyl]-amide |
| 335 | | 482.2 | N-((S)-3-Amino-4-fluoro-butyl)-N-[(R)-2,2-dimethyl-1-(4-phenyl-1-pyridin-3-ylmethyl-1H-imidazol-2-yl)-propyl]-2-methoxy-acetamide |

TABLE 3-continued

| No. | Compound | MH+ | Name |
|---|---|---|---|
| 336 | | 482.2 | N-((R)-3-Amino-4-fluoro-butyl)-N-[(R)-2,2-dimethyl-1-(4-phenyl-1-pyridin-3-ylmethyl-1H-imidazol-2-yl)-propyl]-2-methoxy-acetamide |
| 337 | | 511.1 | N-((S)-3-Amino-4-methoxy-butyl)-N-{(R)-1-[1-benzyl-4-(3-fluoro-phenyl)-1H-imidazol-2-yl]-2,2-dimethyl-propyl}-2-methoxy-acetamide |
| 338 | | 492.3 | N-((R)-3-Amino-2-fluoro-propyl)-N-{(R)-1-[1-benzyl-4-(4-cyano-phenyl)-1H-imidazol-2-yl]-2,2-dimethyl-propyl}-2-methoxy-acetamide |
| 339 | | 497.3 | N-((R)-3-Amino-2-fluoro-propyl)-N-{(R)-1-[1-benzyl-4-(4-methoxy-phenyl)-1H-imidazol-2-yl]-2,2-dimethyl-propyl}-2-methoxy-acetamide |

TABLE 3-continued

| No. | Compound | MH+ | Name |
|---|---|---|---|
| 340 | | 485.3 | N-((R)-3-Amino-2-fluoro-propyl)-N-{(R)-1-[1-(2-fluoro-benzyl)-4-phenyl-1H-imidazol-2-yl]-2,2-dimethyl-propyl}-2-methoxy-acetamide |
| 341 | | 485.3 | N-((R)-3-Amino-2-fluoro-propyl)-N-{(R)-1-[1-(3-fluoro-benzyl)-4-phenyl-1H-imidazol-2-yl]-2,2-dimethyl-propyl}-2-methoxy-acetamide |
| 342 | | 501.2 | N-((R)-3-Amino-2-fluoro-propyl)-N-{(R)-1-[1-(3-chloro-benzyl)-4-phenyl-1H-imidazol-2-yl]-2,2-dimethyl-propyl}-2-methoxy-acetamide |
| 343 | | 492.3 | N-((R)-3-Amino-2-fluoro-propyl)-N-{(R)-1-[1-(3-cyano-benzyl)-4-phenyl-1H-imidazol-2-yl]-2,2-dimethyl-propyl}-2-methoxy-acetamide |

TABLE 3-continued

| No. | Compound | MH+ | Name |
|---|---|---|---|
| 344 | 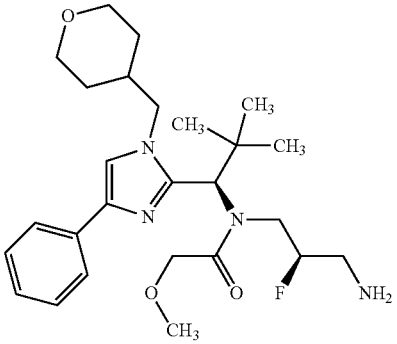 [SMILES: COCC(=O)N(C[C@H](F)CN)[C@@H](c1nc(-c2ccccc2)cn1CC1CCOCC1)C(C)(C)C] | 475.3 | N-((R)-3-Amino-2-fluoro-propyl)-N-{(R)-2,2-dimethyl-1-[4-phenyl-1-(tetrahydro-pyran-4-ylmethyl)-1H-imidazol-2-yl]-propyl}-2-methoxy-acetamide |
| 345 | 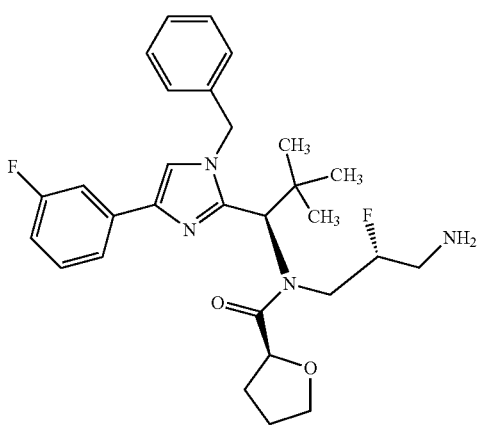 [SMILES: CC(C)(C)[C@H](c1nc(-c2cccc(F)c2)cn1Cc1ccccc1)N(C[C@H](F)CN)C(=O)[C@@H]1CCCO1] | 511.3 | (S)-Tetrahydro-furan-2-carboxylic acid ((R)-3-amino-2-fluoro-propyl)-{(R)-1-[1-benzyl-4-(3-fluoro-phenyl)-1H-imidazol-2-yl]-2,2-dimethyl-propyl}-amide |
| 346 | 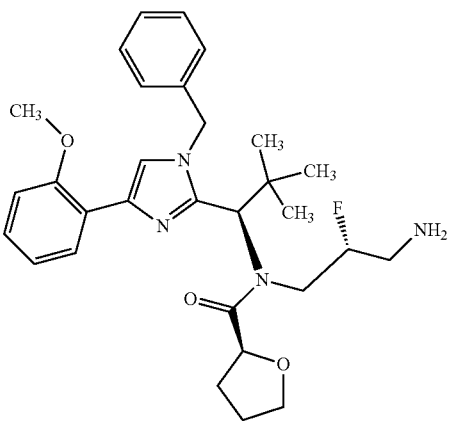 [SMILES: COc1ccccc1-c1cn(Cc2ccccc2)c([C@H](N(C[C@H](F)CN)C(=O)[C@@H]2CCCO2)C(C)(C)C)n1] | 523.3 | (S)-Tetrahydro-furan-2-carboxylic acid ((R)-3-amino-2-fluoro-propyl)-{(R)-1-[1-benzyl-4-(2-methoxy-phenyl)-1H-imidazol-2-yl]-2,2-dimethyl-propyl}-amide |
| 347 | 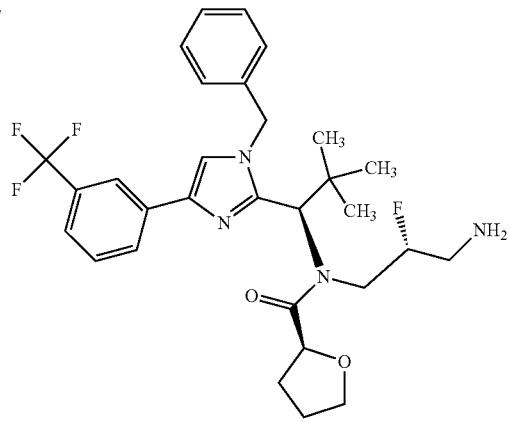 | 561.3 | (S)-Tetrahydro-furan-2-carboxylic acid ((R)-3-amino-2-fluoro-propyl)-{(R)-1-[1-benzyl-4-(3-trifluoromethyl-phenyl)-1H-imidazol-2-yl]-2,2-dimethyl-propyl}-amide |

TABLE 3-continued

| No. | Compound | MH+ | Name |
|---|---|---|---|
| 348 | | 571.2 | (S)-Tetrahydro-furan-2-carboxylic acid ((R)-3-amino-2-fluoro-propyl)-{(R)-1-[1-benzyl-4-(3-bromo-phenyl)-1H-imidazol-2-yl]-2,2-dimethyl-propyl}-amide |
| 349 | | 485.3 | N-((R)-3-Amino-2-fluoro-propyl)-N-{(R)-1-[1-benzyl-4-(3-fluoro-phenyl)-1H-imidazol-2-yl]-2,2-dimethyl-propyl}-2-methoxy-acetamide |
| 350 | | 497.3 | N-((R)-3-Amino-2-fluoro-propyl)-N-{(R)-1-[1-benzyl-4-(2-methoxy-phenyl)-1H-imidazol-2-yl]-2,2-dimethyl-propyl}-2-methoxy-acetamide |

TABLE 3-continued
| No. | Compound | MH+ | Name |
|---|---|---|---|
| 351 | 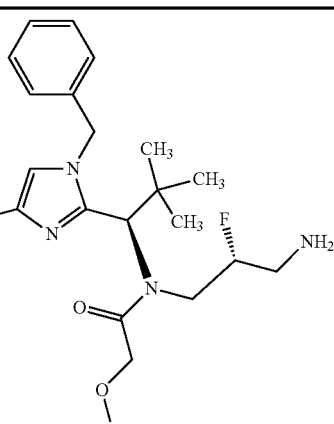 | 535.3 | N-((R)-3-Amino-2-fluoro-propyl)-N-{(R)-1-[1-benzyl-4-(3-trifluoromethyl-phenyl)-1H-imidazol-2-yl]-2,2-dimethyl-propyl}-2-methoxy-acetamide |
| 352 | 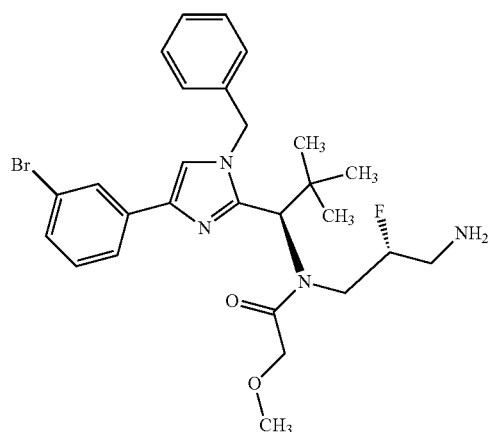 | 545.2 | N-((R)-3-Amino-2-fluoro-propyl)-N-{(R)-1-[1-benzyl-4-(3-bromo-phenyl)-1H-imidazol-2-yl]-2,2-dimethyl-propyl}-2-methoxy-acetamide |
| 353 | 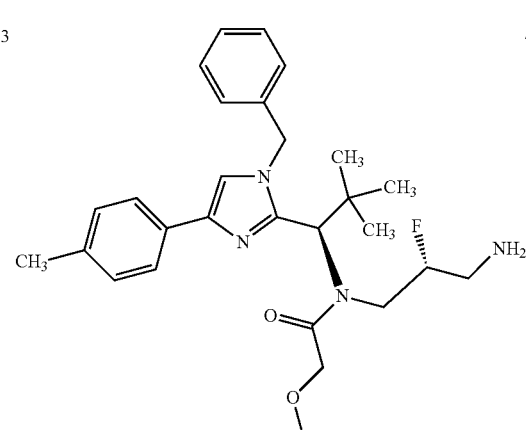 | 481.3 | N-((R)-3-Amino-2-fluoro-propyl)-N-[(R)-1-(1-benzyl-4-p-tolyl-1H-imidazol-2-yl)-2,2-dimethyl-propyl]-2-methoxy-acetamide |

TABLE 3-continued

| No. | Compound | MH+ | Name |
|---|---|---|---|
| 354 | | 482.2 | N-((S)-3-Amino-4-fluoro-butyl)-N-[(R)-2,2-dimethyl-1-(4-phenyl-1-pyridin-4-ylmethyl-1H-imidazol-2-yl)-propyl]-2-methoxy-acetamide |
| 355 | | 482.2 | N-((R)-3-Amino-4-fluoro-butyl)-N-[(R)-2,2-dimethyl-1-(4-phenyl-1-pyridin-4-ylmethyl-1H-imidazol-2-yl)-propyl]-2-methoxy-acetamide |
| 356 | | 486.1 | N-((S)-3-Amino-4-fluoro-butyl)-N-{(R)-2,2-dimethyl-1-[1-(5-methyl-isoxazol-3-ylmethyl)-4-phenyl-1H-imidazol-2-yl]-propyl}-2-methoxy-acetamide |
| 357 | | 486.1 | N-((R)-3-Amino-4-fluoro-butyl)-N-{(R)-2,2-dimethyl-1-[1-(5-methyl-isoxazol-3-ylmethyl)-4-phenyl-1H-imidazol-2-yl]-propyl}-2-methoxy-acetamide |

TABLE 3-continued

| No. | Compound | MH+ | Name |
|---|---|---|---|
| 358 | 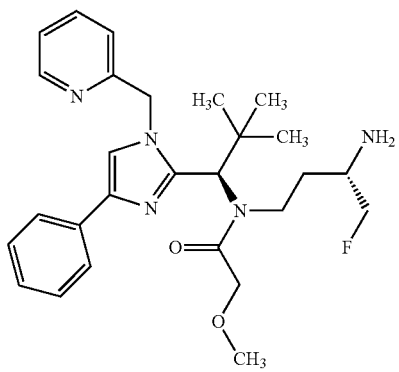 [SMILES: COCC(=O)N(CC[C@H](N)CF)[C@@H](c1nc(-c2ccccc2)cn1Cc1ccccn1)C(C)(C)C] | 482.2 | N-((S)-3-Amino-4-fluoro-butyl)-N-[(R)-2,2-dimethyl-1-(4-phenyl-1-pyridin-2-ylmethyl-1H-imidazol-2-yl)-propyl]-2-methoxy-acetamide |
| 359 | 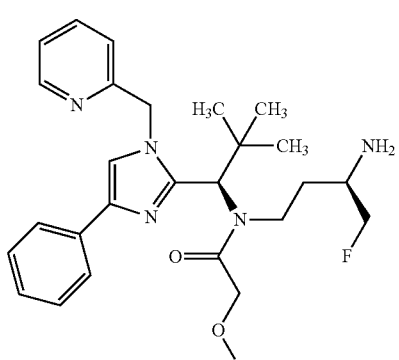 | 482.2 | N-((R)-3-Amino-4-fluoro-butyl)-N-[(R)-2,2-dimethyl-1-(4-phenyl-1-pyridin-2-ylmethyl-1H-imidazol-2-yl)-propyl]-2-methoxy-acetamide |
| 360 | 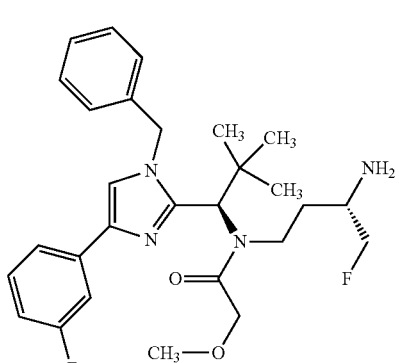 | 499.2 | N-((S)-3-Amino-4-fluoro-butyl)-N-{(R)-1-[1-benzyl-4-(3-fluoro-phenyl)-1H-imidazol-2-yl]-2,2-dimethyl-propyl}-2-methoxy-acetamide |
| 361 | 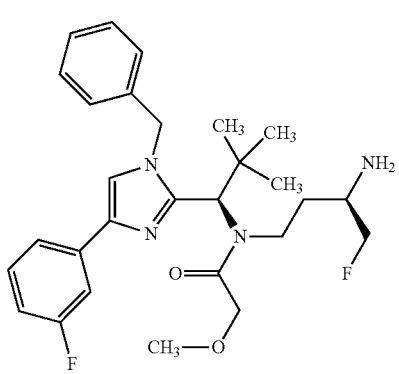 [SMILES: COCC(=O)N(CC[C@@H](N)CF)[C@@H](c1nc(-c2cccc(F)c2)cn1Cc1ccccc1)C(C)(C)C] | 499.2 | N-((R)-3-Amino-4-fluoro-butyl)-N-{(R)-1-[1-benzyl-4-(3-fluoro-phenyl)-1H-imidazol-2-yl]-2,2-dimethyl-propyl}-2-methoxy-acetamide |

TABLE 3-continued
| No. | Compound | MH+ | Name |
|---|---|---|---|
| 362 | 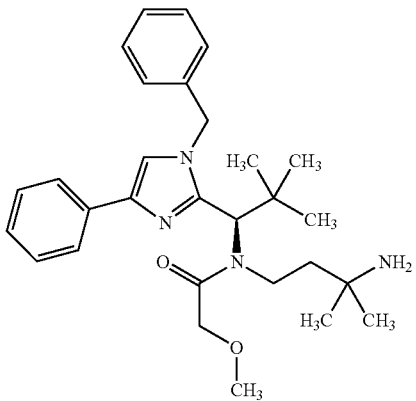 [SMILES: COCC(=O)N(CCC(C)(C)N)[C@@H](c1nc(-c2ccccc2)cn1Cc1ccccc1)C(C)(C)C] | 477.2 | N-(3-Amino-3-methyl-butyl)-N-[(R)-1-(1-benzyl-4-phenyl-1H-imidazol-2-yl)-2,2-dimethyl-propyl]-2-methoxy-acetamide |
| 363 | 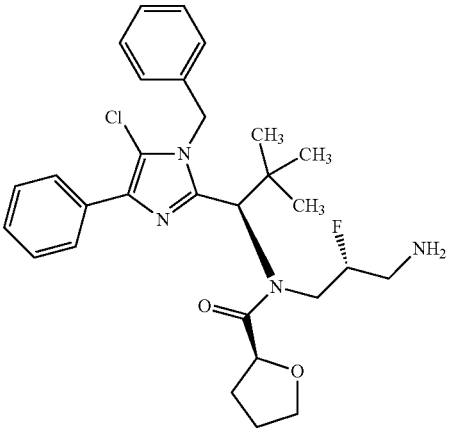 [SMILES: CC(C)(C)[C@H](c1nc(-c2ccccc2)c(Cl)n1Cc1ccccc1)N(C[C@H](F)CN)C(=O)[C@@H]1CCCO1] | 527.2 | (S)-Tetrahydro-furan-2-carboxylic acid ((R)-3-amino-2-fluoro-propyl)-[(R)-1-(1-benzyl-5-chloro-4-phenyl-1H-imidazol-2-yl)-2,2-dimethyl-propyl]-amide |
| 364 | 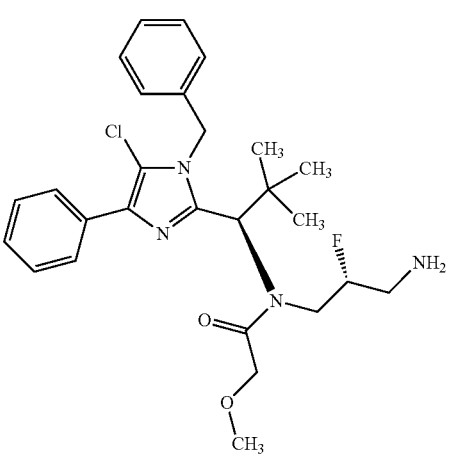 [SMILES: COCC(=O)N(C[C@H](F)CN)[C@@H](c1nc(-c2ccccc2)c(Cl)n1Cc1ccccc1)C(C)(C)C] | 501.2 | N-((R)-3-Amino-2-fluoro-propyl)-N-[(R)-1-(1-benzyl-5-chloro-4-phenyl-1H-imidazol-2-yl)-2,2-dimethyl-propyl]-2-methoxy-acetamide |

TABLE 3-continued

| No. | Compound | MH+ | Name |
|---|---|---|---|
| 365 | | 500.2 | (S)-Tetrahydro-furan-2-carboxylic acid ((R)-3-amino-2-fluoro-propyl)-[(R)-1-(1-benzyl-4-thiazol-2-yl-1H-imidazol-2-yl)-2,2-dimethyl-propyl]-amide |
| 366 | | 525.2 | N-((S)-3-Amino-2-fluoro-propyl)-N-{(R)-2,2-dimethyl-1-[4-phenyl-1-(5-trifluoromethyl-furan-2-ylmethyl)-1H-imidazol-2-yl]-propyl}-2-methoxy-acetamide |
| 367 | | 472.3 | N-((S)-3-Amino-2-fluoro-propyl)-N-{(R)-2,2-dimethyl-1-[1-(5-methyl-isoxazol-3-ylmethyl)-4-phenyl-1H-imidazol-2-yl]-propyl}-2-methoxy-acetamide |

TABLE 3-continued

| No. | Compound | MH+ | Name |
|---|---|---|---|
| 368 | 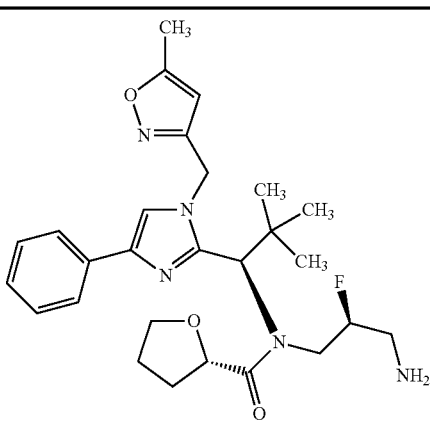 | 498.3 | (S)-Tetrahydro-furan-2-carboxylic acid ((S)-3-amino-2-fluoro-propyl)-{(R)-2,2-dimethyl-1-[1-(5-methyl-isoxazol-3-ylmethyl)-4-phenyl-1H-imidazol-2-yl]-propyl}-amide |
| 369 | 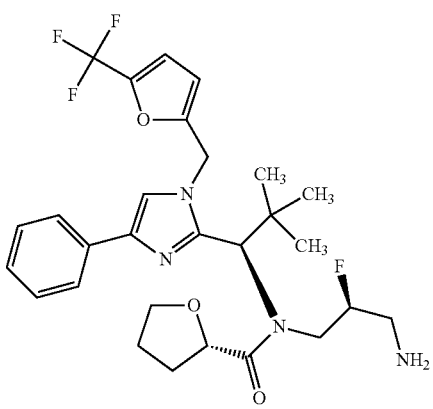 [SMILES: CC(C)(C)[C@H](c1nc(-c2ccccc2)cn1Cc1ccc(C(F)(F)F)o1)N(C[C@@H](F)CN)C(=O)[C@@H]1CCCO1] | 551.3 | (S)-Tetrahydro-furan-2-carboxylic acid ((S)-3-amino-2-fluoro-propyl)-{(R)-2,2-dimethyl-1-[4-phenyl-1-(5-trifluoromethyl-furan-2-ylmethyl)-1H-imidazol-2-yl]-propyl}-amide |
| 370 | 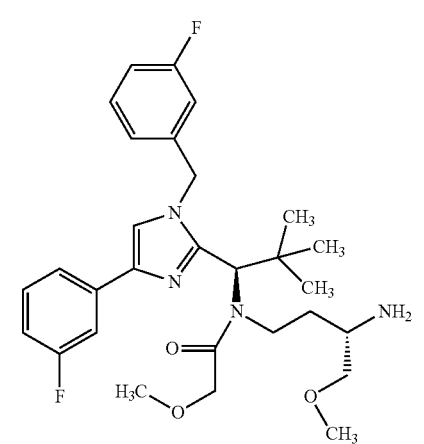 [SMILES: COCC(=O)N(CC[C@H](N)COC)[C@@H](c1nc(-c2cccc(F)c2)cn1Cc1cccc(F)c1)C(C)(C)C] | 529.2 | N-((S)-3-Amino-4-methoxy-butyl)-N-{(R)-1-[1-(3-fluoro-benzyl)-4-(3-fluoro-phenyl)-1H-imidazol-2-yl]-2,2-dimethyl-propyl}-2-methoxy-acetamide |

TABLE 3-continued
| No. | Compound | MH+ | Name |
|---|---|---|---|
| 371 | 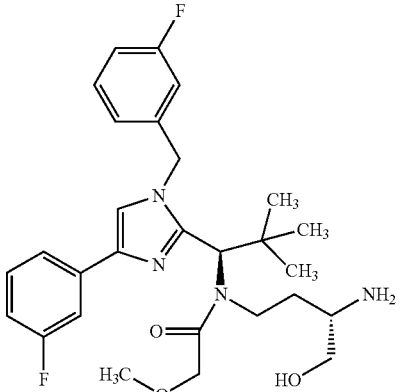 | 515.1 | N-((S)-3-Amino-4-hydroxy-butyl)-N-{(R)-1-[1-(3-fluoro-benzyl)-4-(3-fluoro-phenyl)-1H-imidazol-2-yl]-2,2-dimethyl-propyl}-2-methoxy-acetamide |
| 372 | 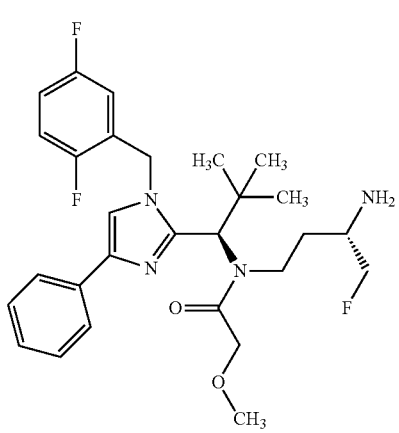 [SMILES: COCC(=O)N(CC[C@H](N)CF)[C@@H](c1nc(-c2ccccc2)cn1Cc1cc(F)ccc1F)C(C)(C)C] | 517.1 | N-((S)-3-Amino-4-fluoro-butyl)-N-{(R)-1-[1-(2,5-difluoro-benzyl)-4-phenyl-1H-imidazol-2-yl]-2,2-dimethyl-propyl}-2-methoxy-acetamide |
| 373 | 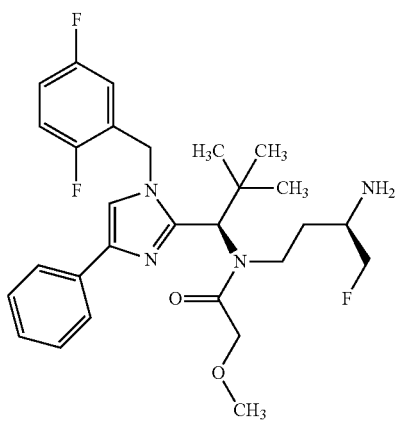 [SMILES: COCC(=O)N(CC[C@@H](N)CF)[C@@H](c1nc(-c2ccccc2)cn1Cc1cc(F)ccc1F)C(C)(C)C] | 517.1 | N-((R)-3-Amino-4-fluoro-butyl)-N-{(R)-1-[1-(2,5-difluoro-benzyl)-4-phenyl-1H-imidazol-2-yl]-2,2-dimethyl-propyl}-2-methoxy-acetamide |

TABLE 3-continued

| No. | Compound | MH+ | Name |
|---|---|---|---|
| 374 | | 485.3 | N-((R)-3-Amino-2-fluoro-propyl)-N-{(R)-1-[1-(4-fluoro-benzyl)-4-phenyl-1H-imidazol-2-yl]-2,2-dimethyl-propyl}-2-methoxy-acetamide |
| 375 | | 497.3 | N-((R)-3-Amino-2-fluoro-propyl)-2-methoxy-N-{(R)-1-[1-(3-methoxy-benzyl)-4-phenyl-1H-imidazol-2-yl]-2,2-dimethyl-propyl}-acetamide |
| 376 | | 581.3 | N-((R)-3-Amino-2-fluoro-propyl)-N-{(R)-2,2-dimethyl-1-[1-(2-methyl-benzyl)-4-phenyl-1H-imidazol-2-yl]-propyl}-2-methoxy-acetamide |
| 377 | | 581.3 | N-((R)-3-Amino-2-fluoro-propyl)-N-{(R)-2,2-dimethyl-1-[1-(3-methyl-benzyl)-4-phenyl-1H-imidazol-2-yl]-propyl}-2-methoxy-acetamide |

TABLE 3-continued
| No. | Compound | MH+ | Name |
|---|---|---|---|
| 378 | 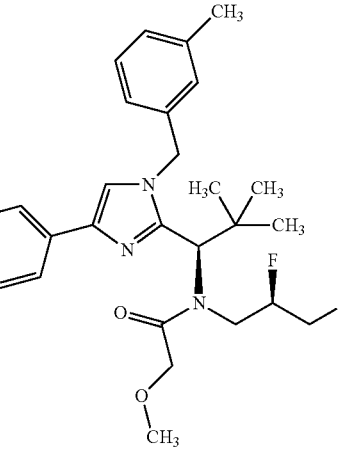 | 581.3 | N-((S)-3-Amino-2-fluoro-propyl)-N-{(R)-2,2-dimethyl-1-[1-(3-methyl-benzyl)-4-phenyl-1H-imidazol-2-yl]-propyl}-2-methoxy-acetamide |
| 379 | 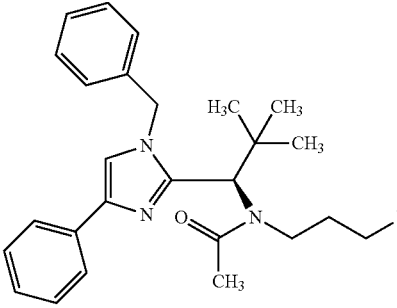 | 419.2 | N-(3-Amino-propyl)-N-[(R)-1-(1-benzyl-4-phenyl-1H-imidazol-2-yl)-2,2-dimethyl-propyl]-acetamide |
| 380 | 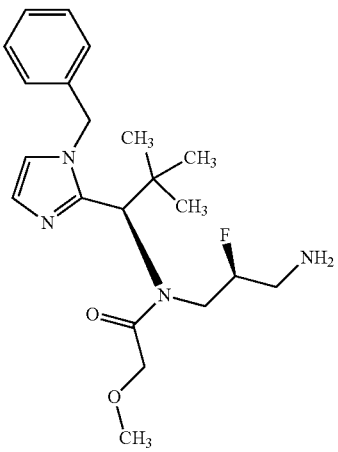 [SMILES: COCC(=O)N(C[C@@H](F)CN)[C@@H](c1nccn1Cc1ccccc1)C(C)(C)C] | 391.2 | N-((S)-3-Amino-2-fluoro-propyl)-N-[(R)-1-(1-benzyl-1H-imidazol-2-yl)-2,2-dimethyl-propyl]-2-methoxy-acetamide |

TABLE 3-continued
| No. | Compound | MH+ | Name |
|---|---|---|---|
| 381 | 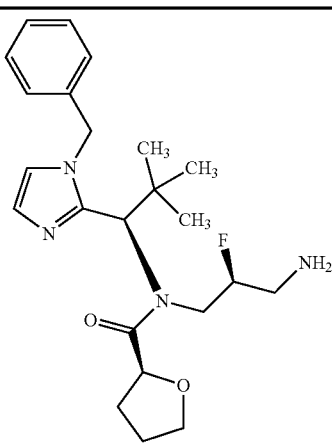 | 417.3 | (S)-Tetrahydro-furan-2-carboxylic acid ((S)-3-amino-2-fluoro-propyl)-[(R)-1-(1-benzyl-1H-imidazol-2-yl)-2,2-dimethyl-propyl]-amide |
| 382 | 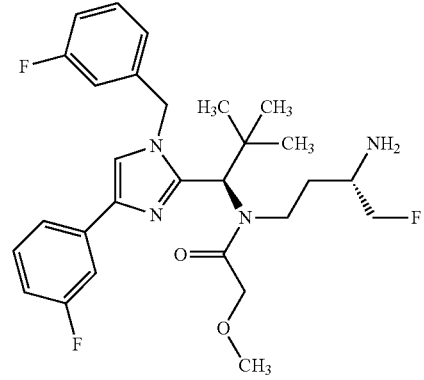 [SMILES: COCC(=O)N(CC[C@H](N)CF)[C@@H](c1nc(-c2cccc(F)c2)cn1Cc1cccc(F)c1)C(C)(C)C] | 517.2 | N-((S)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-2-methoxy-acetamide |
| 383 | 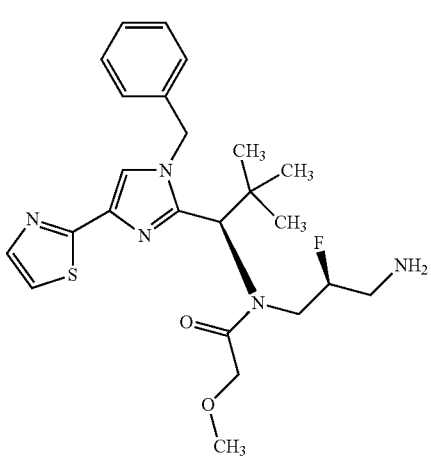 [SMILES: COCC(=O)N(C[C@@H](F)CN)[C@@H](c1nc(-c2nccs2)cn1Cc1ccccc1)C(C)(C)C] | 474.2 | N-((S)-3-Amino-2-fluoro-propyl)-N-[(R)-1-(1-benzyl-4-thiazol-2-yl-1H-imidazol-2-yl)-2,2-dimethyl-propyl]-2-methoxy-acetamide |

TABLE 3-continued

| No. | Compound | MH+ | Name |
|---|---|---|---|
| 384 | | 517.2 | N-((R)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-2-methoxy-acetamide |
| 385 | | 475.3 | N-[2-(1-Amino-cyclopropyl)-ethyl]-N-[(R)-1-(1-benzyl-4-phenyl-1H-imidazol-2-yl)-2,2-dimethyl-propyl]-2-methoxy-acetamide |
| 386 | | 501.3 | (S)-Tetrahydro-furan-2-carboxylic acid [2-(1-amino-cyclopropyl)-ethyl]-[(R)-1-(1-benzyl-4-phenyl-1H-imidazol-2-yl)-2,2-dimethyl-propyl]-amide |
| 387 | | 461.3 | [2-(1-Amino-cyclopropyl)-ethyl]-[(R)-1-(1-benzyl-4-phenyl-1H-imidazol-2-yl)-2,2-dimethyl-propyl]-carbamic acid methyl ester |

TABLE 3-continued

| No. | Compound | MH+ | Name |
|---|---|---|---|
| 388 | | 493.3 | N-[2-(1-Amino-cyclopropyl)-ethyl]-N-{(R)-1-[1-benzyl-4-(3-fluoro-phenyl)-1H-imidazol-2-yl]-2,2-dimethyl-propyl}-2-methoxy-acetamide |
| 389 | | 519.3 | (S)-Tetrahydro-furan-2-carboxylic acid [2-(1-amino-cyclopropyl)-ethyl]-{(R)-1-[1-benzyl-4-(3-fluoro-phenyl)-1H-imidazol-2-yl]-2,2-dimethyl-propyl}-amide |
| 390 | | 485.2 | N-(3-Amino-propyl)-N-{(R)-1-[1-benzyl-4-(2,5-difluoro-phenyl)-1H-imidazol-2-yl]-2,2-dimethyl-propyl}-2-methoxy-acetamide |
| 391 | | 517.2 | N-((S)-3-Amino-4-fluoro-butyl)-N-{(R)-1-[1-benzyl-4-(2,5-difluoro-phenyl)-1H-imidazol-2-yl]-2,2-dimethyl-propyl}-2-methoxy-acetamide |

TABLE 3-continued

| No. | Compound | MH+ | Name |
|---|---|---|---|
| 392 | | 517.2 | N-((R)-3-Amino-4-fluoro-butyl)-N-{(R)-1-[1-benzyl-4-(2,5-difluoro-phenyl)-1H-imidazol-2-yl]-2,2-dimethyl-propyl}-2-methoxy-acetamide |
| 393 | | 457.5 | N-(3-Amino-propyl)-N-{1-[1-(3-fluoro-benzyl)-4-(3-fluoro-phenyl)-1H-imidazol-2-yl]-1-methyl-ethyl}-2-methoxy-acetamide |
| 394 | | 485.6 | N-(3-Amino-propyl)-N-{(R)-1-[1-(3-fluoro-benzyl)-4-(3-fluoro-phenyl)-1H-imidazol-2-yl]-2,2-dimethyl-propyl}-2-methoxy-acetamide |

TABLE 3-continued

| No. | Compound | MH+ | Name |
|---|---|---|---|
| 395 | | 543.3 | (S)-Tetrahydro-furan-2-carboxylic acid ((S)-3-amino-4-fluoro-butyl)-{(R)-1-[1-(3-fluoro-benzyl)-4-(3-fluoro-phenyl)-1H-imidazol-2-yl]-2,2-dimethyl-propyl}-amide |
| 396 | | 499.3 | N-((S)-3-Amino-4-fluoro-butyl)-N-{(R)-1-[1-benzyl-5-(3-fluoro-phenyl)-1H-imidazol-2-yl]-2,2-dimethyl-propyl}-2-methoxy-acetamide |
| 397 | | 531.3 | N-((S)-3-Amino-4-methoxy-butyl)-N-{(R)-1-[4-(3-chloro-phenyl)-1-(3-fluoro-benzyl)-1H-imidazol-2-yl]-2-methyl-propyl}-2-methoxy-acetamide |

TABLE 3-continued
| No. | Compound | MH+ | Name |
|---|---|---|---|
| 398 | 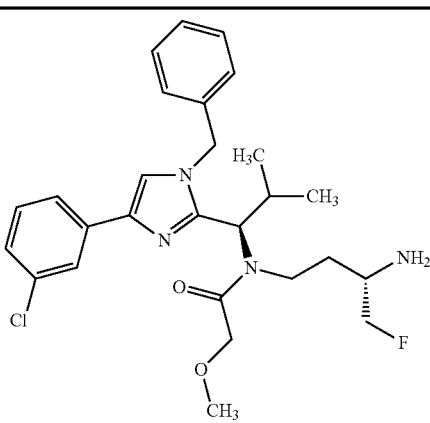 | 501.2 | N-((S)-3-Amino-4-fluoro-butyl)-N-{(R)-1-[1-benzyl-4-(3-chloro-phenyl)-1H-imidazol-2-yl]-2-methyl-propyl}-2-methoxy-aceamide |
| 399 | 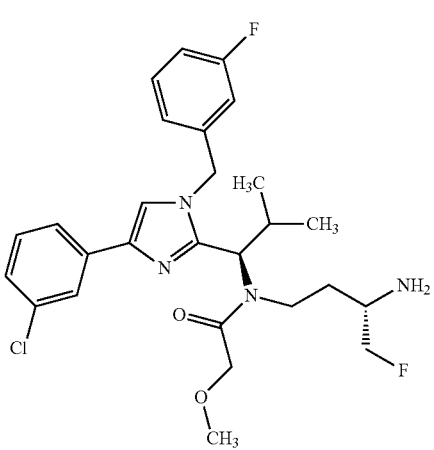 [SMILES: COCC(=O)N(CC[C@H](N)CF)[C@@H](c1nc(-c2cccc(Cl)c2)cn1Cc1cccc(F)c1)C(C)C] | 519.2 | N-((S)-3-Amino-4-fluoro-butyl)-N-{(R)-1-[4-(3-chloro-phenyl)-1-(3-fluoro-benzyl)-1H-imidazol-2-yl]-2-methyl-propyl}-2-methoxy-acetamide |
| 400 | 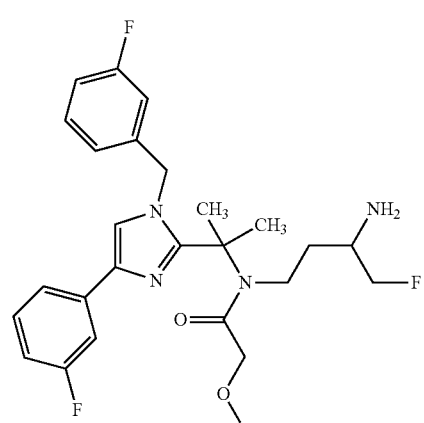 | 489.5 | N-(3-Amino-4-fluoro-butyl)-N-{1-[1-(3-fluoro-benzyl)-4-(3-fluoro-phenyl)-1H-imidazol-2-yl]-1-methyl-ethyl}-2-methoxy-acetamide |

TABLE 3-continued

| No. | Compound | MH+ | Name |
|---|---|---|---|
| 401 | | 487.1 | N-((S)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-acetamide |
| 402 | | 487.1 | N-((R)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-acetamide |
| 403 | | 529.3 | (S)-Tetrahydro-furan-2-carboxylic acid ((S)-3-amino-2-fluoro-propyl)-{(R)-1-[1-(3-fluoro-benzyl)-4-(3-fluoro-phenyl)-1H-imidazol-2-yl]-2,2-dimethyl-propyl}-amide |
| 404 | | 495.2 | (R)-9-{(R)-1-[1-(3-Fluoro-benzyl)-4-(3-fluoro-phenyl)-1H-imidazol-2-yl]-2,2-dimethyl-propyl}-6-oxa-2,9-diaza-spiro[4.5]decan-8-one |

TABLE 3-continued

| No. | Compound | MH+ | Name |
|---|---|---|---|
| 405 | | 503.2 | (3-Amino-4-fluoro-butyl)-{(R)-1-[1-(3-fluoro-benzyl)-4-(3-fluoro-phenyl)-1H-imidazol-2-yl]-2,2-dimethyl-propyl}-carbamic acid methyl ester |
| 406 | | 473.2 | N-((S)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-formamide |
| 407 | | 473.2 | N-((R)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-formamide |
| 408 | | 513.2 | N-(3-Dimethylamino-propyl)-N-{(R)-1-[1-(3-fluoro-benzyl)-4-(3-fluoro-phenyl)-1H-imidazol-2-yl]-2,2-dimethyl-propyl}-2-methoxy-acetamide |

TABLE 3-continued

| No. | Compound | MH+ | Name |
|---|---|---|---|
| 409 | | 499.6 | N-((S)-3-Amino-butyl)-N-{(R)-1-[1-(3-fluoro-benzyl)-4-(3-fluoro-phenyl)-1H-imidazol-2-yl]-2,2-dimethyl-propyl}-2-methoxy-acetamide |
| 410 | | 499.6 | N-((R)-3-Amino-butyl)-N-{(R)-1-[1-(3-fluoro-benzyl)-4-(3-fluoro-phenyl)-1H-imidazol-2-yl]-2,2-dimethyl-propyl}-2-methoxy-acetamide |
| 411 | | 515.2 | N-((S)-3-Amino-4-fluoro-butyl)-N-{(R)-1-[1-(6-amino-pyridin-2-ylmethyl)-4-(3-fluoro-phenyl)-1H-imidazol-2-yl]-2,2-dimethyl-propyl}-2-methoxy-acetamide |

TABLE 3-continued
| No. | Compound | MH+ | Name |
|---|---|---|---|
| 412 | 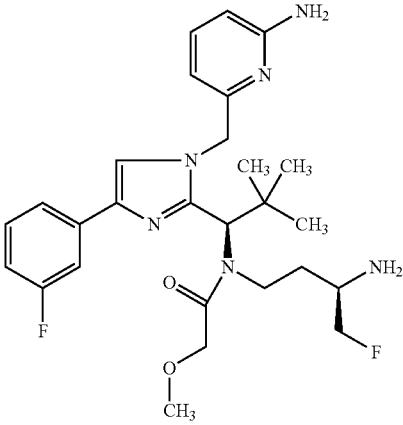 [SMILES: COCC(=O)N(CC[C@@H](N)CF)[C@@H](c1nc(-c2cccc(F)c2)cn1Cc1cccc(N)n1)C(C)(C)C] | 515.2 | N-((R)-3-Amino-4-fluoro-butyl)-N-{(R)-1-[1-(6-amino-pyridin-2-ylmethyl)-4-(3-fluoro-phenyl)-1H-imidazol-2-yl]-2,2-dimethyl-propyl}-2-methoxy-acetamide |
| 413 | 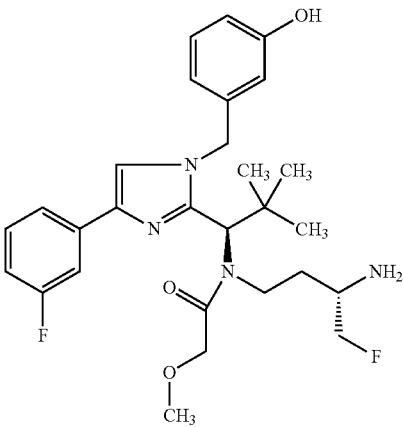 [SMILES: COCC(=O)N(CC[C@H](N)CF)[C@@H](c1nc(-c2cccc(F)c2)cn1Cc1cccc(O)c1)C(C)(C)C] | 515.2 | N-((S)-3-Amino-4-fluoro-butyl)-N-{(R)-1-[4-(3-fluoro-phenyl)-1-(3-hydroxy-benzyl)-1H-imidazol-2-yl]-2,2-dimethyl-propyl}-2-methoxy-acetamide |
| 414 | 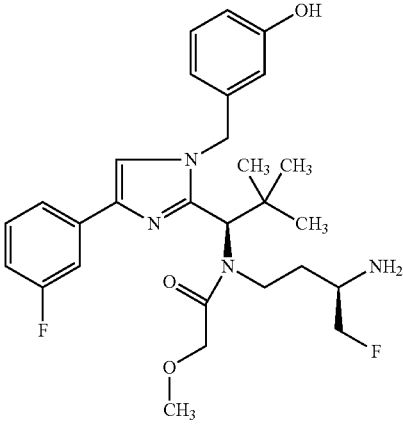 [SMILES: COCC(=O)N(CC[C@@H](N)CF)[C@@H](c1nc(-c2cccc(F)c2)cn1Cc1cccc(O)c1)C(C)(C)C] | 515.2 | N-((R)-3-Amino-4-fluoro-butyl)-N-{(R)-1-[4-(3-fluoro-phenyl)-1-(3-hydroxy-benzyl)-1H-imidazol-2-yl]-2,2-dimethyl-propyl}-2-methoxy-acetamide |

TABLE 3-continued

| No. | Compound | MH+ | Name |
|-----|----------|-----|------|
| 415 | | 488.2 | N-((S)-3-Amino-4-fluoro-butyl)-N-[(R)-1-(1-benzyl-4-thiazol-2-yl-1H-imidazol-2-yl)-2,2-dimethyl-propyl]-2-methoxy-acetamide |
| 416 | | 499.2 | N-{(R)-1-[1-(3-Fluoro-benzyl)-4-(3-fluoro-phenyl)-1H-imidazol-2-yl]-2,2-dimethyl-propyl}-2-methoxy-N-(3-methylamino-propyl)-acetamide |
| 417 | | 455.5 | N-(3-Amino-propyl)-N-{(R)-1-[1-benzyl-4-(2,5-difluoro-phenyl)-1H-imidazol-2-yl]-2,2-dimethyl-propyl}-acetamide |
| 418 | | 471.5 | (3-Amino-propyl)-{(R)-1-[1-benzyl-4-(2,5-difluoro-phenyl)-1H-imidazol-2-yl]-2,2-dimethyl-propyl}-carbamic acid methyl ester |

TABLE 3-continued

| No. | Compound | MH+ | Name |
|---|---|---|---|
| 419 | | 511.6 | (S)-Tetrahydro-furan-2-carboxylic acid (3-amino-propyl)-{(R)-1-[1-benzyl-4-(2,5-difluoro-phenyl)-1H-imidazol-2-yl]-2,2-dimethyl-propyl}-amide |
| 420 | | 499.2 | 3-[{(R)-1-[1-(3-Fluoro-benzyl)-4-(3-fluoro-phenyl)-1H-imidazol-2-yl]-2,2-dimethyl-propyl}-(2-methoxy-acetyl)-amino]-propionamide |
| 421 | | 533.6 | N-(3-Amino-propyl)-N-{(R)-1-[1-benzyl-4-(2,5-difluoro-phenyl)-1H-imidazol-2-yl]-2,2-dimethyl-propyl}-2-methanesulfonyl-acetamide |

TABLE 3-continued

| No. | Compound | MH+ | Name |
|---|---|---|---|
| 422 | | 429.3 | N-((S)-3-Amino-4-methoxy-butyl)-N-{(R)-1-[1-benzyl-4-(2,5-difluoro-phenyl)-1H-imidazol-2-yl]-2,2-dimethyl-propyl}-2-methoxy-acetamide |
| 423 | | 543.3 | (S)-Tetrahydro-furan-2-carboxylic acid ((S)-3-amino-4-fluoro-butyl)-{(R)-1-[1-benzyl-4-(2,5-difluoro-phenyl)-1H-imidazol-2-yl]-2,2-dimethyl-propyl}-amide |
| 424 | | 356.2 | (R)-1-[1-Benzyl-4-(2,5-difluoro-phenyl)-1H-imidazol-2-yl]-2,2-dimethyl-propylamine |
| 425 | | 555.3 | (S)-Tetrahydro-furan-2-carboxylic acid ((S)-3-amino-4-methoxy-butyl)-{(R)-1-[1-benzyl-4-(2,5-difluoro-phenyl)-1H-imidazol-2-yl]-2,2-dimethyl-propyl}-amide |

TABLE 3-continued

| No. | Compound | MH+ | Name |
|---|---|---|---|
| 426 | | 499.6 | N-((R)-3-Amino-butyl)-N-{(R)-1-[1-benzyl-4-(2,5-difluoro-phenyl)-1H-imidazol-2-yl]-2,2-dimethyl-propyl}-2-methoxy-acetamide |
| 427 | | 499.6 | N-((S)-3-Amino-butyl)-N-{(R)-1-[1-benzyl-4-(2,5-difluoro-phenyl)-1H-imidazol-2-yl]-2,2-dimethyl-propyl}-2-methoxy-acetamide |
| 428 | | 509.2 | N-{(R)-1-[1-Benzyl-4-(2,5-difluoro-phenyl)-1H-imidazol-2-yl]-2,2-dimethyl-propyl}-2-methoxy-N-(1H-[1,2,3]triazol-4-ylmethyl)-acetamide |
| 429 | | 487.3 | N-((S)-3-Amino-4-fluoro-butyl)-N-{(R)-1-[1-benzyl-4-(2,5-difluoro-phenyl)-1H-imidazol-2-yl]-2,2-dimethyl-propyl}-acetamide |

TABLE 3-continued

| No. | Compound | MH+ | Name |
|---|---|---|---|
| 430 | | 503.2 | ((S)-3-Amino-4-fluoro-butyl)-{(R)-1-[1-benzyl-4-(2,5-difluoro-phenyl)-1H-imidazol-2-yl]-2,2-dimethyl-propyl}-carbamic acid methyl ester |
| 431 | | 456.2 | {(R)-1-[1-Benzyl-4-(2,5-difluoro-phenyl)-1H-imidazol-2-yl]-2,2-dimethyl-propyl}-carbamic acid tert-butyl ester |
| 432 | Chiral | 424.2 | N-[(1R)-1-(1-benzyl-4-phenyl-1H-imidazol-2-yl)-2-methylpropyl]-4-methylbenzamide |

TABLE 3-continued

| No. | Compound | MH+ | Name |
|---|---|---|---|
| 433 | | 550.2 | N-(3-aminopropyl)-N-[(1R)-1-(1-benzyl-4-phenyl-1H-imidazol-2-yl)-2-methylpropyl]-2-(4-fluorophenoxy)acetamide |

Example 20

Assay for Determining KSP Activity

This example provides a representative in vitro assay for determining KSP activity in vitro. Purified microtubules obtained from bovine brain were purchased from Cytoskeleton Inc. (Denver, Colo., USA). The motor domain of human KSP (Eg 5, KNSL1) was cloned, expressed, and purified to greater than 95% homogeneity. Biomol Green was purchased from Affinity Research Products Ltd. (Matford Court, Exeter, Devon, United Kingdom). Microtubules and KSP motor protein (i.e., the KSP motor domain) were diluted in assay buffer (20 mM Tris-HCl (pH 7.5), 1 mM MgCl$_2$, 10 mM DTT and 0.25 mg/ml BSA) to a final concentration of 35 µg/ml microtubules and 45 nM KSP. The microtubule/KSP mixture was then pre-incubated at 37° C. for 10 min to promote the binding of KSP to microtubules.

To each well of the testing plate (384-well plate) containing 1.25 µl of inhibitor or test compound in DMSO (or DMSO only in the case of controls) were added 25 µl of ATP solution (ATP diluted to a concentration of 300 µM in assay buffer) and 25 µl of the above-described microtubule/KSP solution. The plates were incubated at room temperature for 1 hour. Following incubation, 65 µl of Biomol Green (a malachite green-based dye that detects the release of inorganic phosphate) was added to each well. The plates were incubated for an additional 5-10 minutes then the absorbance at 630 nm was determined using a Victor II plate reader. The amount of absorbance at 630 nm corresponded to the amount of KSP activity in the samples. The IC$_{50}$ of each inhibitor or test compound was then determined based on the decrease in absorbance at 630 nm at each concentration, via nonlinear regression using either XLFit for Excel or Prism data analysis software by GraphPad Software Inc.

Example 21

Inhibition of Cellular Proliferation in Tumor Cell Lines Treated with KSP Inhibitors Cells were plated in 96-well plates at densities from 500 cells/well of a 96-well plate and allowed to adhere/grow for 24 hours. They were then treated with various concentrations of drug for 72 hours. Than 100 µl of CellTiter Glo is added, a tetrazolium-based assay using the reagent 3-(4,5-dimethylthiazol-2-yl) 5-(3-carboxymethoxyphenyl)-2-(4-sulfophenyl)-2H-tetrazolium (MTS) (U.S. Pat. No. 5,185,450) (see Promega product catalog #G3580, CellITiter 96 Aqueous One Solution Cell Proliferation Assay), and incubated in the dark for 30 minutes. The amount of luminescence was determined for each well using a Walloc Trilux plate reader, which correlates with the number of cells/well. The number of viable cells in the wells, that received only DMSO (0.5%) serve as the 0% inhibition data point, while wells without cells serve as 100% inhibition of cell growth. The drug concentration that resulted in a 50% growth inhibition (GI$_{50}$) was determined graphically from sigmoidal dose-response curves of log-transformed dose values versus cell counts (percent of control) at 72 hours of continuous drug exposure.

The cell lines used are listed below.

The cell proliferation assay was performed as described above.

Cancer Cell Lines
Colo 205—colon carcinoma
RPMI 1640+10% FBS+1% L-glutamine+1% P/S+1% NaPyr.+Hepes
+4.5 g/L Glucose+1% NaBicarb.
MDA 435—breast cancer-high met
EMEM+10% FBS+1% P/S+1% L-Glutamine+1% NEAA+1% NaPyr+1% vitamins
HCT-15 and HCT116—colon carcinoma
RPMI 1640+10% FBS+1% L-glutamine+1% P/S
Drug Resistant Cell Lines
KB3.1—colon epidermal carcinoma; parental cell line
Iscove's+10% FBS+1% L-glutamine+1% P/S KBV1—p-glycoprotein associated multi-drug resistant cell line
  RPMI 1640+10% FBS+1% L-glutamine+1% P/S+0.2 ug/ml Vinblastine
KB85—p-glycoprotein associated multi-drug resistant cell line
  DMEM+10% FBS+1% L-glutamine+1% P/S+10 ng/ml Colchicine Example 22

Clonogenic Softagar Assay Protocol

Human cancer cells were plated at a density of $3 \times 10^5$ cells/well in a 6-well plate. The next day compound of interest at a certain concentration is added to each well. After 24 and 48 hrs incubation in the presence of compound of interest the cells were harvested, washed and counted. The following steps were performed using the Multimek 96 robot. Than 500 viable cells/well were plated in a 96-well plate that was coated with PolyHema previously to prevent attachment of the cells to the bottom of the well. Agarose (3% stock) was melted, diluted in warmed media and added to the cells to a final concentration of 0.5%. After the soft agar solidified the plates were incubated at 37° C. for 6 days. Alamar blue dye was added to cells and plates were incubated for additional 6 hrs. The OD change was measured on a Tecan plate reader and is considered to correlate with the number of colonies formed in soft agar.

Preferred compounds of the invention have a biological activity as measured by an $IC_{50}$ of less than about 1 mM in assay protocols described in Examples 20-22, with preferred embodiments having biological activity of less than about 25 µM, with particularly preferred embodiments having biological activity of less than about 1000 nM, and with the most preferred embodiments having biological activity of less than about 100 nM.

Example 23

Cell Lines

The HCT-116 human colon carcinoma cell lines were obtained from the American Type Culture Collection (ATCC; Rockville, Md.).

Cells were cultured using standard technique in RPMI 1640 supplemented with 10% fetal bovine serum, 2 mM glutamine, 1 mM sodium pyruvate (Life Technologies Inc., Gaithersburg, Md.) and maintained routinely in a humidified chamber at 37° C. and 5% carbon dioxide.

Example 24

In Vivo Implantation of Cell Lines and Efficacy Studies

Cells to be implanted in mice were harvested from cell culture flasks during exponential growth, washed once with sterile phosphate-buffered saline (PBS), counted, and resuspended in Hank's Balanced Salt Solution to a suitable concentration prior to implantation.

All animal studies were in accordance with the Institute of Laboratory Animal Research (National Institutes of Health, Bethesda, Md.) *Guide for the Care and Use of Laboratory Animals*. Nine to twelve week old female athymic nu/nu mice purchased from Charles River Laboratories (Wilmington, Mass.) were used.

Mice received subcutaneous injections into the hind flank on Day 0 with $5 \times 10^6$ HCT-116 cells. For multi-dose efficacy studies, animals with established tumors (approximately 300 mm$^3$) were randomized into treatment groups of approximately 10 mice each for efficacy studies. Compounds of interest or their vehicles were administered orally to mice, with the compounds prepared in a vehicle containing 10% Captisol® to appropriate concentrations. Tumor growth was measured twice weekly using Vernier calipers for the duration of the treatment. Tumor volumes were calculated as the product of (length×width$^2$)/2. For stastical analysis, p-values were calculated using the two-tailed Student's t test.

Example 25

In Vivo Mechanistic Studies in HCT-116 Colon Carcinoma Tumors

To evaluate early pharmacodynamic changes to tumors after treatment with a KSP inhibitor, mice bearing tumors ranging from 300-600 mm$^3$ in volume were treated with a single oral dose of compounds of interest at various concentrations. Control animals received an oral dose of vehicle. At predetermined timepoints, individual mice were euthanized, with plasma and half of the resected tumors collected for PK and half of the tumors fixed in 10% buffered formalin, followed by transference to 70% ethanol by 24 hrs of fixation.

Example 26

Phospho-Histone H3, Cleaved PARP and Cleaved Caspase 3 Immunohistochemistry

Sections were prepared from formalin-fixed, paraffin-embedded subcutaneous tumors. For detection of phospho-histone H3, a rabbit polyclonal anti-human antibody (Cat. #9701L, Cell Signaling, Beverley Mass.) was used. A biotinylated anti-rabbit secondary antibody (Jackson Labs, West Grove, Pa.) was also employed in this detection assay. Slides were stained using an automated slide stainer and compatible ancillary reagents (Ventana Medical Systems, Tucson Ariz.). Cell conditioning for phosho-histone H3 was CC2 mild. For detection of cleaved PARP, a rabbit polyclonal antibody (Cat. #44-698G, BioSource, Camarillo Calif.) and a biotinylated anti-rabbit secondary antibody (Jackson Labs, West Grove, Pa.) followed by a peroxidase-based immunostaining protocol (Vectastain® ABC Elite KIT, Vector Laboratories, Burlingame, Calif.) were used. Heat induced epitope retrieval was accomplished using citrate buffer (Decloaker, BioCare, Walnut Creek, Calif.) before staining on an automated stainer (Dako, Carpenteria, Calif.). For detection of cleaved Caspase 3, a rabbit polyclonal antibody (Cat. #44-698G, BioSource, Camarillo Calif.) and a biotinylated anti-rabbit secondary antibody (Jackson Labs, West Grove, Pa.) followed by a peroxidase-based immunostaining protocol (Vectastain® ABC Elite KIT, Vector Laboratories, Burlingame, Calif.) were used. Heat induced epitope retrieval was accomplished using citrate buffer (Decloaker, BioCare, Walnut Creek, Calif.) before staining on an automated stainer (Dako, Carpenteria, Calif.). In all cases the chromogen used for these assays was DAB.

Example 27

KSP Immunohistochemistry

Sections were prepared from formalin-fixed, paraffin-embedded subcutaneous tumors. For detection of KSP, a rabbit polyclonal anti-human antibody (Cat. #AKIN03 from Cytoskeleton) was used. A biotinylated anti-rabbit secondary antibody (Jackson Labs, West Grove, Pa.) was also employed in this detection assay. Slides were stained using an automated slide stainer and compatible ancillary reagents (Ventana Medical Systems, Tucson Ariz.). Cell conditioning for KSP was a CC1 standard. The chromogen used for this assay was DAB.

What is claimed is:

1. A compound of formula I:

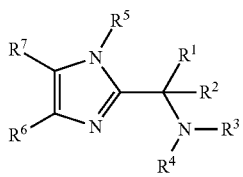

wherein:

$R^1$ is 1 to 6 carbon alkyl optionally substituted with hydroxy or halo;

$R^2$ is selected from the group consisting of hydrogen, methyl, and ethyl;

$R^3$ is —X-A, wherein X is —C(O)—; and

A is a substituted aryl or heteroaryl group selected from 5-methyl-2H-imidazol-4yl, 2-aminothiazol-4-yl, 4-t-butylphenyl, 2-chlorophenyl, 2-chloro-6-methylpyrid-4-yl, 3-chlorophenyl, 4-chlorophenyl, 6-chloropyridin-3-yl, 3,4-dichlorophenyl, 2,4-difluorophenyl, 1,5-dimethyl-1H-pyrazol-3-yl, 2,4-dimethylthiazol-5-yl, 1-ethyl-3-methyl-1H-pyrazol-5-yl, 2-methoxyphenyl, 4-methoxyphenyl, 4-methylisoxazol-3-yl, 5-methylisoxazol-4-yl, 4-methylphenyl, 1-methyl-3-trifluoromethyl-1H-pyrazol-4-yl, 1-methyl-5-chloro-1H-pyrazol-4-yl, 5-methyl-1H-pyrazol-3-yl, 6-methylpyridin-3-yl, 2-pyrrolidin-3-ylphenyl, 4-(trifluoromethyl)phenyl, 6-(trifluoromethyl)pyridin-3-yl, 2,5-dimethyloxazol-4-yl, 2-aminothiazol-4-yl, 4-methylpyrazol-5-yl, 3-trifluoromethylpyrazol-4-yl, 2-methyl-3-trifluoromethylpyrazol-5-yl, 4-chloro-1,3-dimethylpyrazolo[3,4]pyridine, and 1-methylbenzimidazol-2-yl;

$R^4$ is -[alkylene]$_p$-nitrogen-containing heterocyclic, -[alkylene]$_p$-nitrogen-containing substituted heterocyclic, -[alkylene]$_p$-nitrogen-containing heteroaryl, -[alkylene]$_p$-nitrogen-containing substituted heteroaryl, or -[alkylene]$_p$—NR$^{10}$R$^{11}$ wherein p is 1, selected from the group consisting of —(CH$_2$)$_2$—NH$_2$, —CH$_2$-azetidin-3-yl, —CH$_2$-(2,5-dihydropyrrol-3-yl), —(CH$_2$)$_3$-imidazol-1-yl, —CH$_2$-(1H-imidazol-4-yl), —CH$_2$-pyridin-3-yl, —CH$_2$-(2-hydroxypyridin-4-yl), —CH$_2$-(6-hydroxypyridin-3-yl), —CH$_2$-morpholin-2-yl, —CH$_2$-pyrrolidin-3-yl, —CH$_2$-(3-fluoropyrrolidin-3-yl), —CH$_2$-(3-hydroxypyrrolidin-3-yl), —CH$_2$-(4-fluoropyrrolidin-3-yl), —CH$_2$-(4-hydroxypyrrolidin-3-yl), —CH$_2$-(2-hydroxymethylpyrrolidin-3-yl), —CH$_2$-piperidin-3-yl, —CH$_2$-[1H-(1,2,3-triazol-4-yl)], —CH$_2$CH(NH$_2$)CH$_2$OH, —(CH$_2$)$_3$—NH$_2$, —(CH$_2$)$_3$—NHCH$_3$, —(CH$_2$)$_3$—N(CH$_3$)$_2$, —(CH$_2$)$_3$NH-(5-cyanopyridin-2-yl), —(CH$_2$)$_3$NH-cyclopropyl, —(CH$_2$)$_3$NH-cyclobutyl, —(CH$_2$)$_3$-(1H-imidazol-2-yl), —(CH$_2$)$_3$-(2-hydroxyethylpiperidin-1-yl), —(CH$_2$)$_3$NHCH$_2$-cyclopropyl, —CH$_2$CHOHCH$_2$NH$_2$, —CH$_2$CH(CH$_2$OH)CH$_2$NH$_2$, —CH$_2$C(CH$_3$)$_2$CH$_2$—N(CH$_3$)$_2$, —CH$_2$C(CH$_3$)$_2$CH$_2$-(4-methylpiperazin-1-yl), —(CH$_2$)$_2$C(O)NH$_2$, —(CH$_2$)$_2$CH(NH$_2$)C(O)NH$_2$, —(CH$_2$)$_2$CH(NH$_2$)CH$_2$OH, —(CH$_2$)$_2$CH(NH$_2$)CH$_3$, —CH$_2$CHFCH$_2$NH$_2$, —(CH$_2$)$_3$—NHCH$_2$CH$_2$OH, —(CH$_2$)$_3$—N(CH$_2$CH$_2$OH)$_2$, —(CH$_2$)$_3$—NHCH(CH$_2$OH)$_2$, —(CH$_2$)$_3$CH$_3$, —(CH$_2$)$_2$CH(NH$_2$)CH$_2$OH, —(CH$_2$)$_2$C(CH$_3$)$_2$NH$_2$, —(CH$_2$)$_2$CH(NH$_2$)CH$_2$OCH$_3$, —(CH$_2$)$_2$CH(NH$_2$)CH$_2$F, and —CH$_2$CHFCH(NH$_2$)CH$_2$OH;

$R^5$ is L-A$^1$, wherein L is methylene and A$^1$ is selected from the group consisting of phenyl, 6-aminopyridin-2-yl, 3-chlorophenyl, 3-cyanophenyl, 2,4-difluorophenyl, 2,5-difluorophenyl, 3,5-difluorophenyl, 2-fluorophenyl, 3-fluorophenyl, 4-fluorophenyl, 3-hydroxyphenyl, 3-methoxyphenyl, 1-(5-methyl)-isoxazol-3-yl, 2-methylphenyl, 3-methylphenyl, 4-methylphenyl, pyridin-2-yl, pyridin-3-yl, pyridin-4-yl, tetrahydropyran-4-yl, thiazol-4-yl, and 5-trifluoromethylfuran-2-yl;

and $R^6$ is selected from the group consisting of phenyl, 3-bromophenyl, 3-chlorophenyl, 4-cyanophenyl, 2,5-difluorophenyl, 3-fluorophenyl, 2-methoxyphenyl, 3-methoxyphenyl, 4-methoxyphenyl, 4-methylphenyl, pyrazin-2-yl, pyridin-2-yl, thiazol-2-yl, 2-trifluoromethylphenyl, and 3-trifluoromethylphenylR$^7$ is hydrogen, halo, or methyl; or a pharmaceutically acceptable salt thereof.

2. The compound of claim 1, wherein R$^1$ is selected from the group consisting of methyl, iso-propyl, t-butyl, 1-methyl-n-prop-1-yl, and 2-hydroxy-iso-propyl.

3. The compound of claim 1, wherein R$^2$ is hydrogen.

4. The compound of claim 1, wherein R$^7$ is hydrogen.

5. The compound of claim 4, wherein R$^6$ is selected from the group consisting of phenyl, 3-bromophenyl, 3-chlorophenyl, 4-cyanophenyl, 2,5-difluorophenyl, 3-fluorophenyl, and 3-trifluoromethylphenyl.

6. A compound selected from the group consisting of:
N-(3-aminopropyl)-N-[(1R)-1-(1-benzyl-4-phenyl-1H-imidazol-2-yl)-2-methylpropyl]-4-methylbenzamide;
N-(3-aminopropyl)-N-[(1R)-1-(1-benzyl-4-phenyl-1H-imidazol-2-yl)-2-methylpropyl]benzamide;
N-(3-aminopropyl)-N—[(R)-(1-benzyl-4-phenyl-1H-imidazol-2-yl)(phenyl)methyl]-4-methylbenzamide;
N-(3-aminopropyl)-N—[(R)-(1-benzyl-4-phenyl-1H-imidazol-2-yl)(phenyl)methyl]benzamide;
N-(3-aminopropyl)-N-{(1R)-1-[1-benzyl-4-(3-bromophenyl)-1H-imidazol-2-yl]-2-methylpropyl}benzamide;
N-(3-aminopropyl)-N-{(1R)-1-[1-benzyl-4-(3-bromophenyl)-1H-imidazol-2-yl]-2-methylpropyl}-4-methylbenzamide;
N-(3-aminopropyl)-N-{(1R)-1-[1-benzyl-4-(3-bromophenyl)-1H-imidazol-2-yl]-2-methylpropyl}-4-(trifluoromethyl)benzamide;
N-(3-aminopropyl)-N-{(1R)-1-[1-benzyl-4-(3-bromophenyl)-1H-imidazol-2-yl]-2-methylpropyl}-2,4-difluorobenzamide;
N-(3-aminopropyl)-4-methyl-N-{2-methyl-1-[1-(3-methylbenzyl)-4-phenyl-1H-imidazol-2-yl]propyl}benzamide;
N-(3-aminopropyl)-N-{(1R)-1-[1-benzyl-4-(3-methoxyphenyl)-1H-imidazol-2-yl]-2-methylpropyl}benzamide;

N-(3-aminopropyl)-N-{(1R)-1-[1-benzyl-4-(3-methoxyphenyl)-1H-imidazol-2-yl]-2-methylpropyl}-4-methylbenzamide;
N-(3-aminopropyl)-N-{(1R)-1-[1-benzyl-4-(3-methoxyphenyl)-1H-imidazol-2-yl]-2-methylpropyl}-4-(trifluoromethyl)benzamide;
N-(3-aminopropyl)-N-{(1R)-1-[1-benzyl-4-(3-methoxyphenyl)-1H-imidazol-2-yl]-2-methylpropyl}-2,4-difluorobenzamide;
N-(3-aminopropyl)-N-{(1R)-1-[1-benzyl-4-(3-chlorophenyl)-1H-imidazol-2-yl]-2-methylpropyl}benzamide;
N-(3-aminopropyl)-N-{(1R)-1-[1-benzyl-4-(3-chlorophenyl)-1H-imidazol-2-yl]-2-methylpropyl}-4-methylbenzamide;
N-(3-aminopropyl)-N-{(1R)-1-[1-benzyl-4-(3-chlorophenyl)-1H-imidazol-2-yl]-2-methylpropyl}-4-(trifluoromethyl)benzamide;
N-(3-aminopropyl)-N-{(1R)-1-[1-benzyl-4-(3-chlorophenyl)-1H-imidazol-2-yl]-2-methylpropyl}-2,4-difluorobenzamide;
N-(3-aminopropyl)-N-{(1R)-1-[1-benzyl-4-(4-methylphenyl)-1H-imidazol-2-yl]-2-methylpropyl}benzamide;
N-(3-aminopropyl)-N-{(1R)-1-[1-benzyl-4-(4-methylphenyl)-1H-imidazol-2-yl]-2-methylpropyl}-4-methylbenzamide;
N-(3-aminopropyl)-N-{(1R)-1-[1-benzyl-4-(4-methylphenyl)-1H-imidazol-2-yl]-2-methylpropyl}-4-(trifluoromethyl)benzamide;
N-(3-aminopropyl)-N-{(1R)-1-[1-benzyl-4-(4-methylphenyl)-1H-imidazol-2-yl]-2-methylpropyl}-2,4-difluorobenzamide;
N-(3-aminopropyl)-N-[(1R)-1-(1-benzyl-4-phenyl-1H-imidazol-2-yl)-2,2-dimethylpropyl]-4-methylbenzamide;
N-(3-aminopropyl)-N-[(1R)-1-(1-benzyl-4-phenyl-1H-imidazol-2-yl)-2,2-dimethylpropyl]benzamide;
N-(3-aminopropyl)-N-{(1R)-1-[1-(3,5-difluorobenzyl)-4-phenyl-1H-imidazol-2-yl]-2-methylpropyl}-4-methylbenzamide;
N-(3-aminopropyl)-N-{(1R)-1-[1-(3,5-difluorobenzyl)-4-phenyl-1H-imidazol-2-yl]-2-methylpropyl}benzamide;
N-{(1R)-1-[1-benzyl-4-(3-bromophenyl)-1H-imidazol-2-yl]-2-methylpropyl}-4-methyl-N-{3-[(methylsulfonyl)amino]propyl}benzamide;
N-[(1R)-1-(1-benzyl-4-phenyl-1H-imidazol-2-yl)-2-methylpropyl]-N-[(3R)-piperidin-3-ylmethyl]benzamide;
N-[(1R)-1-(1-benzyl-4-phenyl-1H-imidazol-2-yl)-2-methylpropyl]-N-[(3S)-piperidin-3-ylmethyl]benzamide;
N-(3-aminopropyl)-4-methyl-N-{(1R)-2-methyl-1-[1-(4-methylbenzyl)-4-phenyl-1H-imidazol-2-yl]propyl}benzamide;
N-(3-aminopropyl)-N-{(1R)-2-methyl-1-[1-(4-methylbenzyl)-4-phenyl-1H-imidazol-2-yl]propyl}benzamide;
N-(3-aminopropyl)-4-methyl-N-{(1R)-2-methyl-1-[1-(2-methylbenzyl)-4-phenyl-1H-imidazol-2-yl]propyl}benzamide;
N-(3-aminopropyl)-N-{(1R)-2-methyl-1-[1-(2-methylbenzyl)-4-phenyl-1H-imidazol-2-yl]propyl}benzamide;
N-[(1R)-1-(1-benzyl-4-phenyl-1H-imidazol-2-yl)-2-methylpropyl]-N-[2,2-dimethyl-3-(4-methylpiperazin-1-yl)propyl]benzamide;
N-[(1R)-1-(1-benzyl-4-phenyl-1H-imidazol-2-yl)-2-methylpropyl]-N-[2,2-dimethyl-3-(4-methylpiperazin-1-yl)propyl]-4-methylbenzamide;
N-[(1R)-1-(1-benzyl-4-phenyl-1H-imidazol-2-yl)-2-methylpropyl]-4-methyl-N-[(3R)-piperidin-3-ylmethyl]benzamide;
N-[(1R)-1-(1-benzyl-4-phenyl-1H-imidazol-2-yl)-2-methylpropyl]-4-methyl-N-[(3S)-piperidin-3-ylmethyl]benzamide;
N-(3-aminopropyl)-N-((1R)-1-{1-benzyl-4-[2-(trifluoromethyl)phenyl]-1H-imidazol-2-yl}-2-methylpropyl)benzamide;
N-(3-aminopropyl)-N-((1R)-1-{1-benzyl-4-[2-(trifluoromethyl)phenyl]-1H-imidazol-2-yl}-2-methylpropyl)-4-methylbenzamide;
N-(3-aminopropyl)-N-((1R)-1-{1-benzyl-4-[2-(trifluoromethyl)phenyl]-1H-imidazol-2-yl}-2-methylpropyl)-2,4-difluorobenzamide;
N-(3-aminopropyl)-N-{(1R)-1-[1-benzyl-4-(3-chlorophenyl)-1H-imidazol-2-yl]-2-methylpropyl}-4-methoxybenzamide;
N-(3-aminopropyl)-N-{(1R)-1-[1-benzyl-4-(3-chlorophenyl)-1H-imidazol-2-yl]-2-methylpropyl}-3-chlorobenzamide;
N-(3-aminopropyl)-N-{(1R)-1-[1-benzyl-4-(3-chlorophenyl)-1H-imidazol-2-yl]-2-methylpropyl}-4-chlorobenzamide;
N-(3-aminopropyl)-N-{(1R)-1-[1-benzyl-4-(3-chlorophenyl)-1H-imidazol-2-yl]-2-methylpropyl}-4-tert-butylbenzamide;
N-(3-aminopropyl)-N-{(1R)-1-[1-benzyl-4-(3-chlorophenyl)-1H-imidazol-2-yl]-2-methylpropyl}-3,4-dichlorobenzamide;
N-{(1R)-1-[1-benzyl-4-(3-bromophenyl)-1H-imidazol-2-yl]-2-methylpropyl}-N-{3-[(5-cyanopyridin-2-yl)amino]propyl}benzamide;
N-{(1R)-1-[1-benzyl-4-(3-bromophenyl)-1H-imidazol-2-yl]-2-methylpropyl}-N-(3-{[5-(trifluoromethyl)pyridin-2-yl]amino}propyl)benzamide;
N-[(1R)-1-(1-benzyl-4-phenyl-1H-imidazol-2-yl)-2-methylpropyl]-N-piperidin-4-ylbenzamide;
N-[(1R)-1-(1-benzyl-4-phenyl-1H-imidazol-2-yl)-2-methylpropyl]-4-methyl-N-piperidin-4-ylbenzamide;
N-[(1R)-1-(1-benzyl-4-phenyl-1H-imidazol-2-yl)-2-methylpropyl]-2,4-difluoro-N-piperidin-4-ylbenzamide;
N-(3-aminopropyl)-N-{(1R)-1-[1-benzyl-4-(3-chlorophenyl)-1H-imidazol-2-yl]-2-methylpropyl}cyclohexanecarboxamide;
N-(3-aminopropyl)-N-{(1R)-1-[1-benzyl-4-(3-chlorophenyl)-1H-imidazol-2-yl]-2-methylpropyl}-6-chloronicotinamide;
N-(3-aminopropyl)-N-{(1R)-1-[1-benzyl-4-(3-chlorophenyl)-1H-imidazol-2-yl]-2,2-dimethylpropyl}benzamide;
N-(3-aminopropyl)-N-{(1R)-1-[1-benzyl-4-(3-chlorophenyl)-1H-imidazol-2-yl]-2,2-dimethylpropyl}-4-methylbenzamide;
N-(3-aminopropyl)-N-{(1R)-1-[4-(3-chlorophenyl)-1-(2,4-difluorobenzyl)-1H-imidazol-2-yl]-2,2-dimethylpropyl}benzamide;
N-(3-aminopropyl)-N-{(1R)-1-[4-(3-chlorophenyl)-1-(2,4-difluorobenzyl)-1H-imidazol-2-yl]-2,2-dimethylpropyl}-4-methylbenzamide;
N-[(1R)-1-(1-benzyl-4-phenyl-1H-imidazol-2-yl)-2-methylpropyl]-N-[3-(dimethylamino)-2,2-dimethylpropyl]benzamide;

N-[(1R)-1-(1-benzyl-4-phenyl-1H-imidazol-2-yl)-2-methylpropyl]-N-[3-(dimethylamino)-2,2-dimethylpropyl]-4-methylbenzamide;
N-(3-aminopropyl)-N-{(1R)-1-[1-benzyl-4-(3-chlorophenyl)-1H-imidazol-2-yl]-2,2-dimethylpropyl}-6-chloronicotinamide;
N-(3-aminopropyl)-6-chloro-N-{(1R)-1-[4-(3-chlorophenyl)-1-(3,5-difluorobenzyl)-1H-imidazol-2-yl]-2,2-dimethylpropyl}nicotinamide;
N-(3-aminopropyl)-N-[(1R)-1-(1-benzyl-5-methyl-4-phenyl-1H-imidazol-2-yl)-2-methylpropyl]benzamide;
N-(3-aminopropyl)-N-[(1R)-1-(1-benzyl-5-methyl-4-phenyl-1H-imidazol-2-yl)-2-methylpropyl]-4-methylbenzamide;
N-(3-aminopropyl)-N-[(1R)-1-(1-benzyl-5-methyl-4-phenyl-1H-imidazol-2-yl)-2-methylpropyl]-2,4-difluorobenzamide;
N-(3-aminopropyl)-N-[(1R)-1-(1-benzyl-5-methyl-4-phenyl-1H-imidazol-2-yl)-2-methylpropyl]-6-chloronicotinamide;
N-(3-aminopropyl)-N-{(1R)-1-[1-benzyl-4-(3-chlorophenyl)-1H-imidazol-2-yl]-2-methylpropyl}-2-chlorobenzamide;
N-(3-aminopropyl)-N-{(1R)-1-[1-benzyl-4-(3-chlorophenyl)-1H-imidazol-2-yl]-2-methylpropyl}-2-chloro-6-methylisonicotinamide;
N-(3-aminopropyl)-N-{(1R)-1-[1-benzyl-4-(3-chlorophenyl)-1H-imidazol-2-yl]-2-methylpropyl}-3-furamide;
N-(3-aminopropyl)-N-{(1R)-1-[1-benzyl-4-(3-chlorophenyl)-1H-imidazol-2-yl]-2-methylpropyl}-5-methyl-2H-imidazole-4-carboxamide;
N-(3-aminopropyl)-N-{(1R)-1-[1-benzyl-4-(3-chlorophenyl)-1H-imidazol-2-yl]-2-methylpropyl}-2-methoxybenzamide;
N-(3-aminopropyl)-N-{(1R)-1-[1-benzyl-4-(3-chlorophenyl)-1H-imidazol-2-yl]-2-methylpropyl}pyridine-2-carboxamide;
N-(3-aminopropyl)-N-{(1R)-1-[1-benzyl-4-(3-chlorophenyl)-1H-imidazol-2-yl]-2-methylpropyl}-1,5-dimethyl-1H-pyrazole-3-carboxamide;
N-(3-aminopropyl)-N-[(1R)-1-(1-benzyl-4-phenyl-1H-imidazol-2-yl)-1,2-dimethylpropyl]benzamide;
N-(3-aminopropyl)-N-[(1R)-1-(1-benzyl-4-phenyl-1H-imidazol-2-yl)-1,2-dimethylpropyl]-4-methylbenzamide;
N-(2-aminoethyl)-N-[(1R)-1-(1-benzyl-4-phenyl-1H-imidazol-2-yl)-2-methylpropyl]-4-methylbenzamide;
N-(2-aminoethyl)-N-[(1R)-1-(1-benzyl-4-phenyl-1H-imidazol-2-yl)-2-methylpropyl]benzamide;
N-(3-aminopropyl)-N-{(1R)-1-[1-benzyl-4-(3-chlorophenyl)-1H-imidazol-2-yl]-2-methylpropyl}-1,3-thiazole-4-carboxamide;
N-{(1R)-1-[1-benzyl-4-(3-chlorophenyl)-1H-imidazol-2-yl]-2,2-dimethylpropyl}-N-(pyrrolidin-3-ylmethyl)benzamide;
N-{(1R)-1-[4-(3-chlorophenyl)-1-(3,5-difluorobenzyl)-1H-imidazol-2-yl]-2,2-dimethylpropyl}-N-(pyrrolidin-3-ylmethyl)benzamide;
N-(3-aminopropyl)-N-{(1R)-1-[1-benzyl-4-(3-chlorophenyl)-1H-imidazol-2-yl]-2-methylpropyl}benzenesulfonamide;
N-(3-aminopropyl)-N-{(1R)-1-[1-benzyl-4-(3-chlorophenyl)-1H-imidazol-2-yl]-2-methylpropyl}-4-methylisoxazole-3-carboxamide;
N-(3-aminopropyl)-N-{(1R)-1-[1-benzyl-4-(3-chlorophenyl)-1H-imidazol-2-yl]-2-methylpropyl}isoxazole-3-carboxamide;
N-(3-aminopropyl)-N-{(1R)-1-[1-benzyl-4-(3-chlorophenyl)-1H-imidazol-2-yl]-2-methylpropyl}-5-methyl-1H-pyrazole-3-carboxamide;
N-(3-aminopropyl)-N-{(1R)-1-[1-benzyl-4-(3-chlorophenyl)-1H-imidazol-2-yl]-2-methylpropyl}-2,4-dimethyl-1,3-thiazole-5-carboxamide;
N-(3-aminopropyl)-N-{(1R)-1-[1-benzyl-4-(3-chlorophenyl)-1H-imidazol-2-yl]-2-methylpropyl}tetrahydrofuran-3-carboxamide;
N-(3-aminopropyl)-N-{(1R)-1-[1-benzyl-4-(3-chlorophenyl)-1H-imidazol-2-yl]-2-methylpropyl}piperidine-4-carboxamide;
2-amino-N-(3-aminopropyl)-N-{(1R)-1-[1-benzyl-4-(3-chlorophenyl)-1H-imidazol-2-yl]-2-methylpropyl}-1,3-thiazole-4-carboxamide;
N-[(1R)-1-(1-benzyl-4-phenyl-1H-imidazol-2-yl)-2,2-dimethylpropyl]-N-(1H-imidazol-4-ylmethyl)benzamide;
N-[(1R)-1-(1-benzyl-4-phenyl-1H-imidazol-2-yl)-2,2-dimethylpropyl]-N-[(2-hydroxypyridin-4-yl)methyl]benzamide;
N-[(1R)-1-(1-benzyl-4-phenyl-1H-imidazol-2-yl)-2,2-dimethylpropyl]-N-[(6-hydroxypyridin-3-yl)methyl]benzamide;
N-[(1R)-1-(1-benzyl-4-phenyl-1H-imidazol-2-yl)-2,2-dimethylpropyl]-N-(pyridin-3-ylmethyl)benzamide;
N-[(1R)-1-(1-benzyl-4-phenyl-1H-imidazol-2-yl)-2,2-dimethylpropyl]-N-[3-(cyclobutylamino)propyl]benzamide;
N-[(1R)-1-(1-benzyl-4-phenyl-1H-imidazol-2-yl)-2,2-dimethylpropyl]-N-(pyrrolidin-3-ylmethyl)benzamide;
N-(3-aminopropyl)-N-[(1R)-1-(1-benzyl-4-phenyl-1H-imidazol-2-yl)-2,2-dimethylpropyl]-6-methylnicotinamide;
N-[(1R)-1-(1-benzyl-4-phenyl-1H-imidazol-2-yl)-2,2-dimethylpropyl]-N-{3-[(cyclopropylmethyl)amino]propyl}benzamide;
N-[(1R)-1-(1-benzyl-4-phenyl-1H-imidazol-2-yl)-2,2-dimethylpropyl]-N-[3-({[5-(pyridin-3-yloxy)-1H-indazol-3-yl]methyl}amino)propyl]benzamide;
N-[(1R)-1-(1-benzyl-4-phenyl-1H-imidazol-2-yl)-2,2-dimethylpropyl]-N-[(5-methoxy-1H-indazol-3-yl)methyl]benzamide;
N-[(1R)-1-(1-benzyl-4-phenyl-1H-imidazol-2-yl)-2,2-dimethylpropyl]-N-(3-{[(6-fluoro-1H-indazol-3-yl)methyl]amino}propyl)benzamide;
N-[(1R)-1-(1-benzyl-4-phenyl-1H-imidazol-2-yl)-2,2-dimethylpropyl]-N-{[5-(pyridin-3-yloxy)-1H-indazol-3-yl]methyl}benzamide;
N-[(1R)-1-(1-benzyl-4-phenyl-1H-imidazol-2-yl)-2,2-dimethylpropyl]-N-(3-hydroxypropyl)benzamide;
N-(3-aminopropyl)-N-[(1R)-1-(1-benzyl-4-phenyl-1H-imidazol-2-yl)-2,2-dimethylpropyl]-1,5-dimethyl-1H-pyrazole-3-carboxamide;
N-[(1R)-1-(1-benzyl-4-phenyl-1H-imidazol-2-yl)-2,2-dimethylpropyl]-N-[(3R)-3,5-diamino-5-oxopentyl]benzamide;
N-{3-[(aminoacetyl)amino]propyl}-N-[(1R)-1-(1-benzyl-4-phenyl-1H-imidazol-2-yl)-2,2-dimethylpropyl]benzamide;
N-{2-[(aminoacetyl)amino]ethyl}-N-[(1R)-1-(1-benzyl-4-phenyl-1H-imidazol-2-yl)-2,2-dimethylpropyl]benzamide;

N-[(1R)-1-(1-benzyl-4-phenyl-1H-imidazol-2-yl)-2-methylpropyl]-1,5-dimethyl-N-(piperidin-3-ylmethyl)-1H-pyrazole-3-carboxamide;
(2R)—N-(3-aminopropyl)-N-{(1R)-1-[1-benzyl-4-(3-chlorophenyl)-1H-imidazol-2-yl]-2-methylpropyl}tetrahydrofuran-2-carboxamide;
(2S)—N-(3-aminopropyl)-N-{(1R)-1-[1-benzyl-4-(3-chlorophenyl)-1H-imidazol-2-yl]-2-methylpropyl}tetrahydrofuran-2-carboxamide;
N-(3-aminopropyl)-N-{(1R)-1-[1-benzyl-4-(3-chlorophenyl)-1H-imidazol-2-yl]-2-methylpropyl}pyrazine-2-carboxamide;
3-{benzoyl[(1R)-1-(1-benzyl-4-phenyl-1H-imidazol-2-yl)-2,2-dimethylpropyl]amino}propyl benzoate;
N-{(1R)-1-[4-(3-chlorophenyl)-1-(3,5-difluorobenzyl)-1H-imidazol-2-yl]-2,2-dimethylpropyl}-1,5-dimethyl-N-[(3R)-pyrrolidin-3-ylmethyl]-1H-pyrazole-3-carboxamide;
N-{(1R)-1-[4-(3-chlorophenyl)-1-(3,5-difluorobenzyl)-1H-imidazol-2-yl]-2,2-dimethylpropyl}-1,5-dimethyl-N-[(3S)-pyrrolidin-3-ylmethyl]-1H-pyrazole-3-carboxamide;
N-(3-aminopropyl)-N-{(1R)-1-[1-benzyl-4-(3-chlorophenyl)-1H-imidazol-2-yl]-2-methylpropyl}-1-methyl-3-(trifluoromethyl)-1H-pyrazole-4-carboxamide;
N-(3-aminopropyl)-N-{(1R)-1-[1-benzyl-4-(3-chlorophenyl)-1H-imidazol-2-yl]-2-methylpropyl}-5-chloro-1-methyl-1H-pyrazole-4-carboxamide;
N-(3-aminopropyl)-N-{(1R)-1-[1-benzyl-4-(3-chlorophenyl)-1H-imidazol-2-yl]-2-methylpropyl}-2-(dimethylamino)acetamide;
N-[(1R)-1-(1-benzyl-4-phenyl-1H-imidazol-2-yl)-2,2-dimethylpropyl]-N-[3-(1H-imidazol-2-yl)propyl]benzamide;
1-benzyl-6-(1-benzyl-4-phenyl-1H-imidazol-2-yl)piperidin-2-one;
1-benzyl-6-[1-(3-chlorobenzyl)-4-phenyl-1H-imidazol-2-yl]piperidin-2-one;
N-(3-aminopropyl)-N-[(1R)-1-(1-benzyl-4-phenyl-1H-imidazol-2-yl)-2-methylpropyl]-1,5-dimethyl-1H-pyrazole-3-carboxamide;
N-[(1R)-1-(1-benzyl-4-phenyl-1H-imidazol-2-yl)-2,2-dimethylpropyl]-N-{3-[(2-hydroxyethyl)amino]propyl}benzamide;
N-[(1R)-1-(1-benzyl-4-phenyl-1H-imidazol-2-yl)-2,2-dimethylpropyl]-N-[3-(cyclopropylamino)propyl]benzamide;
N-(3-aminopropyl)-N-{(1R)-2-methyl-1-[4-phenyl-1-(1,3-thiazol-4-ylmethyl)-1H-imidazol-2-yl]propyl}benzamide;
N-(3-aminopropyl)-4-methyl-N-{(1R)-2-methyl-1-[4-phenyl-1-(1,3-thiazol-4-ylmethyl)-1H-imidazol-2-yl]propyl}benzamide;
N-(3-aminopropyl)-2,4-difluoro-N-{(1R)-2-methyl-1-[4-phenyl-1-(1,3-thiazol-4-ylmethyl)-1H-imidazol-2-yl]propyl}benzamide;
N-(3-aminopropyl)-6-chloro-N-{(1R)-2-methyl-1-[4-phenyl-1-(1,3-thiazol-4-ylmethyl)-1H-imidazol-2-yl]propyl}nicotinamide;
N-(3-aminopropyl)-N-[(1R)-1-(1-benzyl-4-pyridin-2-yl-1H-imidazol-2-yl)-2,2-dimethylpropyl]benzamide;
N-(3-aminopropyl)-N-[(1R)-1-(1-benzyl-4-pyridin-2-yl-1H-imidazol-2-yl)-2,2-dimethylpropyl]-4-methylbenzamide;
N-(3-aminopropyl)-N-[(1R)-1-(1-benzyl-4-pyridin-2-yl-1H-imidazol-2-yl)-2,2-dimethylpropyl]-2,4-difluorobenzamide;
N-(3-aminopropyl)-N-[(1R)-1-(1-benzyl-4-pyridin-2-yl-1H-imidazol-2-yl)-2,2-dimethylpropyl]-6-chloronicotinamide;
N-(2-amino-3-hydroxypropyl)-N-[(1R)-1-(1-benzyl-4-phenyl-1H-imidazol-2-yl)-2-methylpropyl]benzamide;
N-(3-aminopropyl)-N-[(1R)-1-(1-benzyl-4-phenyl-1H-imidazol-2-yl)-3-methylbutyl]benzamide;
N-(3-aminopropyl)-N-[(1R)-1-(1-benzyl-4-phenyl-1H-imidazol-2-yl)-3-methylbutyl]-4-methylbenzamide;
N-(3-aminopropyl)-N-[(1R,2R)-1-(1-benzyl-4-phenyl-1H-imidazol-2-yl)-2-methylbutyl]benzamide;
N-(3-aminopropyl)-N-[(1R,2R)-1-(1-benzyl-4-phenyl-1H-imidazol-2-yl)-2-methylbutyl]-4-methylbenzamide;
N-(3-aminopropyl)-N-[(1R,2S)-1-(1-benzyl-4-phenyl-1H-imidazol-2-yl)-2-methylbutyl]benzamide;
N-(3-aminopropyl)-N-[(1R,2S)-1-(1-benzyl-4-phenyl-1H-imidazol-2-yl)-2-methylbutyl]-4-methylbenzamide;
N-(3-aminopropyl)-N-{(1R)-1-[1-benzyl-4-(3-chlorophenyl)-1H-imidazol-2-yl]-2-methylpropyl}-5-methylisoxazole-4-carboxamide;
N-(3-aminopropyl)-N-{(1R)-1-[1-benzyl-4-(3-chlorophenyl)-1H-imidazol-2-yl]-2-methylpropyl}acetamide;
N-(3-aminopropyl)-N-{(1R)-1-[1-benzyl-4-(3-chlorophenyl)-1H-imidazol-2-yl]-2-methylpropyl}-2-(4-fluorophenoxy)acetamide;
N-(3-aminopropyl)-N-{(1R)-1-[1-benzyl-4-(3-chlorophenyl)-1H-imidazol-2-yl]-2-methylpropyl}-2-(1H-imidazol-1-yl)acetamide;
N-(3-aminopropyl)-N-{(1R)-1-[1-benzyl-4-(3-chlorophenyl)-1H-imidazol-2-yl]-2-methylpropyl}-2-morpholin-4-ylacetamide;
[(3-{benzoyl[(1R)-1-(1-benzyl-4-phenyl-1H-imidazol-2-yl)-2,2-dimethylpropyl]amino}propyl)amino]acetic acid;
N-(3-aminopropyl)-N-{(1R)-1-[1-benzyl-4-(3-chlorophenyl)-1H-imidazol-2-yl]-2-methylpropyl}-2-hydroxyacetamide;
N-(3-aminopropyl)-N-{(1R)-1-[1-benzyl-4-(3-chlorophenyl)-1H-imidazol-2-yl]-2-methylpropyl}-2-methoxyacetamide;
N-(3-aminopropyl)-N-[(1R)-1-(1-benzyl-4-phenyl-1H-imidazol-2-yl)-2,2-dimethylpropyl]-2-hydroxyacetamide;
N-(3-aminopropyl)-N-[(1R)-1-(1-benzyl-4-phenyl-1H-imidazol-2-yl)-2,2-dimethylpropyl]-2-methoxyacetamide;
N-(3-aminopropyl)-N-{(1R)-1-[1-benzyl-4-(3-chlorophenyl)-1H-imidazol-2-yl]-2-methylpropyl}-1-ethyl-3-methyl-1H-pyrazole-5-carboxamide;
ethyl [(3-{benzoyl[(1R)-1-(1-benzyl-4-phenyl-1H-imidazol-2-yl)-2,2-dimethylpropyl]amino}propyl)amino]acetate;
N-{3-[(2-amino-3-methylbutanoyl)amino]propyl}-N-[(1R)-1-(1-benzyl-4-phenyl-1H-imidazol-2-yl)-2,2-dimethylpropyl]benzamide;
N-(3-aminopropyl)-N-{(1R)-1-[1-benzyl-4-(3-chlorophenyl)-1H-imidazol-2-yl]-2-methylpropyl}tetrahydro-2H-pyran-4-carboxamide;
N-(3-aminopropyl)-N-{(1R)-1-[1-benzyl-4-(3-chlorophenyl)-1H-imidazol-2-yl]-2-methylpropyl}-2-(methylamino)acetamide;
N-[(1R)-1-(1-benzyl-4-phenyl-1H-imidazol-2-yl)-2,2-dimethylpropyl]-N-propylbenzamide;

N-[(1R)-1-(1-benzyl-4-phenyl-1H-imidazol-2-yl)-2,2-dimethylpropyl]-N-butylbenzamide;

N-[(1R)-1-(1-benzyl-4-phenyl-1H-imidazol-2-yl)-2,2-dimethylpropyl]-N-butyl-1,5-dimethyl-1H-pyrazole-3-carboxamide;

[[(1R)-1-(1-benzyl-4-phenyl-1H-imidazol-2-yl)-2,2-dimethylpropyl](butyl)amino](oxo)acetic acid;

[[(1R)-1-(1-benzyl-4-phenyl-1H-imidazol-2-yl)-2,2-dimethylpropyl](propyl)amino](oxo)acetic acid;

N-[(1R)-1-(1-benzyl-4-phenyl-1H-imidazol-2-yl)-2,2-dimethylpropyl]-N-{3-[2-(hydroxymethyl)piperidin-1-yl]propyl}benzamide;

N-[(1R)-1-(1-benzyl-4-phenyl-1H-imidazol-2-yl)-2,2-dimethylpropyl]-N-{3-[bis(2-hydroxyethyl)amino]propyl}benzamide;

1-(2-amino-1-phenylethyl)-6-(1-benzyl-4-phenyl-1H-imidazol-2-yl)piperidin-2-one;

6-(1-benzyl-4-phenyl-1H-imidazol-2-yl)piperidin-2-one;

N-[(2S)-3-amino-2-fluoropropyl]-N-[(1R)-1-(1-benzyl-4-phenyl-1H-imidazol-2-yl)-2,2-dimethylpropyl]benzamide;

N-[(1R)-1-(1-benzyl-4-phenyl-1H-imidazol-2-yl)-2,2-dimethylpropyl]-N-(3-{[2-hydroxy-1-(hydroxymethyl)ethyl]amino}propyl)benzamide;

N-[(1R)-1-(1-benzyl-4-phenyl-1H-imidazol-2-yl)-2,2-dimethylpropyl]-N-(3-{[2-(hydroxymethyl)phenyl]amino}propyl)benzamide;

N-{(1R)-1-[1-benzyl-4-(3-chlorophenyl)-1H-imidazol-2-yl]-2-methylpropyl}-N-piperidin-4-ylbenzamide;

N-{(1R)-1-[1-benzyl-4-(3-chlorophenyl)-1H-imidazol-2-yl]-2-methylpropyl}-N-(piperidin-3-ylmethyl)benzamide;

2-(3-amino-2-oxopyridin-1(2H)-yl)-N-[(1R)-1-(1-benzyl-4-phenyl-1H-imidazol-2-yl)-2,2-dimethylpropyl]acetamide;

N-{(1R)-1-[1-benzyl-4-(3-chlorophenyl)-1H-imidazol-2-yl]-2-methylpropyl}-2-pyrrolidin-3-ylbenzamide;

(1R,3S)-3-{[(2-aminoethyl)sulfonyl]amino}-N-[(1R)-1-(1-benzyl-4-phenyl-1H-imidazol-2-yl)-2,2-dimethylpropyl]cyclohexanecarboxamide;

(1R,3S)-3-[(aminoacetyl)amino]-N-[(1R)-1-(1-benzyl-4-phenyl-1H-imidazol-2-yl)-2,2-dimethylpropyl]cyclohexanecarboxamide;

N-(3-aminopropyl)-N-{(1R)-1-[1-benzyl-4-(3-chlorophenyl)-1H-imidazol-2-yl]-2-methylpropyl}-6-(trifluoromethyl)nicotinamide;

N-[(2R)-3-amino-2-fluoropropyl]-N-[(1R)-1-(1-benzyl-4-phenyl-1H-imidazol-2-yl)-2,2-dimethylpropyl]benzamide;

(3R)—N-(3-aminopropyl)-N-{(1R)-1-[1-benzyl-4-(3-chlorophenyl)-1H-imidazol-2-yl]-2-methylpropyl}piperidine-3-carboxamide;

(3S)—N-(3-aminopropyl)-N-{(1R)-1-[1-benzyl-4-(3-chlorophenyl)-1H-imidazol-2-yl]-2-methylpropyl}piperidine-3-carboxamide;

N-(3-aminopropyl)-N-{(1R)-1-[1-benzyl-4-(3-chlorophenyl)-1H-imidazol-2-yl]-2-methylpropyl}-2-(1H-1,2,4-triazol-1-yl)acetamide;

[(5R)-1-benzoyl-5-(1-benzyl-4-phenyl-1H-imidazol-2-yl)pyrrolidin-2-yl]methylamine;

N-(3-aminopropyl)-N-{(1R)-1-[1-benzyl-4-(3-chlorophenyl)-1H-imidazol-2-yl]-2-methylpropyl}-2-(4H-1,2,4-triazol-4-yl)acetamide;

N-(3-aminopropyl)-N-{(1R)-1-[1-benzyl-4-(3-chlorophenyl)-1H-imidazol-2-yl]-2-methylpropyl}-2,1,3-benzothiadiazole-4-carboxamide;

N-[(2S)-3-amino-2-hydroxypropyl]-N-[(1R)-1-(1-benzyl-4-phenyl-1H-imidazol-2-yl)-2,2-dimethylpropyl]benzamide;

N-[(2S)-3-amino-2-fluoropropyl]-N-[(1R)-1-(1-benzyl-4-phenyl-1H-imidazol-2-yl)-2,2-dimethylpropyl]-1,5-dimethyl-1H-pyrazole-3-carboxamide;

N-[(1R)-1-(1-benzyl-4-phenyl-1H-imidazol-2-yl)-2,2-dimethylpropyl]-1,5-dimethyl-N-[(2S)-morpholin-2-ylmethyl]-1H-pyrazole-3-carboxamide;

N-[(1R)-1-(1-benzyl-4-phenyl-1H-imidazol-2-yl)-2,2-dimethylpropyl]-1,5-dimethyl-N-[(2R)-morpholin-2-ylmethyl]-1H-pyrazole-3-carboxamide;

N-[(2S)-3-amino-2-hydroxypropyl]-N-[(1R)-1-(1-benzyl-4-phenyl-1H-imidazol-2-yl)-2,2-dimethylpropyl]-1,5-dimethyl-1H-pyrazole-3-carboxamide;

N-[(2S)-3-amino-2-hydroxypropyl]-N-[(1R)-1-(1-benzyl-4-phenyl-1H-imidazol-2-yl)-2,2-dimethylpropyl]-2-methoxyacetamide;

N-[(1R)-1-(1-benzyl-4-phenyl-1H-imidazol-2-yl)-2,2-dimethylpropyl]-2-pyrrolidin-3-ylbenzamide;

N-(3-aminopropyl)-N-{(1R)-1-[1-benzyl-4-(3-chlorophenyl)-1H-imidazol-2-yl]-2-methylpropyl}-2-(1H-pyrazol-1-yl)acetamide;

N-[(2R)-3-amino-2-fluoropropyl]-N-[(1R)-1-(1-benzyl-4-phenyl-1H-imidazol-2-yl)-2,2-dimethylpropyl]-1,5-dimethyl-1H-pyrazole-3-carboxamide;

methyl 3-aminopropyl[(1R)-1-(1-benzyl-4-phenyl-1H-imidazol-2-yl)-2,2-dimethylpropyl]carbamate;

N-(3-aminopropyl)-N-[(1R)-1-(1-benzyl-4-phenyl-1H-imidazol-2-yl)-2,2-dimethylpropyl]-2-(1H-tetrazol-1-yl)acetamide;

N-(3-aminopropyl)-N-[(1R)-1-(1-benzyl-4-phenyl-1H-imidazol-2-yl)-2,2-dimethylpropyl]-2-(2H-tetrazol-2-yl)acetamide;

N-(3-aminopropyl)-N-[(1R)-1-(1-benzyl-4-phenyl-1H-imidazol-2-yl)-2,2-dimethylpropyl]-2-(1H-1,2,4-triazol-1-yl)acetamide;

N-(3-aminopropyl)-N-[(1R)-1-(1-benzyl-4-phenyl-1H-imidazol-2-yl)-2,2-dimethylpropyl]-2-(4H-1,2,4-triazol-4-yl)acetamide;

N-[(1R)-1-(1-benzyl-4-phenyl-1H-imidazol-2-yl)-2,2-dimethylpropyl]-2-methoxy-N-[(2S)-morpholin-2-ylmethyl]acetamide;

N-[(1R)-1-(1-benzyl-4-phenyl-1H-imidazol-2-yl)-2,2-dimethylpropyl]-2-methoxy-N-[(2R)-morpholin-2-ylmethyl]acetamide;

N-(3-aminopropyl)-N-[(1S)-1-(1-benzyl-4-phenyl-1H-imidazol-2-yl)-2-hydroxy-2-methylpropyl]benzamide;

N-[(1R)-1-(1-benzyl-4-phenyl-1H-imidazol-2-yl)-2,2-dimethylpropyl]-2-hydroxy-N-[(2S)-morpholin-2-ylmethyl]acetamide;

N-[(1R)-1-(1-benzyl-4-phenyl-1H-imidazol-2-yl)-2,2-dimethylpropyl]-2-hydroxy-N-[(2R)-morpholin-2-ylmethyl]acetamide;

(2S)—N-(3-aminopropyl)-N-[(1R)-1-(1-benzyl-4-phenyl-1H-imidazol-2-yl)-2,2-dimethylpropyl]tetrahydrofuran-2-carboxamide;

N-(3-aminopropyl)-N-{(1R)-1-[4-(3-chlorophenyl)-1-(3-cyanobenzyl)-1H-imidazol-2-yl]-2-methylpropyl}benzamide;

N-(3-aminopropyl)-N-{(1R)-1-[4-(3-chlorophenyl)-1-(3-cyanobenzyl)-1H-imidazol-2-yl]-2-methylpropyl}-4-methylbenzamide;

N-(3-aminopropyl)-N-{(1R)-1-[4-(3-chlorophenyl)-1-(3-methylbenzyl)-1H-imidazol-2-yl]-2-methylpropyl}-4-methylbenzamide;

N-(3-aminopropyl)-N-{(1R)-1-[4-(3-chlorophenyl)-1-(3-methylbenzyl)-1H-imidazol-2-yl]-2-methylpropyl}benzamide;
ethyl 3-aminopropyl[1R)-1-(1-benzyl-4-phenyl-1H-imidazol-2-yl)-2,2-dimethylpropyl]carbamate;
neopentyl 3-aminopropyl[(1R)-1-(1-benzyl-4-phenyl-1H-imidazol-2-yl)-2,2-dimethylpropyl]carbamate;
isobutyl 3-aminopropyl[(1R)-1-(1-benzyl-4-phenyl-1H-imidazol-2-yl)-2,2-dimethylpropyl]carbamate;
propyl 3-aminopropyl[(1R)-1-(1-benzyl-4-phenyl-1H-imidazol-2-yl)-2,2-dimethylpropyl]carbamate;
N-(3-aminopropyl)-N-[(1R)-1-(1-benzyl-4-phenyl-1H-imidazol-2-yl)-2,2-dimethylpropyl]-2-cyanoacetamide;
N-[(1R)-1-(1-benzyl-4-phenyl-1H-imidazol-2-yl)-2,2-dimethylpropyl]-2-methoxy-N-[(3R)-pyrrolidin-3-ylmethyl]acetamide;
N-[(1R)-1-(1-benzyl-4-phenyl-1H-imidazol-2-yl)-2,2-dimethylpropyl]-2-methoxy-N-[(3S)-pyrrolidin-3-ylmethyl]acetamide;
butyl 3-aminopropyl[(1R)-1-(1-benzyl-4-phenyl-1H-imidazol-2-yl)-2,2-dimethylpropyl]carbamate;
N-[(1R)-1-(1-benzyl-4-phenyl-1H-imidazol-2-yl)-2,2-dimethylpropyl]-2-hydroxy-N-[(3R)-pyrrolidin-3-ylmethyl]acetamide;
N-[(1R)-1-(1-benzyl-4-phenyl-1H-imidazol-2-yl)-2,2-dimethylpropyl]-2-hydroxy-N-[(3S)-pyrrolidin-3-ylmethyl]acetamide;
N-[(1R)-1-(1-benzyl-4-phenyl-1H-imidazol-2-yl)-2,2-dimethylpropyl]-N-[(3S)-pyrrolidin-3-ylmethyl]benzamide;
N-[(2R)-3-amino-2-fluoropropyl]-N-[(1R)-1-(1-benzyl-4-phenyl-1H-imidazol-2-yl)-2,2-dimethylpropyl]-2-(2H-tetrazol-2-yl)acetamide;
N-[(2R)-3-amino-2-fluoropropyl]-N-[(1R)-1-(1-benzyl-4-phenyl-1H-imidazol-2-yl)-2,2-dimethylpropyl]-2-(1H-tetrazol-1-yl)acetamide;
N-[(2R)-3-amino-2-fluoropropyl]-N-[(1R)-1-(1-benzyl-4-phenyl-1H-imidazol-2-yl)-2,2-dimethylpropyl]-2-methoxyacetamide;
N-[(2S)-3-amino-2-fluoropropyl]-N-[(1R)-1-(1-benzyl-4-phenyl-1H-imidazol-2-yl)-2,2-dimethylpropyl]-2-methoxyacetamide;
N-[(1R)-1-(1-benzyl-4-phenyl-1H-imidazol-2-yl)-2,2-dimethylpropyl]-N-[(3S)-3,4-diamino-4-oxobutyl]benzamide;
N-[(1R)-1-(1-benzyl-4-phenyl-1H-imidazol-2-yl)-2,2-dimethylpropyl]-N-[(3R)-3,4-diamino-4-oxobutyl]benzamide;
N-[(3S)-3-amino-4-hydroxybutyl]-N-[(1R)-1-(1-benzyl-4-phenyl-1H-imidazol-2-yl)-2,2-dimethylpropyl]benzamide;
(2S)-2-amino-4-{benzoyl[(1R)-1-(1-benzyl-4-phenyl-1H-imidazol-2-yl)-2,2-dimethylpropyl]amino}butanoic acid;
N-[(2R)-3-amino-2-fluoropropyl]-N-[(1R)-1-(1-benzyl-4-phenyl-1H-imidazol-2-yl)-2,2-dimethylpropyl]-2-hydroxyacetamide;
N-(3-aminopropyl)-N-[(1R)-1-(1-benzyl-4-phenyl-1H-imidazol-2-yl)-2,2-dimethylpropyl]-2-(1H-tetrazol-5-yl)acetamide;
N-[(1R)-1-(1-benzyl-4-phenyl-1H-imidazol-2-yl)-2,2-dimethylpropyl]-N-[(3S)-pyrrolidin-3-ylmethyl]-2-(1H-tetrazol-1-yl)acetamide;
N-[(1R)-1-(1-benzyl-4-phenyl-1H-imidazol-2-yl)-2,2-dimethylpropyl]-N-[(3S)-pyrrolidin-3-ylmethyl]-2-(2H-tetrazol-2-yl)acetamide;
N-[(1R)-1-(1-benzyl-4-phenyl-1H-imidazol-2-yl)-2,2-dimethylpropyl]-6-methyl-N-[(3S)-pyrrolidin-3-ylmethyl]nicotinamide;
N-(azetidin-3-ylmethyl)-N-[(1R)-1-(1-benzyl-4-phenyl-1H-imidazol-2-yl)-2,2-dimethylpropyl]-2-methoxyacetamide;
N-{(1R)-1-[1-(3-cyanobenzyl)-4-phenyl-1H-imidazol-2-yl]-2,2-dimethylpropyl}-N-(pyrrolidin-3-ylmethyl)benzamide;
N-{(1R)-2,2-dimethyl-1-[1-(3-methylbenzyl)-4-phenyl-1H-imidazol-2-yl]propyl}-N-(pyrrolidin-3-ylmethyl)benzamide;
N-[(2S)-3-amino-2-hydroxypropyl]-N-[(1R)-1-(1-benzyl-4-phenyl-1H-imidazol-2-yl)-2,2-dimethylpropyl]-2-hydroxyacetamide;
N-[(1R)-1-(1-benzyl-4-phenyl-1H-imidazol-2-yl)-2,2-dimethylpropyl]-N-[3-(methoxyamino)propyl]benzamide;
N-[(2S)-3-amino-2-fluoropropyl]-N-[(1R)-1-(1-benzyl-4-phenyl-1H-imidazol-2-yl)-2,2-dimethylpropyl]-2-(1H-tetrazol-1-yl)acetamide;
N-[(2S)-3-amino-2-fluoropropyl]-N-[(1R)-1-(1-benzyl-4-phenyl-1H-imidazol-2-yl)-2,2-dimethylpropyl]-2-(2H-tetrazol-2-yl)acetamide;
N-{(1R)-1-[1-(3-cyanobenzyl)-4-phenyl-1H-imidazol-2-yl]-2,2-dimethylpropyl}-2-methoxy-N-[(3S)-pyrrolidin-3-ylmethyl]acetamide;
N-{(1R)-1-[1-(3-cyanobenzyl)-4-phenyl-1H-imidazol-2-yl]-2,2-dimethylpropyl}-2-methoxy-N-[(3R)-pyrrolidin-3-ylmethyl]acetamide;
N-(3-aminopropyl)-N-{(1R)-1-[1-(3-cyanobenzyl)-4-phenyl-1H-imidazol-2-yl]-2,2-dimethylpropyl}benzamide;
N-(3-aminopropyl)-N-{(1R)-1-[1-(3-cyanobenzyl)-4-phenyl-1H-imidazol-2-yl]-2,2-dimethylpropyl}-2-methoxyacetamide;
2-hydroxy-N-{(1R)-1-[1-(3-hydroxybenzyl)-4-phenyl-1H-imidazol-2-yl]-2,2-dimethylpropyl}-N-(pyrrolidin-3-ylmethyl)acetamide;
N-{(1R)-2,2-dimethyl-1-[1-(3-methylbenzyl)-4-phenyl-1H-imidazol-2-yl]propyl}-2-methoxy-N-[(3S)-pyrrolidin-3-ylmethyl]acetamide;
N-{(1R)-2,2-dimethyl-1-[1-(3-methylbenzyl)-4-phenyl-1H-imidazol-2-yl]propyl}-2-methoxy-N-[(3R)-pyrrolidin-3-ylmethyl]acetamide;
N-(3-aminopropyl)-N-{(1R)-2,2-dimethyl-1-[1-(3-methylbenzyl)-4-phenyl-1H-imidazol-2-yl]propyl}-2-methoxyacetamide;
N-[(3S)-3-amino-4-hydroxybutyl]-N-[(1R)-1-(1-benzyl-4-phenyl-1H-imidazol-2-yl)-2,2-dimethylpropyl]-1,5-dimethyl-1H-pyrazole-3-carboxamide;
N-(3-amino-2-hydroxypropyl)-N-[(1R)-1-(1-benzyl-4-phenyl-1H-imidazol-2-yl)-2,2-dimethylpropyl]-2-(1H-tetrazol-1-yl)acetamide;
N-(3-amino-2-hydroxypropyl)-N-[(1R)-1-(1-benzyl-4-phenyl-1H-imidazol-2-yl)-2,2-dimethylpropyl]-2-(2H-tetrazol-2-yl)acetamide;
N-[(1R)-1-(1-benzyl-4-phenyl-1H-imidazol-2-yl)-2,2-dimethylpropyl]-1,5-dimethyl-N-[(3S)-pyrrolidin-3-ylmethyl]-1H-pyrazole-3-carboxamide;
N-(3-aminopropyl)-N-{(1R)-2,2-dimethyl-1-[1-(3-methylbenzyl)-4-phenyl-1H-imidazol-2-yl]propyl}benzamide;
N-(azetidin-3-ylmethyl)-N-[(1R)-1-(1-benzyl-4-phenyl-1H-imidazol-2-yl)-2,2-dimethylpropyl]benzamide;

N-(azetidin-3-ylmethyl)-N-[(1R)-1-(1-benzyl-4-phenyl-1H-imidazol-2-yl)-2,2-dimethylpropyl]-2-hydroxyacetamide;

N-(azetidin-3-ylmethyl)-N-[(1R)-1-(1-benzyl-4-phenyl-1H-imidazol-2-yl)-2,2-dimethylpropyl]-1,5-dimethyl-1H-pyrazole-3-carboxamide;

N-[(3S)-3-amino-4-hydroxybutyl]-N-[(1R)-1-(1-benzyl-4-phenyl-1H-imidazol-2-yl)-2,2-dimethylpropyl]-2-methoxyacetamide;

N-[(2S)-3-amino-2-fluoropropyl]-N-[(1R)-1-(1-benzyl-4-phenyl-1H-imidazol-2-yl)-2,2-dimethylpropyl]-2-(1H-1,2,3-triazol-1-yl)acetamide;

N-[(2S)-3-amino-2-fluoropropyl]-N-[(1R)-1-(1-benzyl-4-phenyl-1H-imidazol-2-yl)-2,2-dimethylpropyl]-2-(2H-1,2,3-triazol-2-yl)acetamide;

N-[(3S)-3-amino-4-hydroxybutyl]-N-[(1R)-1-(1-benzyl-4-phenyl-1H-imidazol-2-yl)-2,2-dimethylpropyl]-2-(1H-tetrazol-1-yl)acetamide;

N-[(3S)-3-amino-4-hydroxybutyl]-N-[(1R)-1-(1-benzyl-4-phenyl-1H-imidazol-2-yl)-2,2-dimethylpropyl]-2-(2H-tetrazol-2-yl)acetamide;

N-[(3S)-3-amino-4-hydroxybutyl]-N-[(1R)-1-(1-benzyl-4-phenyl-1H-imidazol-2-yl)-2,2-dimethylpropyl]-2-(1H-1,2,3-triazol-1-yl)acetamide;

N-[(1R)-1-(1-benzyl-4-phenyl-1H-imidazol-2-yl)-2,2-dimethylpropyl]-N-[(3-fluoropyrrolidin-3-yl)methyl]amine;

N-[(1R)-1-(1-benzyl-4-phenyl-1H-imidazol-2-yl)-2,2-dimethylpropyl]-N-{[(3S)-3-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3R)-3-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-[(3-hydroxypyrrolidin-3-yl)methyl]-2-methoxyacetamide;

N-(azetidin-3-ylmethyl)-N-[(1R)-1-(1-benzyl-4-phenyl-1H-imidazol-2-yl)-2,2-dimethylpropyl]-6-methylnicotinamide;

N-[(1R)-1-(1-benzyl-4-phenyl-1H-imidazol-2-yl)-2,2-dimethylpropyl]-N-{[(3S)-3-fluoropyrrolidin-3-yl]methyl}-1,5-dimethyl-1H-pyrazole-3-carboxamide;

N-[(1R)-1-(1-benzyl-4-phenyl-1H-imidazol-2-yl)-2,2-dimethylpropyl]-N-{[(3R)-3-fluoropyrrolidin-3-yl]methyl}-1,5-dimethyl-1H-pyrazole-3-carboxamide;

N-[(1R)-1-(1-benzyl-4-phenyl-1H-imidazol-2-yl)-2,2-dimethylpropyl]-N-[(3-fluoropyrrolidin-3-yl)methyl]-1,5-dimethyl-1H-pyrazole-3-carboxamide;

N-[(1R)-1-(1-benzyl-4-phenyl-1H-imidazol-2-yl)-2,2-dimethylpropyl]-N-{[(3S)-3-fluoropyrrolidin-3-yl]methyl}benzamide;

N-[(1R)-1-(1-benzyl-4-phenyl-1H-imidazol-2-yl)-2,2-dimethylpropyl]-N-{[(3R)-3-fluoropyrrolidin-3-yl]methyl}benzamide;

N-[(1R)-1-(1-benzyl-4-phenyl-1H-imidazol-2-yl)-2,2-dimethylpropyl]-N-[(3-fluoropyrrolidin-3-yl)methyl]benzamide;

N-(3-aminopropyl)-2-hydroxy-N-{(1R)-1-[1-(3-hydroxybenzyl)-4-phenyl-1H-imidazol-2-yl]-2,2-dimethylpropyl}acetamide;

N-{(1R)-1-[1-(3-hydroxybenzyl)-4-phenyl-1H-imidazol-2-yl]-2,2-dimethylpropyl}-N-(pyrrolidin-3-ylmethyl)benzamide;

N-(3-aminopropyl)-N-{(1R)-2,2-dimethyl-1-[1-(3-methylbenzyl)-4-phenyl-1H-imidazol-2-yl]propyl}-1,5-dimethyl-1H-pyrazole-3-carboxamide;

N-{(1R)-2,2-dimethyl-1-[1-(3-methylbenzyl)-4-phenyl-1H-imidazol-2-yl]propyl}-1,5-dimethyl-N-(pyrrolidin-3-ylmethyl)-1H-pyrazole-3-carboxamide;

N-(3-aminopropyl)-N-{(1R)-1-[1-(3-hydroxybenzyl)-4-phenyl-1H-imidazol-2-yl]-2,2-dimethylpropyl}benzamide;

N-(3-aminopropyl)-N-{(1R)-1-[1-(3-methoxybenzyl)-4-phenyl-1H-imidazol-2-yl]-2,2-dimethylpropyl}benzamide;

N-(3-aminopropyl)-2-methoxy-N-{(1R)-1-[1-(3-methoxybenzyl)-4-phenyl-1H-imidazol-2-yl]-2,2-dimethylpropyl}acetamide;

N-(3-aminopropyl)-N-{(1R)-1-[1-(3-cyanobenzyl)-4-phenyl-1H-imidazol-2-yl]-2,2-dimethylpropyl}-2-hydroxyacetamide;

N-(3-aminopropyl)-N-{(1R)-1-[1-(3-methoxybenzyl)-4-phenyl-1H-imidazol-2-yl]-2,2-dimethylpropyl}-1,5-dimethyl-1H-pyrazole-3-carboxamide;

N-[(3S)-3-amino-4-methoxybutyl]-N-[(1R)-1-(1-benzyl-4-phenyl-1H-imidazol-2-yl)-2,2-dimethylpropyl]benzamide;

N-(3-aminopropyl)-N-{(1R)-1-[1-(3-cyanobenzyl)-4-phenyl-1H-imidazol-2-yl]-2,2-dimethylpropyl}-1,5-dimethyl-1H-pyrazole-3-carboxamide;

N-{(1R)-1-[1-(3-cyanobenzyl)-4-phenyl-1H-imidazol-2-yl]-2,2-dimethylpropyl}-1,5-dimethyl-N-(pyrrolidin-3-ylmethyl)-1H-pyrazole-3-carboxamide;

N-{(1R)-1-[1-(3-cyanobenzyl)-4-phenyl-1H-imidazol-2-yl]-2,2-dimethylpropyl}-2-hydroxy-N-[(3S)-pyrrolidin-3-ylmethyl]acetamide;

N-[(2R)-3-amino-2-fluoropropyl]-N-[(1R)-1-(1-benzyl-4-phenyl-1H-imidazol-2-yl)-2,2-dimethylpropyl]-2-(1H-1,2,3-triazol-1-yl)acetamide;

N-[(2R)-3-amino-2-fluoropropyl]-N-[(1R)-1-(1-benzyl-4-phenyl-1H-imidazol-2-yl)-2,2-dimethylpropyl]-2-(2H-1,2,3-triazol-2-yl)acetamide;

N-[(1R)-1-(1-benzyl-4-phenyl-1H-imidazol-2-yl)-2,2-dimethylpropyl]-N-{[(3S)-3-hydroxypyrrolidin-3-yl]methyl}benzamide;

N-[(1R)-1-(1-benzyl-4-phenyl-1H-imidazol-2-yl)-2,2-dimethylpropyl]-N-{[(3R)-3-hydroxypyrrolidin-3-yl]methyl}benzamide;

N-[(1R)-1-(1-benzyl-4-phenyl-1H-imidazol-2-yl)-2,2-dimethylpropyl]-N-[(3-hydroxypyrrolidin-3-yl)methyl]benzamide;

N-[(1R)-1-(1-benzyl-4-phenyl-1H-imidazol-2-yl)-2,2-dimethylpropyl]-2-ethoxy-N-[(3S)-pyrrolidin-3-ylmethyl]acetamide;

N-(3-aminopropyl)-N-[(1R)-1-(1-benzyl-4-phenyl-1H-imidazol-2-yl)-2,2-dimethylpropyl]-2-ethoxyacetamide;

N-[(1R)-1-(1-benzyl-4-phenyl-1H-imidazol-2-yl)-2,2-dimethylpropyl]-N-{[(3S)-3-hydroxypyrrolidin-3-yl]methyl}-1,5-dimethyl-1H-pyrazole-3-carboxamide;

N-[(1R)-1-(1-benzyl-4-phenyl-1H-imidazol-2-yl)-2,2-dimethylpropyl]-N-{[(3R)-3-hydroxypyrrolidin-3-yl]methyl}-1,5-dimethyl-1H-pyrazole-3-carboxamide;

N-[(1R)-1-(1-benzyl-4-phenyl-1H-imidazol-2-yl)-2,2-dimethylpropyl]-N-[(3-hydroxypyrrolidin-3-yl)methyl]-1,5-dimethyl-1H-pyrazole-3-carboxamide;

N-[(2S)-3-amino-2-fluoropropyl]-N-[(1S)-1-(1-benzyl-4-phenyl-1H-imidazol-2-yl)-2-hydroxy-2-methylpropyl]-2-(1H-tetrazol-1-yl)acetamide;

N-[(2S)-3-amino-2-fluoropropyl]-N-[(1S)-1-(1-benzyl-4-phenyl-1H-imidazol-2-yl)-2-hydroxy-2-methylpropyl]-2-(2H-tetrazol-2-yl)acetamide;

N-[(2S)-3-amino-2-fluoropropyl]-N-{(1R)-1-[1-benzyl-4-(3-fluorophenyl)-1H-imidazol-2-yl]-2,2-dimethylpropyl}-2-(1H-tetrazol-1-yl)acetamide;

N-[(2S)-3-amino-2-fluoropropyl]-N-{(1R)-1-[1-benzyl-4-(3-fluorophenyl)-1H-imidazol-2-yl]-2,2-dimethylpropyl}-2-(2H-tetrazol-2-yl)acetamide;

N-[(2S)-3-amino-2-(hydroxymethyl)propyl]-N-[(1R)-1-(1-benzyl-4-phenyl-1H-imidazol-2-yl)-2,2-dimethylpropyl]-N'-methylethanediamide;

N-[(2R)-3-amino-2-(hydroxymethyl)propyl]-N-[(1R)-1-(1-benzyl-4-phenyl-1H-imidazol-2-yl)-2,2-dimethylpropyl]-N'-methylethanediamide;

N-[(3R)-3-amino-4-hydroxybutyl]-N-[(1R)-1-(1-benzyl-4-phenyl-1H-imidazol-2-yl)-2,2-dimethylpropyl]-2-methoxyacetamide;

N-[(3R)-3-amino-4-hydroxybutyl]-N-[(1R)-1-(1-benzyl-4-phenyl-1H-imidazol-2-yl)-2,2-dimethylpropyl]-2-(1H-tetrazol-1-yl)acetamide;

N-[(3R)-3-amino-4-hydroxybutyl]-N-[(1R)-1-(1-benzyl-4-phenyl-1H-imidazol-2-yl)-2,2-dimethylpropyl]-2-(2H-tetrazol-2-yl)acetamide;

N-[(1R)-1-(1-benzyl-4-phenyl-1H-imidazol-2-yl)-2,2-dimethylpropyl]-N-{[(3S)-3-fluoropyrrolidin-3-yl]methyl}-2-methoxyacetamide;

N-[(1R)-1-(1-benzyl-4-phenyl-1H-imidazol-2-yl)-2,2-dimethylpropyl]-N-{[(3R)-3-fluoropyrrolidin-3-yl]methyl}-2-methoxyacetamide;

N-[(1R)-1-(1-benzyl-4-phenyl-1H-imidazol-2-yl)-2,2-dimethylpropyl]-N-{[(3R,4R)-4-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3S,4S)-4-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3R,4R)-4-hydroxypyrrolidin-3-yl]methyl}benzamide;

N-[(1R)-1-(1-benzyl-4-phenyl-1H-imidazol-2-yl)-2,2-dimethylpropyl]-N-{[(3S,4S)-4-hydroxypyrrolidin-3-yl]methyl}benzamide;

N-[(3S)-3-amino-4-hydroxybutyl]-N-{(1R)-1-[1-benzyl-4-(3-fluorophenyl)-1H-imidazol-2-yl]-2,2-dimethylpropyl}-2-(1H-tetrazol-1-yl)acetamide;

N-[(3S)-3-amino-4-hydroxybutyl]-N-{(1R)-1-[1-benzyl-4-(3-fluorophenyl)-1H-imidazol-2-yl]-2,2-dimethylpropyl}-2-(2H-tetrazol-2-yl)acetamide;

N-[(3S)-3-amino-4-methoxybutyl]-N-[(1R)-1-(1-benzyl-4-phenyl-1H-imidazol-2-yl)-2,2-dimethylpropyl]-2-methoxyacetamide;

N-[(3S)-3-amino-4-hydroxybutyl]-N-{(1R)-1-[1-benzyl-4-(3-fluorophenyl)-1H-imidazol-2-yl]-2,2-dimethylpropyl}-2-methoxyacetamide;

N-[(1R)-1-(1-benzyl-4-phenyl-1H-imidazol-2-yl)-2,2-dimethylpropyl]-N-{[(3S)-3-fluoropyrrolidin-3-yl]methyl}-2-(2H-tetrazol-2-yl)acetamide;

N-[(1R)-1-(1-benzyl-4-phenyl-1H-imidazol-2-yl)-2,2-dimethylpropyl]-N-{[(3R)-3-fluoropyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(3S,4S)-4-hydroxypyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(3S,4S)-4-hydroxypyrrolidin-3-yl]methyl}-2-(2H-tetrazol-2-yl)acetamide;

N-[(1R)-1-(1-benzyl-4-phenyl-1H-imidazol-2-yl)-2,2-dimethylpropyl]-N-{[(3R,4R)-4-hydroxypyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(3R,4R)-4-hydroxypyrrolidin-3-yl]methyl}-2-(2H-tetrazol-2-yl)acetamide;

N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}-2-(2H-tetrazol-2-yl)acetamide;

N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}-2-methoxyacetamide;

N-[(1R)-1-(1-benzyl-4-phenyl-1H-imidazol-2-yl)-2,2-dimethylpropyl]-N-{[(2S,3S)-2-(hydroxymethyl)pyrrolidin-3-yl]methyl}benzamide;

N-[(2R)-3-amino-2-fluoropropyl]-N-[(1R)-1-(1-benzyl-4-phenyl-1H-imidazol-2-yl)-2,2-dimethylpropyl]-2-(5-methyl-2H-tetrazol-2-yl)acetamide;

N-[(2R)-3-amino-2-fluoropropyl]-N-[(1R)-1-(1-benzyl-4-phenyl-1H-imidazol-2-yl)-2,2-dimethylpropyl]-2-(5-methyl-1H-tetrazol-1-yl)acetamide;

N-[(1R)-1-(1-benzyl-4-phenyl-1H-imidazol-2-yl)-2,2-dimethylpropyl]-N-{[(3R)-3-hydroxypyrrolidin-3-yl]methyl}-2-(1H-tetrazol-1-yl)acetamide;

N-[(1R)-1-(1-benzyl-4-phenyl-1H-imidazol-2-yl)-2,2-dimethylpropyl]-N-{[(3S)-3-hydroxypyrrolidin-3-yl]methyl}-2-(1H-tetrazol-1-yl)acetamide;

(5S)-3-[(1R)-1-(1-benzyl-4-phenyl-1H-imidazol-2-yl)-2,2-dimethylpropyl]-1-oxa-3,7-diazaspiro[4.4]nonan-2-one;

(5R)-3-[(1R)-1-(1-benzyl-4-phenyl-1H-imidazol-2-yl)-2,2-dimethylpropyl]-1-oxa-3,7-diazaspiro[4.4]nonan-2-one;

N-[(2S,3R)-3-amino-2-fluoro-4-hydroxybutyl]-N-[(1R)-1-(1-benzyl-4-phenyl-1H-imidazol-2-yl)-2,2-dimethylpropyl]-2-methoxyacetamide;

N-[(3S)-3-amino-4-fluorobutyl]-N-[(1R)-1-(1-benzyl-4-phenyl-1H-imidazol-2-yl)-2,2-dimethylpropyl]-2-methoxyacetamide;

N-[(3R)-3-amino-4-fluorobutyl]-N-[(1R)-1-(1-benzyl-4-phenyl-1H-imidazol-2-yl)-2,2-dimethylpropyl]-2-methoxyacetamide;

N-[(1R)-1-(1-benzyl-4-phenyl-1H-imidazol-2-yl)-2,2-dimethylpropyl]-N-{[(3R,4S)-4-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3S,4R)-4-hydroxypyrrolidin-3-yl]methyl}-2-methoxyacetamide;

N-[(1R)-1-(1-benzyl-4-phenyl-1H-imidazol-2-yl)-2,2-dimethylpropyl]-N-{[(3R,4S)-4-fluoropyrrolidin-3-yl]methyl}-2-methoxyacetamide;

N-[(1R)-1-(1-benzyl-4-phenyl-1H-imidazol-2-yl)-2,2-dimethylpropyl]-N-(2,5-dihydro-1H-pyrrol-3-ylmethyl)-2-methoxyacetamide;

N—((R)-3-Amino-2-fluoro-propyl)-N—[(R)-1-(1-benzyl-4-pyrazin-2-yl-1H-imidazol-2-yl)-2,2-dimethylpropyl]-2-methoxy-acetamide;

N—((R)-3-Amino-2-fluoro-propyl)-N-{(R)-1-[1-benzyl-4-(3-methoxy-phenyl)-1H-imidazol-2-yl]-2,2-dimethyl-propyl}-2-ethoxy-acetamide;

N—((R)-3-Amino-2-fluoro-propyl)-N-{(R)-1-[1-benzyl-4-(3-methoxy-phenyl)-1H-imidazol-2-yl]-2,2-dimethyl-propyl}-2-methoxy-acetamide;

(S)-Tetrahydro-furan-2-carboxylic acid ((R)-3-amino-2-fluoro-propyl)-[(R)-1-(1-benzyl-4-pyrazin-2-yl-1H-imidazol-2-yl)-2,2-dimethyl-propyl]-amide;

N—((R)-3-Amino-2-fluoro-propyl)-N—[(R)-1-(1-benzyl-4-pyrazin-2-yl-1H-imidazol-2-yl)-2,2-dimethyl-propyl]-2-ethoxy-acetamide;
N—((R)-3-Amino-2-fluoro-propyl)-N—[(R)-1-(1-benzyl-4-phenyl-1H-imidazol-2-yl)-2,2-dimethyl-propyl]-2-ethoxy-acetamide;
(S)-Tetrahydro-furan-2-carboxylic acid ((R)-3-amino-2-fluoro-propyl)-[(R)-1-(1-benzyl-4-phenyl-1H-imidazol-2-yl)-2,2-dimethyl-propyl]-amide;
N—((S)-3-Amino-4-fluoro-butyl)-N—[(R)-2,2-dimethyl-1-(4-phenyl-1-pyridin-3-ylmethyl-1H-imidazol-2-yl)-propyl]-2-methoxy-acetamide;
N—((R)-3-Amino-4-fluoro-butyl)-N—[(R)-2,2-dimethyl-1-(4-phenyl-1-pyridin-3-ylmethyl-1H-imidazol-2-yl)-propyl]-2-methoxy-acetamide;
N—((S)-3-Amino-4-methoxy-butyl)-N-{(R)-1-[1-benzyl-4-(3-fluoro-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(4-cyano-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(4-methoxy-phenyl)-1H-imidazol-2-yl]-2,2-dimethyl-propyl}-2-methoxy-acetamide;
N—((R)-3-Amino-2-fluoro-propyl)-N-{(R)-1-[1-(2-fluoro-benzyl)-4-phenyl-1H-imidazol-2-yl]-2,2-dimethyl-propyl}-2-methoxy-acetamide;
N—((R)-3-Amino-2-fluoro-propyl)-N-{(R)-1-[1-(3-fluoro-benzyl)-4-phenyl-1H-imidazol-2-yl]-2,2-dimethyl-propyl}-2-methoxy-acetamide;
N—((R)-3-Amino-2-fluoro-propyl)-N-{(R)-1-[1-(3-chloro-benzyl)-4-phenyl-1H-imidazol-2-yl]-2,2-dimethyl-propyl}-2-methoxy-acetamide;
N—((R)-3-Amino-2-fluoro-propyl)-N-{(R)-1-[1-(3-cyano-benzyl)-4-phenyl-1H-imidazol-2-yl]-2,2-dimethyl-propyl}-2-methoxy-acetamide;
N—((R)-3-Amino-2-fluoro-propyl)-N-{(R)-2,2-dimethyl-1-[4-phenyl-1-(tetrahydro-pyran-4-ylmethyl)-1H-imidazol-2-yl]-propyl}-2-methoxy-acetamide;
(S)-Tetrahydro-furan-2-carboxylic acid ((R)-3-amino-2-fluoro-propyl)-{(R)-1-[1-benzyl-4-(3-fluoro-phenyl)-1H-imidazol-2-yl]-2,2-dimethyl-propyl}-amide;
(S)-Tetrahydro-furan-2-carboxylic acid ((R)-3-amino-2-fluoro-propyl)-{(R)-1-[1-benzyl-4-(2-methoxy-phenyl)-1H-imidazol-2-yl]-2,2-dimethyl-propyl}-amide;
(S)-Tetrahydro-furan-2-carboxylic acid ((R)-3-amino-2-fluoro-propyl)-{(R)-1-[1-benzyl-4-(3-trifluoromethyl-phenyl)-1H-imidazol-2-yl]-2,2-dimethyl-propyl}-amide;
(S)-Tetrahydro-furan-2-carboxylic acid ((R)-3-amino-2-fluoro-propyl)-{(R)-1-[1-benzyl-4-(3-bromo-phenyl)-1H-imidazol-2-yl]-2,2-dimethyl-propyl}-amide;
N—((R)-3-Amino-2-fluoro-propyl)-N-{(R)-1-[1-benzyl-4-(3-fluoro-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(2-methoxy-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(3-trifluoromethyl-phenyl)-1H-imidazol-2-yl]-2,2-dimethyl-propyl}-2-methoxy-acetamide;
N—((R)-3-Amino-2-fluoro-propyl)-N-{(R)-1-[1-benzyl-4-(3-bromo-phenyl)-1H-imidazol-2-yl]-2,2-dimethyl-propyl}-2-methoxy-acetamide;
N—((R)-3-Amino-2-fluoro-propyl)-N—[(R)-1-(1-benzyl-4-p-tolyl-1H-imidazol-2-yl)-2,2-dimethyl-propyl]-2-methoxy-acetamide;
N—((S)-3-Amino-4-fluoro-butyl)-N—[(R)-2,2-dimethyl-1-(4-phenyl-1-pyridin-4-ylmethyl-1H-imidazol-2-yl)-propyl]-2-methoxy-acetamide;
N—((R)-3-Amino-4-fluoro-butyl)-N—[(R)-2,2-dimethyl-1-(4-phenyl-1-pyridin-4-ylmethyl-1H-imidazol-2-yl)-propyl]-2-methoxy-acetamide;
N—((S)-3-Amino-4-fluoro-butyl)-N-{(R)-2,2-dimethyl-1-[1-(5-methyl-isoxazol-3-ylmethyl)-4-phenyl-1H-imidazol-2-yl]-propyl}-2-methoxy-acetamide;
N—((R)-3-Amino-4-fluoro-butyl)-N-{(R)-2,2-dimethyl-1-[1-(5-methyl-isoxazol-3-ylmethyl)-4-phenyl-1H-imidazol-2-yl]-propyl}-2-methoxy-acetamide;
N—((S)-3-Amino-4-fluoro-butyl)-N—[(R)-2,2-dimethyl-1-(4-phenyl-1-pyridin-2-ylmethyl-1H-imidazol-2-yl)-propyl]-2-methoxy-acetamide;
N—((R)-3-Amino-4-fluoro-butyl)-N—[(R)-2,2-dimethyl-1-(4-phenyl-1-pyridin-2-ylmethyl-1H-imidazol-2-yl)-propyl]-2-methoxy-acetamide;
N—((S)-3-Amino-4-fluoro-butyl)-N-{(R)-1-[1-benzyl-4-(3-fluoro-phenyl)-1H-imidazol-2-yl]-2,2-dimethyl-propyl}-2-methoxy-acetamide;
N—((R)-3-Amino-4-fluoro-butyl)-N-{(R)-1-[1-benzyl-4-(3-fluoro-phenyl)-1H-imidazol-2-yl]-2,2-dimethyl-propyl}-2-methoxy-acetamide;
N-(3-Amino-3-methyl-butyl)-N—[(R)-1-(1-benzyl-4-phenyl-1H-imidazol-2-yl)-2,2-dimethyl-propyl]-2-methoxy-acetamide;
(S)-Tetrahydro-furan-2-carboxylic acid ((R)-3-amino-2-fluoro-propyl)-[(R)-1-(1-benzyl-5-chloro-4-phenyl-1H-imidazol-2-yl)-2,2-dimethyl-propyl]-amide;
N—((R)-3-Amino-2-fluoro-propyl)-N—[(R)-1-(1-benzyl-5-chloro-4-phenyl-1H-imidazol-2-yl)-2,2-dimethyl-propyl]-2-methoxy-acetamide;
(S)-Tetrahydro-furan-2-carboxylic acid ((R)-3-amino-2-fluoro-propyl)-[(R)-1-(1-benzyl-4-thiazol-2-yl-1H-imidazol-2-yl)-2,2-dimethyl-propyl]-amide;
N—((S)-3-Amino-2-fluoro-propyl)-N-{(R)-2,2-dimethyl-1-[4-phenyl-1-(5-trifluoromethyl-furan-2-ylmethyl)-1H-imidazol-2-yl]-propyl}-2-methoxy-acetamide;
N—((S)-3-Amino-2-fluoro-propyl)-N-{(R)-2,2-dimethyl-1-[1-(5-methyl-isoxazol-3-ylmethyl)-4-phenyl-1H-imidazol-2-yl]-propyl}-2-methoxy-acetamide;
(S)-Tetrahydro-furan-2-carboxylic acid ((S)-3-amino-2-fluoro-propyl)-{(R)-2,2-dimethyl-1-[1-(5-methyl-isoxazol-3-ylmethyl)-4-phenyl-1H-imidazol-2-yl]-propyl}-amide;
(S)-Tetrahydro-furan-2-carboxylic acid ((S)-3-amino-2-fluoro-propyl)-{(R)-2,2-dimethyl-1-[4-phenyl-1-(5-trifluoromethyl-furan-2-ylmethyl)-1H-imidazol-2-yl]-propyl}-amide;
N—((S)-3-Amino-4-methoxy-butyl)-N-{(R)-1-[1-(3-fluoro-benzyl)-4-(3-fluoro-phenyl)-1H-imidazol-2-yl]-2,2-dimethyl-propyl}-2-methoxy-acetamide;
N—((S)-3-Amino-4-hydroxy-butyl)-N-{(R)-1-[1-(3-fluoro-benzyl)-4-(3-fluoro-phenyl)-1H-imidazol-2-yl]-2,2-dimethyl-propyl}-2-methoxy-acetamide;
N—((S)-3-Amino-4-fluoro-butyl)-N-{(R)-1-[1-(2,5-difluoro-benzyl)-4-phenyl-1H-imidazol-2-yl]-2,2-dimethyl-propyl}-2-methoxy-acetamide;
N—((R)-3-Amino-4-fluoro-butyl)-N-{(R)-1-[1-(2,5-difluoro-benzyl)-4-phenyl-1H-imidazol-2-yl]-2,2-dimethyl-propyl}-2-methoxy-acetamide;
N—((R)-3-Amino-2-fluoro-propyl)-N-{(R)-1-[1-(4-fluoro-benzyl)-4-phenyl-1H-imidazol-2-yl]-2,2-dimethyl-propyl}-2-methoxy-acetamide;

N—((R)-3-Amino-2-fluoro-propyl)-2-methoxy-N-{(R)-1-[1-(3-methoxy-benzyl)-4-phenyl-1H-imidazol-2-yl]-2,2-dimethyl-propyl}-acetamide;
N—((R)-3-Amino-2-fluoro-propyl)-N-{(R)-2,2-dimethyl-1-[1-(2-methyl-benzyl)-4-phenyl-1H-imidazol-2-yl]-propyl}-2-methoxy-acetamide;
N—((R)-3-Amino-2-fluoro-propyl)-N-{(R)-2,2-dimethyl-1-[1-(3-methyl-benzyl)-4-phenyl-1H-imidazol-2-yl]-propyl}-2-methoxy-acetamide;
N—((S)-3-Amino-2-fluoro-propyl)-N-{(R)-2,2-dimethyl-1-[1-(3-methyl-benzyl)-4-phenyl-1H-imidazol-2-yl]-propyl}-2-methoxy-acetamide;
N-(3-Amino-propyl)-N—[(R)-1-(1-benzyl-4-phenyl-1H-imidazol-2-yl)-2,2-dimethyl-propyl]-acetamide;
N—((S)-3-Amino-2-fluoro-propyl)-N—[(R)-1-(1-benzyl-1H-imidazol-2-yl)-2,2-dimethyl-propyl]-2-methoxy-acetamide;
(S)-Tetrahydro-furan-2-carboxylic acid ((S)-3-amino-2-fluoro-propyl)-[(R)-1-(1-benzyl-1H-imidazol-2-yl)-2,2-dimethyl-propyl]-amide;
N—((S)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-2-methoxy-acetamide;
N—((S)-3-Amino-2-fluoro-propyl)-N—[(R)-1-(1-benzyl-4-thiazol-2-yl-1H-imidazol-2-yl)-2,2-dimethyl-propyl]-2-methoxy-acetamide;
N—((R)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-2-methoxy-acetamide;
N-[2-(1-Amino-cyclopropyl)-ethyl]-N—[(R)-1-(1-benzyl-4-phenyl-1H-imidazol-2-yl)-2,2-dimethyl-propyl]-2-methoxy-acetamide;
(S)-Tetrahydro-furan-2-carboxylic acid [2-(1-amino-cyclopropyl)-ethyl]-[(R)-1-(1-benzyl-4-phenyl-1H-imidazol-2-yl)-2,2-dimethyl-propyl]-amide;
[2-(1-Amino-cyclopropyl)-ethyl]-[(R)-1-(1-benzyl-4-phenyl-1H-imidazol-2-yl)-2,2-dimethyl-propyl]-carbamic acid methyl ester;
N-[2-(1-Amino-cyclopropyl)-ethyl]-N-{(R)-1-[1-benzyl-4-(3-fluoro-phenyl)-1H-imidazol-2-yl]-2,2-dimethyl-propyl}-2-methoxy-acetamide;
(S)-Tetrahydro-furan-2-carboxylic acid [2-(1-amino-cyclopropyl)-ethyl]-{(R)-1-[1-benzyl-4-(3-fluoro-phenyl)-1H-imidazol-2-yl]-2,2-dimethyl-propyl}-amide;
N-(3-Amino-propyl)-N-{(R)-1-[1-benzyl-4-(2,5-difluoro-phenyl)-1H-imidazol-2-yl]-2,2-dimethyl-propyl}-2-methoxy-acetamide;
N—((S)-3-Amino-4-fluoro-butyl)-N-{(R)-1-[1-benzyl-4-(2,5-difluoro-phenyl)-1H-imidazol-2-yl]-2,2-dimethyl-propyl}-2-methoxy-acetamide;
N—((R)-3-Amino-4-fluoro-butyl)-N-{(R)-1-[1-benzyl-4-(2,5-difluoro-phenyl)-1H-imidazol-2-yl]-2,2-dimethyl-propyl}-2-methoxy-acetamide;
N-(3-Amino-propyl)-N-{1-[1-(3-fluoro-benzyl)-4-(3-fluoro-phenyl)-1H-imidazol-2-yl]-1-methyl-ethyl}-2-methoxy-acetamide;
N-(3-Amino-propyl)-N-{(R)-1-[1-(3-fluoro-benzyl)-4-(3-fluoro-phenyl)-1H-imidazol-2-yl]-2,2-dimethyl-propyl}-2-methoxy-acetamide;
(S)-Tetrahydro-furan-2-carboxylic acid ((S)-3-amino-4-fluoro-butyl)-{(R)-1-[1-(3-fluoro-benzyl)-4-(3-fluoro-phenyl)-1H-imidazol-2-yl]-2,2-dimethyl-propyl}-amide;
N—((S)-3-Amino-4-fluoro-butyl)-N-{(R)-1-[1-benzyl-5-(3-fluoro-phenyl)-1H-imidazol-2-yl]-2,2-dimethyl-propyl}-2-methoxy-acetamide;
N—((S)-3-Amino-4-methoxy-butyl)-N-{(R)-1-[4-(3-chloro-phenyl)-1-(3-fluoro-benzyl)-1H-imidazol-2-yl]-2-methyl-propyl}-2-methoxy-acetamide;
N—((S)-3-Amino-4-fluoro-butyl)-N-{(R)-1-[1-benzyl-4-(3-chloro-phenyl)-1H-imidazol-2-yl]-2-methyl-propyl}-2-methoxy-acetamide;
N—((S)-3-Amino-4-fluoro-butyl)-N-{(R)-1-[4-(3-chloro-phenyl)-1-(3-fluoro-benzyl)-1H-imidazol-2-yl]-2-methyl-propyl}-2-methoxy-acetamide;
N-(3-Amino-4-fluoro-butyl)-N-{1-[1-(3-fluoro-benzyl)-4-(3-fluoro-phenyl)-1H-imidazol-2-yl]-1-methyl-ethyl}-2-methoxy-acetamide;
N—((S)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-acetamide;
N—((R)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-acetamide;
(S)-Tetrahydro-furan-2-carboxylic acid ((S)-3-amino-2-fluoro-propyl)-{(R)-1-[1-(3-fluoro-benzyl)-4-(3-fluoro-phenyl)-1H-imidazol-2-yl]-2,2-dimethyl-propyl}-amide;
(R)-9-{(R)-1-[1-(3-Fluoro-benzyl)-4-(3-fluoro-phenyl)-1H-imidazol-2-yl]-2,2-dimethyl-propyl}-6-oxa-2,9-diaza-spiro[4.5]decan-8-one;
(3-Amino-4-fluoro-butyl)-{(R)-1-[1-(3-fluoro-benzyl)-4-(3-fluoro-phenyl)-1H-imidazol-2-yl]-2,2-dimethyl-propyl}-carbamic acid methyl ester;
N—((S)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-formamide;
N—((R)-3-Amino-4-fluoro-butyl)-N-{(R)-1-[1-(3-fluoro-benzyl)-4-(3-fluoro-phenyl)-1H-imidazol-2-yl]-2,2-dimethyl-propyl}-formamide;
N-(3-Dimethylamino-propyl)-N-{(R)-1-[1-(3-fluoro-benzyl)-4-(3-fluoro-phenyl)-1H-imidazol-2-yl]-2,2-dimethyl-propyl}-2-methoxy-acetamide;
N—((S)-3-Amino-butyl)-N-{(R)-1-[1-(3-fluoro-benzyl)-4-(3-fluoro-phenyl)-1H-imidazol-2-yl]-2,2-dimethyl-propyl}-2-methoxy-acetamide;
N—((R)-3-Amino-butyl)-N-{(R)-1-[1-(3-fluoro-benzyl)-4-(3-fluoro-phenyl)-1H-imidazol-2-yl]-2,2-dimethyl-propyl}-2-methoxy-acetamide;
N—((S)-3-Amino-4-fluoro-butyl)-N-{(R)-1-[1-(6-amino-pyridin-2-ylmethyl)-4-(3-fluoro-phenyl)-1H-imidazol-2-yl]-2,2-dimethyl-propyl}-2-methoxy-acetamide;
N—((R)-3-Amino-4-fluoro-butyl)-N-{(R)-1-[1-(6-amino-pyridin-2-ylmethyl)-4-(3-fluoro-phenyl)-1H-imidazol-2-yl]-2,2-dimethyl-propyl}-2-methoxy-acetamide;
N—((S)-3-Amino-4-fluoro-butyl)-N-{(R)-1-[4-(3-fluoro-phenyl)-1-(3-hydroxy-benzyl)-1H-imidazol-2-yl]-2,2-dimethyl-propyl}-2-methoxy-acetamide;
N—((R)-3-Amino-4-fluoro-butyl)-N-{(R)-1-[4-(3-fluoro-phenyl)-1-(3-hydroxy-benzyl)-1H-imidazol-2-yl]-2,2-dimethyl-propyl}-2-methoxy-acetamide;
N—((S)-3-Amino-4-fluoro-butyl)-N—[(R)-1-(1-benzyl-4-thiazol-2-yl-1H-imidazol-2-yl)-2,2-dimethyl-propyl]-2-methoxy-acetamide;
N-{(R)-1-[1-(3-Fluoro-benzyl)-4-(3-fluoro-phenyl)-1H-imidazol-2-yl]-2,2-dimethyl-propyl}-2-methoxy-N-(3-methylamino-propyl)-acetamide;
N-(3-Amino-propyl)-N-{(R)-1-[1-benzyl-4-(2,5-difluoro-phenyl)-1H-imidazol-2-yl]-2,2-dimethyl-propyl}-acetamide;

(3-Amino-propyl)-{(R)-1-[1-benzyl-4-(2,5-difluoro-phenyl)-1H-imidazol-2-yl]-2,2-dimethyl-propyl}-carbamic acid methyl ester;
(S)-Tetrahydro-furan-2-carboxylic acid (3-amino-propyl)-{(R)-1-[1-benzyl-4-(2,5-difluoro-phenyl)-1H-imidazol-2-yl]-2,2-dimethyl-propyl}-amide;
3-[{(R)-1-[1-(3-Fluoro-benzyl)-4-(3-fluoro-phenyl)-1H-imidazol-2-yl]-2,2-dimethyl-propyl}-(2-methoxy-acetyl)-amino]-propionamide;
N-(3-Amino-propyl)-N-{(R)-1-[1-benzyl-4-(2,5-difluoro-phenyl)-1H-imidazol-2-yl]-2,2-dimethyl-propyl}-2-methanesulfonyl-acetamide;
N—((S)-3-Amino-4-methoxy-butyl)-N-{(R)-1-[1-benzyl-4-(2,5-difluoro-phenyl)-1H-imidazol-2-yl]-2,2-dimethyl-propyl}-2-methoxy-acetamide;
(S)-Tetrahydro-furan-2-carboxylic acid ((S)-3-amino-4-fluoro-butyl)-{(R)-1-[1-benzyl-4-(2,5-difluoro-phenyl)-1H-imidazol-2-yl]-2,2-dimethyl-propyl}-amide;
(R)-1-[1-Benzyl-4-(2,5-difluoro-phenyl)-1H-imidazol-2-yl]-2,2-dimethyl-propylamine;
(S)-Tetrahydro-furan-2-carboxylic acid ((S)-3-amino-4-methoxy-butyl)-{(R)-1-[1-benzyl-4-(2,5-difluoro-phenyl)-1H-imidazol-2-yl]-2,2-dimethyl-propyl}-amide;
N—((R)-3-Amino-butyl)-N-{(R)-1-[1-benzyl-4-(2,5-difluoro-phenyl)-1H-imidazol-2-yl]-2,2-dimethyl-propyl}-2-methoxy-acetamide;
N—((S)-3-Amino-butyl)-N-{(R)-1-[1-benzyl-4-(2,5-difluoro-phenyl)-1H-imidazol-2-yl]-2,2-dimethyl-propyl}-2-methoxy-acetamide;
N-{(R)-1-[1-Benzyl-4-(2,5-difluoro-phenyl)-1H-imidazol-2-yl]-2,2-dimethyl-propyl}-2-methoxy-N-(1H-[1,2,3]triazol-4-ylmethyl)-acetamide;
N—((S)-3-Amino-4-fluoro-butyl)-N-{(R)-1-[1-benzyl-4-(2,5-difluoro-phenyl)-1H-imidazol-2-yl]-2,2-dimethyl-propyl}-acetamide;
((S)-3-Amino-4-fluoro-butyl)-{(R)-1-[1-benzyl-4-(2,5-difluoro-phenyl)-1H-imidazol-2-yl]-2,2-dimethyl-propyl}-carbamic acid methyl ester;
{(R)-1-[1-Benzyl-4-(2,5-difluoro-phenyl)-1H-imidazol-2-yl]-2,2-dimethyl-propyl}-carbamic acid tert-butyl ester;
N-[(1R)-1-(1-benzyl-4-phenyl-1H-imidazol-2-yl)-2-methylpropyl]-4-methylbenzamide;
N-(3-aminopropyl)-N-[(1R)-1-(1-benzyl-4-phenyl-1H-imidazol-2-yl)-2-methylpropyl]-2-(4-fluorophenoxy)acetamide; and
pharmaceutically acceptable salts thereof.

7. A pharmaceutical composition comprising a therapeutically effective amount of a compound of claim 1 and a pharmaceutically acceptable carrier.

8. The composition of claim 7 further comprising at least one additional agent for the treatment of cancer selected from the group consisting of irinotecan, topotecan, gemcitabine, imatinib, 5-fluorouracil, leucovorin, carboplatin, cisplatin, docetaxel, paclitaxel, tezacitabine, cyclophosphamide, vinca alkaloids, anthracyclines, rituximab, and trastuzumab.

9. The compound of claim 1, wherein A is selected from 4-t-butylphenyl, 2-chlorophenyl, 3-chlorophenyl, 4-chlorophenyl, 3,4-dichlorophenyl, 2,4-difluorophenyl, 2-methoxyphenyl, 4-methoxyphenyl, 4-methylphenyl, 2-pyrrolidin-3-ylphenyl, 4-(trifluoromethyl)phenyl.

10. The compound of claim 1, wherein $R^4$ is selected —$(CH_2)_2$—$NH_2$, —$CH_2$-azetidin-3-yl, —$CH_2$-(2,5-dihydropyrrol-3-yl), —$CH_2$-morpholin-2-yl, —$CH_2$-pyrrolidin-3-yl, —$CH_2$-(3-fluoropyrrolidin-3-yl), —$CH_2$-(3-hydroxypyrrolidin-3-yl), —$CH_2$-(4-fluoropyrrolidin-3-yl), —$CH_2$-(4-hydroxypyrrolidin-3-yl), —$CH_2$-(2-hydroxymethylpyrrolidin-3-yl), —$CH_2$-piperidin-3-yl, —$CH_2CH(NH_2)CH_2OH$, —$(CH_2)_3$—$NH_2$, —$(CH_2)_3$—$NHCH_3$, —$(CH_2)_3$—$N(CH_3)_2$, —$(CH_2)_3NH$-cyclopropyl, —$(CH_2)_3NH$-cyclobutyl, —$(CH_2)_3NHCH_2$-cyclopropyl, —$CH_2CHOHCH_2NH_2$, —$CH_2CH(CH_2OH)CH_2NH_2$, —$CH_2C(CH_3)_2CH_2$—$N(CH_3)_2$, —$CH_2C(CH_3)_2CH_2$-(4-methylpiperazin-1-yl), —$(CH_2)_2CH(NH_2)CH_3$, —$CH_2CHFCH_2NH_2$, —$(CH_2)_2C(CH_3)_2NH_2$, —$(CH_2)_2CH(NH_2)CH_2OCH_3$, —$(CH_2)_2CH(NH_2)CH_2F$, and —$CH_2CHFCH(NH_2)CH_2OH$.

11. The compound of claim 1, wherein $A^1$ is selected from the group consisting of phenyl, 3-chlorophenyl, 3-cyanophenyl, 2-fluorophenyl, 3-fluorophenyl, 4-fluorophenyl, 3-hydroxyphenyl, 3-methoxyphenyl, 2-methylphenyl, and 3-methylphenyl.

* * * * *